(12) United States Patent
Gotoh et al.

(10) Patent No.: US 10,155,905 B2
(45) Date of Patent: Dec. 18, 2018

(54) LIQUID CRYSTAL COMPOUND HAVING VINYLENE GROUP, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Keiji Kimura, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

(21) Appl. No.: 15/046,452

(22) Filed: Feb. 18, 2016

(65) Prior Publication Data
US 2016/0244670 A1    Aug. 25, 2016

(30) Foreign Application Priority Data
Feb. 24, 2015  (JP) ................. 2015-033914

(51) Int. Cl.
| | | |
|---|---|---|
| *C09K 19/30* | (2006.01) | |
| *C09K 19/34* | (2006.01) | |
| *C07C 43/225* | (2006.01) | |
| *C07C 43/192* | (2006.01) | |
| *C07D 309/06* | (2006.01) | |
| *C07D 309/12* | (2006.01) | |
| *C07D 309/10* | (2006.01) | |
| *C07D 239/26* | (2006.01) | |
| *C07D 239/28* | (2006.01) | |
| *C07D 239/34* | (2006.01) | |
| *C07D 319/06* | (2006.01) | |
| *C07D 213/68* | (2006.01) | |
| *C07D 213/30* | (2006.01) | |
| *C07D 213/79* | (2006.01) | |
| *C07C 69/753* | (2006.01) | |
| *C09K 19/04* | (2006.01) | |

(52) U.S. Cl.
CPC ........ *C09K 19/3458* (2013.01); *C07C 43/192* (2013.01); *C07C 43/225* (2013.01); *C07C 69/753* (2013.01); *C07D 213/30* (2013.01); *C07D 213/68* (2013.01); *C07D 213/79* (2013.01); *C07D 239/26* (2013.01); *C07D 239/28* (2013.01); *C07D 239/34* (2013.01); *C07D 309/06* (2013.01); *C07D 309/10* (2013.01); *C07D 309/12* (2013.01); *C07D 319/06* (2013.01); *C09K 19/3048* (2013.01); *C09K 19/3066* (2013.01); *C07C 2601/14* (2017.05); *C09K 2019/0466* (2013.01); *C09K 2019/3004* (2013.01); *C09K 2019/3009* (2013.01); *C09K 2019/3077* (2013.01); *C09K 2019/3083* (2013.01); *C09K 2019/3422* (2013.01)

(58) Field of Classification Search
CPC .................................. C09K 19/3001
See application file for complete search history.

(56) References Cited

U.S. PATENT DOCUMENTS

| | | | |
|---|---|---|---|
| 5,728,319 A | 3/1998 | Matsui et al. | |
| 6,007,740 A * | 12/1999 | Andou | C07C 43/225 252/299.01 |
| 6,231,934 B1 * | 5/2001 | Kondo | C07C 43/176 252/299.61 |

FOREIGN PATENT DOCUMENTS

| | | |
|---|---|---|
| JP | 10-204016 | 8/1998 |
| WO | 96/011897 | 4/1996 |

* cited by examiner

*Primary Examiner* — Chanceity N Robinson
(74) *Attorney, Agent, or Firm* — JCIPRNET

(57) ABSTRACT

A compound is represented by formula (1).

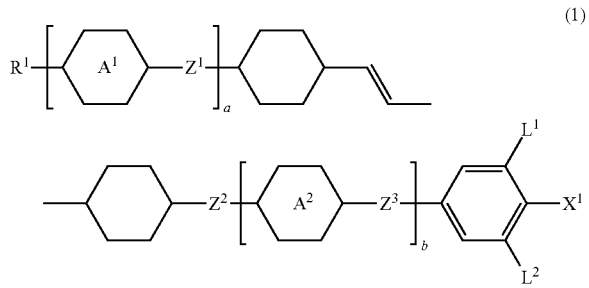

(1)

In formula (1), $R^1$ is hydrogen, fluorine, alkyl or the like; ring $A^1$ and ring $A^2$ are independently 1,4-cyclohexylene, 1,4-phenylene or the like; $Z^1$, $Z^2$ and $Z^3$ are independently a single bond, —COO— or the like; $X^1$ is hydrogen, fluorine, —CF$_3$, or —OCF$_3$; $L^1$ and $L^2$ are independently hydrogen or fluorine; and a is 0 or 1, and b is 0 or 1.

12 Claims, No Drawings

LIQUID CRYSTAL COMPOUND HAVING VINYLENE GROUP, LIQUID CRYSTAL COMPOSITION AND LIQUID CRYSTAL DISPLAY DEVICE

CROSS-REFERENCE TO RELATED APPLICATION

This application claims the priority benefit of Japan application serial no. 2015-033914, filed on Feb. 24, 2015. The entirety of the above-mentioned patent application is hereby incorporated by reference herein and made a part of this specification.

FIELD OF THE INVENTION

The invention relates to a liquid crystal compound having a vinylene group, a liquid crystal composition and a liquid crystal display device. More specifically, the invention relates to a liquid crystal compound having a cyclohexane ring-vinylene group-cyclohexane ring structure, a liquid crystal composition containing this compound and having a nematic phase, and a liquid crystal display device containing this composition.

Liquid crystal display devices are widely utilized in displays of personal computers, televisions and so on. These devices utilize physical properties such as optical anisotropy and dielectric anisotropy of liquid crystal compounds. Operating modes of a liquid crystal display device include phase change (PC), twisted nematic (TN), super twisted nematic (STN), bistable twisted nematic (BTN), electrically controlled birefringence (ECB), optically compensated bend (OCB), in-plane switching (IPS), vertical alignment (VA), fringe field switching (FFS), and polymer sustained alignment (PSA) modes, etc.

In such a liquid crystal display device, a liquid crystal composition with suitable physical properties is used. To further improve characteristics of the device, a liquid crystal compound contained in this composition preferably has physical properties shown in the following (1) to (8): (1) high stability to heat or light; (2) a high clearing point; (3) low minimum temperature of a liquid crystal phase; (4) small viscosity ($\eta$); (5) suitable optical anisotropy ($\Delta n$); (6) large dielectric anisotropy ($\Delta \varepsilon$); (7) a suitable elastic constant (K); and (8) excellent compatibility with other liquid crystal compounds.

Effects of the physical properties of the liquid crystal compound on the characteristics of the device are as follows. A compound having high stability to heat or light as described in (1) increases a voltage holding ratio of the device. Accordingly, service life of the device is increased. A compound having a high clearing point as described in (2) broadens a temperature range in which the device can be used. A compound having low minimum temperature of a liquid crystal phase such as a nematic phase, a smectic phase and so on as described in (3), particularly a compound having low minimum temperature of a nematic phase, also broadens the temperature range in which the device can be used. A compound having small viscosity as described in (4) decreases response time of the device.

Depending on the design of the device, a compound having suitable optical anisotropy, namely large or small optical anisotropy, is required. To decrease the response time by decreasing a cell gap of the device, a compound having large optical anisotropy is suitable. A compound having large dielectric anisotropy as described in (6) decreases a threshold voltage of the device. Accordingly, electric power consumption of the device is decreased. On the other hand, a compound having small dielectric anisotropy decreases the response time of the device by reducing viscosity of a composition. This compound broadens the temperature range in which the device can be used by increasing a maximum temperature of a nematic phase.

With respect to (7), a compound having a large elastic constant decreases the response time of the device. A compound having a small elastic constant decreases the threshold voltage of the device. Accordingly, a suitable elastic constant is required according to the characteristics that are desirably improved. A compound having excellent compatibility with other liquid crystal compounds as described in (8) is preferred, because physical properties of a composition are adjusted by mixing liquid crystal compounds having different physical properties.

Until now, various liquid crystal compounds having large dielectric anisotropy have been synthesized, and various liquid crystal compounds having large optical anisotropy have also been synthesized. This is because excellent physical properties which conventional compounds do not have are expected to be found in a new compound, and because a suitable balance between at least two physical properties of a composition is expected to be obtained by adding a new compound to a liquid crystal composition. Under such a circumstance, a compound having excellent physical properties and a suitable balance with regard to the above (1) to (8) is desired.

PRIOR-ART DOCUMENTS

Patent Documents

[Patent Document 1] WO 1996/011897
[Patent Document 2] JP H10-204016

SUMMARY OF THE INVENTION

Problems to be Solved

A first subject is to provide a liquid crystal compound that satisfies at least one of physical properties such as high stability to heat or light, a high clearing point (or high maximum temperature of a nematic phase), low minimum temperature of a liquid crystal phase, small viscosity, suitable optical anisotropy, large dielectric anisotropy, a suitable elastic constant and excellent compatibility with other liquid crystal compounds, etc., and particularly to provide a compound that has excellent compatibility with other liquid crystal compounds. A second subject is to provide a liquid crystal composition that contains this compound and that satisfies at least one of physical properties such as high stability to heat or light, high maximum temperature of a nematic phase, low minimum temperature of a nematic phase, small viscosity, suitable optical anisotropy, large dielectric anisotropy, large specific resistance, and a suitable elastic constant, etc., and this subject is to provide a liquid crystal composition having a suitable balance between at least two of the physical properties. A third subject is to provide a liquid crystal display device that contains this composition and that has a wide temperature range in which the device can be used, short response time, a large voltage holding ratio, a low threshold voltage, a large contrast ratio, and long service life.

Means for Solving the Problems

The invention relates to a compound represented by formula (1), a liquid crystal composition containing the compound, and a liquid crystal display device containing the composition.

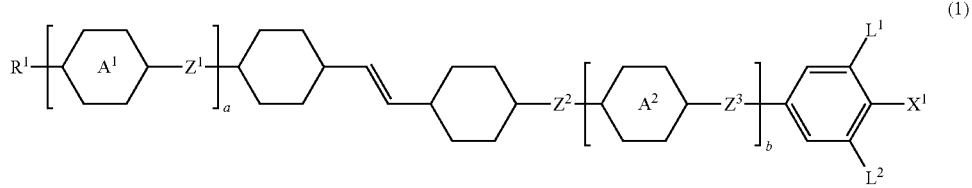

In formula (1), $R^1$ is hydrogen, fluorine, or alkyl having 1 to 10 carbons, wherein at least one —$CH_2$— in the alkyl is optionally replaced with —O— or —S—, and at least one —$CH_2CH_2$— in the alkyl is optionally replaced with —CH=CH—, and wherein at least one hydrogen in these groups is optionally replaced with fluorine; ring $A^1$ and ring $A^2$ are independently 1,4-cyclohexylene, 1,4-phenylene, 1,4-phenylene in which at least one hydrogen has been replaced with fluorine, tetrahydropyran-2,5-diyl, 1,3-dioxane-2,5-diyl, pyridine-2,5-diyl, or pyrimidine-2,5-diyl; $Z^1$, $Z^2$ and $Z^3$ are independently a single bond, —COO—, —$OCH_2$—, —$CF_2O$—, —$CH_2CH_2$—, —$CF_2CF_2$—, —CH=CH—, —CF=CF—, —C≡C—, —$(CH_2)_4$—, or —$CH_2CH=CHCH_2$—, wherein at least one of $Z^1$, $Z^2$ and $Z^3$ is —$CF_2O$—; $X^1$ is hydrogen, fluorine, —$CF_3$, or —$OCF_3$; $L^1$ and $L^2$ are independently hydrogen or fluorine; and a is 0 or 1, b is 0 or 1, and the sum of a and b is 0 or 1.

Effects of the Invention

A first advantage is to provide a liquid crystal compound that satisfies at least one of physical properties such as high stability to heat or light, a high clearing point (or high maximum temperature of a nematic phase), low minimum temperature of a liquid crystal phase, small viscosity, suitable optical anisotropy, large dielectric anisotropy, a suitable elastic constant and excellent compatibility with other liquid crystal compounds, etc., and particularly to provide a compound that has excellent compatibility with other liquid crystal compounds (see Comparative Example 2). A second advantage is to provide a liquid crystal composition that contains this compound and that satisfies at least one of physical properties such as high stability to heat or light, high maximum temperature of a nematic phase, low minimum temperature of a nematic phase, small viscosity, suitable optical anisotropy, large dielectric anisotropy, large specific resistance, and a suitable elastic constant, etc., and this advantage is to provide a liquid crystal composition having a suitable balance between at least two of the physical properties. A third advantage is to provide a liquid crystal display device that contains this composition and that has a wide temperature range in which the device can be used, short response time, a large voltage holding ratio, a low threshold voltage, a large contrast ratio, and long service life.

DESCRIPTION OF THE EMBODIMENTS

The terms in this specification are defined as follows. The terms "liquid crystal compound," "liquid crystal composition" and "liquid crystal display device" are sometimes simply referred to as "compound," "composition," and "device," respectively. "Liquid crystal compound" is a generic term for compounds having a liquid crystal phase such as nematic phase or smectic phase, etc., and compounds having no liquid crystal phase but are added for adjusting physical properties such as maximum temperature, minimum temperature, viscosity, and dielectric anisotropy of a composition. This compound has a six-membered ring such as 1,4-cyclohexylene or 1,4-phenylene, and a rod-like molecular structure. "Liquid crystal display device" is a generic term for liquid crystal display panels and liquid crystal display modules. "Polymerizable compound" is a compound that is added for producing a polymer in the composition.

A liquid crystal composition is prepared by mixing a plurality of liquid crystal compounds. The ratio (content) of the liquid crystal compound is expressed by a weight percentage (wt %) based on the weight of the liquid crystal composition. An additive such as a polymerizable compound, a polymerization initiator, a polymerization inhibitor, an optically active compound, an antioxidant, an ultraviolet absorbent, a light stabilizer, a heat stabilizer, a dye, or a defoamer is added to this composition if necessary. Similarly to the liquid crystal compound, a ratio (amount added) of the additive is expressed by a weight percentage (wt %) based on the weight of the liquid crystal composition. Parts per million (ppm) may also be used. A ratio of the polymerization initiator or polymerization inhibitor is exceptionally expressed based on the weight of the polymerizable compound.

"Clearing point" is the transition temperature between a liquid crystal phase and an isotropic phase in a liquid crystal compound. The "minimum temperature of a liquid crystal phase" is the transition temperature between solids and a liquid crystal phase (a smectic phase, a nematic phase and so on) in a liquid crystal compound. The "maximum temperature of a nematic phase" is the transition temperature between a nematic phase and an isotropic phase in a mixture of a liquid crystal compound and a mother liquid crystal or a liquid crystal composition, and is sometimes simply referred to as "maximum temperature." The "minimum temperature of a nematic phase" is sometimes simply referred to as "minimum temperature." The expression "increase the dielectric anisotropy" means that when the composition has positive dielectric anisotropy, the value of the dielectric anisotropy increases positively, and that when the composition has negative dielectric anisotropy, the value of the dielectric anisotropy increases negatively.

A compound represented by formula (1) is sometimes simply referred to as a compound (1). At least one compound selected from the group consisting of compounds represented by formula (1) is sometimes simply referred to as a compound (1). "Compound (1)" means one compound represented by formula (1), a mixture of two compounds represented by formula (1), or a mixture of three or more compounds represented by formula (1). These rules also apply to compounds represented by the other formulae. In formulae (1) to (15), symbols $A^1$, $B^1$, $C^1$ and so on surrounded by a hexagon correspond to ring $A^1$, ring $B^1$, ring $C^1$ and so on, respectively. The hexagon represents a six-membered ring such as cyclohexane or benzene. The hexagon sometimes represents a fused ring such as naphthalene, or a cross-linked ring such as adamantane.

In chemical formulae of component compounds, the symbol of the terminal group $R^1$ is used for a plurality of the compounds. In these compounds, two groups represented by arbitrary two $R^1$'s may be the same or different. For example, in one case, $R^1$ represents ethyl in both compounds (1-1) and (1-2). In another case, $R^1$ represents ethyl in the compound (1-1), and represents propyl in the compound (1-2). This rule also applies to symbols such as $R^{11}$, $Z^{11}$ and so on. In a compound (8), when i is 2, two rings $D^1$ are present. In this compound, the two groups represented by the two rings $D^1$ may be the same or different. When i is greater than 2, the same rule also applies to arbitrary two rings $D^1$. This rule also applies to the other symbols.

diyl, which is formed by removing two hydrogens from a ring.

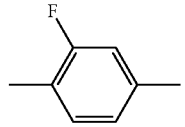

(L)

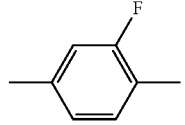

(R)

The invention includes the following items.

Item 1 is a compound represented by formula (1).

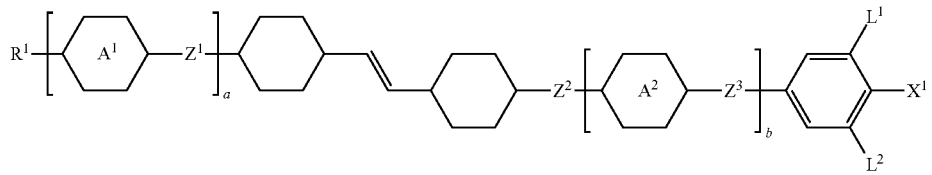

(1)

The expression "at least one 'A'" means the number of 'A' is arbitrary. The expression "at least one 'A' is optionally replaced with 'B'" means that when the number of 'A' is one, the position of 'A' is arbitrary, and when the number of 'A' is two or more, the positions of 'A's can be selected without any restriction. This rule also applies to the expression "at least one 'A' has been replaced with 'B'." The expression "at least one 'A' is optionally replaced with 'B,' 'C' or 'D'" includes the case where arbitrary 'A' has been replaced with 'B,' the case where arbitrary 'A' has been replaced with 'C' and the case where arbitrary 'A' has been replaced with 'D,' and further the case where a plurality of 'A's have been replaced with at least two of 'B', 'C' and/or 'D.' For example, the scope of "alkyl in which at least one —$CH_2$— is optionally replaced with —O— or —CH=CH—" includes alkyl, alkoxy, alkoxyalkyl, alkenyl, alkoxyalkenyl and alkenyloxyalkyl. Moreover, it is undesirable that two successive —$CH_2$— be replaced with —O— to form —O—O—, and it is also undesirable that —$CH_2$— in a methyl moiety (—$CH_2$—H) in alkyl or the like be replaced with —O— to form —O—H.

Halogen includes fluorine, chlorine, bromine and iodine. The halogen is preferably fluorine or chlorine, and more preferably fluorine. In a liquid crystal compound, alkyl is straight or branched, and does not include cyclic alkyl. Generally, straight alkyl is preferred to branched alkyl. These also apply to terminal groups such as alkoxy and alkenyl, etc. To increase the maximum temperature, the stereo configuration of 1,4-cyclohexylene is preferably trans rather than cis. 2-fluoro-1,4-phenylene means the following two divalent groups. In a chemical formula, fluorine may be leftward (L) or rightward (R). This rule also applies to an asymmetrical divalent group such as tetrahydropyran-2,5-

In formula (1), $R^1$ is hydrogen, fluorine, or alkyl having 1 to 10 carbons, wherein at least one —$CH_2$— in the alkyl is optionally replaced with —O— or —S—, and at least one —$CH_2CH_2$— in the alkyl is optionally replaced with —CH=CH—, and wherein at least one hydrogen in these groups is optionally replaced with fluorine; ring $A^1$ and ring $A^2$ are independently 1,4-cyclohexylene, 1,4-phenylene, 1,4-phenylene in which at least one hydrogen has been replaced with fluorine, tetrahydropyran-2,5-diyl, 1,3-dioxane-2,5-diyl, pyridine-2,5-diyl, or pyrimidine-2,5-diyl; $Z^1$, $Z^2$ and $Z^3$ are independently a single bond, —COO—, —$OCH_2$—, —$CF_2O$—, —$CH_2CH_2$—, —$CF_2CF_2$—, —CH=CH—, —CF=CF—, —C≡C—, —$(CH_2)_4$—, or —$CH_2CH=CHCH_2$—, wherein at least one of $Z^1$, $Z^2$ and $Z^3$ is —$CF_2O$—; $X^1$ is hydrogen, fluorine, —$CF_3$, or —$OCF_3$; $L^1$ and $L^2$ are independently hydrogen or fluorine; and a is 0 or 1, b is 0 or 1, and the sum of a and b is 0 or 1.

Item 2 is the compound described in item 1, wherein in formula (1) described in item 1, $R^1$ is hydrogen, fluorine, or alkyl having 1 to 10 carbons, wherein at least one —$CH_2$— in the alkyl is optionally replaced with —O—, and at least one —$CH_2CH_2$— in the alkyl is optionally replaced with —CH=CH—, and wherein at least one hydrogen in these groups is optionally replaced with fluorine; ring $A^1$ and ring $A^2$ are independently 1,4-cyclohexylene, 1,4-phenylene, 1,4-phenylene in which at least one hydrogen has been replaced with fluorine, tetrahydropyran-2,5-diyl, 1,3-dioxane-2,5-diyl, or pyrimidine-2,5-diyl; $Z^1$, $Z^2$ and $Z^3$ are independently a single bond, —COO—, —$OCH_2$—, —$CF_2O$—, —$CH_2CH_2$—, or —CH=CH—, wherein at least one of $Z^1$, $Z^2$ and $Z^3$ is —$CF_2O$—; $X^1$ is hydrogen, fluorine, —$CF_3$, or —$OCF_3$; $L^1$ and $L^2$ are independently hydrogen or fluorine; and a is 0 or 1, b is 0 or 1, and the sum of a and b is 0 or 1.

Item 3 is the compound described in item 1 or 2, represented by any one of formulae (1-1) to (1-3).

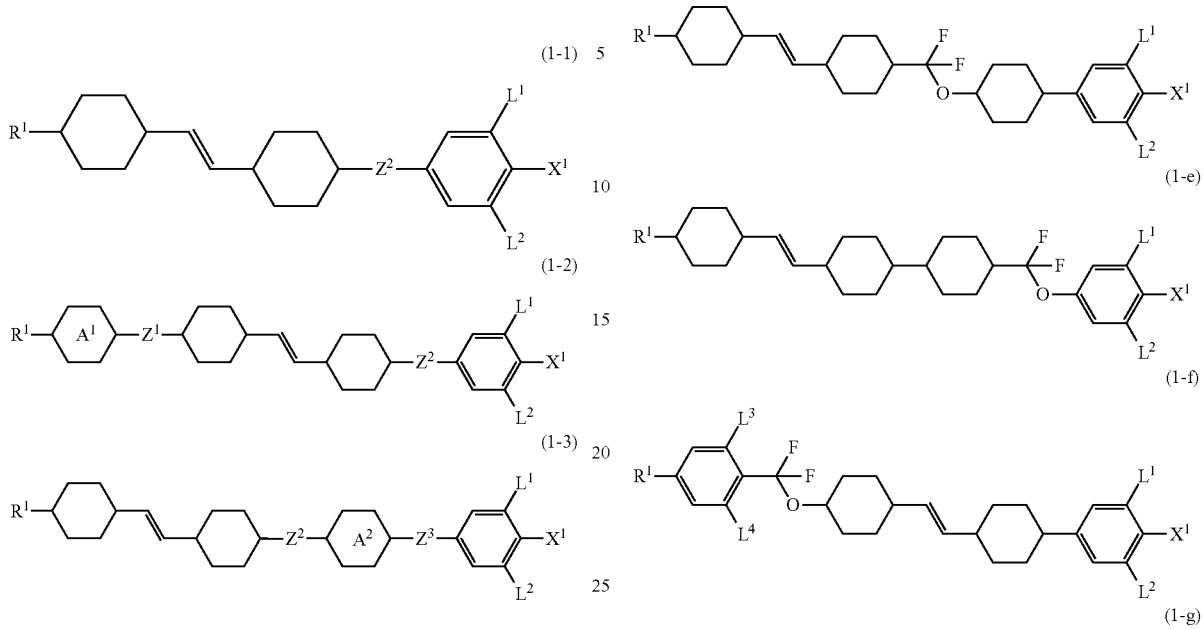

In formulae (1-1) to (1-3), R¹ is alkyl having 1 to 10 carbons or alkenyl having 2 to 10 carbons, wherein at least one —CH₂— in the alkyl and alkenyl is optionally replaced with —O—; ring A¹ and ring A² are independently 1,4-cyclohexylene, 1,4-phenylene, 1,4-phenylene in which at least one hydrogen has been replaced with fluorine, or tetrahydropyran-2,5-diyl; Z¹, Z² and Z³ are independently a single bond, —COO—, —OCH₂—, —CF₂O—, or —CH=CH—, wherein at least one of Z¹, Z² and Z³ is —CF₂O—; X¹ is hydrogen, fluorine, —CF₃, or —OCF₃; and L¹ and L² are independently hydrogen or fluorine.

Item 4 is the compound described in any one of items 1 to 3, represented by any one of formulae (1-a) to (1-i).

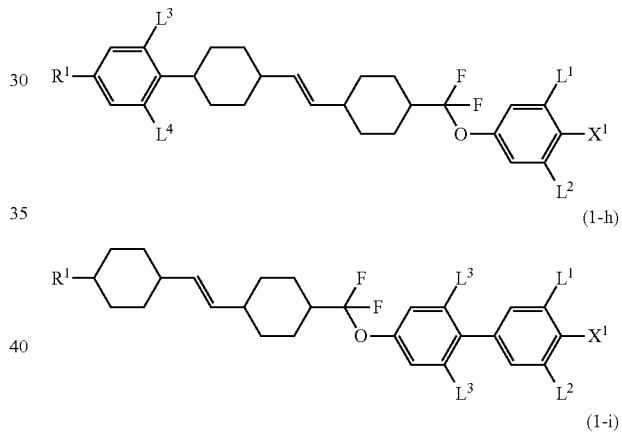

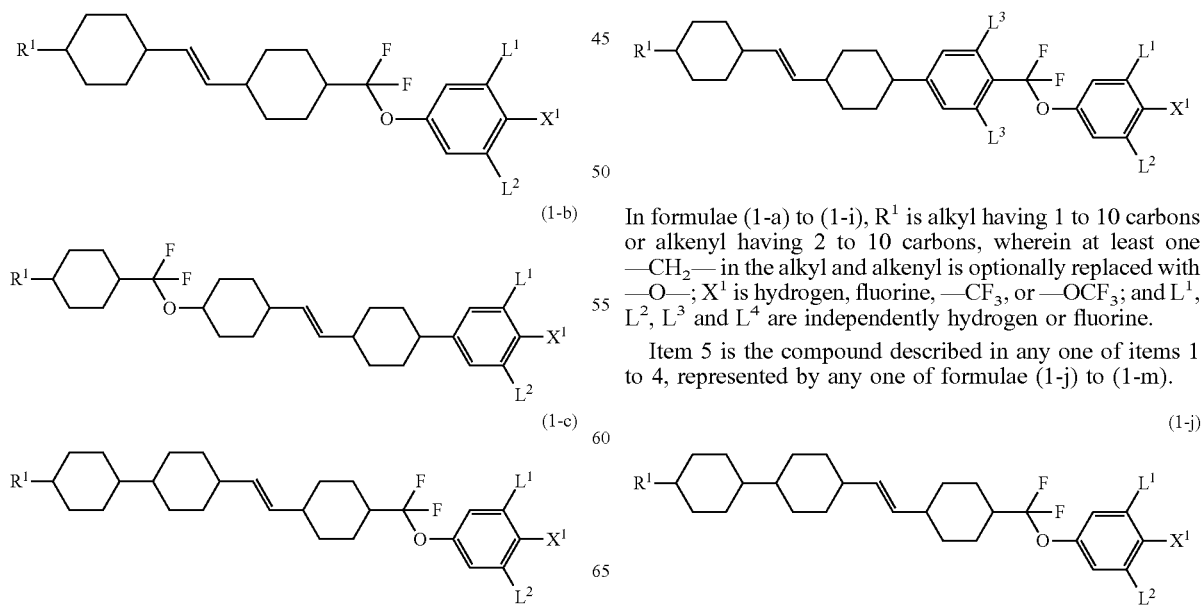

In formulae (1-a) to (1-i), R¹ is alkyl having 1 to 10 carbons or alkenyl having 2 to 10 carbons, wherein at least one —CH₂— in the alkyl and alkenyl is optionally replaced with —O—; X¹ is hydrogen, fluorine, —CF₃, or —OCF₃; and L¹, L², L³ and L⁴ are independently hydrogen or fluorine.

Item 5 is the compound described in any one of items 1 to 4, represented by any one of formulae (1-j) to (1-m).

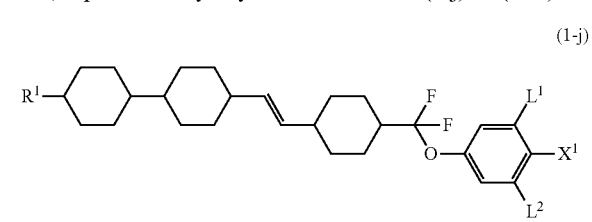

-continued (1-k)
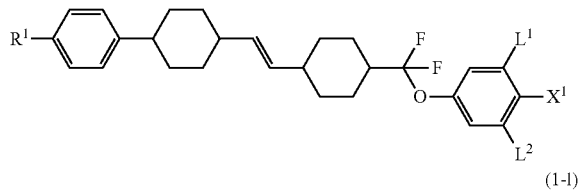

(1-l)
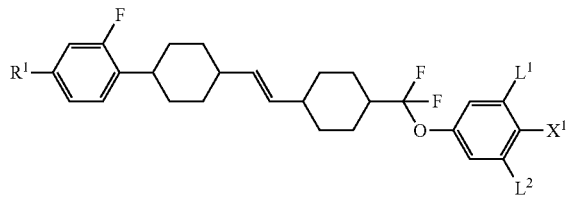

(1-m)
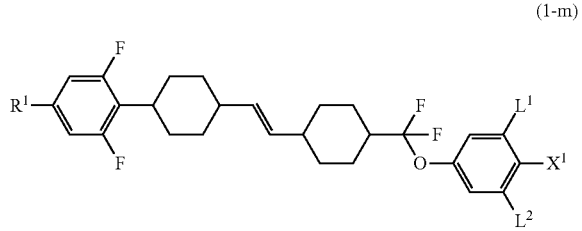

In formulae (1-j) to (1-m), $R^1$ is alkyl having 1 to 5 carbons or alkenyl having 2 to 5 carbons, wherein at least one —CH$_2$— in the alkyl and alkenyl is optionally replaced with —O—; $X^1$ is hydrogen, fluorine, —CF$_3$, or —OCF$_3$; and $L^1$ and $L^2$ are independently hydrogen or fluorine.

Item 6 is the compound described in item 5, wherein in formulae (1-j) to (1-m) described in item 5, $R^1$ is alkyl having 1 to 5 carbons or alkenyl having 2 to 5 carbons; $X^1$ is fluorine; and $L^1$ and $L^2$ are independently hydrogen or fluorine.

Item 7 is the compound described in item 5, wherein in formulae (1-j) to (1-m) described in item 5, $R^1$ is alkyl having 1 to 5 carbons or alkenyl having 2 to 5 carbons; $X^1$ is —CF$_3$; and $L^1$ and $L^2$ are independently hydrogen or fluorine.

Item 8 is the compound described in item 5, wherein in formulae (1-j) to (1-m) described in item 5, $R^1$ is alkyl having 1 to 5 carbons or alkenyl having 2 to 5 carbons; $X^1$ is —OCF$_3$; and $L^1$ and $L^2$ are independently hydrogen or fluorine.

Item 9 is a liquid crystal composition containing at least one compound described in any one of items 1 to 8.

Item 10 is the liquid crystal composition described in item 9, further containing at least one compound selected from the group consisting of compounds represented by formulae (2) to (4).

(2)
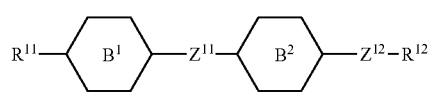

(3)
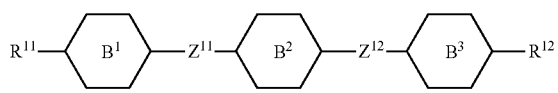

(4)
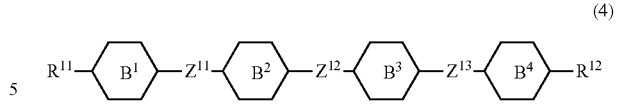

In formulae (2) to (4), $R^{11}$ and $R^{12}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; ring $B^1$, ring $B^2$, ring $B^3$, and ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —CH$_2$CH$_2$—, —CH=CH—, —C≡C—, or —COO—.

Item 11 is the liquid crystal composition described in item 9 or 10, further containing at least one compound selected from the group consisting of compounds represented by formulae (5) to (7).

(5)
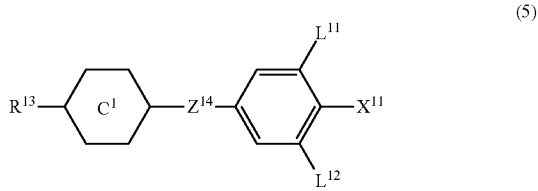

(6)
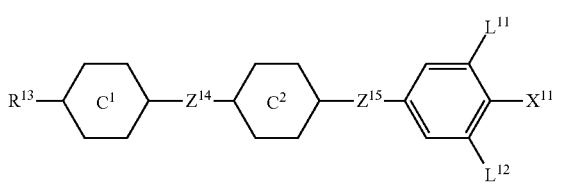

(7)
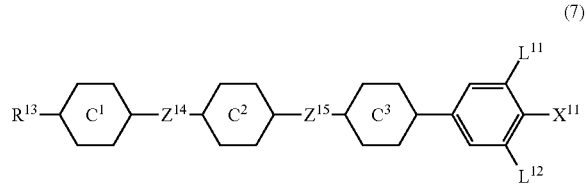

In formulae (5) to (7), $R^{13}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; $X^{11}$ is fluorine, chlorine, —OCF$_3$, —OCHF$_2$, —CF$_3$, —CHF$_2$, —CH$_2$F, —OCF$_2$CHF$_2$, or —OCF$_2$CHFCF$_3$; ring $C^1$, ring $C^2$ and ring $C^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl; $Z^{14}$, $Z^{15}$, and $Z^{16}$ are independently a single bond, —CH$_2$CH$_2$—, —CH=CH—, —C≡C—, —COO—, —CF$_2$O—, —OCF$_2$—, —CH$_2$O—, or —(CH$_2$)$_4$—; and $L^{11}$ and $L^{12}$ are independently hydrogen or fluorine.

Item 12 is the liquid crystal composition described in any one of items 9 to 11, further containing at least one compound selected from the group consisting of compounds represented by formula (8).

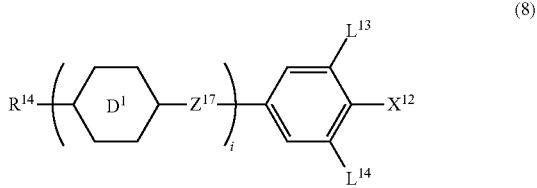

(8)

In formula (8), $R^{14}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; $X^{12}$ is —C≡N or —C≡C—C≡N; ring $D^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl; $Z^{17}$ is a single bond, —$CH_2CH_2$—, —C≡C—, —COO—, —$CF_2O$—, —$OCF_2$—, or —$CH_2O$—; $L^{13}$ and $L^{14}$ are independently hydrogen or fluorine; and i is 1, 2, 3, or 4.

Item 13 is the liquid crystal composition described in any one of items 9 to 12, further containing at least one compound selected from the group consisting of compounds represented by formulae (9) to (15).

In formulae (9) to (15), $R^{15}$ and $R^{16}$ are independently alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; $R^{17}$ is hydrogen, fluorine, alkyl having 1 to 10 carbons, or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; ring $E^1$, ring $E^2$, ring $E^3$, and ring $E^4$ are independently 1,4-cyclohexylene, 1,4-cyclohexenylene, 1,4-phenylene in which at least one hydrogen is optionally replaced with fluorine, tetrahydropyran-2,5-diyl, or decahydronaphthalene-2,6-diyl; ring $E^5$ and ring $E^6$ are independently 1,4-cyclohexylene, 1,4-cyclohexenylene, 1,4-phenylene, tetrahydropyran-2,5-diyl, or decahydronaphthalene-2,6-diyl; $Z^{18}$, $Z^{19}$, $Z^{20}$, and $Z^{21}$ are independently a single bond, —$CH_2CH_2$—, —COO—, —$CH_2O$—, —$OCF_2$—, or —$OCF_2CH_2CH_2$—; $L^{15}$ and $L^{16}$ are independently fluorine or chlorine; $S^{11}$ is hydrogen or methyl; X is —CHF— or —$CF_2$—; and j, k, m, n, p, q, r and s are independently 0 or 1, the sum of k, m, n and p is 1 or 2, the sum of q, r and s is 0, 1, 2, or 3, and t is 1, 2, or 3.

Item 14 is the liquid crystal composition described in any one of items 9 to 13, further containing at least one additive selected from the group consisting of a polymerizable com-

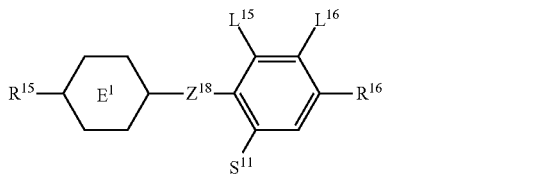

(9)

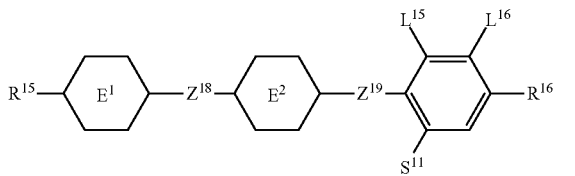

(10)

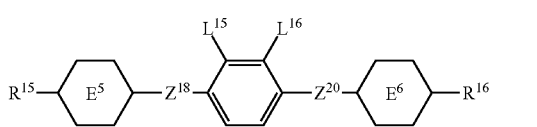

(11)

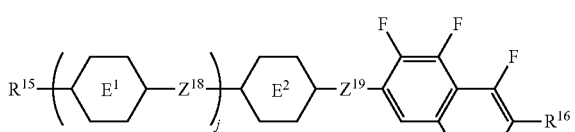

(12)

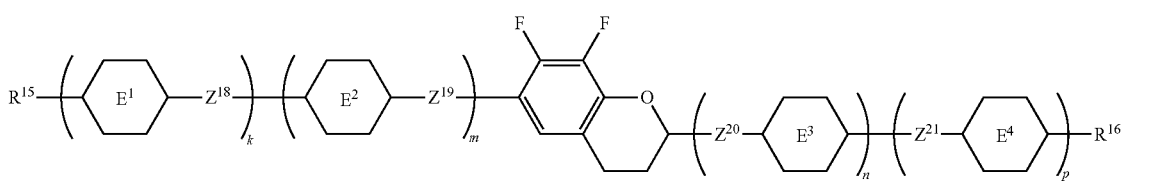

(13)

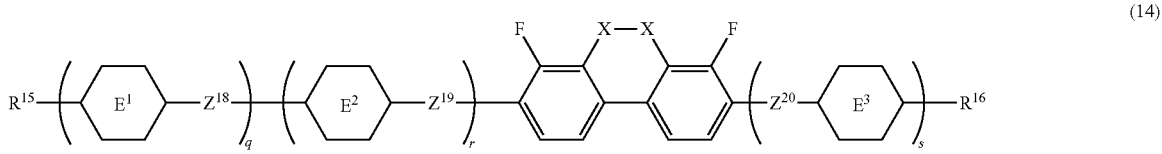

(14)

(15)

pound, a polymerization initiator, a polymerization inhibitor, an optically active compound, an antioxidant, an ultraviolet absorbent, a light stabilizer, a heat stabilizer, a dye and a defoamer.

Item 15 is a liquid crystal display device containing the liquid crystal composition described in any one of items 9 to 14.

The invention also includes the following items: (a) the composition, further containing one, two, or at least three additives selected from the group consisting of a polymerizable compound, a polymerization initiator, a polymerization inhibitor, an optically active compound, an antioxidant, an ultraviolet absorbent, a light stabilizer, a heat stabilizer, a dye and a defoamer; (b) the liquid crystal composition, having a maximum temperature of a nematic phase of 70° C. or higher, optical anisotropy (measured at 25° C.) at a wavelength of 589 nm of 0.07 or more, and dielectric anisotropy (measured at 25° C.) at a frequency of 1 kHz of 2 or more; and (c) the liquid crystal display device, wherein an operating mode of the liquid crystal display device is a TN mode, an ECB mode, an OCB mode, an IPS mode, or an FPA mode, and a driving method for the liquid crystal display device is an active matrix (AM) method.

Embodiments of the compound (1), a synthesis method of the compound (1), the liquid crystal composition and the liquid crystal display device are explained in sequence.

1. Embodiments of Compound (1)

The compound (1) of the invention has a cyclohexane ring-vinylene group-cyclohexane ring structure. The compound (1) is particularly characterized by excellent compatibility with other liquid crystal compounds (see Comparative Example 2). Preferred examples of the compound (1) are explained. Preferred examples of the terminal groups $R^1$ and $X^1$, rings $A^1$ and $A^2$, linking groups $Z^1$, $Z^2$ and $Z^3$, and substituents $L^1$ and $L^2$ in the compound (1) are also applicable to sub-formulae of the compound (1). In the compound (1), by a suitable combination of these groups, the physical properties can be arbitrarily adjusted. The compound (1) may contain an isotope such as $^2H$ (deuterium) and $^{13}C$ in an amount larger than the natural abundance since there is no large difference in physical properties of the compound. Moreover, definitions of the symbols in the compound (1) are as described in item 1.

enyloxyalkyl, or alkoxyalkenyl, more preferably alkyl, alkoxy, alkoxyalkyl, alkenyl, or alkenyloxy, particularly preferably alkyl or alkenyl, and most preferably alkyl.

The alkyl is preferably —$CH_3$, —$C_2H_5$, —$C_3H_7$, —$C_4H_9$, —$C_5H_{11}$, —$C_6H_{13}$, or —$C_7H_{15}$.

The alkoxy is preferably —$OCH_3$, —$OC_2H_5$, —$OC_3H_7$, —$OC_4H_9$, —$OC_5H_{11}$, —$OC_6H_{13}$, or —$OC_7H_{15}$.

The alkoxyalkyl is preferably —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$, or —$(CH_2)_5$—$OCH_3$.

The alkenyl is preferably —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$, or —$(CH_2)_3$—CH=$CH_2$.

The alkenyloxy is preferably —$OCH_2$CH=$CH_2$, —$OCH_2$CH=$CHCH_3$, or —$OCH_2$CH=$CHC_2H_5$.

$R^1$ is preferably hydrogen, —$CH_3$, —$C_2H_5$, —$C_3H_7$, —$C_4H_9$, —$C_5H_{11}$, —$C_6H_{13}$, —$OCH_3$, —$OC_2H_5$, —$OC_3H_7$, —$OC_4H_9$, —$OC_5H_{11}$, —$CH_2OCH_3$, —CH=$CH_2$, —CH=$CHCH_3$, —$(CH_2)_2$—CH=$CH_2$, —$CH_2$CH=$CHC_2H_5$, —$(CH_2)_2$—CH=$CHCH_3$, —$OCH_2$CH=$CH_2$, —$OCH_2$CH=$CHCH_3$, or —$OCH_2$CH=$CHC_2H_5$, and—more preferably —$C_3H_7$, —$C_4H_9$, —$C_5H_{11}$, —$C_6H_{13}$, —$(CH_2)_2$—CH=$CH_2$, or —$(CH_2)_2$—CH=$CHCH_3$.

When $R^1$ is straight, the temperature range of a liquid crystal phase is wide, and the viscosity is small. When $R^1$ is branched, the compatibility with other liquid crystal compounds is good. A compound having optically active $R^1$ is useful as a chiral dopant. By addition of the compound to the composition, generation of a reverse twisted domain in the liquid crystal display device can be prevented. A compound having non-optically active $R^1$ is useful as a component of the composition. When $R^1$ is alkenyl, its preferred stereo configuration depends on the position of the double bond. An alkenyl compound having a preferred stereo configuration has small viscosity, high maximum temperature or a wide temperature range of a liquid crystal phase.

The preferred stereo configuration of —CH=CH— in the alkenyl depends on the position of the double bond. The trans-configuration is preferred for alkenyl having a double bond at an odd position, such as —CH=$CHCH_3$,

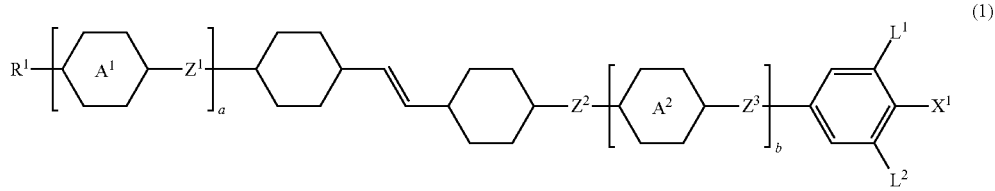

(1)

In formula (1), $R^1$ is hydrogen, fluorine, or alkyl having 1 to 10 carbons, wherein at least one —$CH_2$— in the alkyl is optionally replaced with —O— or —S—, and at least one —$CH_2CH_2$— in the alkyl is optionally replaced with —CH=CH—, and wherein at least one hydrogen in these groups is optionally replaced with fluorine.

Examples of $R^1$ include hydrogen, alkyl, alkoxy, alkoxyalkyl, alkoxyalkoxy, alkenyl, alkenyloxy, alkenyloxyalkyl, alkoxyalkenyl, alkylthio, alkylthioalkyl, alkenylthio, alkenylthioalkyl, and alkylthioalkenyl. $R^1$ is preferably alkyl, alkoxy, alkoxyalkyl, alkoxyalkoxy, alkenyl, alkenyloxy, alk- —CH=$CHC_2H_5$, —CH=$CHC_3H_7$, —CH=$CHC_4H_9$, —$C_2H_4$CH=$CHCH_3$, and —$C_2H_4$CH=$CHC_2H_5$. The cis-configuration is preferred for alkenyl having a double bond at an even position, such as —$CH_2$CH=$CHCH_3$, —$CH_2$CH=$CHC_2H_5$, and —$CH_2$CH=$CHC_3H_7$. An alkenyl compound having a preferred stereo configuration has a high clearing point or a wide temperature range of a liquid crystal phase. A detailed explanation is given in Mol. Cryst. Liq. Cryst., 1985, 131, 109 and Mol. Cryst. Liq. Cryst., 1985, 131, 327.

In formula (1), ring $A^1$ and ring $A^2$ are independently 1,4-cyclohexylene, 1,4-phenylene, 1,4-phenylene in which at least one hydrogen has been replaced with fluorine, tetrahydropyran-2,5-diyl, 1,3-dioxane-2,5-diyl, pyridine-2,5-diyl, or pyrimidine-2,5-diyl.

Ring $A^1$ or ring $A^2$ is preferably 1,4-cyclohexylene, 1,4-phenylene, 2-fluoro-1,4-phenylene, 2,3-difluoro-1,4-phenylene, 2,6-difluoro-1,4-phenylene, 2,3,5-trifluoro-1,4-phenylene, tetrahydropyran-2,5-diyl, 1,3-dioxane-2,5-diyl, or pyrimidine-2,5-diyl, more preferably 1,4-cyclohexylene, 1,4-phenylene, 2-fluoro-1,4-phenylene, 2,6-difluoro-1,4-phenylene, or tetrahydropyran-2,5-diyl, and particularly preferably 1,4-cyclohexylene, 1,4-phenylene, 2-fluoro-1,4-phenylene, or 2,6-difluoro-1,4-phenylene.

When ring $A^1$ or ring $A^2$ is 1,4-cyclohexylene, the clearing point is high, and the viscosity is small. When ring $A^1$ or ring $A^2$ is 1,4-phenylene, or 1,4-phenylene in which at least one hydrogen has been replaced with fluorine, the optical anisotropy is large, and the orientational order parameter is relatively large. When ring $A^1$ or ring $A^2$ is 1,4-phenylene in which at least one hydrogen has been replaced with fluorine, the dielectric anisotropy is large.

In formula (1), $Z^1$, $Z^2$ and $Z^3$ are independently a single bond, —COO—, —OCH$_2$—, —CF$_2$O—, —CH$_2$CH$_2$—, —CF$_2$CF$_2$—, —CH=CH—, —CF=CF—, —C≡C—, —CH$_2$CH=CHCH$_2$—, or —(CH$_2$)$_4$—, wherein at least one of $Z^1$, $Z^2$ and $Z^3$ is —CF$_2$O—.

$Z^1$, $Z^2$ or $Z^3$ is preferably a single bond, —COO—, —OCH$_2$—, —CF$_2$O—, —CH$_2$CH$_2$—, or —CH=CH—, more preferably a single bond, —COO—, —OCH$_2$—, —CF$_2$O—, or —CH=CH—, particularly preferably a single bond or —CF$_2$O—, and most preferably a single bond.

When $Z^1$, $Z^2$ or $Z^3$ is a single bond, the chemical stability is high, and the viscosity is small. When $Z^1$, $Z^2$ or $Z^3$ is —CF$_2$O—, the viscosity is small, the dielectric anisotropy is large, and the maximum temperature is high.

In formula (1), $X^1$ is hydrogen, fluorine, —CF$_3$, or —OCF$_3$, preferably fluorine, —CF$_3$, or —OCF$_3$, and more preferably fluorine or —OCF$_3$.

When $X^1$ is fluorine, the viscosity is small. When $X^1$ is —CF$_3$, the dielectric anisotropy is large. When $X^1$ is —OCF$_3$, the compatibility with other liquid crystal compounds is excellent.

In formula (1), $L^1$ and $L^2$ are independently hydrogen or fluorine. $L^1$ and $L^2$ are preferably a combination of hydrogen and fluorine. $L^1$ and $L^2$ are more preferably a combination of fluorine and fluorine.

When $L^1$ and $L^2$ are a combination of hydrogen and fluorine, the dielectric anisotropy is large. When $L^1$ and $L^2$ are a combination of fluorine and fluorine, the dielectric anisotropy is particularly large.

In formula (1), a is 0 or 1, b is 0 or 1, and the sum of a and b is 0 or 1. a is preferably 1, b is preferably 0, and the sum of a and b is preferably 1.

When the sum of a and b is 0, the viscosity is small. When the sum of a and b is 1, the clearing point is high.

Preferred examples of the compound (1) include the compounds (1-1) to (1-3) described in item 3. More preferred examples of the compound (1) include the compounds (1-a) to (1-i) described in item 4. Most preferred examples of the compound (1) include the compounds (1-j) to (1-m) described in item 5.

The compound (1-a) is preferred in view of high stability to heat or light and small viscosity. The compounds (1-b) to (1-e) are preferred in view of a high clearing point and excellent compatibility. The compounds (1-f) to (1-i) are preferred in view of a high clearing point and large optical anisotropy.

2. Synthesis of Compound (1)

The synthesis method of the compound (1) is explained. The compound (1) can be synthesized by a suitable combination of methods in organic synthetic chemistry. The methods for introducing target terminal groups, rings and linking groups into starting materials are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza, in Japanese)" (Maruzen Co., Ltd.), etc.

2-1. Formation of Linking Group Z

With regard to a method for forming the linking groups $Z^1$ to $Z^3$, first of all, a scheme is shown. Next, the reactions described in the scheme are explained in methods (1) to (11). In this scheme, MSG$^1$ (or MSG$^2$) is a monovalent organic group having at least one ring. Monovalent organic groups represented by a plurality of the MSG$^1$ (or MSG$^2$) used in the scheme may be the same or different. Compounds (1A) to (1J) correspond to the compound (1).

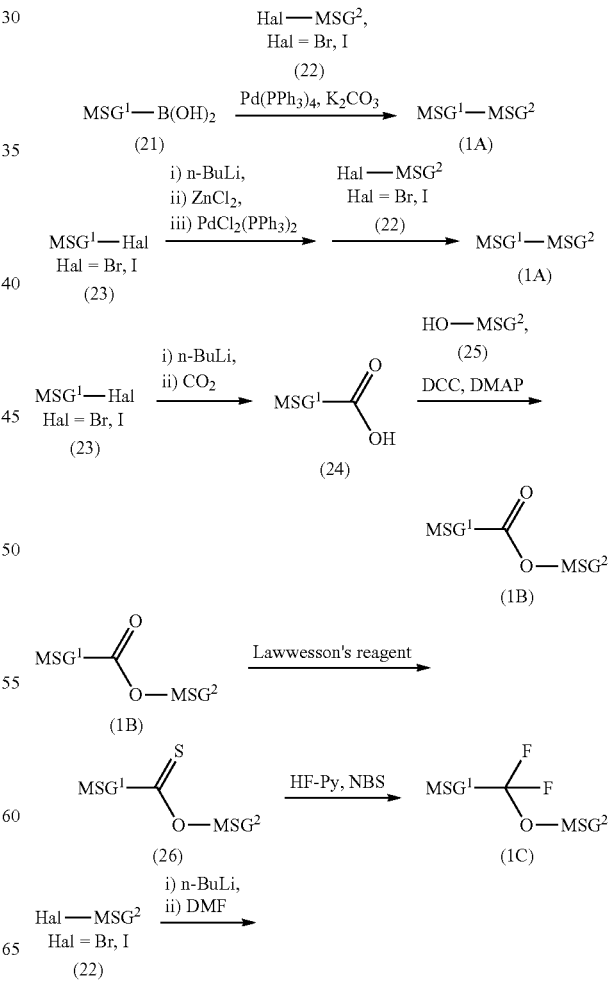

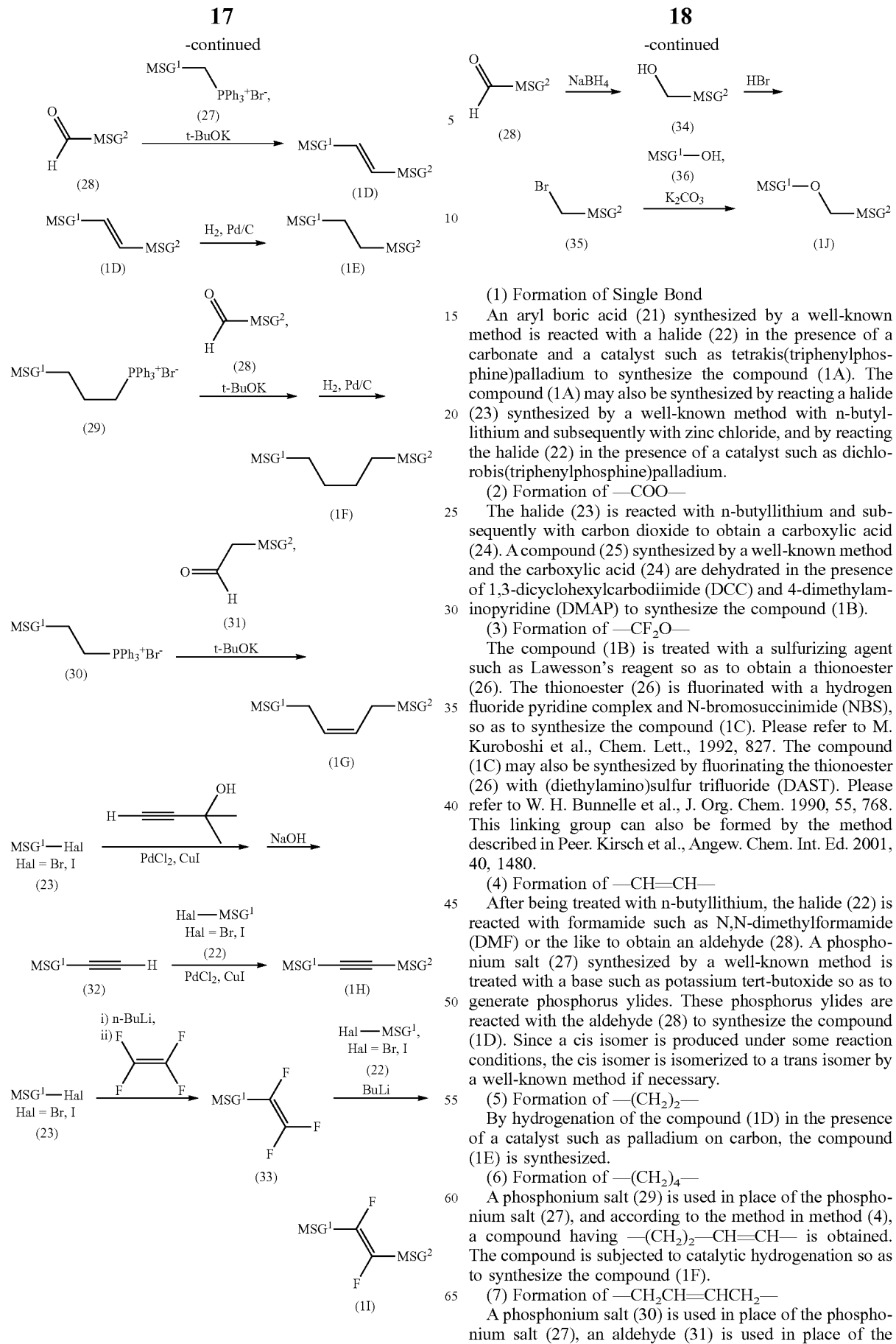

(1) Formation of Single Bond

An aryl boric acid (21) synthesized by a well-known method is reacted with a halide (22) in the presence of a carbonate and a catalyst such as tetrakis(triphenylphosphine)palladium to synthesize the compound (1A). The compound (1A) may also be synthesized by reacting a halide (23) synthesized by a well-known method with n-butyllithium and subsequently with zinc chloride, and by reacting the halide (22) in the presence of a catalyst such as dichlorobis(triphenylphosphine)palladium.

(2) Formation of —COO—

The halide (23) is reacted with n-butyllithium and subsequently with carbon dioxide to obtain a carboxylic acid (24). A compound (25) synthesized by a well-known method and the carboxylic acid (24) are dehydrated in the presence of 1,3-dicyclohexylcarbodiimide (DCC) and 4-dimethylaminopyridine (DMAP) to synthesize the compound (1B).

(3) Formation of —CF$_2$O—

The compound (1B) is treated with a sulfurizing agent such as Lawesson's reagent so as to obtain a thionoester (26). The thionoester (26) is fluorinated with a hydrogen fluoride pyridine complex and N-bromosuccinimide (NBS), so as to synthesize the compound (1C). Please refer to M. Kuroboshi et al., Chem. Lett., 1992, 827. The compound (1C) may also be synthesized by fluorinating the thionoester (26) with (diethylamino)sulfur trifluoride (DAST). Please refer to W. H. Bunnelle et al., J. Org. Chem. 1990, 55, 768. This linking group can also be formed by the method described in Peer. Kirsch et al., Angew. Chem. Int. Ed. 2001, 40, 1480.

(4) Formation of —CH═CH—

After being treated with n-butyllithium, the halide (22) is reacted with formamide such as N,N-dimethylformamide (DMF) or the like to obtain an aldehyde (28). A phosphonium salt (27) synthesized by a well-known method is treated with a base such as potassium tert-butoxide so as to generate phosphorus ylides. These phosphorus ylides are reacted with the aldehyde (28) to synthesize the compound (1D). Since a cis isomer is produced under some reaction conditions, the cis isomer is isomerized to a trans isomer by a well-known method if necessary.

(5) Formation of —(CH$_2$)$_2$—

By hydrogenation of the compound (1D) in the presence of a catalyst such as palladium on carbon, the compound (1E) is synthesized.

(6) Formation of —(CH$_2$)$_4$—

A phosphonium salt (29) is used in place of the phosphonium salt (27), and according to the method in method (4), a compound having —(CH$_2$)$_2$—CH═CH— is obtained. The compound is subjected to catalytic hydrogenation so as to synthesize the compound (1F).

(7) Formation of —CH$_2$CH═CHCH$_2$—

A phosphonium salt (30) is used in place of the phosphonium salt (27), an aldehyde (31) is used in place of the aldehyde (28), and according to the method in method (4), the compound (1G) is synthesized. Since a trans isomer is produced under some reaction conditions, the trans isomer is isomerized to a cis isomer by a well-known method if necessary.

(8) Formation of —C≡C—

The halide (23) is reacted with 2-methyl-3-butyn-2-ol in the presence of catalysts including dichloropalladium and a copper halide, followed by deprotection under a basic condition, so as to obtain a compound (32). In the presence of catalysts including dichloropalladium and a copper halide, the compound (32) is reacted with the halide (22) to synthesize the compound (1H).

(9) Formation of —CF=CF—

After being treated with n-butyllithium, the halide (23) is reacted with tetrafluoroethylene to obtain a compound (33). After being treated with n-butyllithium, the halide (22) is reacted with the compound (33) to obtain the compound (1I).

(10) Formation of —OCH$_2$—

The aldehyde (28) is reduced with a reducing agent such as sodium borohydride or the like so as to obtain a compound (34). The compound (34) is brominated with hydrobromic acid or the like so as to obtain a bromide (35). The bromide (35) is reacted with a compound (36) in the presence of a base such as potassium carbonate or the like to synthesize the compound (1J).

(11) Formation of —(CF$_2$)$_2$—

In accordance with the method described in J. Am. Chem. Soc., 2001, 123, 5414, a diketone (—COCO—) is fluorinated with sulfur tetrafluoride in the presence of a hydrogen fluoride catalyst, so as to obtain a compound having —(CF$_2$)$_2$—.

2-2. Formation of Ring A$^1$ and Ring A$^2$

Starting materials are commercially available, or synthesis methods are well-known with regard to the rings such as 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl, pyrimidine-2,5-diyl, or pyridine-2,5-diyl, etc.

2-3. Method for Synthesizing Compound (1)

An example of a method for synthesizing the compound (1) is as follows. A bromide (41) synthesized by a well-known method is reacted with mercaptophenyltetrazole (42) in the presence of tetrabutylammonium hydrogen sulfate and potassium hydroxide to obtain a sulfide (43). The sulfide (43) is oxidized with hydrogen peroxide in the presence of hexaammonium heptamolybdate tetrahydrate so as to obtain a sulfone (44). The sulfone (44) is reacted with an aldehyde (45) synthesized by a well-known method in the presence of potassium hexamethyldisilazane (KHMDS) to synthesize the compound (1). In these compounds, definitions of the symbols such as R$^1$, ring A$^1$ and so on are the same as those described in item 1.

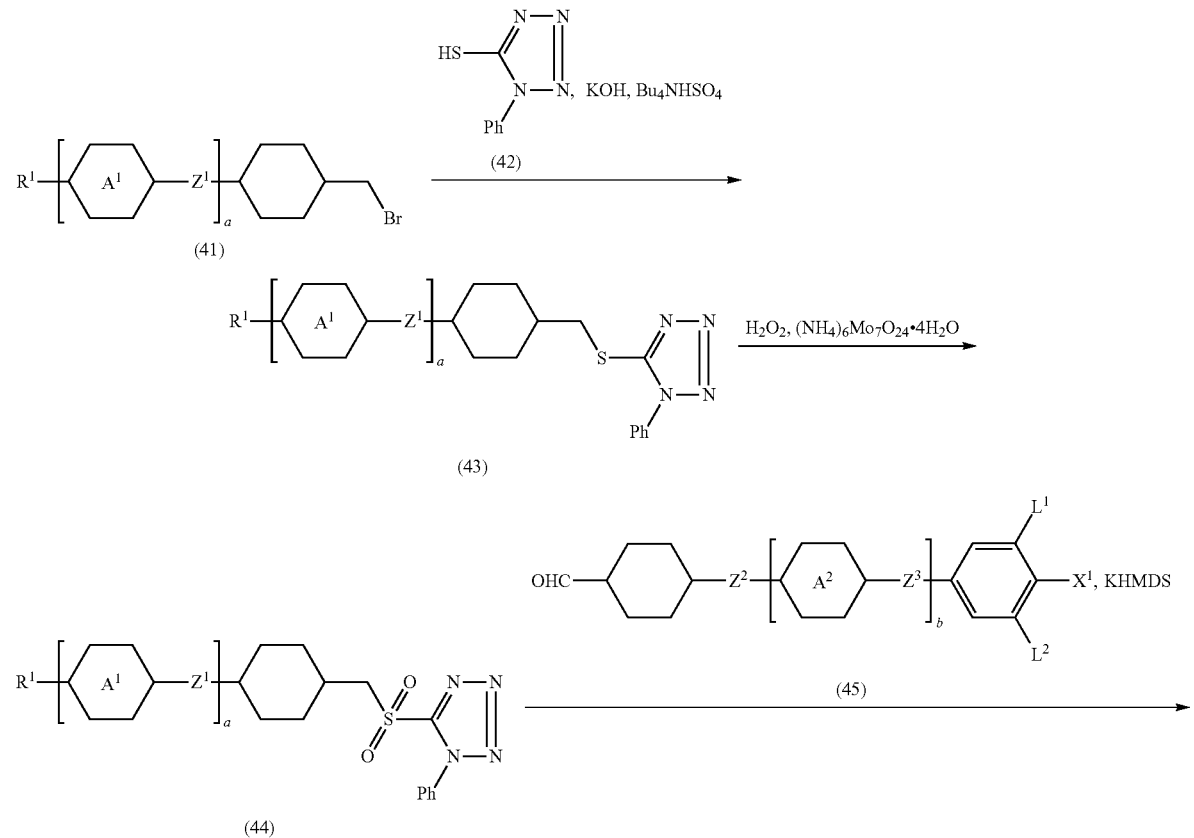

-continued

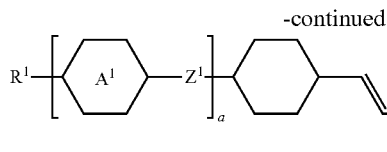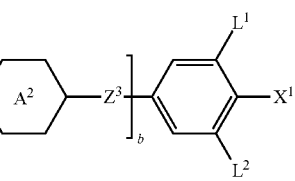

(1)

3. Liquid Crystal Composition

3-1. Component Compounds

The liquid crystal composition of the invention is explained. This composition contains at least one compound (1) as a component A. This composition may contain two, or three or more compounds (1). The composition may contain the compound (1) as the only component. The composition preferably contains at least one compound (1) in a range of 1 to 99 wt % for exhibiting excellent physical properties. In the composition having positive dielectric anisotropy, a preferred content of the compound (1) ranges from 5 to 60 wt %. In the composition having negative dielectric anisotropy, a preferred content of the compound (1) is 30 wt % or less. The composition may contain the compound (1) and a liquid crystal compound that is not described in this specification.

Preferably, this composition contains the compound (1) as the component A, and further contains a liquid crystal compound selected from components B, C, D and E shown below. The component B includes compounds (2) to (4). The component C includes compounds (5) to (7). The component D includes a compound (8). The component E includes compounds (9) to (15). This composition may contain other liquid crystal compounds different from the compounds (2) to (15). In preparing this composition, it is preferred to select the components B, C, D and E by taking the polarity and magnitude of the dielectric anisotropy into consideration. The composition in which the components are suitably selected has high stability to heat or light, high maximum temperature, low minimum temperature, small viscosity, suitable (large or small) optical anisotropy, large dielectric anisotropy, large specific resistance, and a suitable (large or small) elastic constant.

The component B is a compound in which two terminal groups are alkyl or the like. Preferred examples of the component B include compounds (2-1) to (2-11), compounds (3-1) to (3-19) and compounds (4-1) to (4-7). In these compounds, $R^{11}$ and $R^{12}$ are independently alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine.

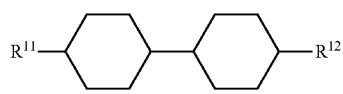
(2-1)

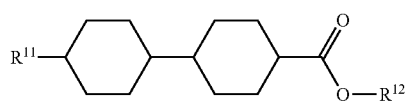
(2-2)

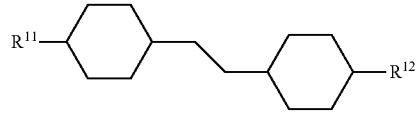
(2-3)

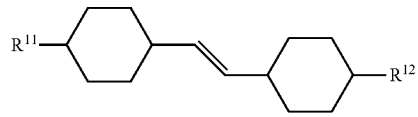
(2-4)

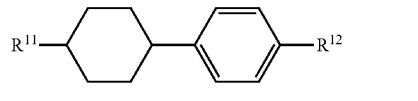
(2-5)

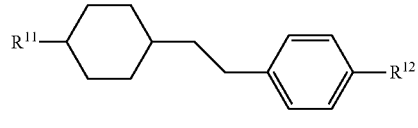
(2-6)

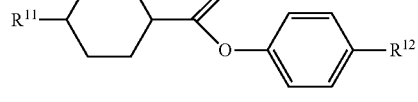
(2-7)

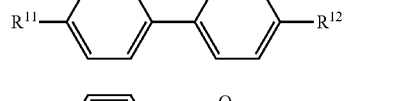
(2-8)

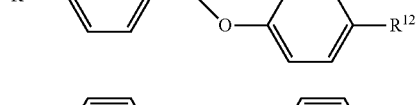
(2-9)

(2-10)

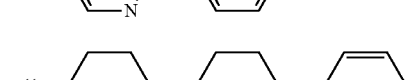
(2-11)

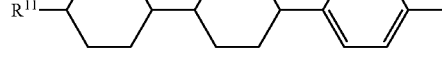
(3-1)

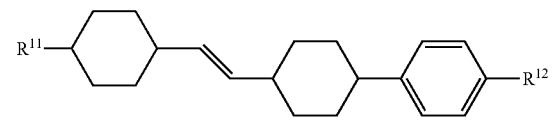
(3-2)

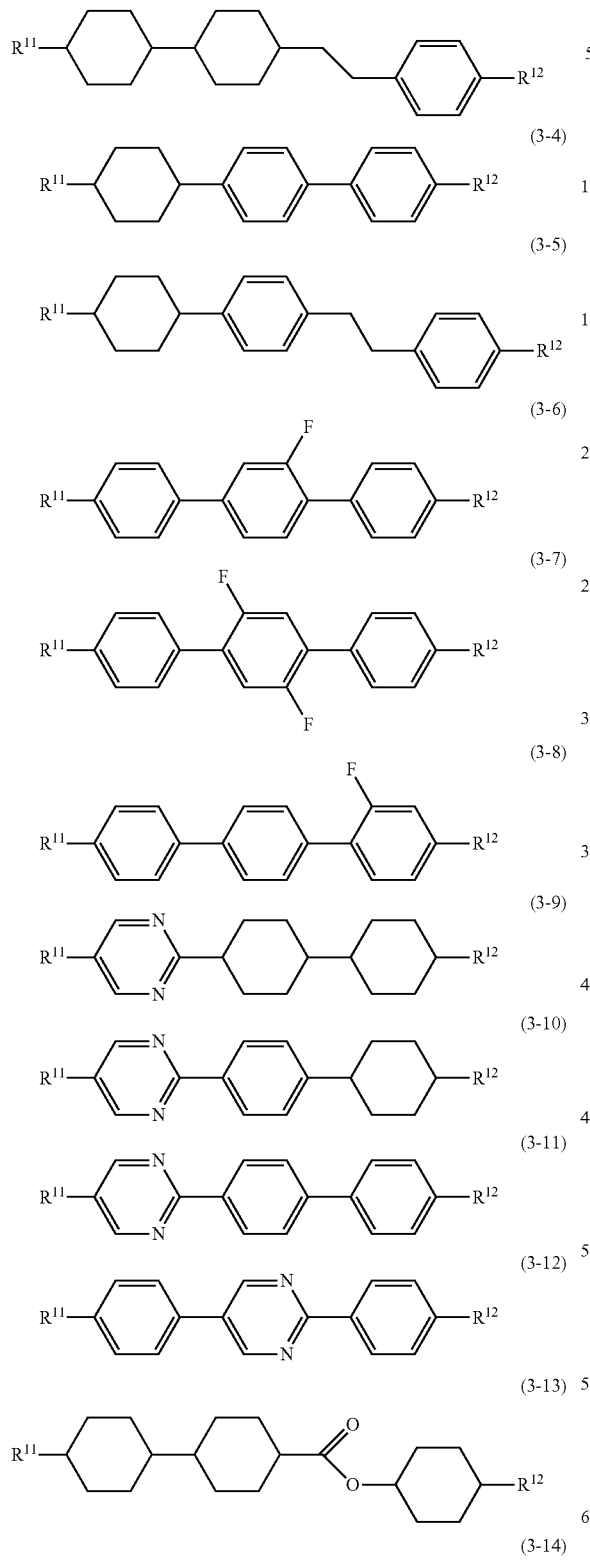
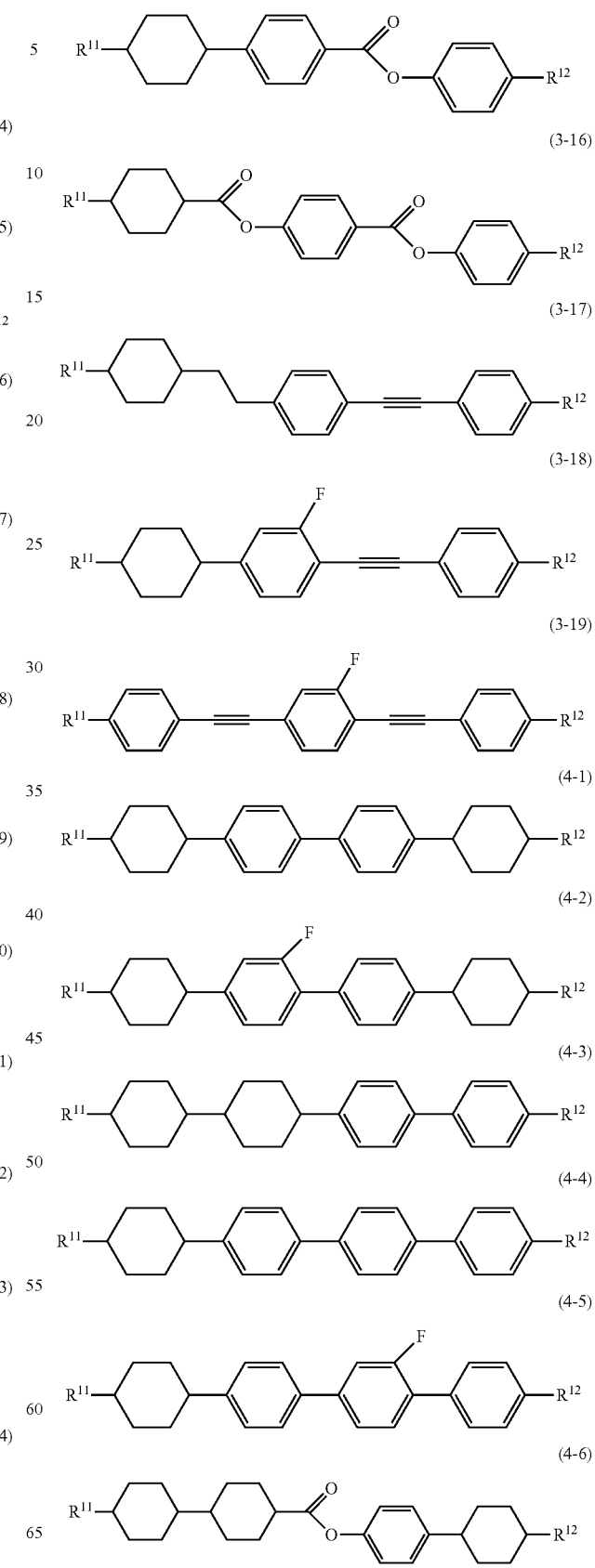

(4-7)

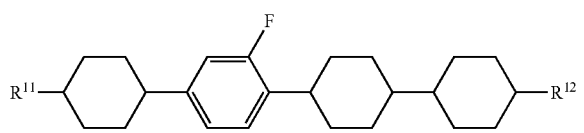

The component B has small dielectric anisotropy, and is nearly neutral. The compound (2) has an effect of reducing viscosity or adjusting optical anisotropy. The compounds (3) and (4) have an effect of broadening the temperature range of a nematic phase by increasing the maximum temperature, or an effect of adjusting optical anisotropy.

As the content of the component B is increased, the viscosity of the composition is reduced and the dielectric anisotropy is reduced. Therefore, the content is preferably as high as possible as long as a required value of threshold voltage of the device is satisfied. In preparing the composition for use in modes such as IPS and VA, etc., the content of the component B is preferably 30 wt % or more, more preferably 40 wt % or more, based on the weight of the liquid crystal composition.

The component C is a compound having halogen or a fluorine-containing group in the right terminal. Preferred examples of the component C include compounds (5-1) to (5-16), compounds (6-1) to (6-113) and compounds (7-1) to (7-57). In these compounds, $R^{13}$ is alkyl having 1 to 10 carbons or alkenyl having 2 to 10 carbons, wherein at least one —$CH_2$— in the alkyl and alkenyl is optionally replaced with —O—, and at least one hydrogen in the alkyl and alkenyl is optionally replaced with fluorine; and $X^{11}$ is fluorine, chlorine, —$OCF_3$, —$OCHF_2$, —$CF_3$, —$CHF_2$, —$CH_2F$, —$OCF_2CHF_2$, or —$OCF_2CHFCF_3$.

(5-1)

(5-2)

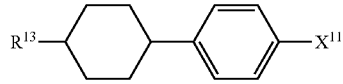

(5-3)

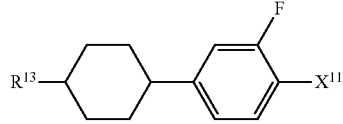

(5-4)

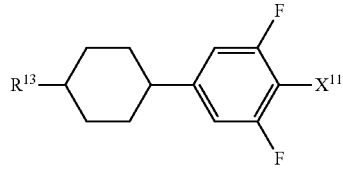

(5-5)

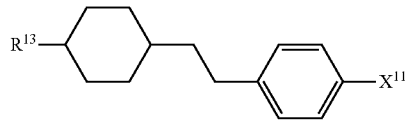

(5-6)

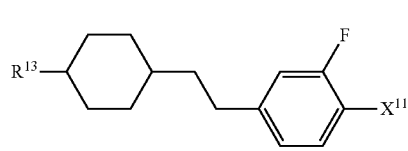

(5-7)

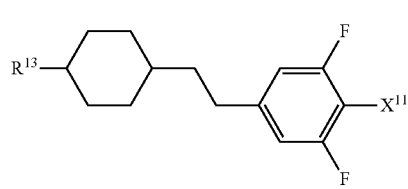

(5-8)

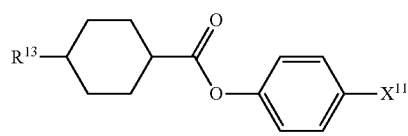

(5-9)

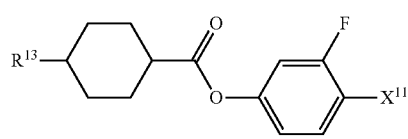

(5-10)

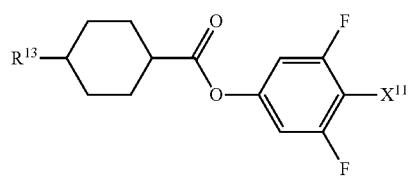

(5-11)

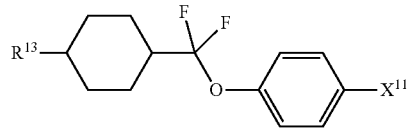

(5-12)

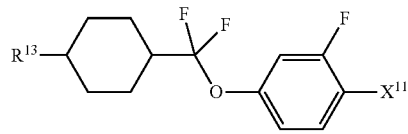

(5-13)

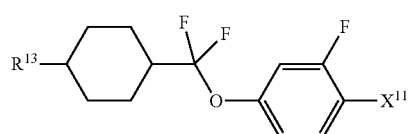

(5-14)

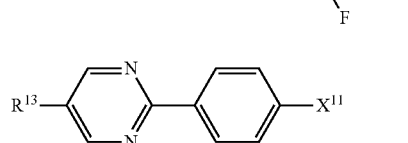

(5-15)

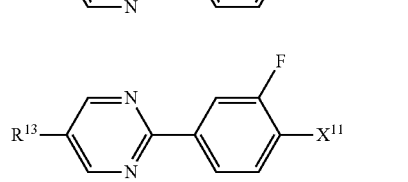

(5-16) 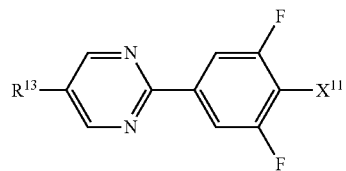
(6-1) 
(6-2) 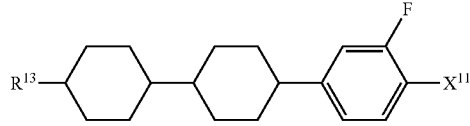
(6-3) 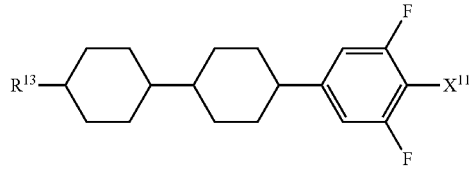
(6-4) 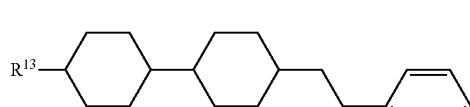
(6-5) 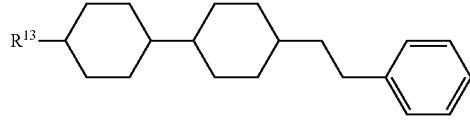
(6-6) 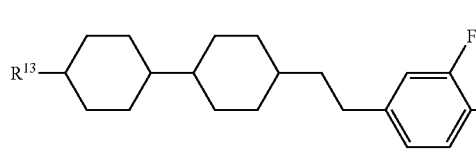
(6-7) 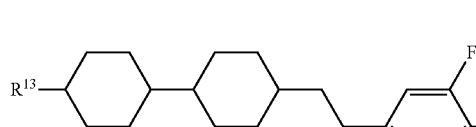
(6-8) 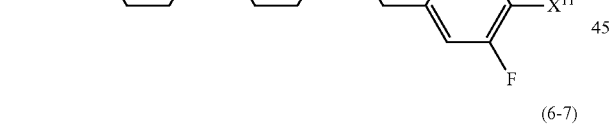
(6-9) 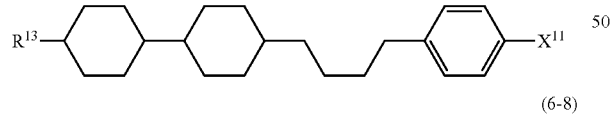
(6-10) 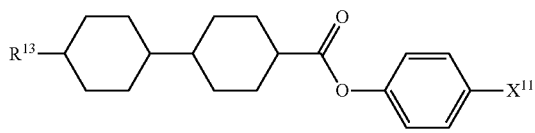
(6-11) 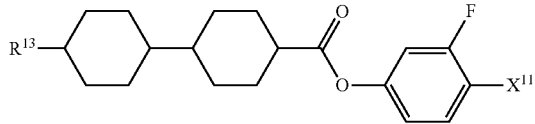
(6-12) 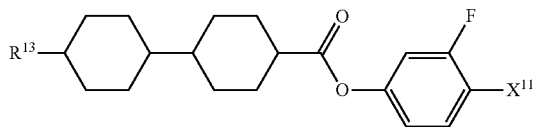
(6-13) 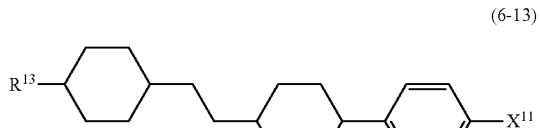
(6-14) 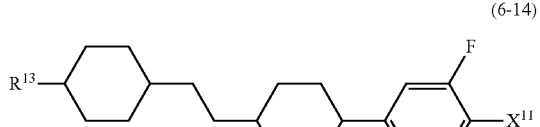
(6-15) 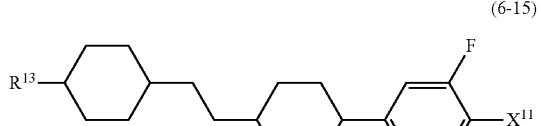
(6-16) 
(6-17) 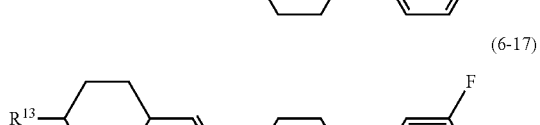
(6-18) 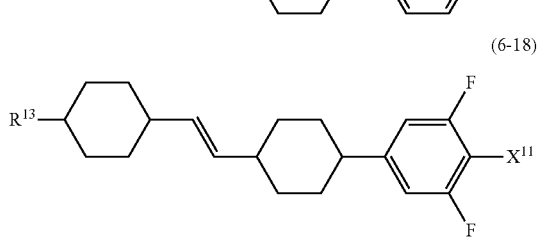

(6-19) 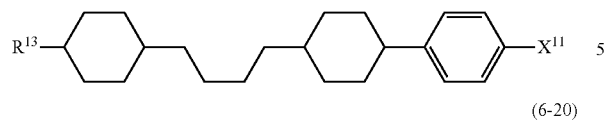
(6-20) 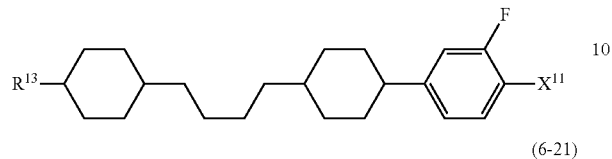
(6-21) 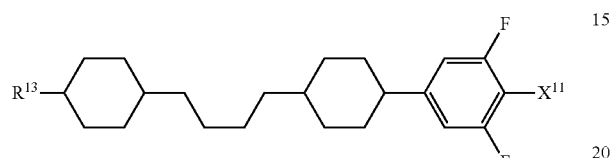
(6-22) 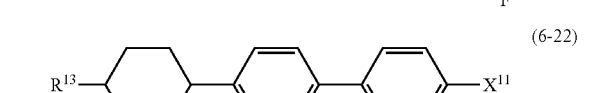
(6-23) 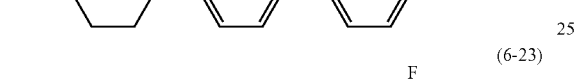
(6-24) 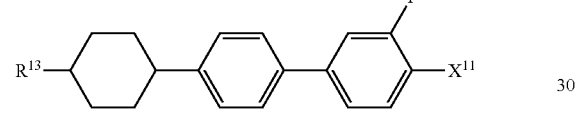
(6-25) 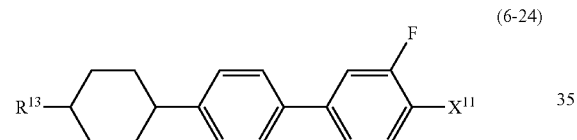
(6-26) 
(6-27) 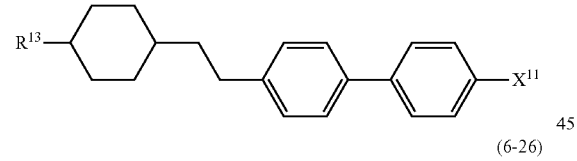
(6-28) 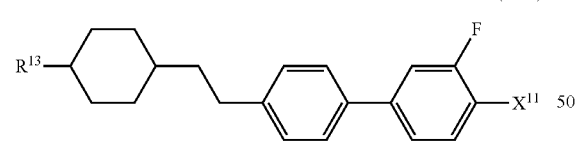
(6-29) 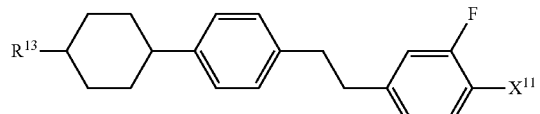
(6-30) 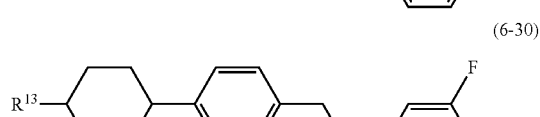
(6-31) 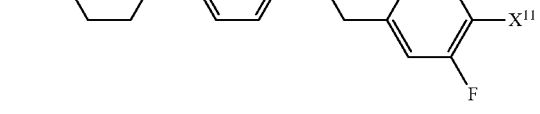
(6-32) 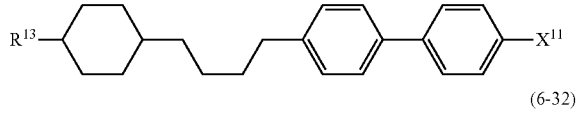
(6-33) 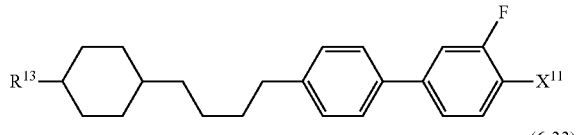
(6-34) 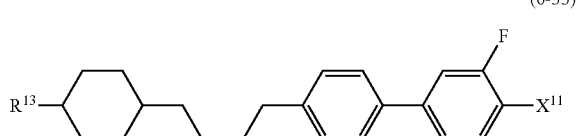
(6-35) 
(6-36) 
(6-37) 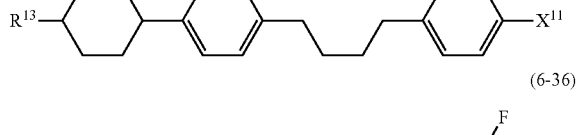
(6-38) 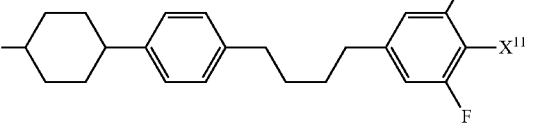

(6-39) 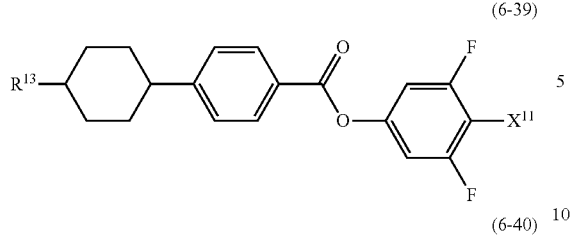
(6-40) 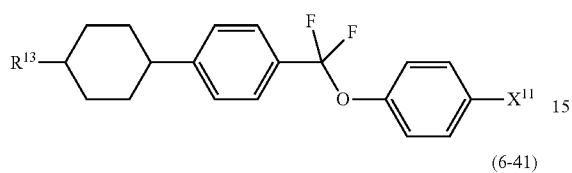
(6-41) 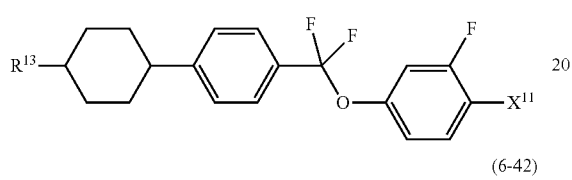
(6-42) 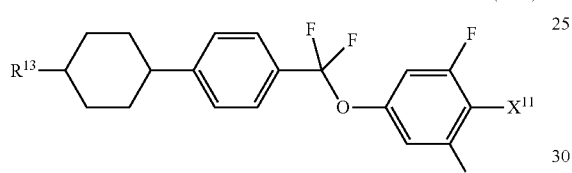
(6-43) 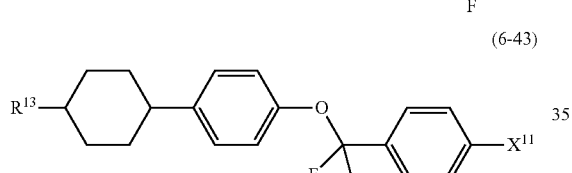
(6-44) 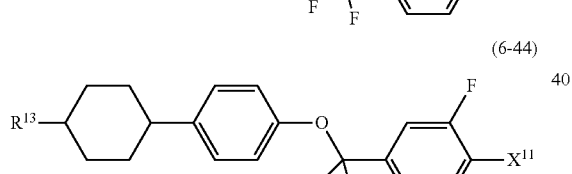
(6-45) 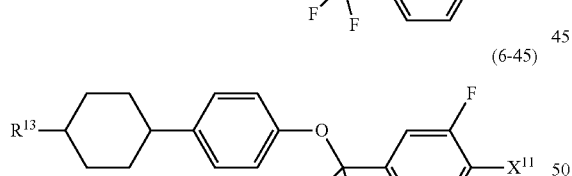
(6-46) 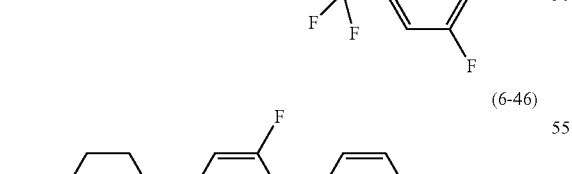
(6-47) 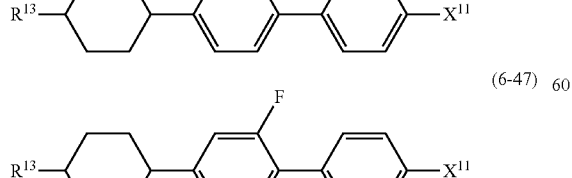
(6-48) 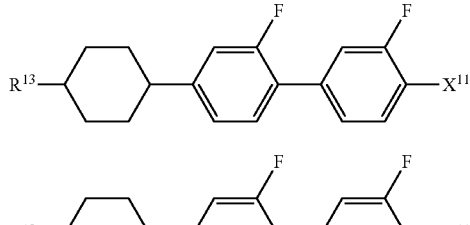
(6-49) 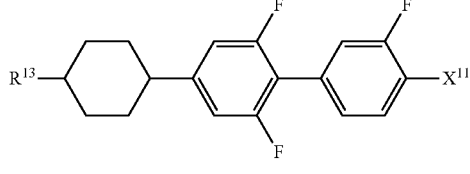
(6-50) 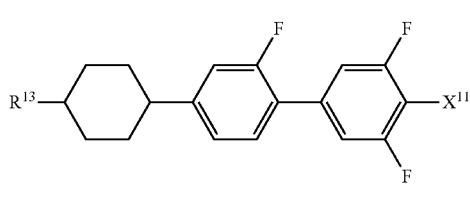
(6-51) 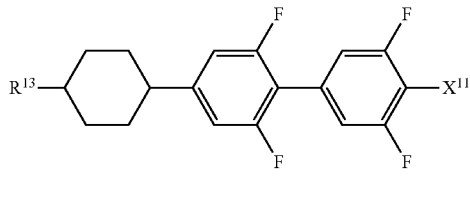
(6-52) 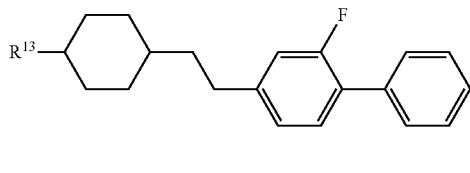
(6-53) 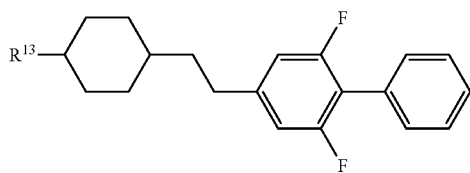
(6-54) 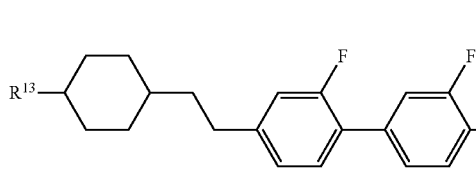
(6-55) 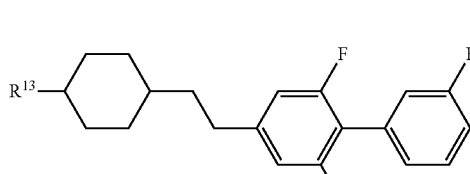
(6-56) 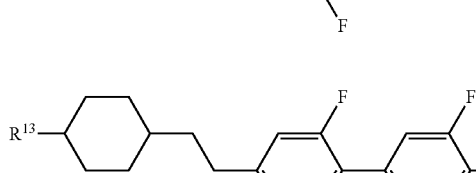

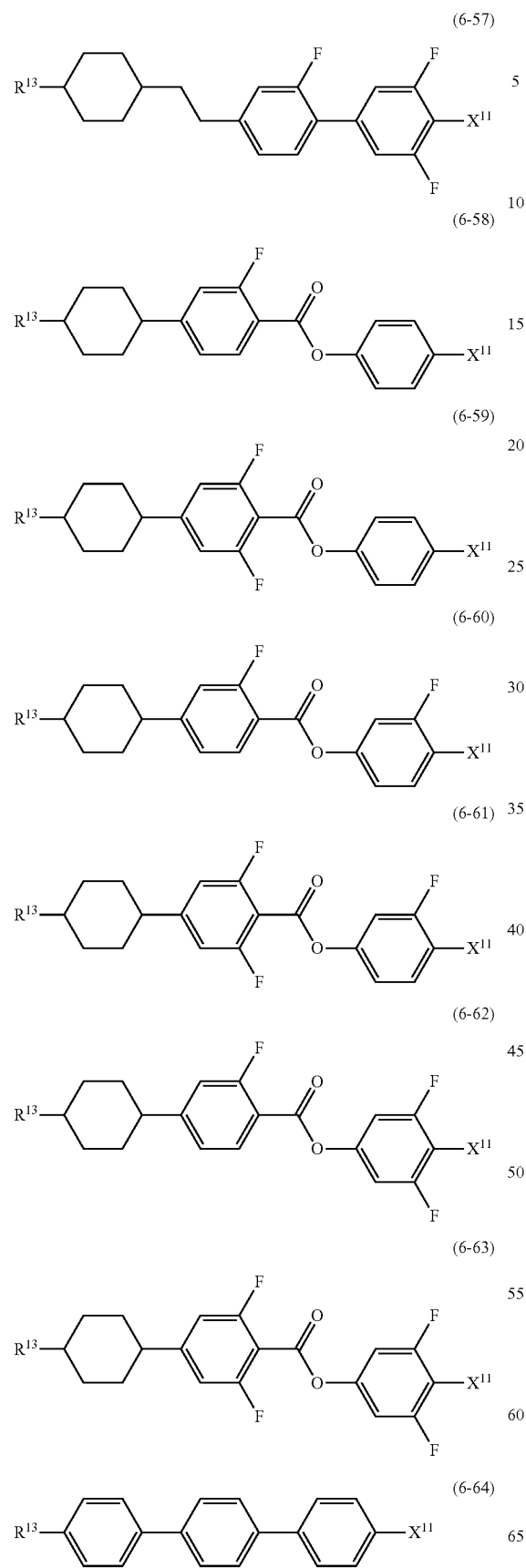
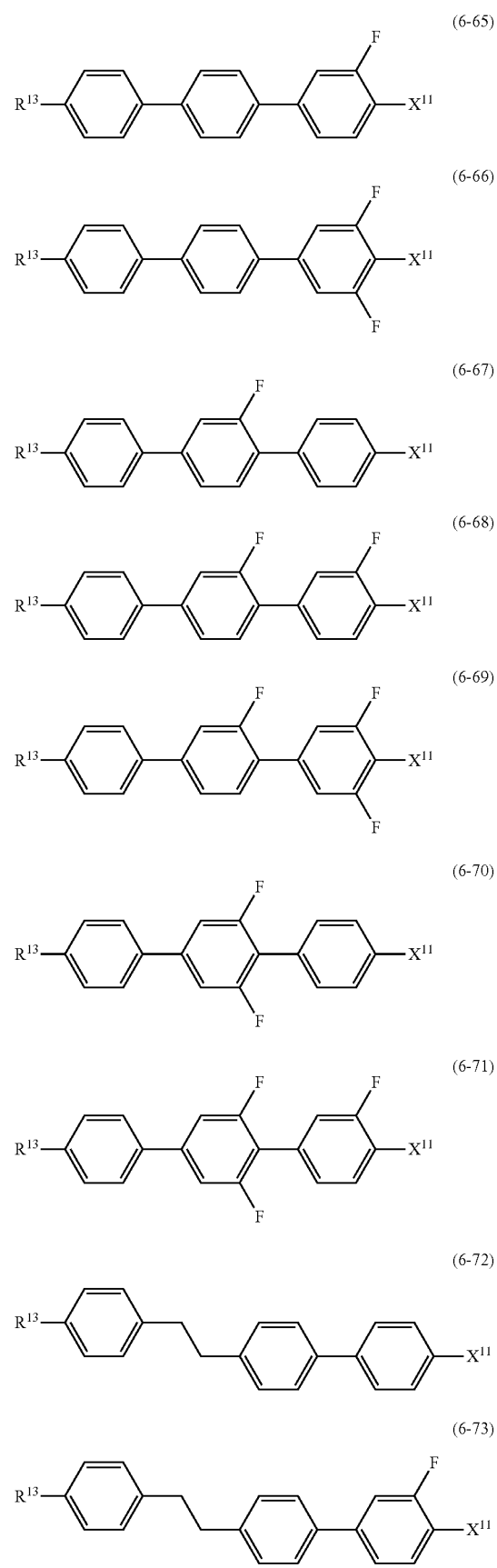

(6-74) 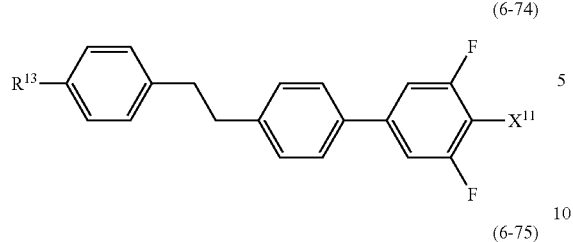
(6-75) 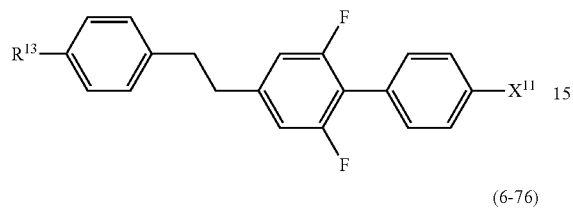
(6-76) 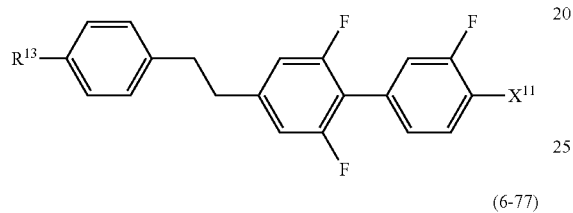
(6-77) 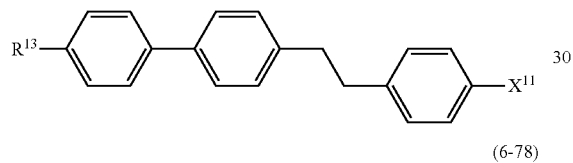
(6-78) 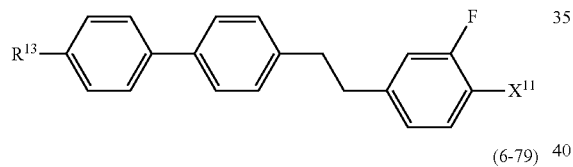
(6-79) 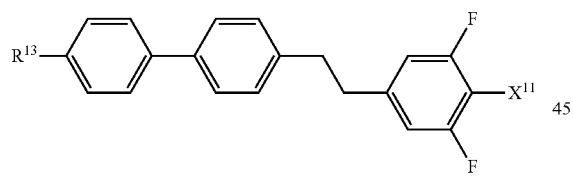
(6-80) 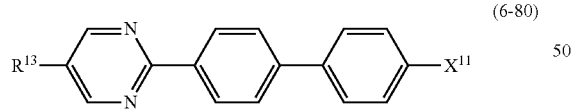
(6-81) 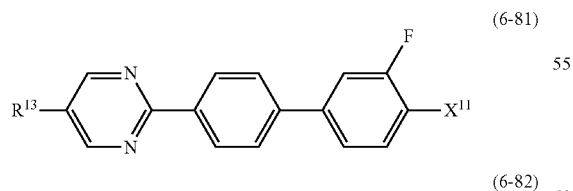
(6-82) 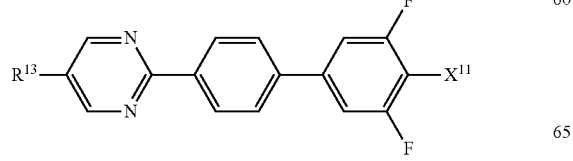
(6-83) 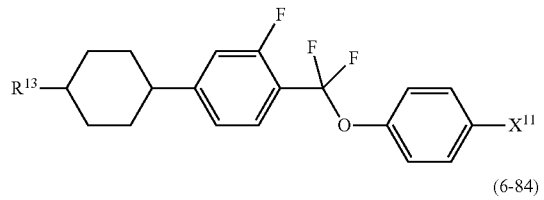
(6-84) 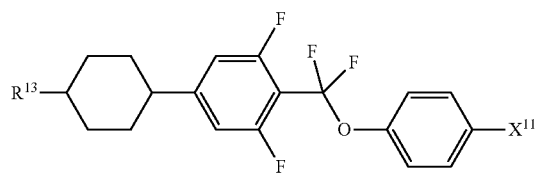
(6-85) 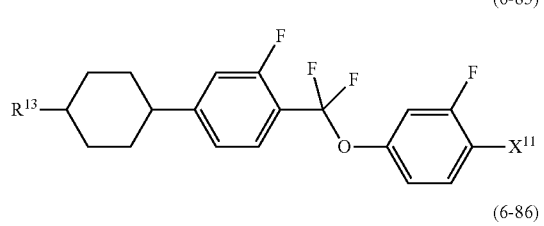
(6-86) 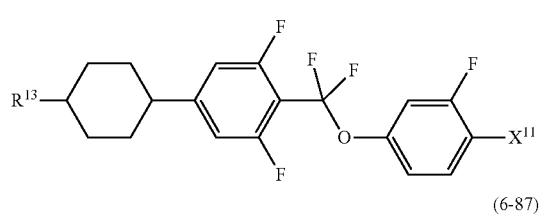
(6-87) 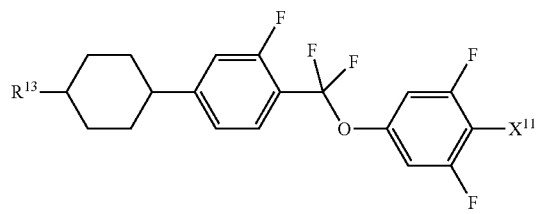
(6-88) 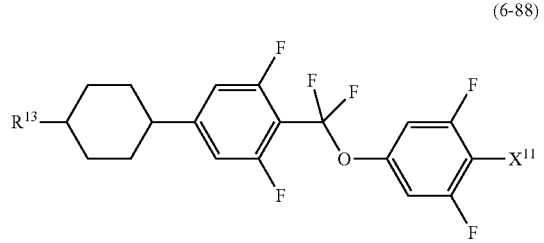
(6-89) 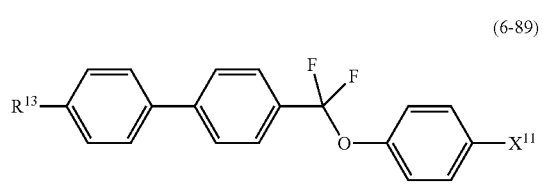
(6-90) 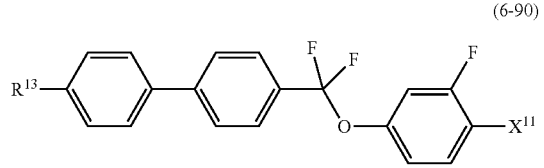

(6-91) 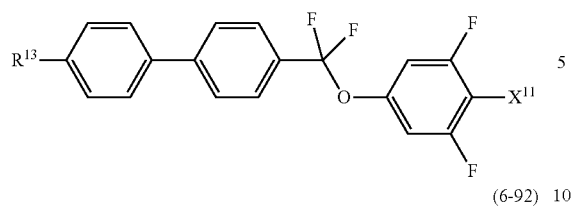
(6-92) 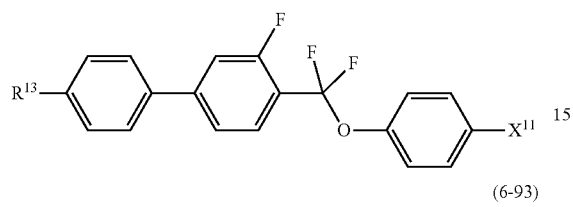
(6-93) 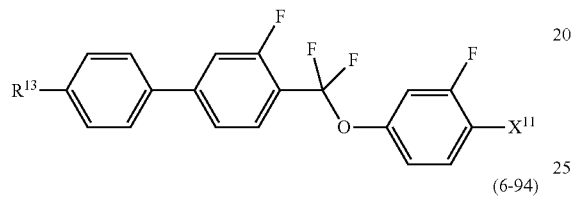
(6-94) 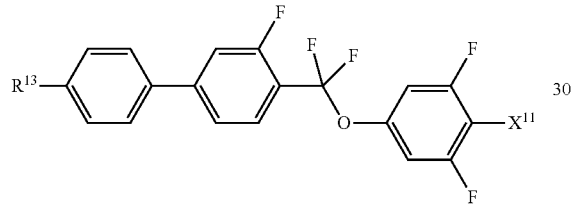
(6-95) 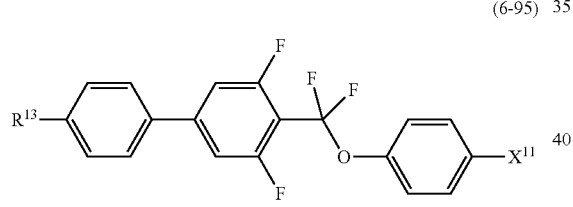
(6-96) 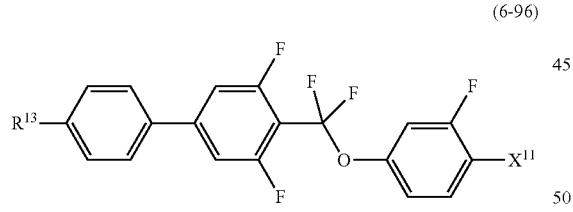
(6-97) 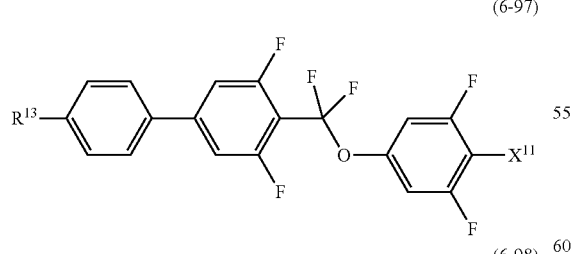
(6-98) 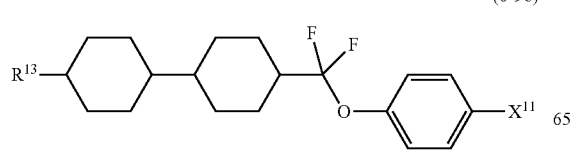
(6-99) 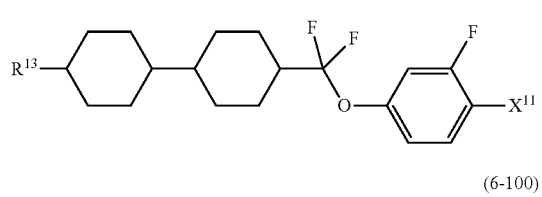
(6-100) 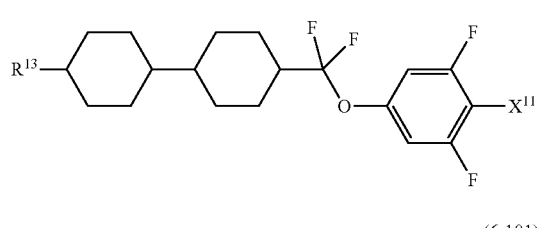
(6-101) 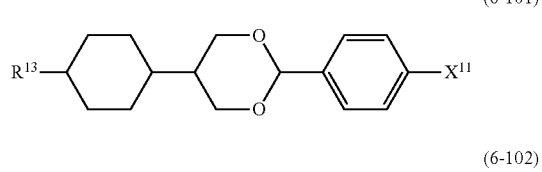
(6-102) 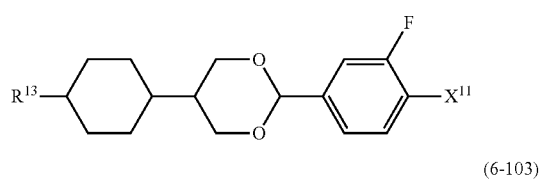
(6-103) 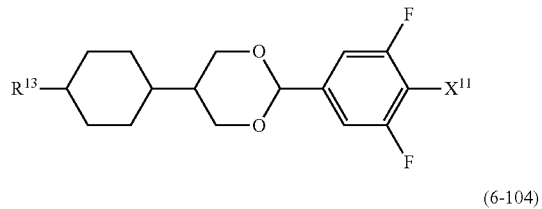
(6-104) 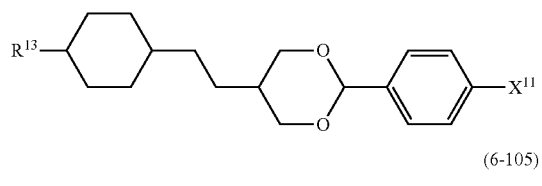
(6-105) 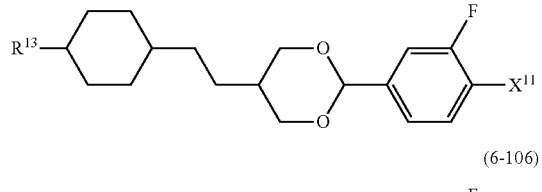
(6-106) 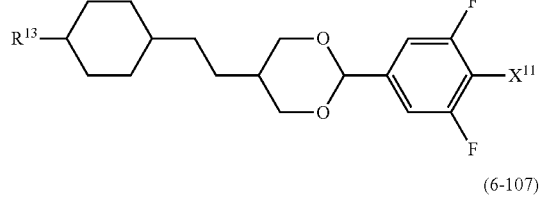
(6-107) 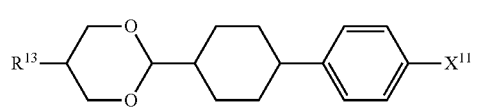

(6-108)
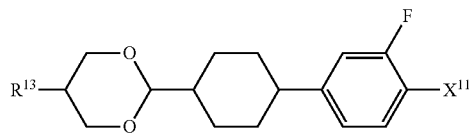
(6-109)
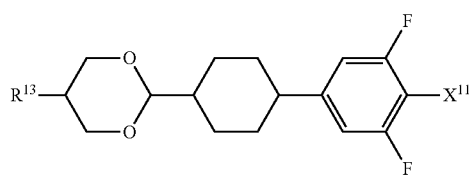
(6-110)
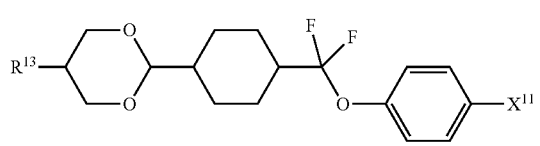
(6-111)
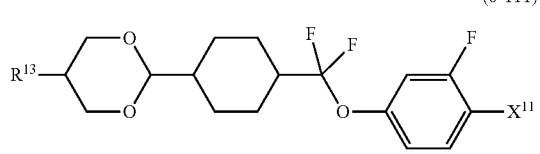
(6-112)
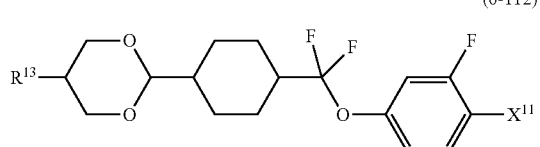
(6-113)
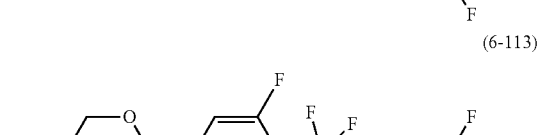
(7-1)
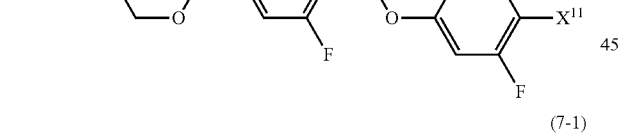
(7-2)
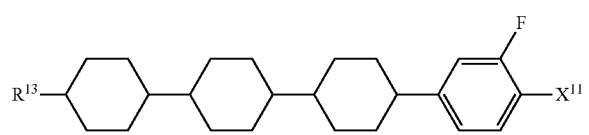
(7-3)
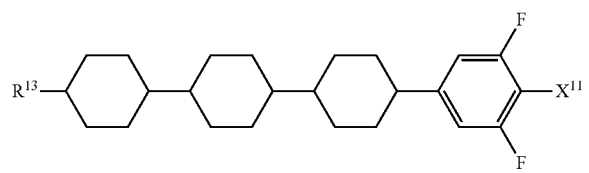
(7-4)
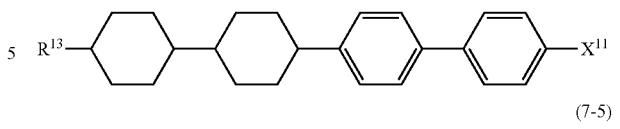
(7-5)
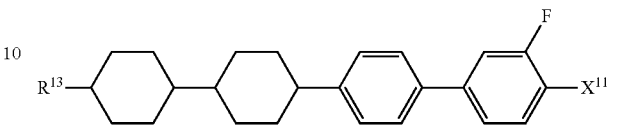
(7-6)
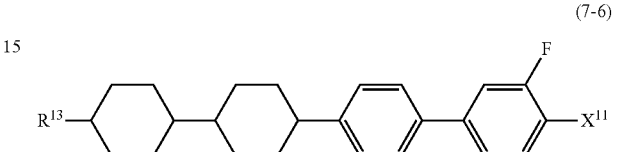
(7-7)
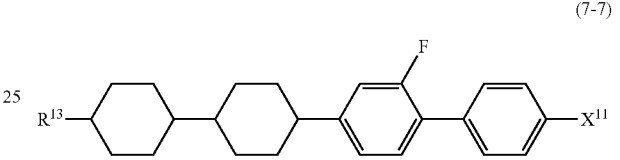
(7-8)
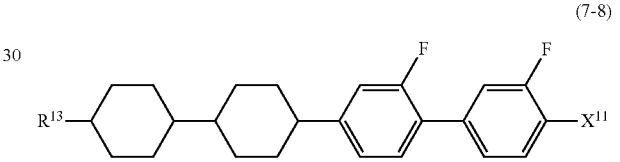
(7-9)
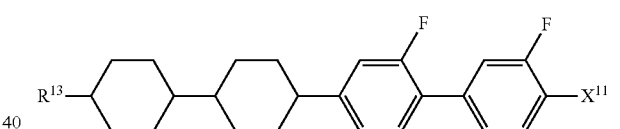
(7-10)
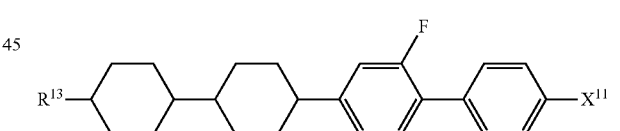
(7-11)
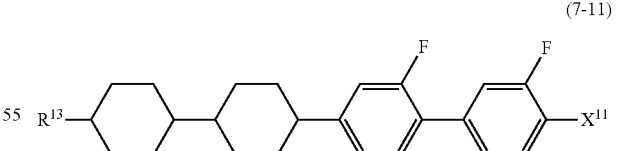
(7-12)
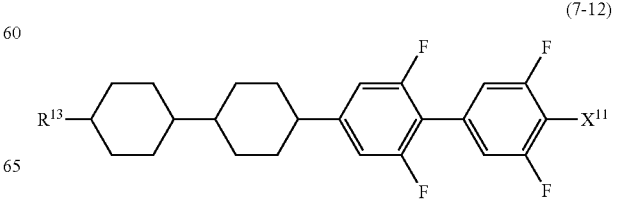

(7-13) 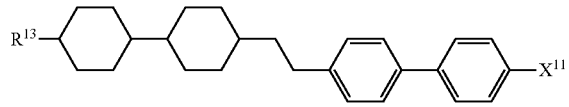
(7-14) 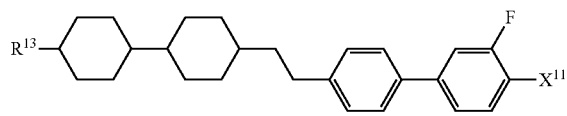
(7-15) 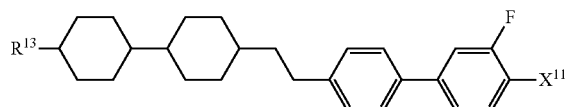
(7-16) 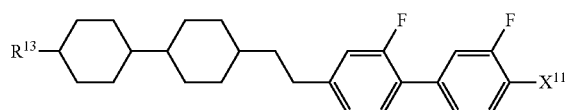
(7-17) 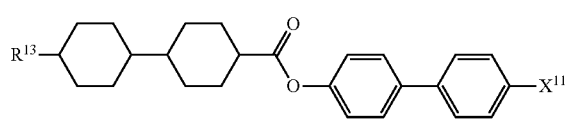
(7-18) 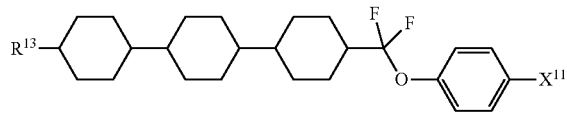
(7-19) 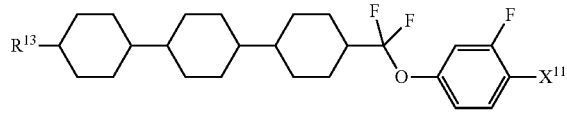
(7-20) 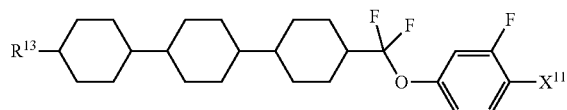
(7-21) 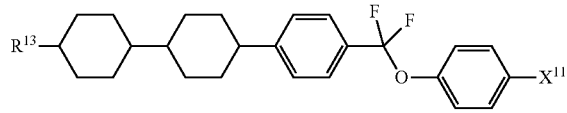
(7-22) 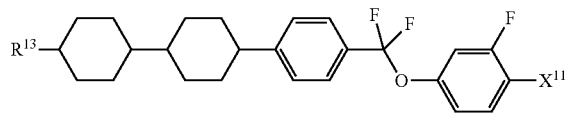
(7-23) 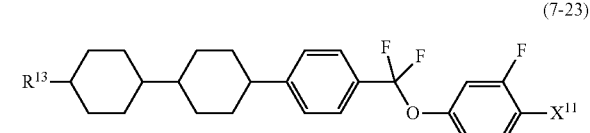
(7-24) 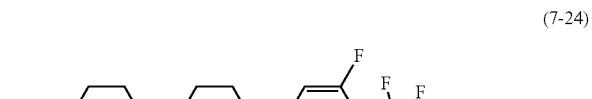
(7-25) 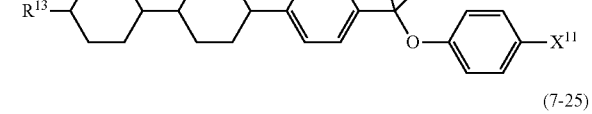
(7-26) 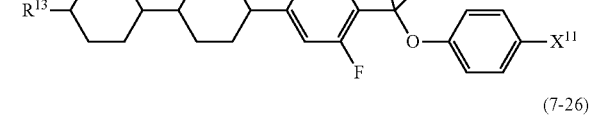
(7-27) 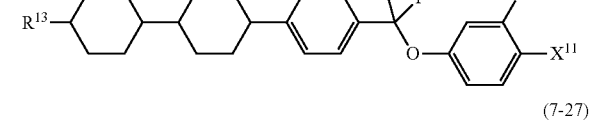
(7-28) 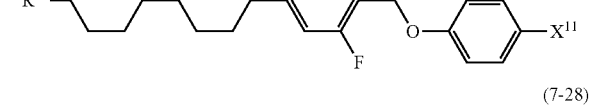
(7-29) 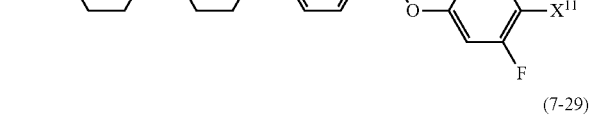
(7-30) 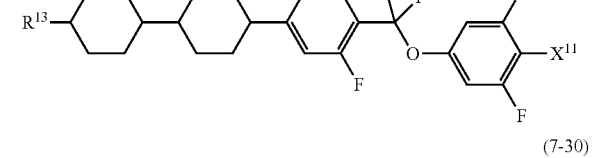
(7-31) 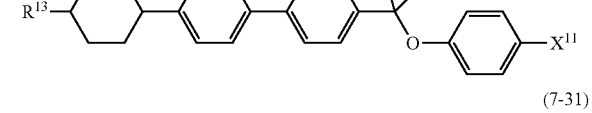

(7-32) 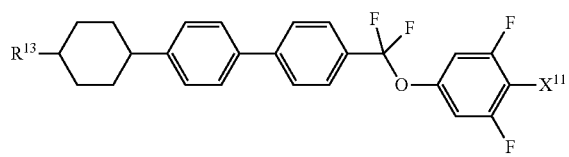
(7-33) 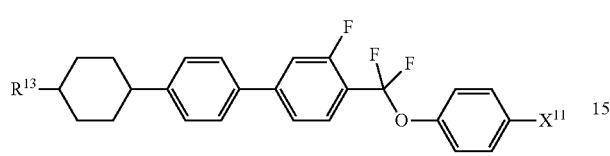
(7-34) 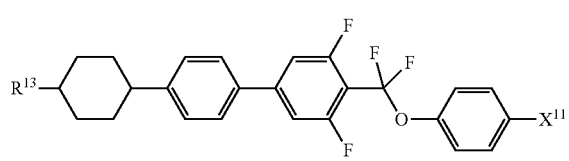
(7-35) 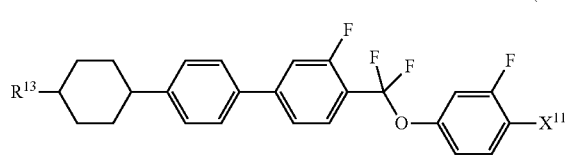
(7-36) 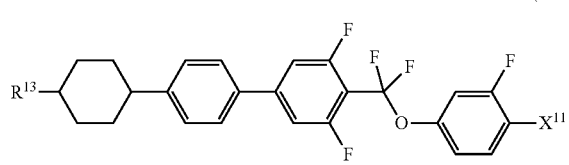
(7-37) 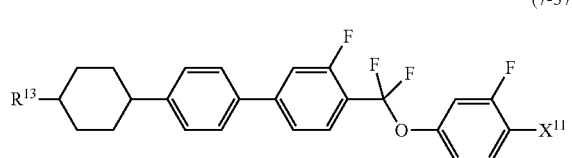
(7-38) 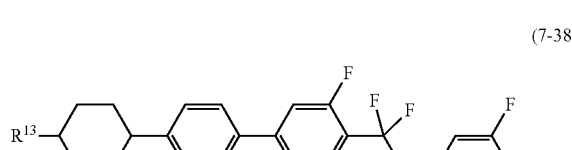
(7-39) 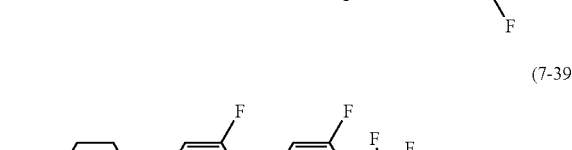
(7-40) 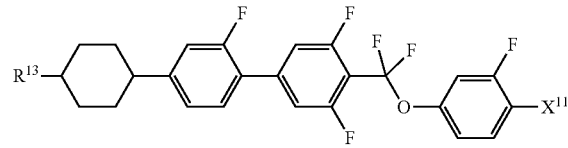
(7-41) 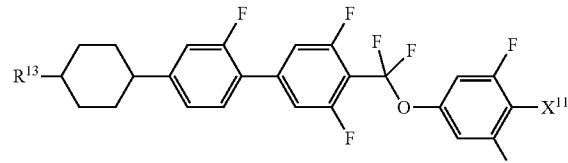
(7-42) 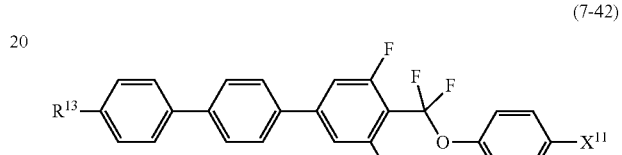
(7-43) 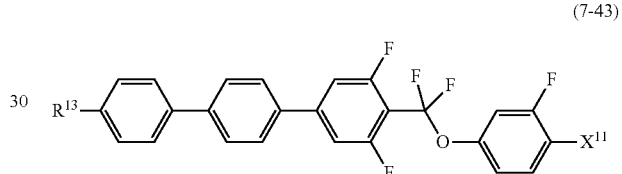
(7-44) 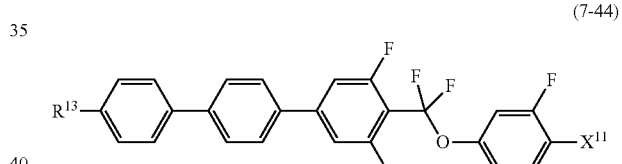
(7-45) 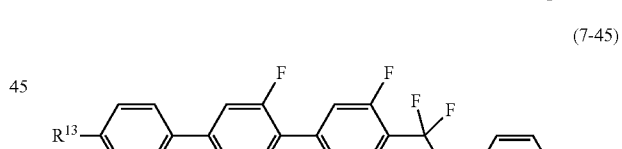
(7-46) 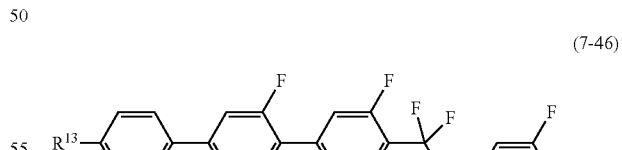
(7-47) 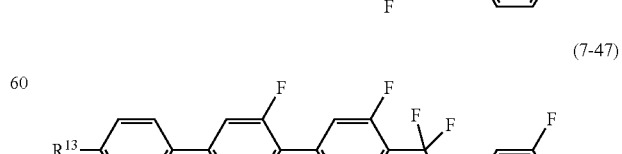

(7-48)
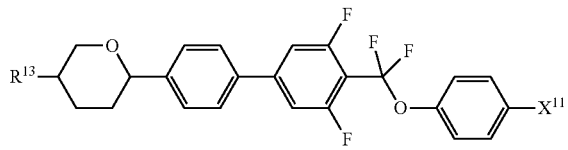

(7-49)
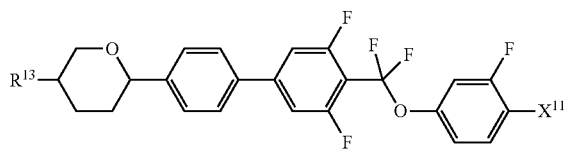

(7-50)
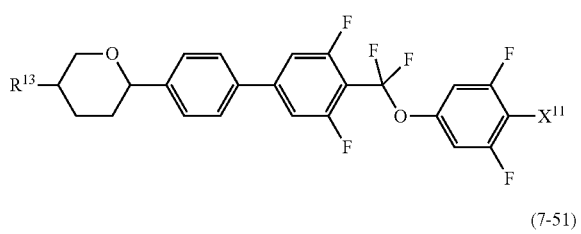

(7-51)
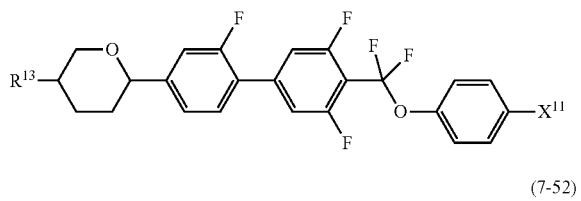

(7-52)
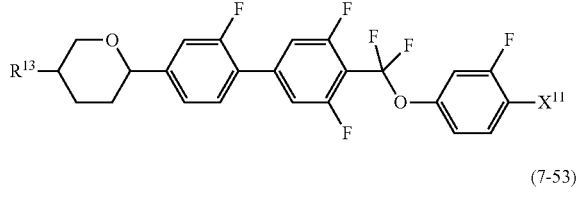

(7-53)
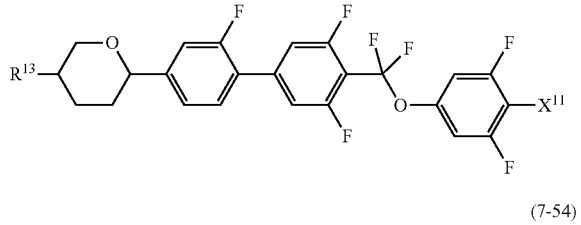

(7-54)
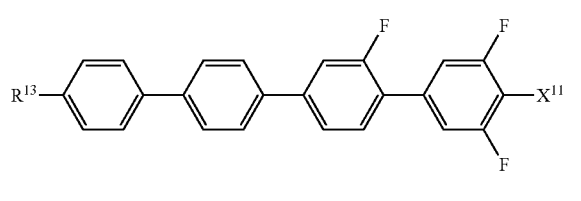

(7-55)
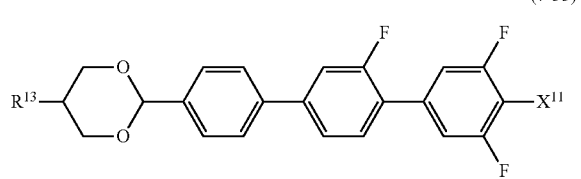

(7-56)
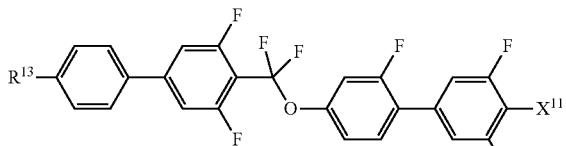

(7-57)
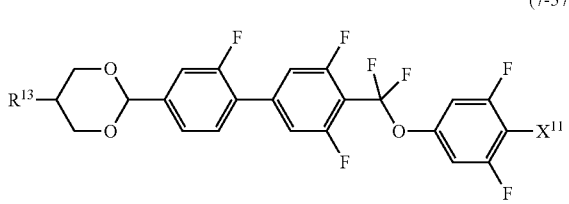

The component C has positive dielectric anisotropy and very excellent stability to heat or light, etc., and can thus be used for preparing the composition for use in modes such as IPS, FFS, and OCB, etc. The content of the component C is suitably 1 to 99 wt %, preferably 10 to 97 wt %, and more preferably 40 to 95 wt %, based on the weight of the liquid crystal composition. When the component C is added to a composition having negative dielectric anisotropy, the content of the component C is preferably 30 wt % or less. By addition of the component C, the elastic constant of the composition can be adjusted, and a voltage-transmittance curve of the device can be adjusted.

The component D is the compound (8) in which the right terminal group is —C≡N or —C≡C—C≡N. Preferred examples of the component D include compounds (8-1) to (8-64). In these compounds, $R^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; and $X^{12}$ is —C≡N or —C≡C—C≡N.

(8-1)
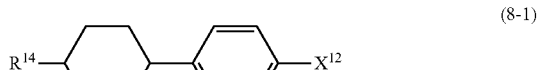

(8-2)
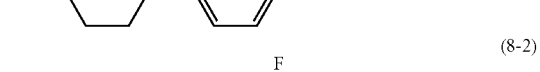

(8-3)
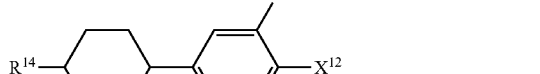

(8-4)
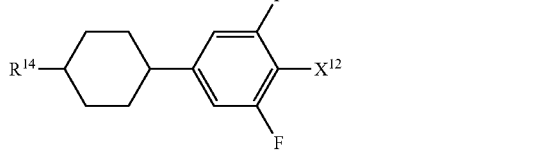

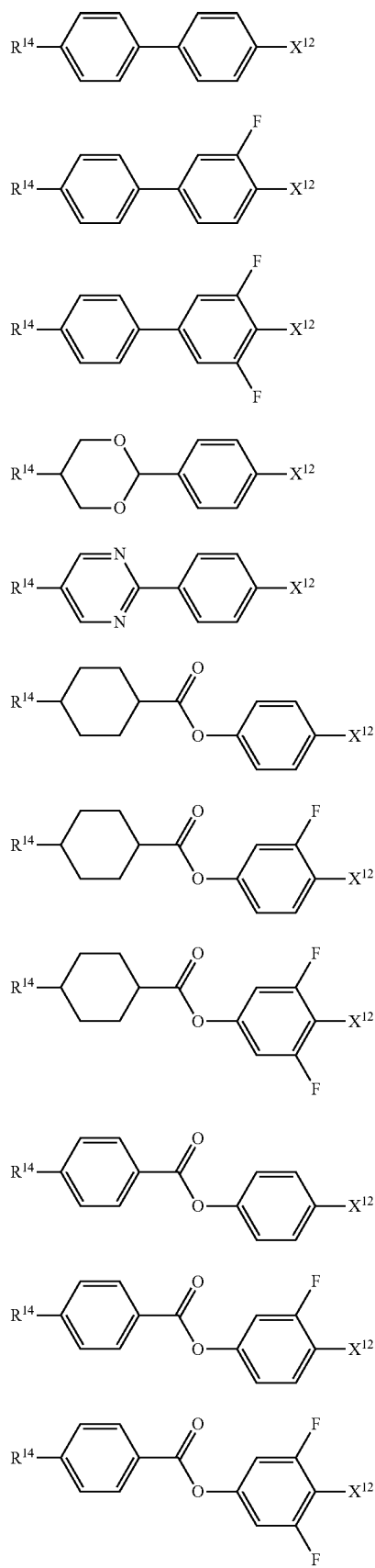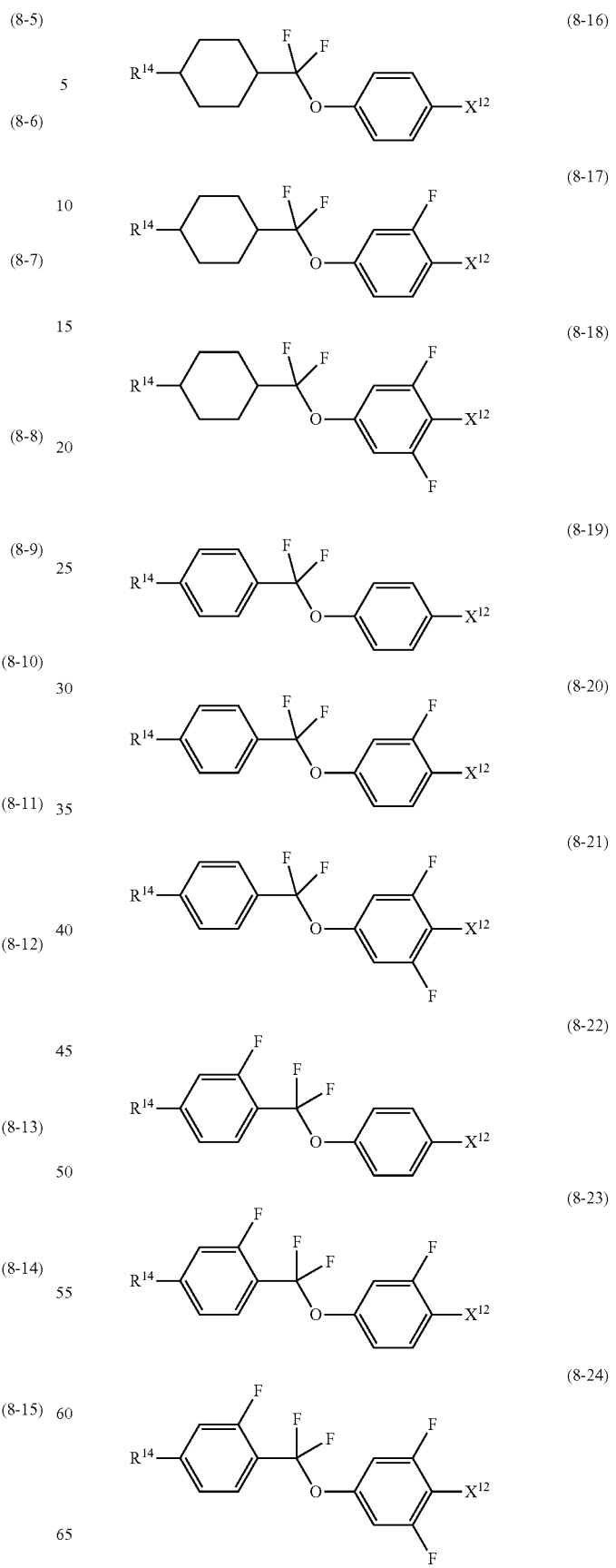

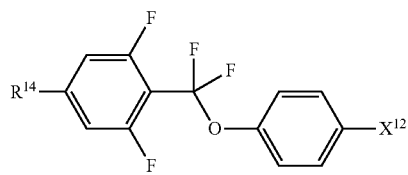 (8-25)
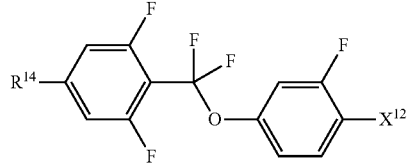 (8-26)
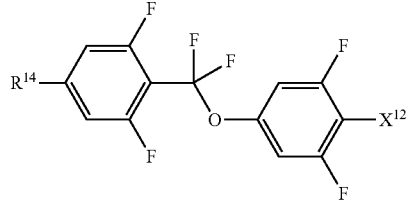 (8-27)
 (8-28)
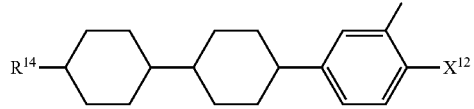 (8-29)
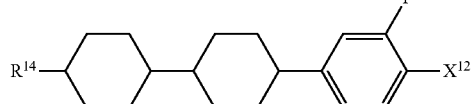 (8-30)
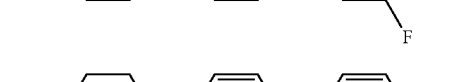 (8-31)
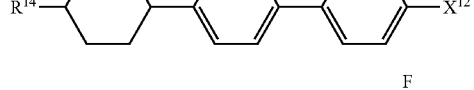 (8-32)
 (8-33)
 (8-34)
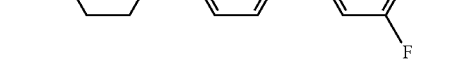 (8-35)
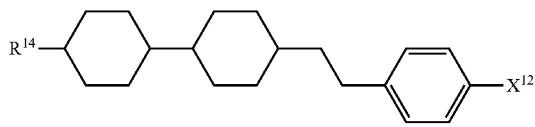 (8-36)
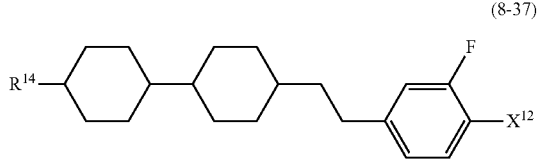 (8-37)
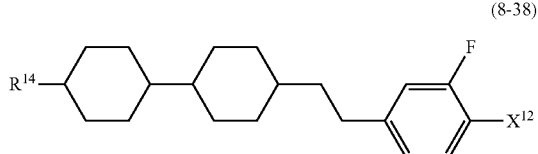 (8-38)
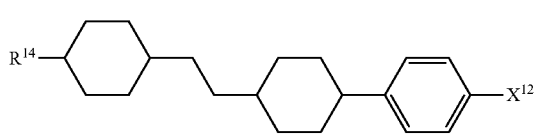 (8-39)
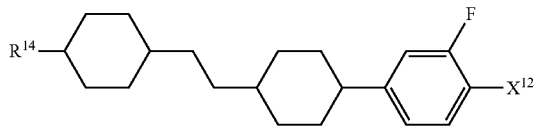 (8-40)
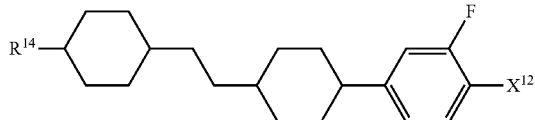 (8-41)
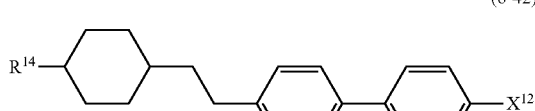 (8-42)
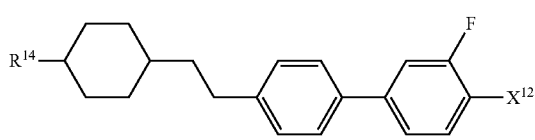 (8-43)
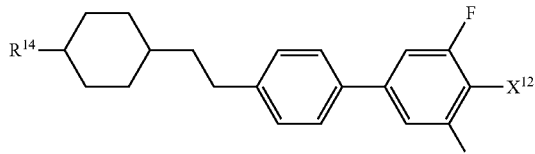 (8-44)

(8-45)
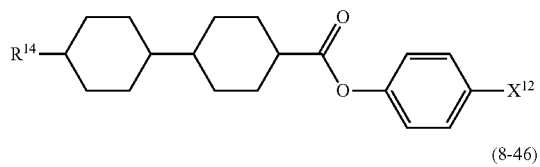
(8-46)
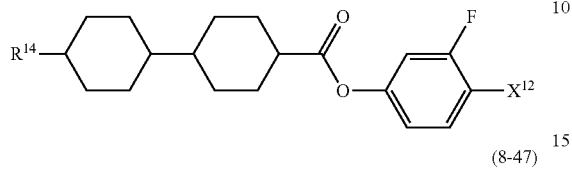
(8-47)
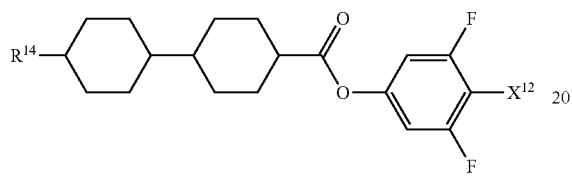
(8-48)
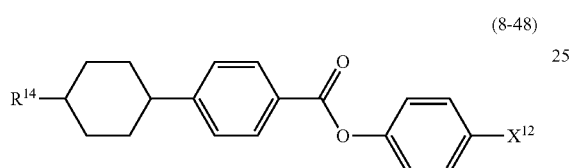
(8-49)
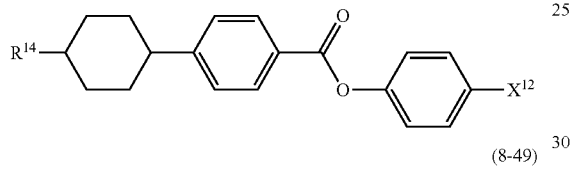
(8-50)
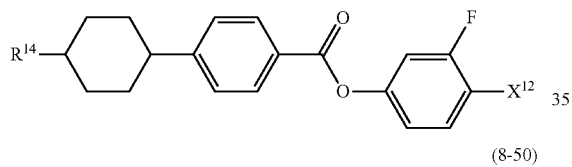
(8-51)
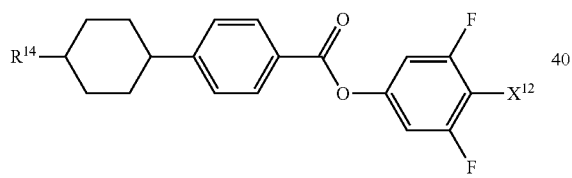
(8-52)
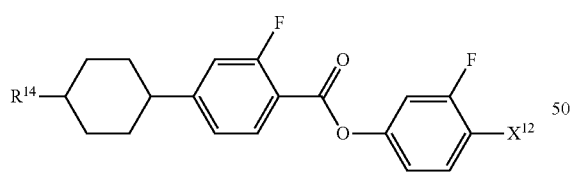
(8-53)
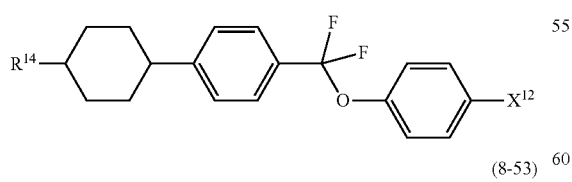
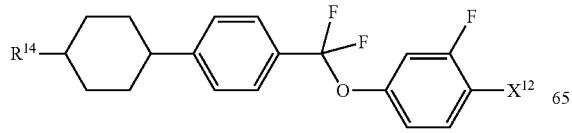
(8-54)
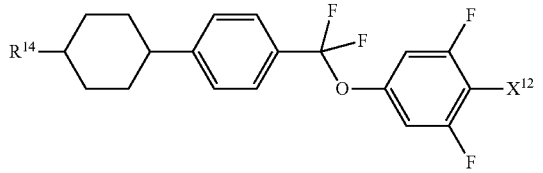
(8-55)
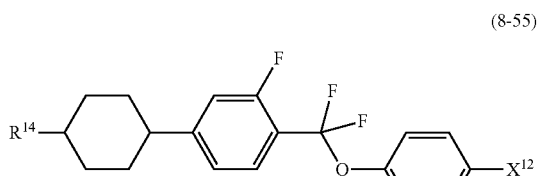
(8-56)
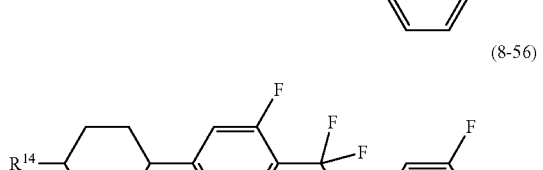
(8-57)
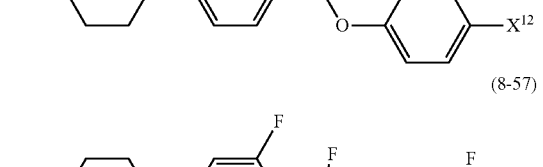
(8-58)
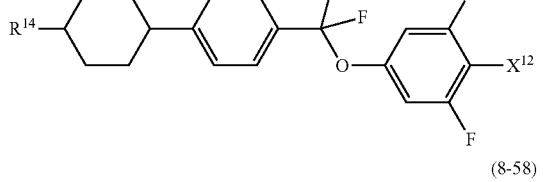
(8-59)
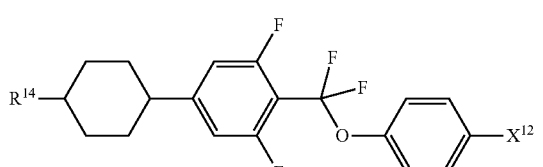
(8-60)
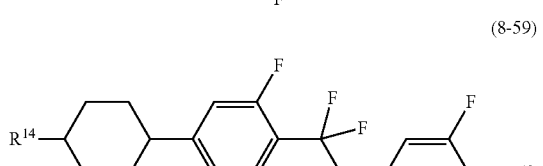
(8-61)
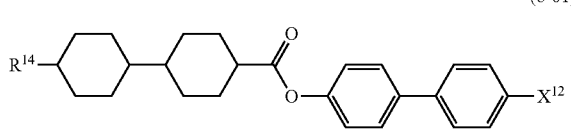

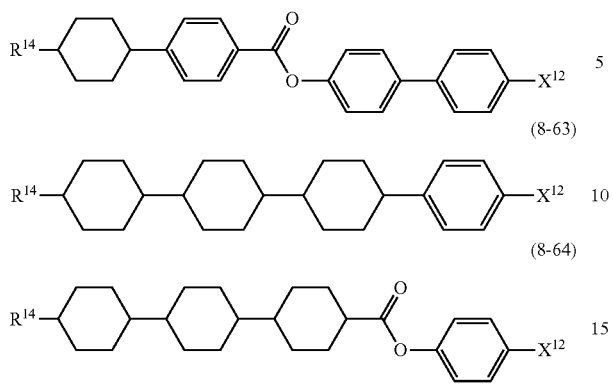

The component D has large positive dielectric anisotropy, and can thus be used for preparing the composition for use in modes such as TN and so on. By addition of the component D, the dielectric anisotropy of the composition can be increased. The component D has an effect of broadening a temperature range of a liquid crystal phase, adjusting viscosity, or adjusting optical anisotropy. The component D is also useful for adjusting the voltage-transmittance curve of the device.

In preparing the composition for use in modes such as TN and so on, the content of the component D is suitably 1 to 99 wt %, preferably 10 to 97 wt %, and more preferably 40 to 95 wt %, based on the weight of the liquid crystal composition. When the component D is added to a composition having negative dielectric anisotropy, the content of the component D is preferably 30 wt % or less. By addition of the component D, the elastic constant of the composition can be adjusted, and the voltage-transmittance curve of the device can be adjusted.

The component E includes compounds (9) to (15). These compounds have phenylene in which lateral positions have been replaced with two halogens, such as 2,3-difluoro-1,4-phenylene. Preferred examples of the component E include compounds (9-1) to (9-8), compounds (10-1) to (10-17), compound (11-1), compounds (12-1) to (12-3), compounds (13-1) to (13-11), compounds (14-1) to (14-3), and compounds (15-1) to (15-3). In these compounds, $R^{15}$ and $R^{16}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine; $R^{17}$ is hydrogen, fluorine, alkyl having 1 to 10 carbons, or alkenyl having 2 to 10 carbons, wherein at least one —CH$_2$— in the alkyl and alkenyl is optionally replaced with —O—, and at least one hydrogen in the alkyl and alkenyl is optionally replaced with fluorine.

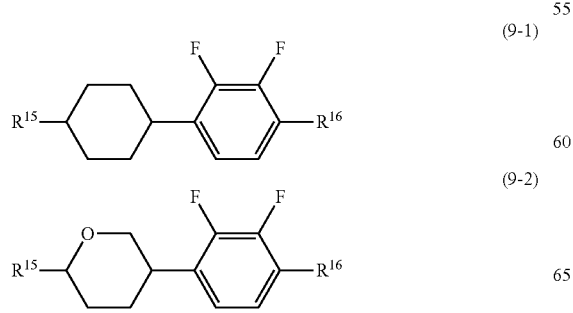

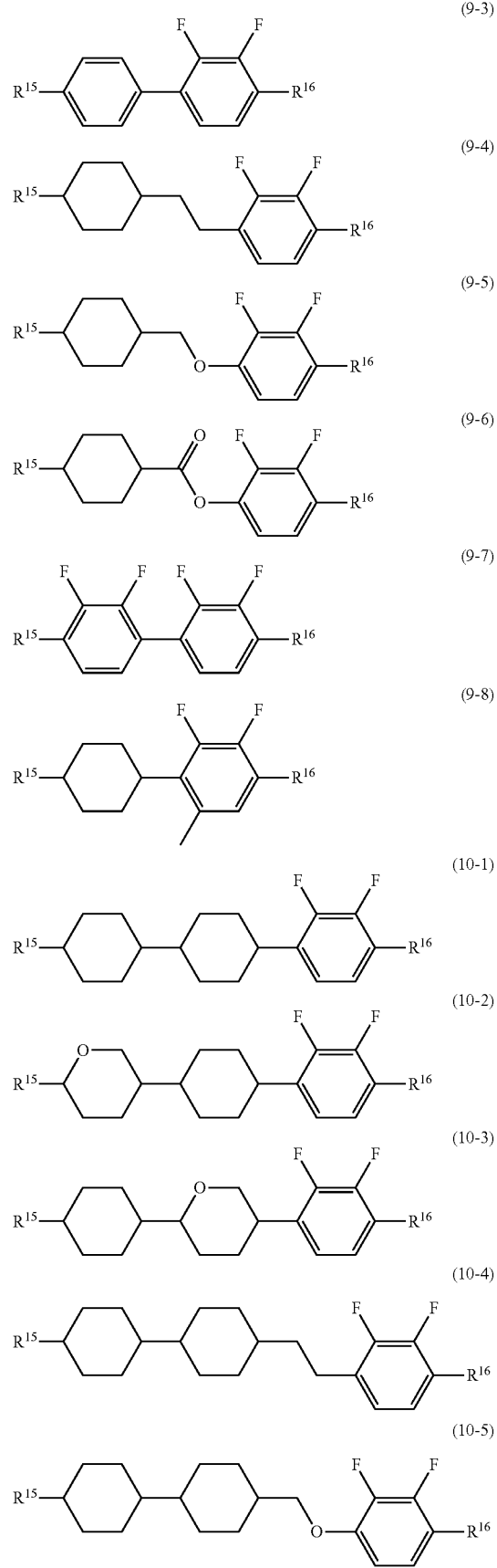

(10-6) 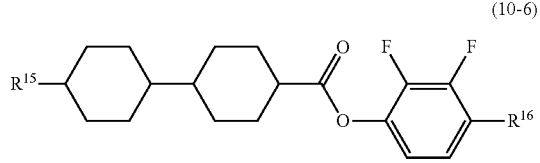
(10-7) 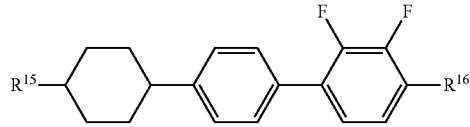
(10-8) 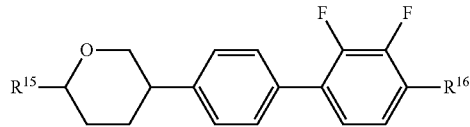
(10-9) 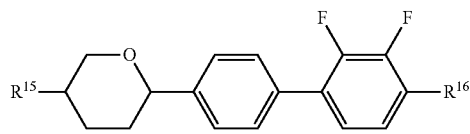
(10-10) 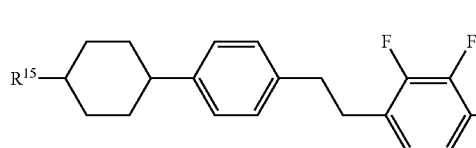
(10-11) 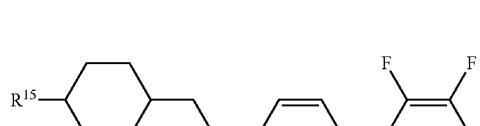
(10-12) 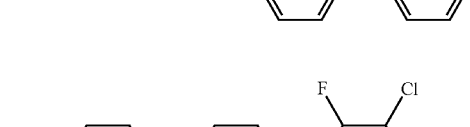
(10-13) 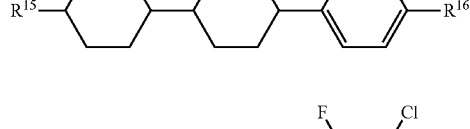
(10-14) 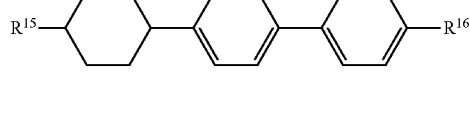
(10-15) 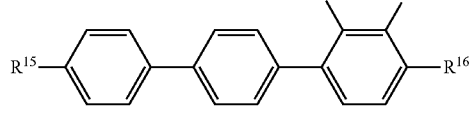
(10-16) 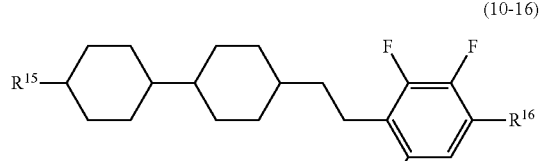
(10-17) 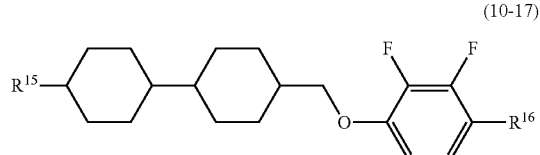
(11-1) 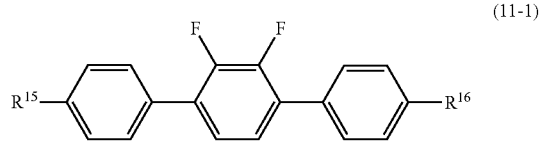
(12-1) 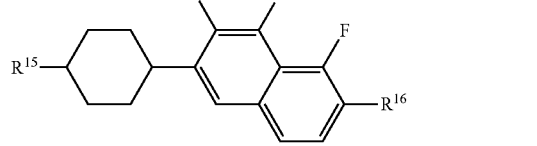
(12-2) 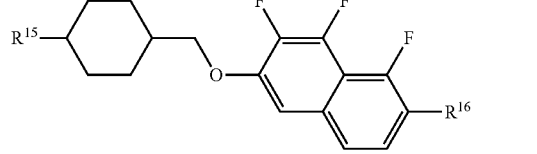
(12-3) 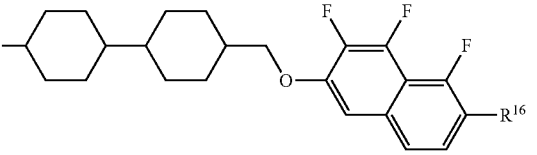
(13-1) 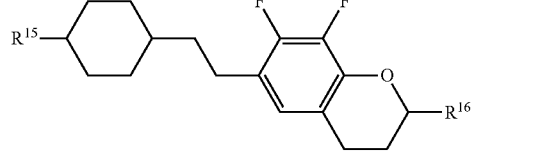
(13-2) 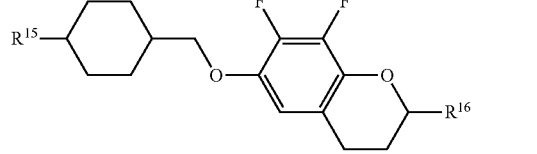
(13-3) 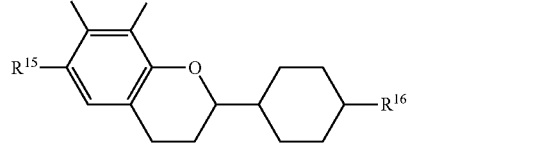

(13-4)
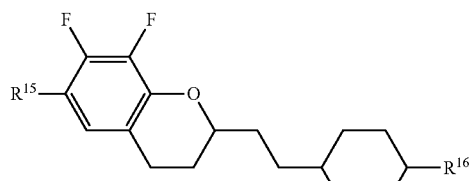

(13-5)
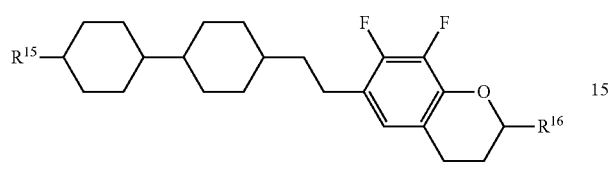

(13-6)
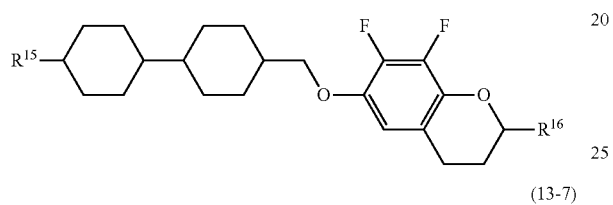

(13-7)
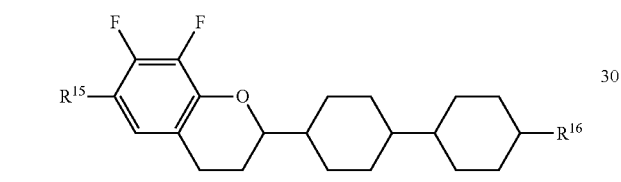

(13-8)
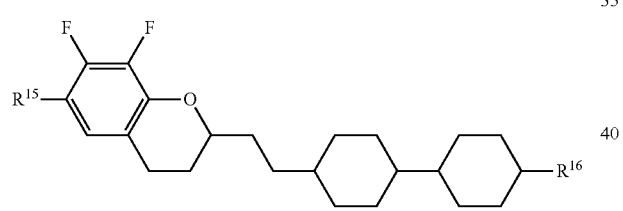

(13-9)
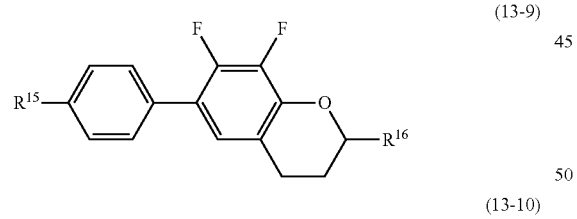

(13-10)
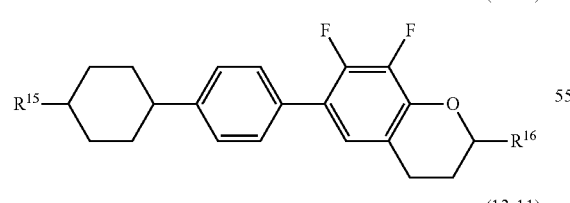

(13-11)
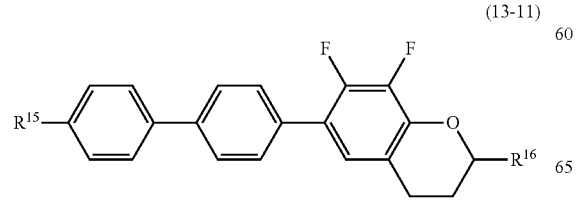

(14-1)
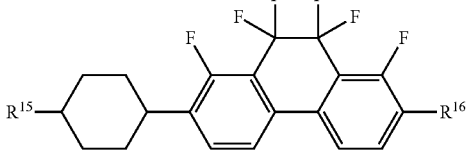

(14-2)
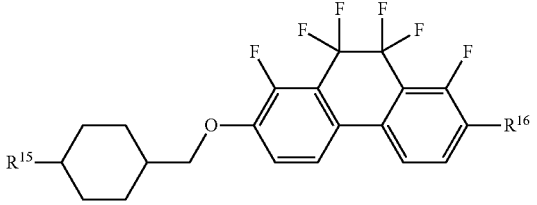

(14-3)
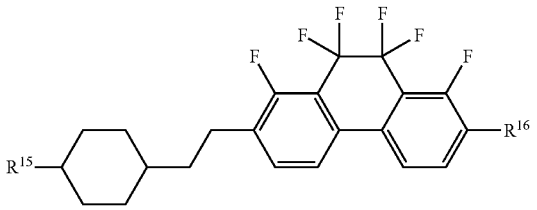

(15-1)
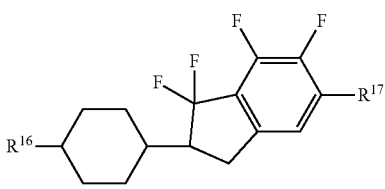

(15-2)
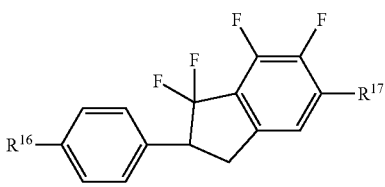

(15-3)
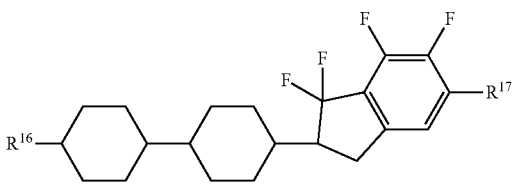

The component E has large negative dielectric anisotropy. The component E can be used for preparing the composition for use in modes such as IPS, VA, and PSA, etc. As the content of the component E is increased, the dielectric anisotropy of the composition is increased negatively but the viscosity is increased. Therefore, the content is preferably as low as possible as long as a required value of threshold voltage of the device is satisfied. When considering that the dielectric anisotropy is about −5, the content is preferably 40 wt % or more to perform sufficient voltage driving.

In the component E, the compound (9) is a bicyclic compound, and thus has an effect of reducing viscosity, adjusting optical anisotropy or increasing dielectric anisotropy. The compounds (10) and (11) are tricyclic compounds, and thus have an effect of increasing the maximum temperature, increasing optical anisotropy or increasing dielectric anisotropy. The compounds (12) to (15) have an effect of increasing dielectric anisotropy.

In preparing the composition for use in modes such as IPS, VA, and PSA, etc., the content of the component E is preferably 40 wt % or more, more preferably 50 to 95 wt %, based on the weight of the liquid crystal composition. When the component E is added to a composition having positive dielectric anisotropy, the content of the component E is preferably 30 wt % or less. By addition of the component E, the elastic constant of the composition can be adjusted, and the voltage-transmittance curve of the device can be adjusted.

By a suitable combination of the aforementioned components B, C, D and E, a liquid crystal composition that satisfies at least one of physical properties such as high stability to heat or light, high maximum temperature, low minimum temperature, small viscosity, suitable optical anisotropy, large dielectric anisotropy, large specific resistance, and a suitable elastic constant, etc. can be prepared. A liquid crystal compound different from the components B, C, D and E may be added if necessary.

3-2. Additives

The liquid crystal composition is prepared by a well-known method. For example, the component compounds are mixed together and dissolve in each other by heating. An additive may be added to the composition according to the use. Examples of the additive include a polymerizable compound, a polymerization initiator, a polymerization inhibitor, an optically active compound, an antioxidant, an ultraviolet absorbent, a light stabilizer, a heat stabilizer, a dye, and a defoamer, etc. Such additives are well-known to persons skilled in the art and have been described in literatures.

In a liquid crystal display device having a polymer sustained alignment (PSA) mode, the composition contains a polymer. The polymerizable compound is added for producing the polymer in the composition. The polymer is produced in the composition by irradiation with ultraviolet light to polymerize the polymerizable compound while a voltage is applied between electrodes. By this method, a suitable pretilt is achieved, and a device having shortened response time and improved image burn-in can thus be fabricated.

Preferred examples of the polymerizable compound include an acrylate, a methacrylate, a vinyl compound, a vinyloxy compound, propenyl ether, an epoxy compound (oxirane, oxetane), and vinyl ketone. More preferred examples include a compound having at least one acryloyloxy and a compound having at least one methacryloyloxy. More preferred examples also include a compound having both acryloyloxy and methacryloyloxy.

More preferred examples include compounds (M-1) to (M-17). In these compounds, $R^{25}$ to $R^{31}$ are independently hydrogen or methyl; s, v and x are independently 0 or 1; and t and u are independently an integer of 1 to 10. $L^{21}$ to $L^{26}$ are independently hydrogen or fluorine; and $L^{27}$ and $L^{28}$ are independently hydrogen, fluorine, or methyl.

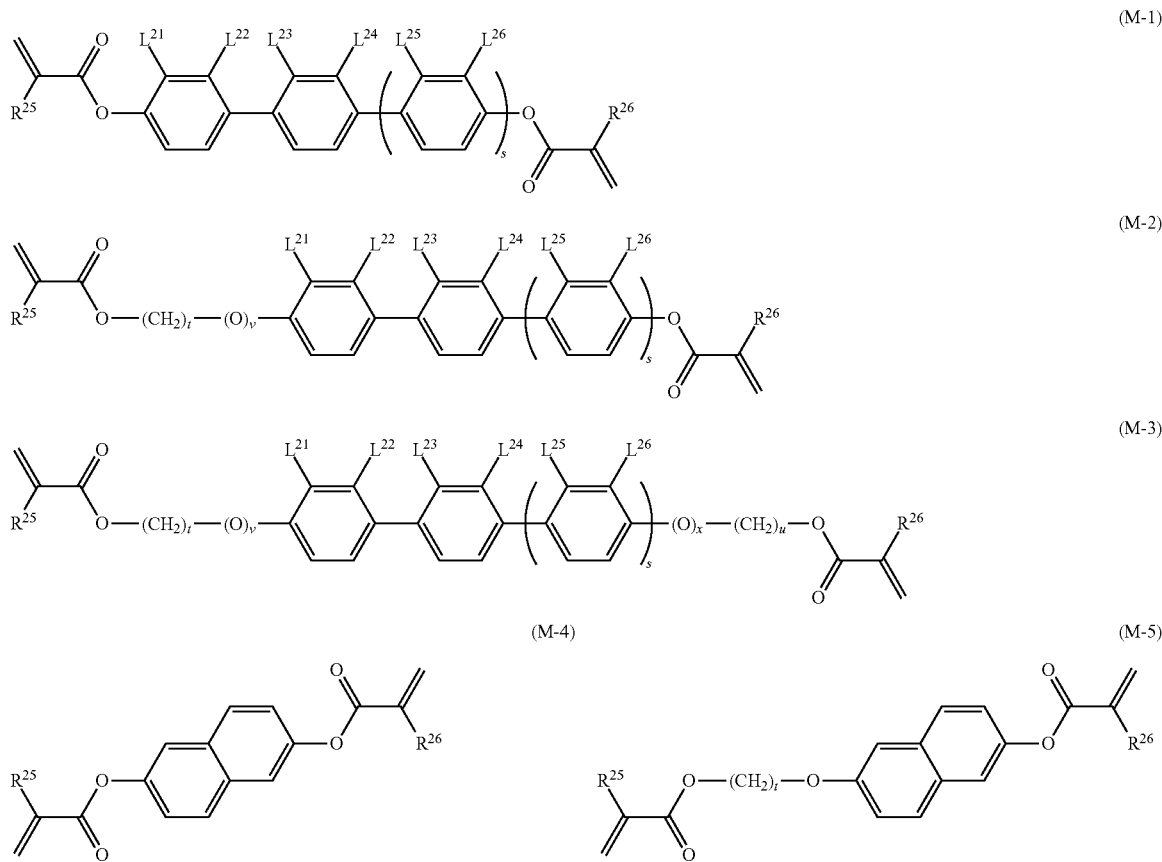

-continued
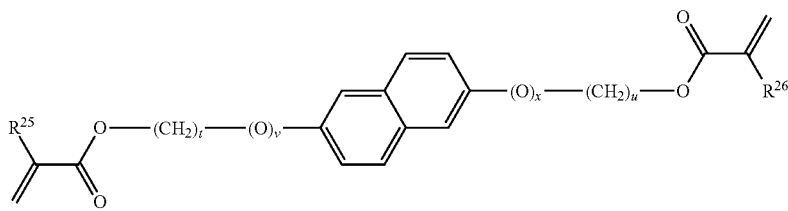
(M-6)
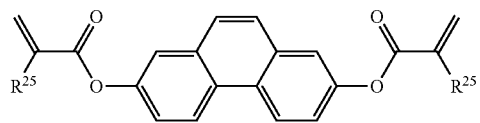
(M-7)
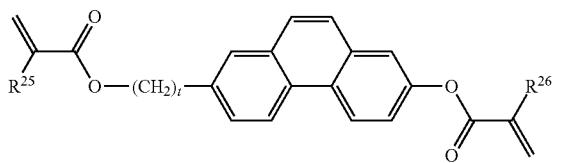
(M-8)
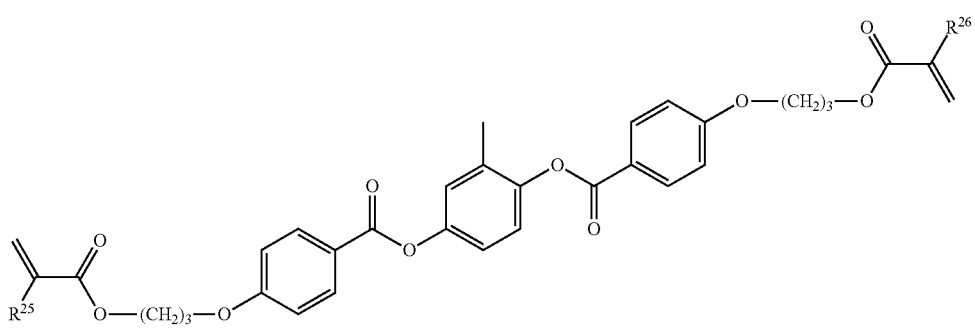
(M-9)
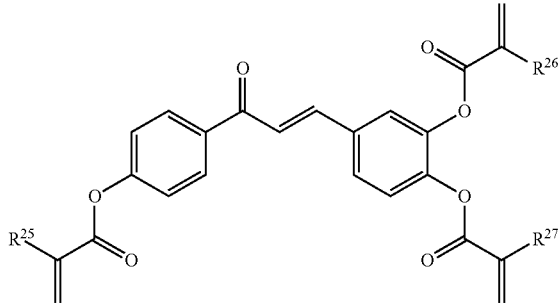
(M-10)
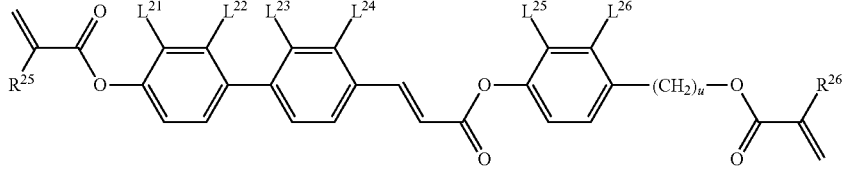
(M-11)
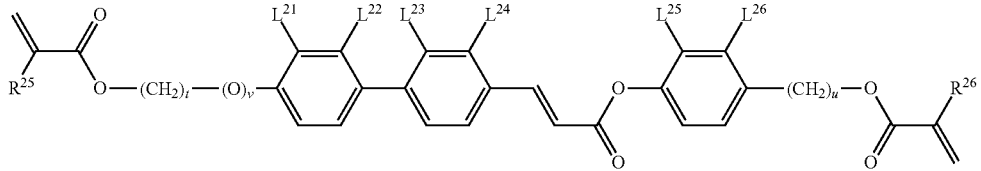
(M-12)
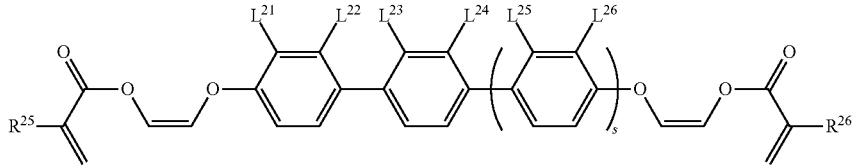
(M-13)

-continued

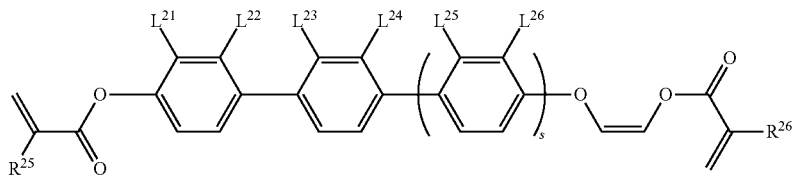
(M-14)

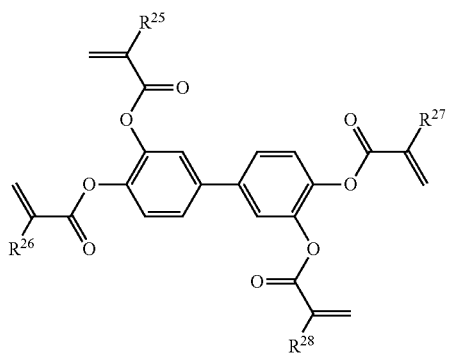
(M-15)

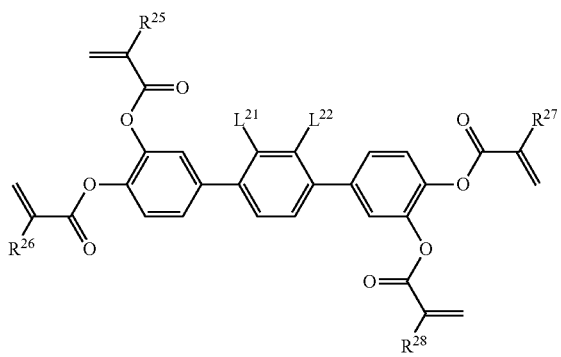
(M-16)

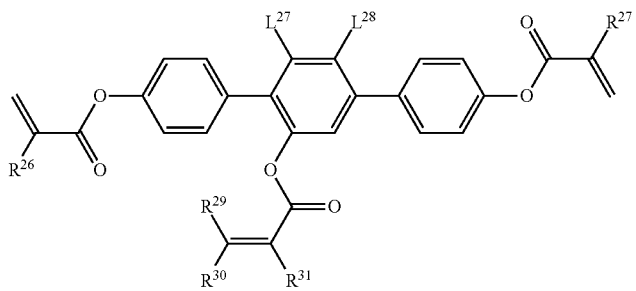
(M-17)

The polymerizable compound can be promptly polymerized by addition of a polymerization initiator. By optimization of a reaction temperature, the amount of remaining polymerizable compound can be reduced. Examples of a photo-radical polymerization initiator include TPO, 1173 and 4265 from Darocur series, and 184, 369, 500, 651, 784, 819, 907, 1300, 1700, 1800, 1850, and 2959 from Irgacure series, all made by BASF.

Additional examples of the photo-radical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/methyl p-dimethylaminobenzoate mixture, and a benzophenone/methyltriethanolamine mixture.

After the photo-radical polymerization initiator is added to the liquid crystal composition, polymerization can be carried out by irradiation with ultraviolet light in a state in which an electric field has been applied. However, an unreacted polymerization initiator or a decomposition product of the polymerization initiator might cause display defects of the device, such as image burn-in. In order to prevent this, the photopolymerization may also be carried out with no addition of the polymerization initiator. The irradiated light has a wavelength of preferably 150 to 500 nm, more preferably 250 to 450 nm, and most preferably 300 to 400 nm.

During storage of the polymerizable compound, a polymerization inhibitor may be added in order to prevent polymerization. The polymerizable compound is usually added to the composition without removing the polymerization inhibitor. Examples of the polymerization inhibitor include hydroquinone, a hydroquinone derivative such as methylhydroquinone, 4-t-butylcatechol, 4-methoxyphenol, and phenothiazine, etc.

The optically active compound has an effect of inducing a helical structure in liquid crystal molecules to give a necessary torsion angle so as to prevent reverse torsion. By addition of the optically active compound, a helical pitch can be adjusted. Two or more optically active compounds may be added for adjusting temperature dependence of the helical pitch. Preferred examples of the optically active compound include the following compounds (Op-1) to (Op-18). In the compound (Op-18), ring J is 1,4-cyclohexylene or 1,4-phenylene, and $R^{28}$ is alkyl having 1 to 10 carbons. The * mark represents an asymmetric carbon.

65
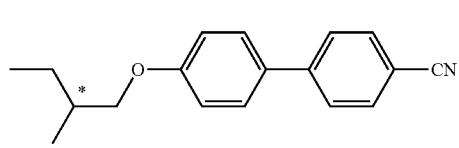 (Op-1)
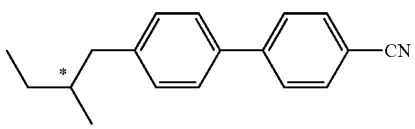 (Op-2)
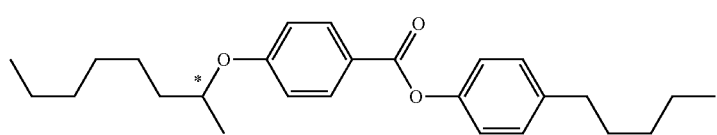 (Op-3)
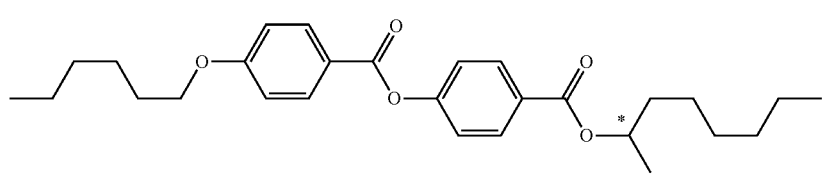 (Op-4)
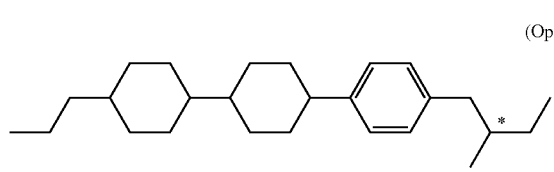 (Op-5)
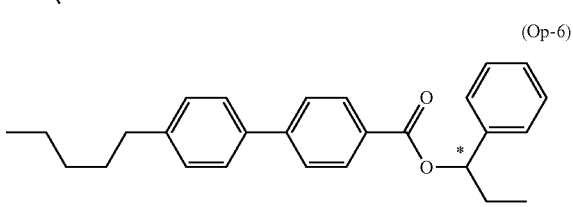 (Op-6)
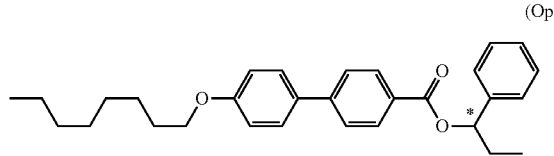 (Op-7)
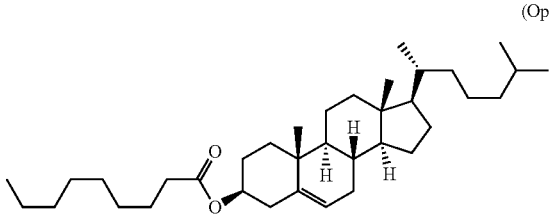 (Op-8)
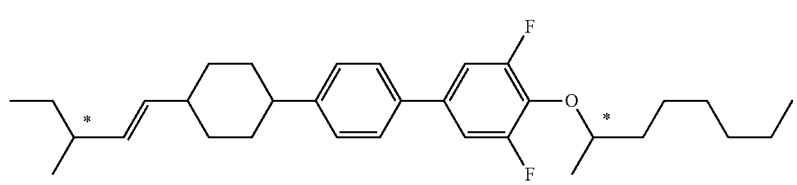 (Op-9)
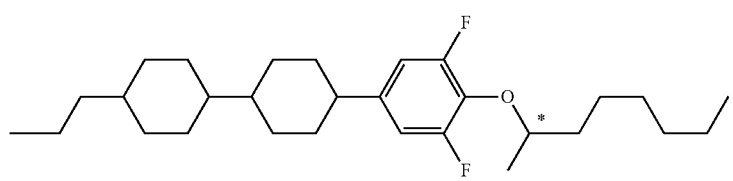 (Op-10)
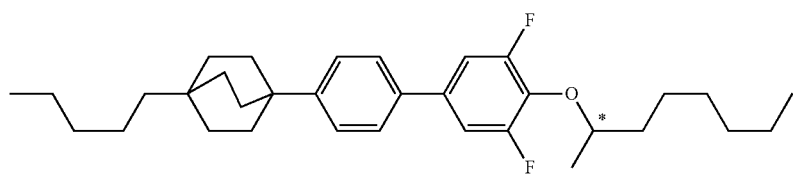 (Op-11)
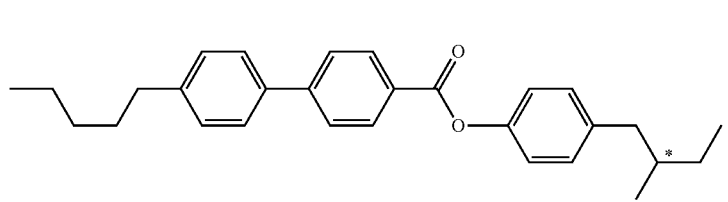 (Op-12)

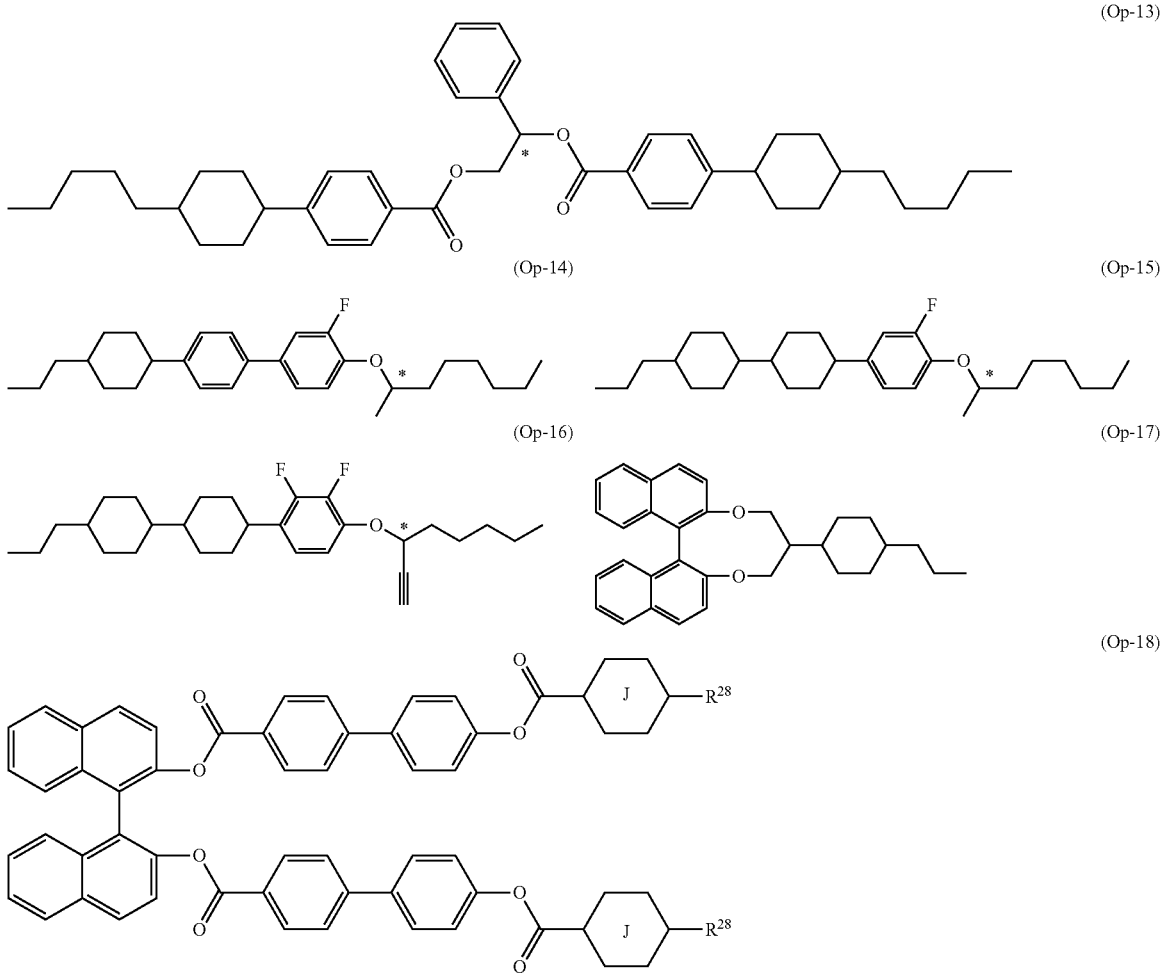

The antioxidant is effective for maintaining a large voltage holding ratio. Preferred examples of the antioxidant include the following compounds (AO-1) and (AO-2), IRGANOX 415, IRGANOX 565, IRGANOX 1010, IRGANOX 1035, IRGANOX 3114, and IRGANOX 1098 (trade names, made by BASF). The ultraviolet absorbent is effective for preventing reduction in the maximum temperature. Preferred examples of the ultraviolet absorbent include a benzophenone derivative, a benzoate derivative, and a triazole derivative, etc. Specific examples thereof include the following compounds (AO-3) and (AO-4), TINUVIN 329, TINUVIN P, TINUVIN 326, TINUVIN 234, TINUVIN 213, TINUVIN 400, TINUVIN 328, and TINUVIN 99-2 (trade names, made by BASF), and 1,4-diazabicyclo[2.2.2]octane (DABCO).

The light stabilizer such as an amine having steric hindrance is preferred for maintaining a large voltage holding ratio. Preferred examples of the light stabilizer include the following compounds (AO-5) and (AO-6), TINUVIN 144, TINUVIN 765 and TINUVIN 770DF (trade names, made by BASF). The heat stabilizer is also effective for maintaining a large voltage holding ratio, and preferred examples thereof include IRGAFOS 168 (trade name, made by BASF). A dichroic dye such as an azo dye, an anthraquinone dye or the like is added to the composition in order to suit a device in a guest host (GH) mode. The defoamer is effective for preventing foaming. Preferred examples of the defoamer include dimethyl silicone oil and methyl phenyl silicone oil, etc.

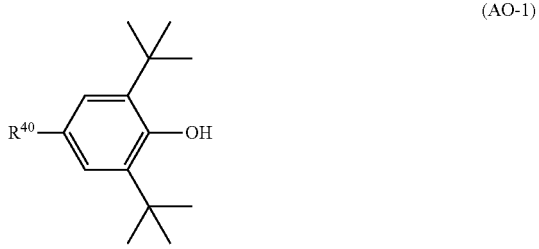

(AO-1)

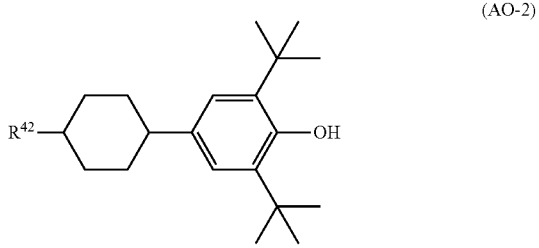

(AO-2)

-continued

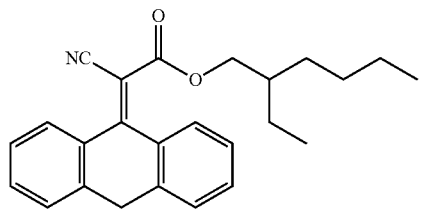
(AO-3)

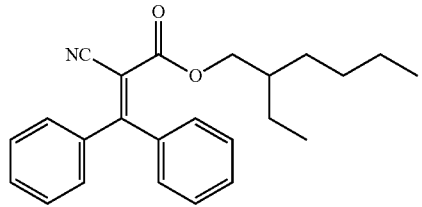
(AO-4)

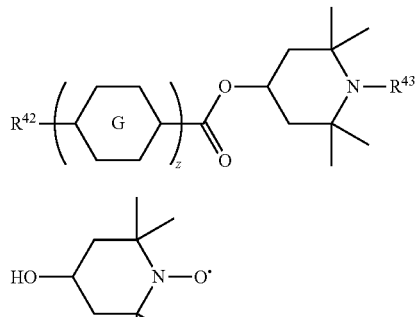
(AO-5)

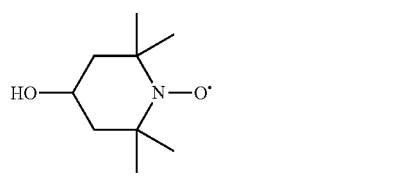
(AO-6)

In the compound (AO-1), $R^{40}$ is alkyl having 1 to 20 carbons, alkoxy having 1 to 20 carbons, —COOR$^{41}$ or —CH$_2$CH$_2$COOR$^{41}$, wherein $R^{41}$ is alkyl having 1 to 20 carbons. In the compounds (AO-2) and (AO-5), $R^{42}$ is alkyl having 1 to 20 carbons. In the compound (AO-5), $R^{43}$ is hydrogen, methyl, or O (oxygen radical); ring G is 1,4-cyclohexylene or 1,4-phenylene; and z is 1, 2, or 3.

4. Liquid Crystal Display Device

The liquid crystal composition can be used in a liquid crystal display device having an operating mode such as PC, TN, STN, OCB, or PSA, etc. and driven by an active matrix (AM) method. This composition can also be used in a liquid crystal display device having an operating mode such as PC, TN, STN, OCB, VA, or IPS, etc. and driven by a passive matrix (PM) method. These devices may be of any of a reflective type, a transmissive type and a transflective type.

The composition is also applicable to a nematic curvilinear aligned phase (NCAP) device in which the composition is microencapsulated. The composition can also be used in a polymer dispersed liquid crystal display (PDLCD) device or a polymer network liquid crystal display (PNLCD) device. In these compositions, a large amount of polymerizable compounds are added. On the other hand, when the polymerizable compound is added in an amount of 10 wt % or less based on the weight of the liquid crystal composition, a liquid crystal display device in the PSA mode is fabricated. A preferred ratio is 0.1 to 2 wt %, and a more preferred ratio is 0.2 to 1.0 wt %. The device in the PSA mode can be driven by methods such as an active matrix (AM) method and a passive matrix (PM) method. Such a device may be of any of a reflective type, a transmissive type and a transflective type.

EXAMPLES

The invention is further explained in detail according to examples (including synthesis examples and use examples). The invention is not limited to these examples. The invention includes a mixture of a composition of Use Example 1 and a composition of Use Example 2. The invention also includes a composition prepared by mixing at least two compositions of the use examples.

1. Examples of Compound (1)

The compound (1) was synthesized by the following procedure. The synthesized compound was identified by methods such as NMR analysis, etc. The physical properties of the compound or the composition, and the characteristics of the device were measured by the following methods.

NMR analysis: DRX-500 made by Bruker BioSpin K.K. was used for the measurement. In the measurement of $^1$H-NMR, a sample was dissolved in a deuterated solvent such as CDCl$_3$, and measured at 500 MHz at room temperature in 16 times of accumulation. Tetramethylsilane was used as the internal standard. The measurement of $^{19}$F-NMR was carried out using CFCl$_3$ as the internal standard in 24 times of accumulation. In the explanation of the nuclear magnetic resonance spectrum, "s" denotes singlet, "d" denotes doublet, "t" denotes triplet, "q" denotes quartet, "quin" denotes quintet, "sex" denotes sextet, "m" denotes multiplet, and "br" denotes broad.

Gas chromatography (GC) analysis: GC-2010 Gas Chromatograph made by Shimadzu Corporation was used for the measurement. The capillary column DB-1 (length=60 m, inner diameter=0.25 mm, film thickness=0.25 μm) made by Agilent Technologies Inc. was used as the column. Helium (1 ml/min) was used as the carrier gas. The sample evaporation chamber was set at 300° C., and the detector (flame ionization detector, FID) was set at 300° C. The sample was dissolved in acetone so as to prepare a solution of 1 wt %, and 1 μl of the obtained solution was poured into the sample evaporation chamber. The GCsolution system made by Shimadzu Corporation or the like was used as the recorder.

HPLC analysis: Prominence (LC-20AD; SPD-20A) made by Shimadzu Corporation was used for the measurement. YMC-Pack ODS-A (length=150 mm, inner diameter=4.6 mm, particle diameter=5 μm) made by YMC Co., Ltd. was used as the column. A mixture obtained by properly mixing acetonitrile with water was used as the eluent. A UV detector, an RI detector, or a Corona detector or the like was properly used as the detector. When the UV detector was used, the detection wavelength was 254 nm. The sample was dissolved in acetonitrile so as to prepare a solution of 0.1 wt %, and 1 μL of the solution was introduced to the sample chamber. C-R7Aplus made by Shimadzu Corporation was used as the recorder.

Ultraviolet-visible spectroscopic analysis: PharmaSpec UV-1700 made by Shimadzu Corporation was used for the measurement. The detection wavelength was 190 to 700 nm. The sample was dissolved in acetonitrile so as to prepare a 0.01 mmol/L solution, and the solution was placed in a quartz cell (optical path length=1 cm) and then measured.

Measurement sample: A compound itself was used as a sample when the phase structure and the transition temperature (clearing point, melting point, polymerization start temperature, etc.) were measured. A mixture of a compound and a mother liquid crystal was used as a sample in measuring the physical properties such as the maximum temperature of a nematic phase, viscosity, optical anisotropy, and dielectric anisotropy, etc.

When the sample obtained by mixing the compound with the mother liquid crystal was used, an extrapolated value was calculated by the following equation and was recorded. <Extrapolated value>=(100×<measured value of the sample>−<wt % of the mother liquid crystal>×<measured value of the mother liquid crystal>)/<wt % of the compound>.

Mother liquid crystal (A): When the dielectric anisotropy of the compound was zero or positive, the following mother liquid crystal (A) was used. The ratio of each component was expressed by wt %.

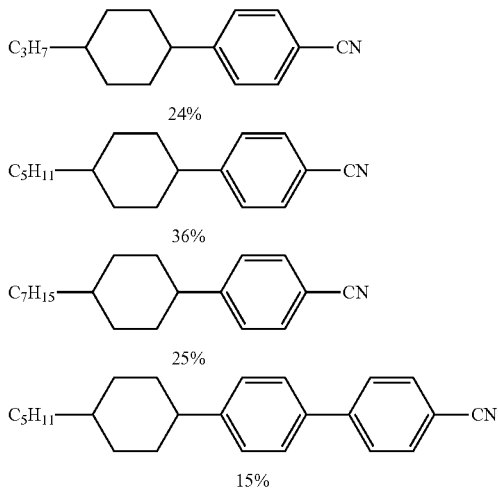

A ratio of the compound to the mother liquid crystal (A) was set to 15 wt %:85 wt %. If crystals (or a smectic phase) were precipitated at 25° C. at this ratio, the ratio of the compound to the mother liquid crystal (A) was changed to 10 wt %:90 wt %, 5 wt %:95 wt % and 1 wt %:99 wt % in order. The sample was measured at the ratio at which the crystals (or the smectic phase) were no longer precipitated at 25° C. Moreover, the ratio of the compound to the mother liquid crystal (A) was 15 wt %:85 wt % unless specified otherwise.

Mother liquid crystal (B): In Comparative Example 2, a mother liquid crystal (B) having the following fluorine-based compounds as components was also used. The ratios of the components of the mother liquid crystal (B) were expressed by wt %.

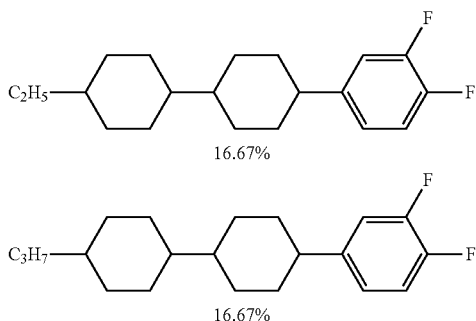

-continued

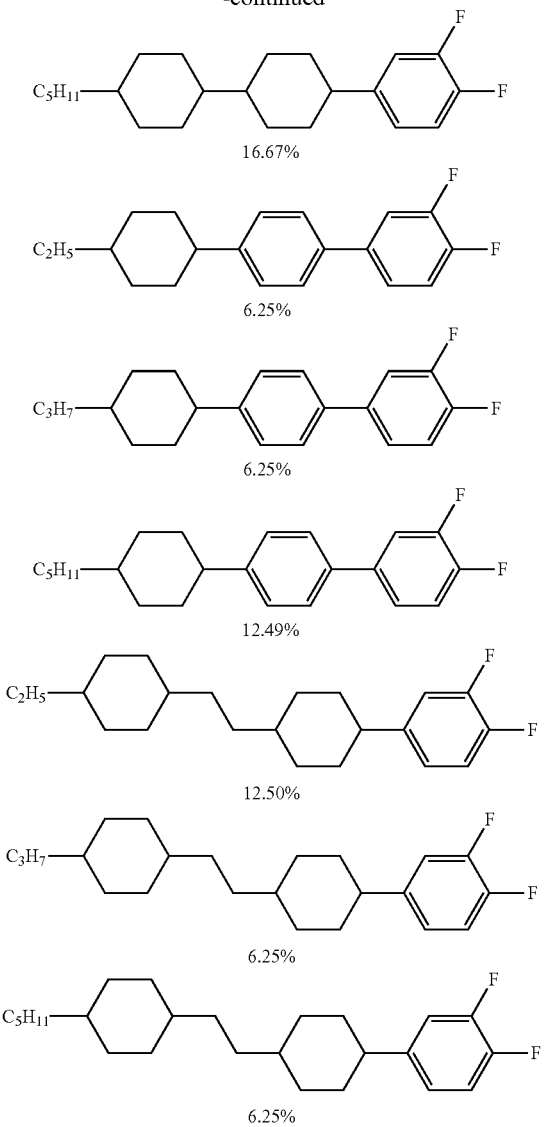

A ratio of the compound to the mother liquid crystal (B) was set to 20 wt %:80 wt %. If crystals (or a smectic phase) were precipitated at 25° C. at this ratio, the ratio of the compound to the mother liquid crystal (B) was changed to 15 wt %:85 wt %, 10 wt %:90 wt %, 5 wt %:95 wt % and 1 wt %:99 wt % in order. The physical properties of the sample were measured at the ratio at which the crystals (or the smectic phase) were no longer precipitated at 25° C. Moreover, the ratio of the compound to the mother liquid crystal (B) was 20 wt %:80 wt % unless specified otherwise.

Measurement method: The physical properties were measured by the following methods. Most of these methods are described in the JEITA Standards (JEITA•ED-2521B) deliberated and established by the Japan Electronics and Information Technology Industries Association (JEITA). Modifications of the above methods were also employed. No thin-film transistor (TFT) was attached to a TN device used for the measurement.

(1) Phase structure: The sample was placed on a hot plate (FP52 Hot Stage made by Mettler Toledo International Inc.) of a melting point apparatus equipped with a polarizing microscope. A state of phase and a change thereof were observed with the polarizing microscope while the sample was heated at a rate of 3° C./min, and a phase type was specified.

(2) Transition temperature (° C.): A scanning calorimeter, Diamond DSC System made by PerkinElmer, Inc., or a high sensitivity differential scanning calorimeter, X-DSC7000 made by SII NanoTechnology Inc., was used for the measurement. The sample was heated and then cooled at a rate of 3° C./min. A starting point of an endothermic peak or an exothermic peak caused by a phase change of the sample was calculated by extrapolation, and the transition temperature was determined. The melting point and the polymerization start temperature of the compound were also measured using this apparatus. The temperature at which the compound changes from solid to a liquid crystal phase such as smectic phase or nematic phase is sometimes simply referred to as "minimum temperature of a liquid crystal phase." The temperature at which the compound changes from a liquid crystal phase to liquid is sometimes simply referred to as "clearing point."

Crystals were expressed as C. When types of the crystals were distinguishable, the crystals were respectively expressed as $C_1$ or $C_2$. The smectic phase was expressed as S and the nematic phase as N. When a smectic A phase, a smectic B phase, a smectic C phase or a smectic F phase was distinguishable in the smectic phases, it was expressed as $S_A$, $S_B$, $S_C$ or $S_F$. A liquid (isotropic) was expressed as I. The transition temperature was expressed as, e.g., "C 50.0 N 100.0 I." This means that the transition temperature from crystals to a nematic phase is 50.0° C., and the transition temperature from a nematic phase to liquid is 100.0° C.

(3) Low-temperature compatibility: The sample was prepared by mixing the mother liquid crystal with the compound such that the ratio of the compound became 20 wt %, 15 wt %, 10 wt %, 5 wt %, 3 wt %, or 1 wt %, and the sample was placed in a glass bottle. The glass bottle was stored in a freezer at −10° C. or −20° C. for a certain period, and was then observed for whether or not crystals or a smectic phase was precipitated.

(4) Maximum temperature of nematic phase ($T_{NI}$ or NI; ° C.): The sample was placed on a hot plate of a melting point measuring apparatus equipped with a polarizing microscope, and was heated at a rate of 1° C./min. The temperature at which a part of the sample changed from a nematic phase to an isotropic liquid was measured. When the sample was a mixture of the compound (1) and a mother liquid crystal, the maximum temperature was represented by the symbol $T_{NI}$. When the sample was a mixture of the compound (1) and a compound such as the component B, C or D, the maximum temperature was represented by the symbol NI. The maximum temperature of a nematic phase is sometimes simply referred to as "maximum temperature."

(5) Minimum temperature of nematic phase ($T_C$; ° C.): The sample having a nematic phase was placed in a glass bottle and stored in a freezer at 0° C., −10° C., −20° C., −30° C. or −40° C. for 10 days, and was then observed for the liquid crystal phase. For example, when the sample maintained the nematic phase at −20° C. and changed to crystals or a smectic phase at −30° C., the $T_C$ was recorded as "<20° C." The minimum temperature of a nematic phase is sometimes simply referred to as "minimum temperature."

(6) Viscosity (bulk viscosity; η; measured at 20° C.; mPa·s): An E-type rotational viscometer made by Tokyo Keiki Inc. was used for the measurement.

(7) Viscosity (rotational viscosity; γ1; measured at 25° C.; mPa·s): The measurement was carried out in accordance with the method described in M. Imai et al., Molecular Crystals and Liquid Crystals, Vol. 259, 37 (1995). The sample was placed into a TN device with a twist angle of 0° and a distance (cell gap) of 5 μm between two glass substrates. The device was applied with a voltage in a range of 16 to 19.5 V, stepwise by 0.5 V. After a period of 0.2 second with no voltage application, application was repeated under the conditions of only one rectangular wave (rectangular pulse; 0.2 second) and no application (2 seconds). The peak current and the peak time of a transient current resulting from this application were measured. The value of rotational viscosity was obtained according to these measured values and Equation (8) on page 40 of the paper of M. Imai et al. The value of dielectric anisotropy required for this calculation was obtained by the method described below using the device by which the rotational viscosity was measured.

(8) Optical anisotropy (refractive index anisotropy; measured at 25° C.; Δn): The measurement was carried out using light of 589 nm, with an Abbe refractometer having a polarizing plate mounted on an ocular lens. The surface of the main prism was rubbed in a direction, and then the sample was dripped onto the main prism. The refractive index (n∥) was measured when the direction of polarized light was parallel to that of the rubbing, and the refractive index (n⊥) was measured when the direction of polarized light was perpendicular to that of the rubbing. The value of optical anisotropy (Δn) was calculated from an equation of "Δn=n∥−n⊥."

(9) Dielectric anisotropy (Δε; measured at 25° C.): The sample was placed into a TN device with a distance (cell gap) of 9 μm between two glass substrates and a twist angle of 80 degrees. The device was applied with a sine wave (10 V, 1 kHz), and the dielectric constant (ε∥) in the major-axis direction of the liquid crystal molecule was measured after 2 seconds. The device was applied with a sine wave (0.5 V, 1 kHz), and the dielectric constant (ε⊥) in the minor-axis direction of the liquid crystal molecule was measured after 2 seconds. The value of dielectric anisotropy was calculated from an equation of "Δε=ε∥−ε⊥."

(10) Elastic constant (K; measured at 25° C.; pN): An LCR meter, HP 4284A made by Yokogawa-Hewlett-Packard, Ltd., was used for the measurement. The sample was placed into a horizontal alignment device with a distance (cell gap) of 20 μm between two glass substrates. The device was applied with an electric charge of 0 to 20 V, and electrostatic capacity and applied voltage were measured. The measured values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and values of $K_{11}$ and $K_{33}$ were obtained from Equation (2.99). Next, $K_{22}$ was calculated from Equation (3.18) on page 171 using the previously obtained values of $K_{11}$ and $K_{33}$. The elastic constant K was an average value of $K_{11}$, $K_{22}$ and $K_{33}$ thus obtained.

(11) Threshold voltage (Vth; measured at 25° C.; V) A luminance meter, Model LCD5100 made by Otsuka Electronics Co., Ltd., was used for the measurement. The light source was a halogen lamp. The sample was placed into a TN device in a normally white mode with a distance (cell gap) of 0.45/Δn(μm) between two glass substrates and a twist angle of 80 degrees. A voltage (32 Hz, rectangular wave) applied to the device was increased stepwise from 0 V to 10 V at an increment of 0.02 V. On this occasion, the device was irradiated with light in the vertical direction, and the amount of light passing through the device was measured. A voltage-transmittance curve was plotted in a manner that the transmittance was 100% when the amount of light became the maximum and the transmittance was 0% when the amount of light was the minimum. The threshold voltage was the voltage corresponding to the transmittance of 90%.

(12) Voltage holding ratio (VHR-1; measured at 25° C.; %): The TN device used for the measurement had a polyimide alignment film, and had a distance (cell gap) of 5 μm between two glass substrates. The sample was placed into the device, and then the device was sealed with an adhesive curable on irradiation with ultraviolet light. The device was charged at 25° C. by applying a pulse voltage (60 microseconds at 5 V). A decaying voltage was measured for 16.7 milliseconds with a high-speed voltmeter, and an area A between a voltage curve and a horizontal axis per unit cycle was calculated. An area B was an area without decay. A voltage holding ratio was expressed by a percentage of the area A relative to the area B.

(13) Voltage holding ratio (VHR-2; measured at 80° C.; %): The voltage holding ratio was measured by the above method except that the measurement was carried out at 80° C. instead of 25° C. The results obtained were represented by the symbol VHR-2.

(14) Specific resistance (p; measured at 25° C.; Ωcm): 1.0 mL of the sample was poured into a vessel equipped with electrodes. DC voltage (10 V) was applied to the vessel, and the DC current after 10 seconds was measured. The specific resistance was calculated from the following equation: (specific resistance)=[(voltage)×(electric capacity of vessel)]/[(DC current)×(dielectric constant in vacuum)].

(15) Response time (τ; measured at 25° C.; ms): A luminance meter, Model LCD5100 made by Otsuka Electronics Co., Ltd., was used for the measurement. The light source was a halogen lamp. The low-pass filter was set at 5 kHz. The sample was placed into a TN device in a normally white mode with a distance (cell gap) of 5.0 μm between two glass substrates and a twist angle of 80 degrees. A rectangular wave (60 Hz, 5 V, 0.5 second) was applied to the device. On this occasion, the device was irradiated with light in the vertical direction, and the amount of light passing through the device was measured. The transmittance was regarded as 100% when the amount of light became the maximum and the transmittance was regarded as 0% when the amount of light was the minimum. Rise time (τr; millisecond) was the time required for a change in transmittance from 90% to 10%. Fall time (τf; millisecond) was the time required for a change in transmittance from 10% to 90%. The response time was the sum of the rise time and the fall time thus obtained.

Raw materials: SOLMIX® A-11 is a mixture of ethanol (85.5%), methanol (13.4%) and isopropanol (1.1%), and was available from Japan Alcohol Trading Company Limited. Tetrahydrofuran is sometimes simply referred to as THF. Tetrabutylammonium bromide is sometimes simply referred to as TBAB. N,N-dimethylformamide is sometimes simply referred to as DMF. 2-propanol is sometimes simply referred to as IPA. 1,2-dimethoxyethane is sometimes simply referred to as DME. Potassium hexamethyldisilazane is sometimes simply referred to as KHMDS.

Synthesis Example 1

Synthesis of Compound (No. 3)

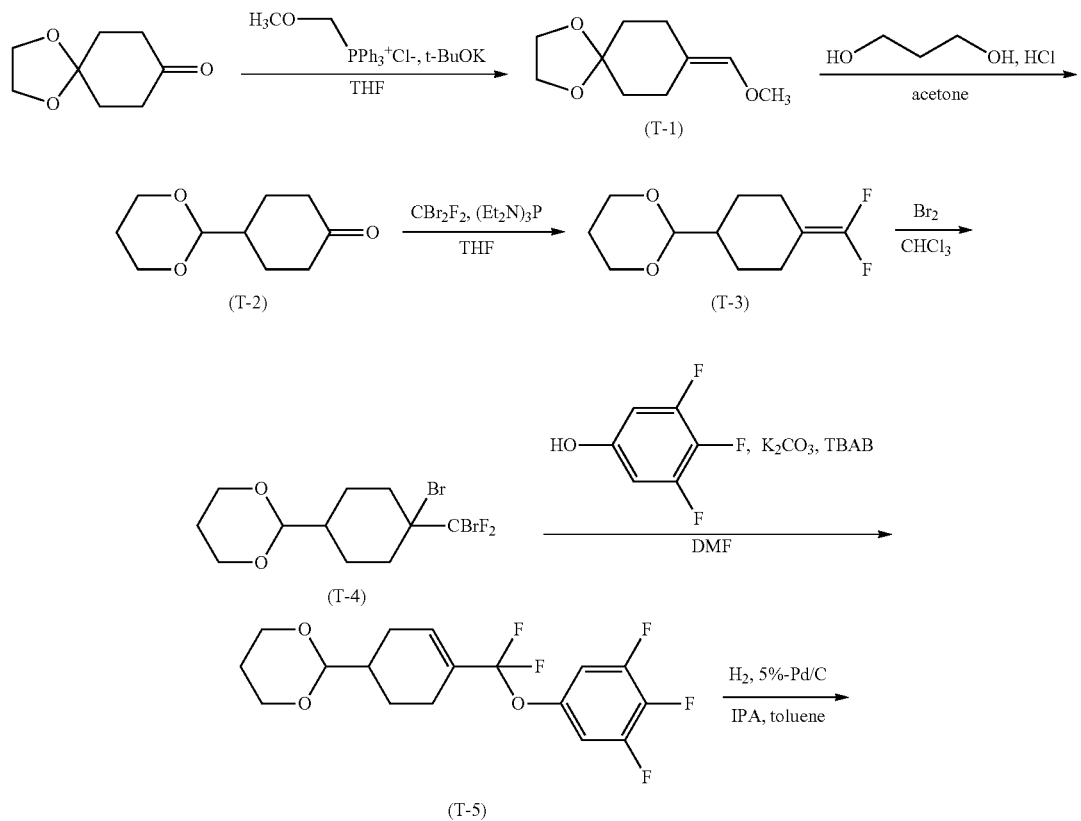

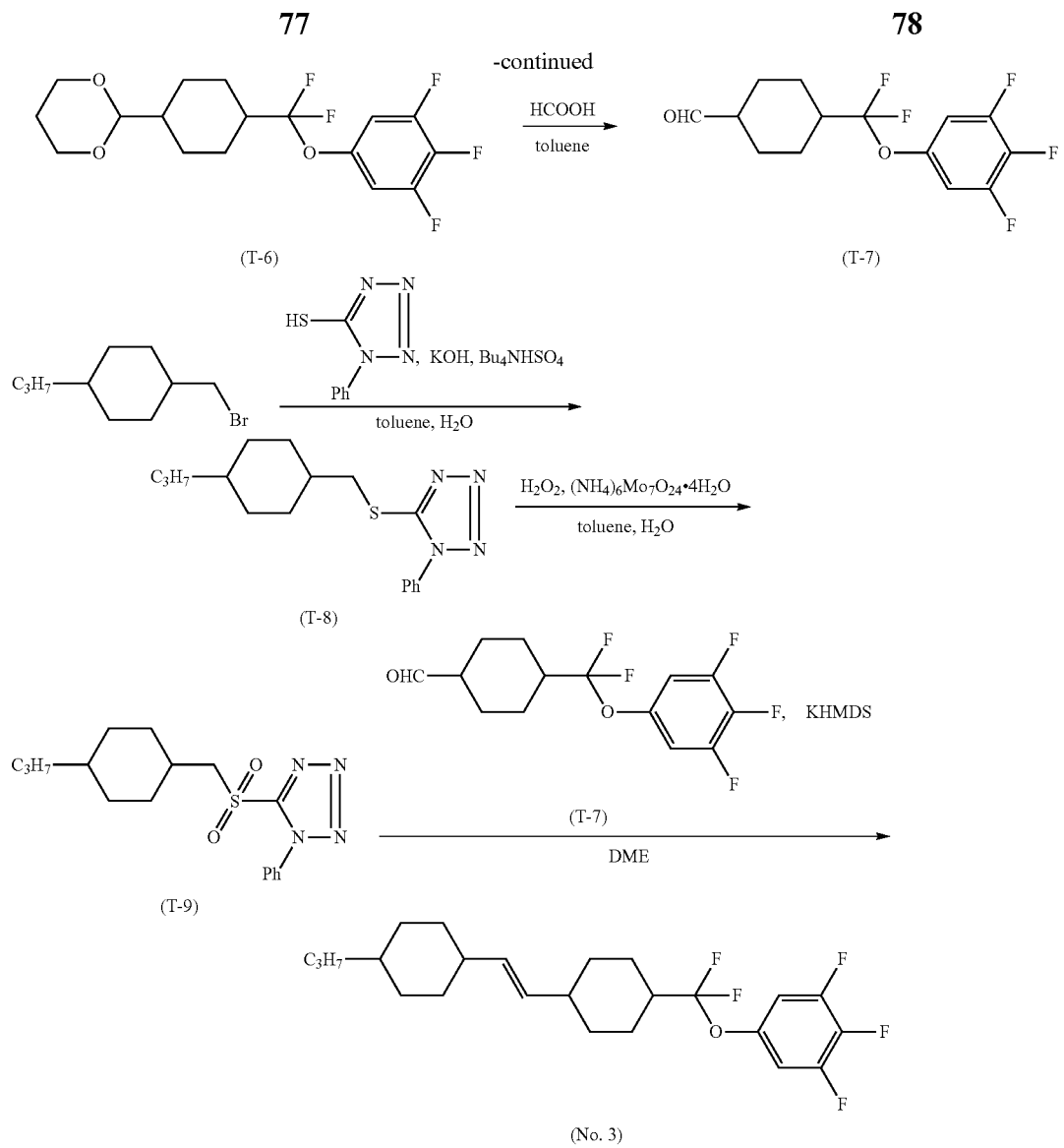

First Process

Under a nitrogen atmosphere, (methoxymethyl)triphenylphosphonium chloride (131.69 g, 381.17 mmol) and THF (1000 ml) were placed in a reactor and cooled to −30° C. Potassium tert-butoxide (43.11 g, 381.17 mmol) was added thereto, and the resultant was stirred for 1 hour while the temperature was maintained at −30° C. Next, a THF (250 ml) solution of 1,4-cyclohexanedione monoethylene ketal (50.00 g, 320.15 mmol) was slowly dripped in, and after the dripping, the resultant was heated to room temperature. The reaction mixture was poured into water, and the water layer was extracted with toluene. The combined organic layer was washed with saturated saline solution and water in order, and was dried with anhydrous magnesium sulfate. This solution was concentrated under reduced pressure, and the residue was purified by silica gel column chromatography (toluene/ethyl acetate=9/1 (volume ratio)), so as to obtain a compound (T-1) (54.73 g, yield=92.8%).

Second Process

Under a nitrogen atmosphere, the compound (T-1) (54.73 g, 297.09 mmol), 1,3-propanediol (24.87 g, 326.80 mmol), 6N hydrochloric acid (75 ml) and acetone (150 ml) were placed in a reactor and stirred at room temperature for 24 hours. The reaction mixture was poured into water and neutralized with sodium hydrogen carbonate. The water layer was extracted with toluene, and the combined organic layer was washed with water and dried with anhydrous magnesium sulfate. This solution was concentrated under reduced pressure, and the residue was purified by silica gel column chromatography (toluene/ethyl acetate=7/3 (volume ratio)), so as to obtain a compound (T-2) (39.74 g, yield=72.6%).

Third Process

Under a nitrogen atmosphere, dibromodifluoromethane (67.89 g, 323.58 mmol) and THF (100 ml) were placed in a reactor and cooled to 0° C. A THF (300 ml) solution of tris(diethylamino)phosphine (165.42 g, 668.74 mmol) was slowly dripped therein, and after the dripping, the resultant was stirred for 1 hour while the temperature was maintained at 0° C. Next, a THF (150 ml) solution of the compound (T-2) (39.74 g, 215.72 mmol) was slowly dripped in. After the dripping, the resultant was heated to room temperature, and was further stirred at room temperature for 12 hours. The reaction mixture was poured into water, and the water layer was extracted with ethyl acetate. The combined organic layer was washed with water and dried with anhydrous magnesium sulfate. This solution was concentrated under reduced pressure, and the residue was purified by silica gel column chromatography (toluene/ethyl acetate=19/1 (volume ratio)), so as to obtain a compound (T-3) (35.73 g, yield=75.9%).

Fourth Process

Under a nitrogen atmosphere, the compound (T-3) (35.73 g, 163.72 mmol) and chloroform (700 ml) were placed in a reactor and cooled to −60° C. A chloroform (300 ml) solution of bromine (28.78 g, 180.09 mmol) was slowly dripped therein, and after the dripping, the resultant was stirred for 3 hours while the temperature was maintained at −60° C. The reaction mixture was poured into saturated sodium thiosulfate aqueous solution, and the water layer was extracted with toluene. The combined organic layer was washed with saturated sodium thiosulfate aqueous solution and water in order, and was dried with anhydrous magnesium sulfate. This solution was concentrated under reduced pressure, and the residue was purified by silica gel column chromatography (toluene/ethyl acetate=9/1 (volume ratio)), so as to obtain a compound (T-4) (58.28 g, yield=94.2%).

Fifth Process

Under a nitrogen atmosphere, 3,4,5-trifluorophenol (34.24 g, 231.24 mmol), potassium carbonate (63.92 g, 462.48 mmol), TBAB (2.48 g, 7.71 mmol) and DMF (250 ml) were placed in a reactor, heated to 70° C. and stirred for 1 hour. A DMF (120 ml) solution of the compound (T-4) (58.28 g, 154.16 mmol) was slowly dripped therein, and after the dripping, the resultant was stirred for 10 hours while the temperature was maintained at 70° C. The reaction mixture was poured into water, and the water layer was extracted with toluene. The combined organic layer was washed with water and dried with anhydrous magnesium sulfate. This solution was concentrated under reduced pressure, and the residue was purified by silica gel column chromatography (toluene/ethyl acetate=19/1 (volume ratio)). The resultant was further purified by recrystallization from IPA so as to obtain a compound (T-5) (22.58 g, yield=40.2%).

Sixth Process

The compound (T-5) (22.58 g, 61.98 mmol), 5% palladium on carbon (2.26 g), IPA (100 ml), and toluene (100 ml) were placed in an autoclave, heated to 40° C. under pressurized hydrogen and stirred for 4 days. The 5% palladium on carbon was removed, the filtrate was concentrated, and the residue was purified by silica gel column chromatography (toluene/ethyl acetate=19/1 (volume ratio)). The resultant was further purified by recrystallization from IPA so as to obtain a compound (T-6) (8.70 g, yield=38.3%).

Seventh Process

Under a nitrogen atmosphere, the compound (T-6) (8.70 g, 23.75 mmol), formic acid (45 ml), and toluene (85 ml) were placed in a reactor and stirred under reflux for 3 hours. The organic layer was separated, washed with water, saturated sodium hydrogen carbonate aqueous solution and water in order, and dried with anhydrous magnesium sulfate. This solution was concentrated under reduced pressure, and the residue was purified by silica gel column chromatography (toluene), so as to obtain a compound (T-7) (7.20 g, yield=98.3%).

Eighth Process

Under a nitrogen atmosphere, 1-(bromomethyl)-4-propylcyclohexane (20.00 g, 91.25 mmol), mercaptophenyltetrazole (17.89 g, 100.39 mmol), tetrabutylammonium hydrogen sulfate (1.55 g, 4.57 mmol), and toluene (200 ml) were placed in a reactor and stirred at room temperature. An aqueous (120 ml) solution of potassium hydroxide (6.14 g, 109.43 mmol) was slowly dripped therein, and after the dripping, the resultant was stirred at 70° C. for 6 hours. The reaction mixture was extracted with toluene, and the combined organic layer was washed with water and dried with anhydrous magnesium sulfate. This solution was concentrated under reduced pressure, and a compound (T-8) (27.43 g, yield=95.0%) was obtained.

Ninth Process

Under a nitrogen atmosphere, the compound (T-8) (27.43 g, 86.67 mmol) and SOLMIX A-11 (250 ml) were placed in a reactor and cooled to 0° C. A 35% hydrogen peroxide aqueous (84.22 g, 866.72 mmol) solution of hexaammonium heptamolybdate tetrahydrate (10.71 g, 8.67 mmol) was slowly dripped therein. After the dripping, the resultant was heated to room temperature, and was further stirred at room temperature for 12 hours. The resultant was then heated to 50° C. and stirred for 12 hours. The reaction mixture was extracted with toluene, and the combined organic layer was washed with saturated sodium thiosulfate aqueous solution and water in order and dried with anhydrous magnesium sulfate. This solution was concentrated under reduced pressure, and the residue was purified by silica gel chromatography (toluene). The resultant was further purified by recrystallization from a mixed solvent of ethanol/toluene=1/1 (volume ratio), so as to obtain a compound (T-9) (24.07 g, yield=79.7%).

Tenth Process

Under a nitrogen atmosphere, the compound (T-7) (3.00 g, 9.73 mmol), the compound (T-9) (4.41 g, 12.65 mmol), and DME (50 ml) were placed in a reactor and cooled to −70° C. KHMDS (1.00 M; THF solution; 14.60 ml) was slowly dripped therein, and after the dripping, the resultant was heated to room temperature. The resultant was then stirred under reflux for 7 hours. The reaction mixture was extracted with toluene, and the combined organic layer was washed with saturated saline solution and dried with anhydrous magnesium sulfate. This solution was concentrated under reduced pressure, and the residue was purified by silica gel chromatography (heptane). The resultant was further purified by recrystallization from ethanol so as to obtain a compound (No. 3) (2.18 g, yield=52.0%).

$^1$H-NMR (ppm; CDCl$_3$): δ6.83 (dd, J=8.1 Hz, J=6.0 Hz, 2H), 5.35 (dd, J=15.6 Hz, J=6.1 Hz, 1H), 5.29 (dd, J=15.7 Hz, J=5.9 Hz, 1H), 2.02-1.94 (m, 3H), 1.92-1.78 (m, 4H), 1.75-1.69 (m, 4H), 1.38 (dddd, J=13.0 Hz, J=13.0 Hz, J=13.0 Hz, J=3.3 Hz, 2H), 1.31 (sex, J=7.2 Hz, 2H), 1.17-1.13 (m, 3H), 1.12 (dddd, J=11.8 Hz, J=11.8 Hz, J=11.8 Hz, J=2.9 Hz, 2H), 1.04 (dddd, J=12.7 Hz, J=12.7 Hz, J=12.7 Hz, J=3.0 Hz, 2H), 0.89 (dddd, J=12.5 Hz, J=12.5 Hz, J=12.5 Hz, J=2.6 Hz, 2H), 0.87 (t, J=7.5 Hz, 3H).

Transition temperature: C 32.0 N 106.7 I.

Maximum temperature ($T_{NI}$)=85.7° C.; dielectric anisotropy (Δε)=12.2; optical anisotropy (Δn)=0.077; and viscosity (η)=18.0 mPa·s.

Synthesis Example 2

Synthesis of Compound (No. 5)

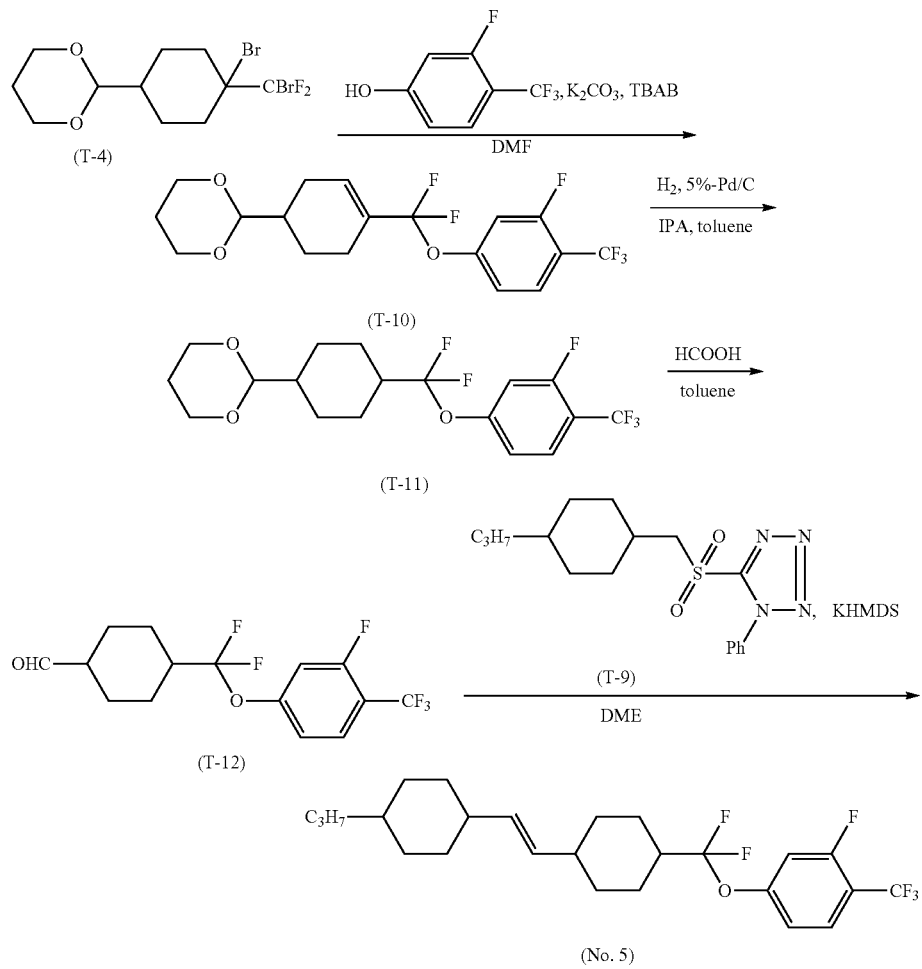

First Process

Under a nitrogen atmosphere, 3-fluoro-4-(trifluoromethyl)phenol (100.00 g, 555.25 mmol), potassium carbonate (215.00 g, 1555.65 mmol), TBAB (4.86 g, 15.08 mmol) and DMF (650 ml) were placed in a reactor, heated to 70° C. and stirred for 1 hour. A DMF (380 ml) solution of the compound (T-4) (190.00 g, 502.58 mmol) was slowly dripped therein, and after the dripping, the resultant was stirred for 10 hours while the temperature was maintained at 70° C. The reaction mixture was poured into water, and the water layer was extracted with toluene. The combined organic layer was washed with water and dried with anhydrous magnesium sulfate. This solution was concentrated under reduced pressure, and the residue was purified by silica gel column chromatography (toluene/ethyl acetate=19/1 (volume ratio)). The resultant was further purified by recrystallization from IPA so as to obtain a compound (T-10) (82.00 g, yield=41.2%).

Second Process

The compound (T-10) (82.00 g, 206.90 mmol), 5% palladium on carbon (8.20 g), IPA (400 ml), and toluene (400 ml) were placed in an autoclave, heated to 40° C. under pressurized hydrogen and stirred for 4 days. The 5% palladium on carbon was removed, the filtrate was concentrated, and the residue was purified by silica gel column chromatography (toluene/ethyl acetate=19/1 (volume ratio)). The resultant was further purified by recrystallization from IPA so as to obtain a compound (T-11) (23.70 g, yield=28.8%).

Third Process

Under a nitrogen atmosphere, the compound (T-11) (23.70 g, 59.50 mmol), formic acid (130 ml), and toluene (250 ml) were placed in a reactor and stirred under reflux for 3 hours. The organic layer was separated, washed with water, saturated sodium hydrogen carbonate aqueous solution and water in order, and dried with anhydrous magnesium sulfate. This solution was concentrated under reduced pressure, and the residue was purified by silica gel column chromatography (toluene), so as to obtain a compound (T-12) (17.60 g, yield=87.0%).

Fourth Process

Under a nitrogen atmosphere, the compound (T-12) (3.00 g, 8.82 mmol), the compound (T-9) (3.99 g, 11.46 mmol), and DME (50 ml) were placed in a reactor and cooled to −70° C. KHMDS (1.00 M; THF solution; 13.23 ml) was slowly dripped therein, and after the dripping, the resultant was heated to room temperature. The resultant was then stirred under reflux for 7 hours. The reaction mixture was extracted with toluene, and the combined organic layer was washed with saturated saline solution and dried with anhydrous magnesium sulfate. This solution was concentrated under reduced pressure, and the residue was purified by silica gel chromatography (heptane). The resultant was further purified by recrystallization from ethanol so as to obtain a compound (No. 5) (2.07 g, yield=50.8%).

$^1$H-NMR (ppm; CDCl$_3$): δ7.56 (dd, J=8.3 Hz, J=8.3 Hz, 1H), 7.06-7.04 (m, 2H), 5.35 (dd, J=15.6 Hz, J=6.2 Hz, 1H), 5.29 (dd, J=15.6 Hz, J=5.8 Hz, 1H), 2.04-2.02 (m, 3H), 1.93-1.84 (m, 4H), 1.75-1.69 (m, 4H), 1.40 (dddd, J=13.1 Hz, J=13.1 Hz, J=13.1 Hz, J=2.5 Hz, 2H), 1.31 (sex, J=7.4 Hz, 2H), 1.16-1.00 (m, 7H), 0.93-0.86 (m, 5H).

Transition temperature: C 71.6 N 119.1 I.

Maximum temperature (T$_{NI}$)=91.0° C.; dielectric anisotropy (Δε)=15.5; optical anisotropy (Δn)=0.084; and viscosity (η)=34.6 mPa·s.

Synthesis Example 3

Synthesis of Compound (No. 23)

water and dried with anhydrous magnesium sulfate. This solution was concentrated under reduced pressure, and a compound (T-13) (117.46 g, yield=92.0%) was obtained.

Second Process

Under a nitrogen atmosphere, the compound (T-13) (117.46 g, 294.67 mmol) and SOLMIX A-11 (1000 ml) were placed in a reactor and cooled to 0° C. A 35% hydrogen peroxide aqueous (286.34 g, 2946.75 mmol) solution of hexaammonium heptamolybdate tetrahydrate (36.78 g, 29.46 mmol) was slowly dripped therein. After the dripping, the resultant was heated to room temperature, and was further stirred at room temperature for 12 hours. The resultant was then heated to 50° C. and stirred for 12 hours. The reaction mixture was extracted with toluene, and the combined organic layer was washed with saturated sodium thiosulfate aqueous solution and water in order and dried with anhydrous magnesium sulfate. This solution was concentrated under reduced pressure, and the residue was purified by silica gel chromatography (toluene). The resultant

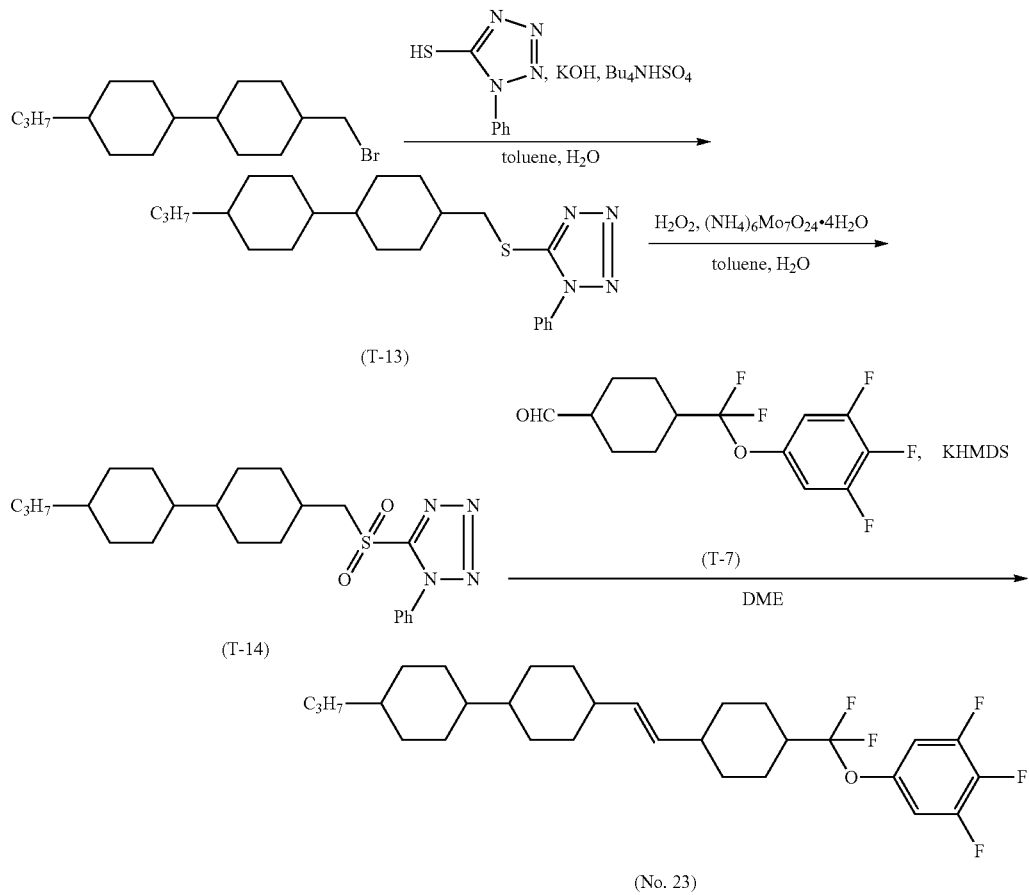

First Process

Under a nitrogen atmosphere, 4-(bromomethyl)-4'-propyl-1,1'-bi(cyclohexane) (96.56 g, 320.47 mmol), mercaptophenyltetrazole (62.82 g, 352.51 mmol), tetrabutylammonium hydrogen sulfate (5.44 g, 16.02 mmol), and toluene (1000 ml) were placed in a reactor and stirred at room temperature. An aqueous (500 ml) solution of potassium hydroxide (25.39 g, 384.63 mmol) was slowly dripped therein, and after the dripping, the resultant was stirred at 70° C. for 6 hours. The reaction mixture was extracted with toluene, and the combined organic layer was washed with was further purified by recrystallization from a mixed solvent of ethanol/toluene=1/1 (volume ratio), so as to obtain a compound (T-14) (103.93 g, yield=81.9%).

Third Process

Under a nitrogen atmosphere, the compound (T-7) (4.19 g, 13.59 mmol), the compound (T-14) (7.61 g, 17.67 mmol), and DME (50 ml) were placed in a reactor and cooled to −70° C. KHMDS (1.00 M; THF solution; 20.39 ml) was slowly dripped therein, and after the dripping, the resultant was heated to room temperature. The resultant was then stirred under reflux for 7 hours. The reaction mixture was extracted with toluene, and the combined organic layer was washed with saturated saline solution and dried with anhydrous magnesium sulfate. This solution was concentrated under reduced pressure, and the residue was purified by silica gel chromatography (heptane). The resultant was further purified by recrystallization from a mixed solvent of ethanol/heptane=3/2 (volume ratio), so as to obtain a compound (No. 23) (0.58 g, yield=8.3%).

$^1$H-NMR (ppm; CDCl$_3$): δ6.84 (dd, J=8.0 Hz, J=5.9 Hz, 2H), 5.34 (dd, J=15.6 Hz, J=6.1 Hz, 1H), 5.28 (dd, J=15.6 Hz, J=5.9 Hz, 1H), 1.99-1.68 (m, 15H), 1.38 (dddd, J=13.1 Hz, J=13.1 Hz, J=13.1 Hz, J=3.0 Hz, 2H), 1.30 (sex, J=7.1 Hz, 2H), 1.14-0.92 (m, 13H), 0.88-0.80 (m, 5H).

Transition temperature: C –10.3 C 49.4 S$_B$ 149.2 N 274.3

Maximum temperature (T$_{NI}$)=203.0° C.; dielectric anisotropy (Δε)=12.2; optical anisotropy (Δn)=0.104; and viscosity (η)=48.0 mPa·s.

Synthesis Example 4

Synthesis of Compound (No. 26)

First Process

Under a nitrogen atmosphere, 3,5-difluoro-4-(trifluoromethyl)phenol (60.00 g, 302.89 mmol), potassium carbonate (83.73 g, 605.82 mmol), TBAB (3.25 g, 10.08 mmol) and DMF (400 ml) were placed in a reactor, heated to 70° C. and stirred for 1 hour. A DMF (150 ml) solution of the compound (T-4) (76.34 g, 201.93 mmol) was slowly dripped therein, and after the dripping, the resultant was stirred for 10 hours while the temperature was maintained at 70° C. The reaction mixture was poured into water, and the water layer was extracted with toluene. The combined organic layer was washed with water and dried with anhydrous magnesium sulfate. This solution was concentrated under reduced pressure, and the residue was purified by silica gel column chromatography (toluene/ethyl acetate=19/1 (volume ratio)). The resultant was further purified by recrystallization from IPA so as to obtain a compound (T-15) (32.80 g, yield=39.2%).

Second Process

The compound (T-15) (32.80 g, 79.17 mmol), 5% palladium on carbon (3.28 g), IPA (160 ml), and toluene (160 ml)

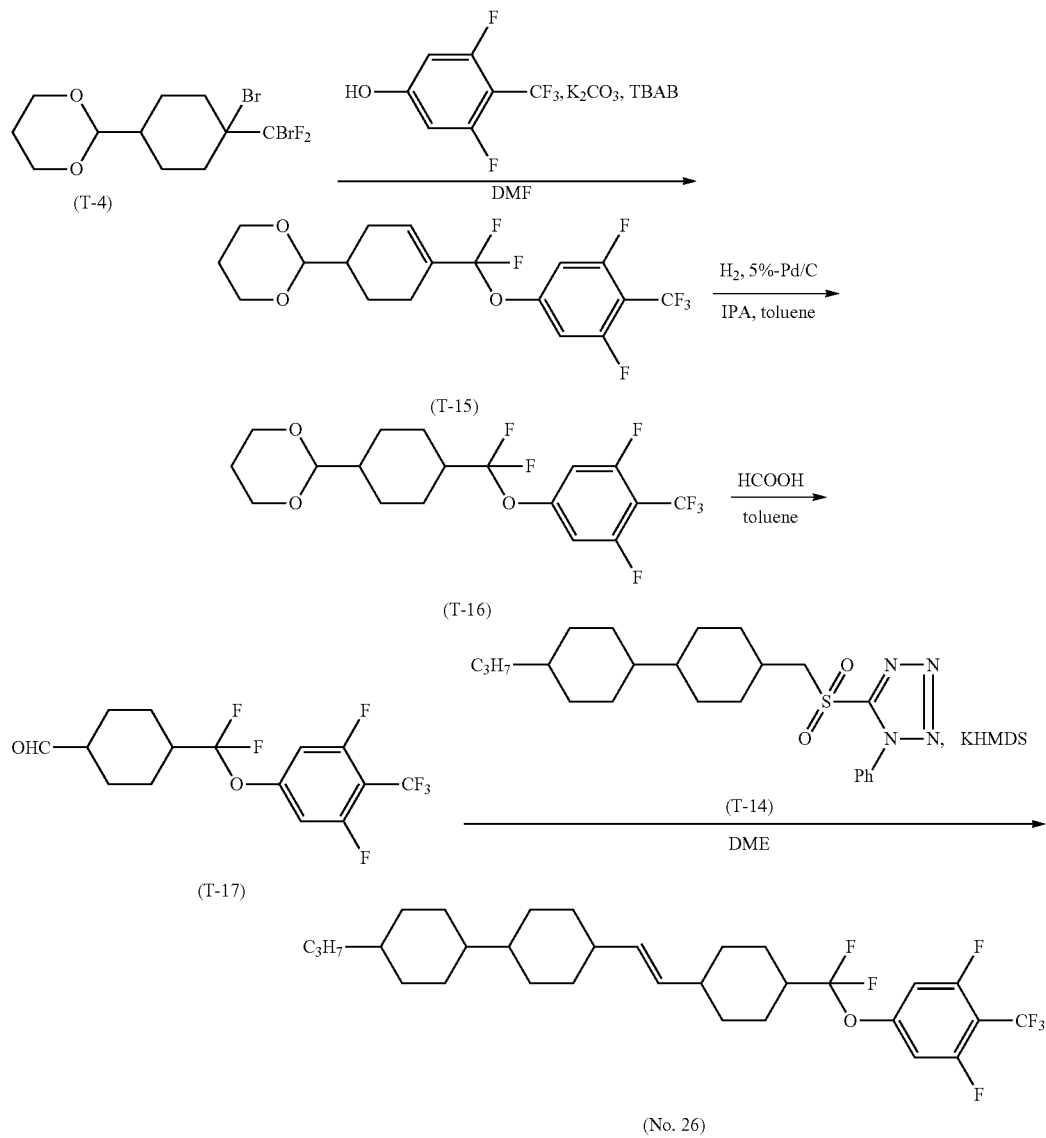

were placed in an autoclave, heated to 40° C. under pressurized hydrogen and stirred for 4 days. The 5% palladium on carbon was removed, the filtrate was concentrated, and the residue was purified by silica gel column chromatography (toluene/ethyl acetate=19/1 (volume ratio)). The resultant was further purified by recrystallization from IPA so as to obtain a compound (T-16) (11.63 g, yield=35.3%).

Third Process

Under a nitrogen atmosphere, the compound (T-16) (11.63 g, 27.93 mmol), formic acid (60 ml), and toluene (120 ml) were placed in a reactor and stirred under reflux for 3 hours. The organic layer was separated, washed with water, saturated sodium hydrogen carbonate aqueous solution and water in order, and dried with anhydrous magnesium sulfate. This solution was concentrated under reduced pressure, and the residue was purified by silica gel column chromatography (toluene), so as to obtain a compound (T-17) (9.65 g, yield=96.4%).

Fourth Process

Under a nitrogen atmosphere, the compound (T-17) (9.28 g, 25.90 mmol), the compound (T-14) (14.50 g, 33.67 mmol), and DME (100 ml) were placed in a reactor and cooled to −70° C. KHMDS (1.00 M; THF solution; 38.86 ml) was slowly dripped therein, and after the dripping, the resultant was heated to room temperature. The resultant was then stirred under reflux for 7 hours. The reaction mixture was extracted with toluene, and the combined organic layer was washed with saturated saline solution and dried with anhydrous magnesium sulfate. This solution was concentrated under reduced pressure, and the residue was purified by silica gel chromatography (heptane). The resultant was further purified by recrystallization from a mixed solvent of ethanol/heptane=2/1 (volume ratio), so as to obtain a compound (No. 26) (1.14 g, yield=7.8%).

$^1$H-NMR (ppm; CDCl$_3$): δ6.86 (d, J=10.3 Hz, 2H), 5.34 (dd, J=15.6 Hz, J=6.2 Hz, 1H), 5.28 (dd, J=15.7 Hz, J=6.0 Hz, 1H), 2.02-1.68 (m, 15H), 1.38 (dddd, J=12.9 Hz, J=12.9 Hz, J=12.9 Hz, J=2.8 Hz, 2H), 1.30 (sex, J=7.4 Hz, 2H), 1.14-0.92 (m, 13H), 0.88-0.80 (m, 5H).

Transition temperature: C 95.3 C 98.8 S$_B$ 142.0 N 263.4 I.

Maximum temperature (T$_{NI}$)=187.7° C.; dielectric anisotropy (Δε)=18.1; optical anisotropy (Δn)=0.097; and viscosity (η)=60.9 mPa·s.

Moreover, the measurement sample was prepared from 5 wt % of the compound (No. 26) and 95 wt % of the mother liquid crystal (A). This is because crystals were precipitated at the usual ratio (15 wt %:85 wt %).

Synthesis Example 5

Synthesis of Compound (No. 223)

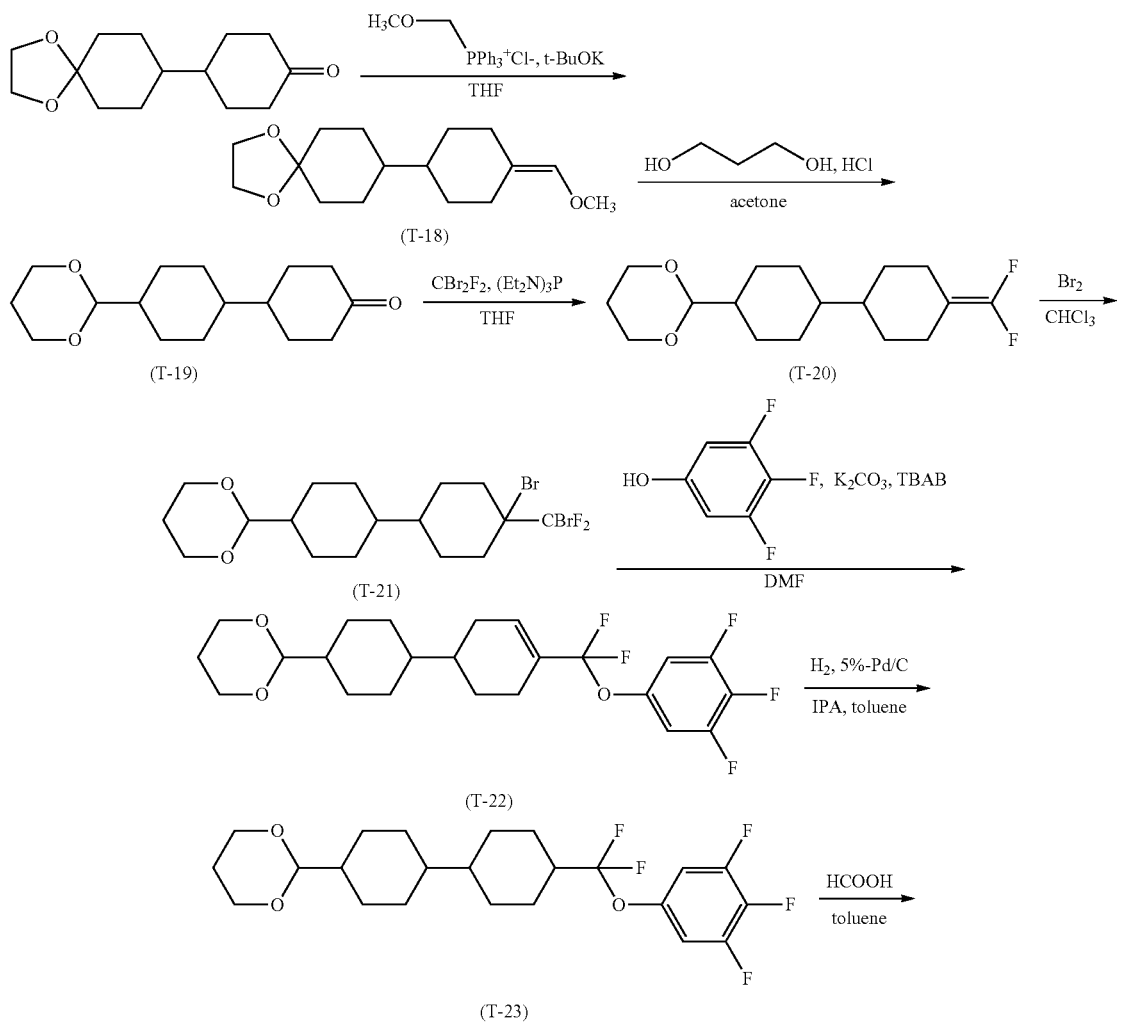

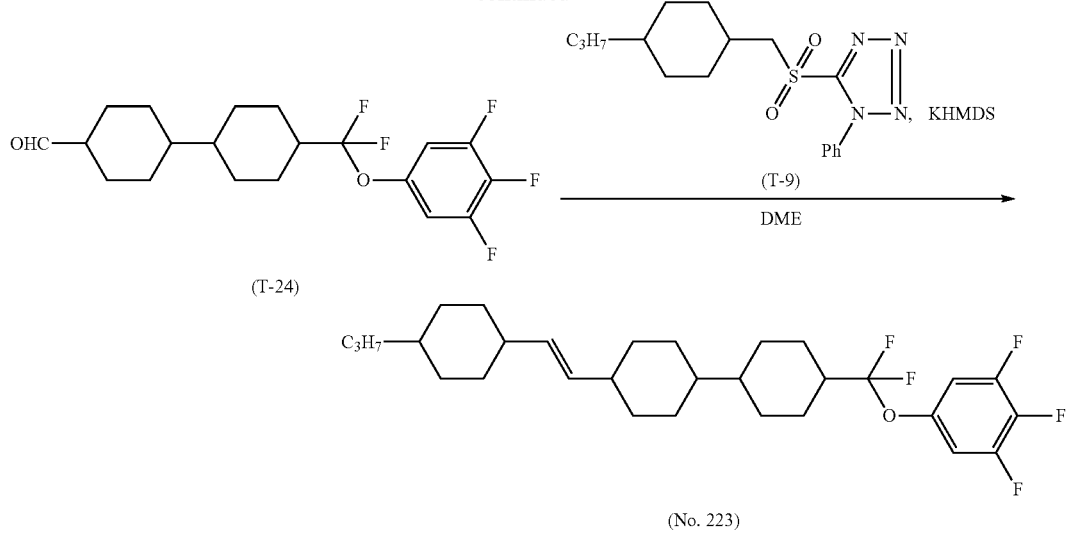

(No. 223)

First Process

Under a nitrogen atmosphere, (methoxymethyl)triphenylphosphonium chloride (86.30 g, 251.75 mmol) and THF (850 ml) were placed in a reactor and cooled to −30° C. Potassium tert-butoxide (28.25 g, 251.76 mmol) was added thereto, and the resultant was stirred for 1 hour while the temperature was maintained at −30° C. Next, a THF (250 ml) solution of bicyclohexane-4,4'-dione monoethylene ketal (50.00 g, 209.79 mmol) was slowly dripped in, and after the dripping, the resultant was heated to room temperature. The reaction mixture was poured into water, and the water layer was extracted with toluene. The combined organic layer was washed with saturated saline solution and water in order, and was dried with anhydrous magnesium sulfate. This solution was concentrated under reduced pressure, and the residue was purified by silica gel column chromatography (toluene/ethyl acetate=9/1 (volume ratio)), so as to obtain a compound (T-18) (49.23 g, yield=88.1%).

Second Process

Under a nitrogen atmosphere, the compound (T-18) (49.23 g, 184.81 mmol), 1,3-propanediol (15.47 g, 203.31 mmol), 6N hydrochloric acid (45 ml) and acetone (150 ml) were placed in a reactor and stirred at room temperature for 24 hours. The reaction mixture was poured into water and neutralized with sodium hydrogen carbonate. The water layer was extracted with toluene, and the combined organic layer was washed with water and dried with anhydrous magnesium sulfate. This solution was concentrated under reduced pressure, and the residue was purified by silica gel column chromatography (toluene/ethyl acetate=7/3 (volume ratio)), so as to obtain a compound (T-19) (38.69 g, yield=78.6%).

Third Process

Under a nitrogen atmosphere, dibromodifluoromethane (45.71 g, 217.85 mmol) and THF (70 ml) were placed in a reactor and cooled to 0° C. A THF (200 ml) solution of tris(diethylamino)phosphine (111.37 g, 450.23 mmol) was slowly dripped therein, and after the dripping, the resultant was stirred for 1 hour while the temperature was maintained at 0° C. Next, a THF (150 ml) solution of the compound (T-19) (38.69 g, 145.24 mmol) was slowly dripped in. After the dripping, the resultant was heated to room temperature, and was further stirred at room temperature for 12 hours. The reaction mixture was poured into water, and the water layer was extracted with ethyl acetate. The combined organic layer was washed with water and dried with anhydrous magnesium sulfate. This solution was concentrated under reduced pressure, and the residue was purified by silica gel column chromatography (toluene/ethyl acetate=19/1 (volume ratio)), so as to obtain a compound (T-20) (30.67 g, yield=70.3%).

Fourth Process

Under a nitrogen atmosphere, the compound (T-20) (30.67 g, 102.10 mmol) and chloroform (600 ml) were placed in a reactor and cooled to −60° C. A chloroform (180 ml) solution of bromine (17.95 g, 112.32 mmol) was slowly dripped therein, and after the dripping, the resultant was stirred for 3 hours while the temperature was maintained at −60° C. The reaction mixture was poured into saturated sodium thiosulfate aqueous solution, and the water layer was extracted with toluene. The combined organic layer was washed with saturated sodium thiosulfate aqueous solution and water in order, and was dried with anhydrous magnesium sulfate. This solution was concentrated under reduced pressure, and the residue was purified by silica gel column chromatography (toluene/ethyl acetate=9/1 (volume ratio)), so as to obtain a compound (T-21) (45.29 g, yield=96.4%).

Fifth Process

Under a nitrogen atmosphere, 3,4,5-trifluorophenol (21.86 g, 147.62 mmol), potassium carbonate (40.80 g, 295.20 mmol), TBAB (2.48 g, 7.71 mmol) and DMF (250 ml) were placed in a reactor, heated to 70° C. and stirred for 1 hour. A DMF (120 ml) solution of the compound (T-21) (45.29 g, 98.41 mmol) was slowly dripped therein, and after the dripping, the resultant was stirred for 10 hours while the temperature was maintained at 70° C. The reaction mixture was poured into water, and the water layer was extracted with toluene. The combined organic layer was washed with water and dried with anhydrous magnesium sulfate. This solution was concentrated under reduced pressure, and the residue was purified by silica gel column chromatography (toluene/ethyl acetate=19/1 (volume ratio)). The resultant was further purified by recrystallization from IPA so as to obtain a compound (T-22) (19.99 g, yield=45.5%).

Sixth Process

The compound (T-22) (19.99 g, 44.77 mmol), 5% palladium on carbon (2.00 g), IPA (100 ml), and toluene (100 ml) were placed in an autoclave, heated to 40° C. under pressurized hydrogen and stirred for 4 days. The 5% palladium on carbon was removed, the filtrate was concentrated, and the residue was purified by silica gel column chromatography (toluene/ethyl acetate=19/1 (volume ratio)). The resultant was further purified by recrystallization from IPA so as to obtain a compound (T-23) (6.20 g, yield=30.9%).

Seventh Process

Under a nitrogen atmosphere, the compound (T-23) (6.20 g, 13.82 mmol), formic acid (30 ml), and toluene (60 ml) were placed in a reactor and stirred under reflux for 3 hours. The organic layer was separated, washed with water, saturated sodium hydrogen carbonate aqueous solution and water in order, and dried with anhydrous magnesium sulfate. This solution was concentrated under reduced pressure, and the residue was purified by silica gel column chromatography (toluene), so as to obtain a compound (T-24) (4.86 g, yield=90.1%).

Eighth Process

Under a nitrogen atmosphere, the compound (T-24) (4.86 g, 12.45 mmol), the compound (T-9) (5.64 g, 16.19 mmol), and DME (50 ml) were placed in a reactor and cooled to −70° C. KHMDS (1.00 M; THF solution; 18.68 ml) was slowly dripped therein, and after the dripping, the resultant was heated to room temperature. The resultant was then stirred under reflux for 7 hours. The reaction mixture was extracted with toluene, and the combined organic layer was washed with saturated saline solution and dried with anhydrous magnesium sulfate. This solution was concentrated under reduced pressure, and the residue was purified by silica gel chromatography (heptane). The resultant was further purified by recrystallization from a mixed solvent of ethanol/heptane=3/2 (volume ratio), so as to obtain a compound (No. 223) (0.69 g, yield=10.8%).

$^1$H-NMR (ppm; CDCl$_3$): δ6.83 (dd, J=8.0 Hz, J=6.0 Hz, 2H), 5.33-5.26 (m, 2H), 2.02-1.68 (m, 15H), 1.36-1.27 (m, 4H), 1.16-0.98 (m, 13H), 0.88 (dddd, J=13.0 Hz, J=13.0 Hz, J=13.0 Hz, J=2.3 Hz, 2H), 0.87 (t, J=7.4 Hz, 3H).

Transition temperature: C 69.6 S$_B$ 127.8 N 254.7 I.

Maximum temperature (T$_{NI}$)=195.0° C.; dielectric anisotropy (Δε)=12.2; optical anisotropy (Δn)=0.104; and viscosity (η)=59.4 mPa·s.

Comparative Examples

The compound (1) was compared with similar compounds in view of physical properties. When a sample is a mixture of a compound and a mother liquid crystal, the ratio therebetween is determined by the method described in the paragraphs under the heading "Mother liquid crystal (A)" or "Mother liquid crystal (B)."

Comparative Example 1

Comparison of Physical Properties

The following compound (S-1) was selected as a comparative compound. This is because all the linking groups of this compound are single bonds, which is different from the compound of the invention. This compound was synthesized in accordance with the method described in JP H10-204016.

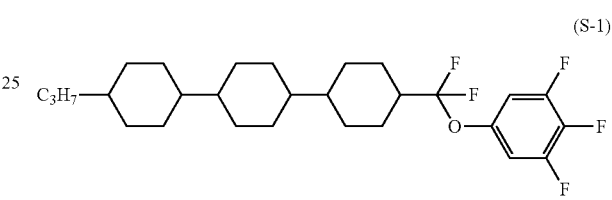

(S-1)

$^1$H-NMR (ppm; CDCl$_3$): δ6.86 (dd, J=8.0 Hz, J=6.0 Hz, 2H), 2.04-1.95 (m, 3H), 1.88-1.85 (m, 2H), 1.77-1.70 (m, 8H), 1.39-1.29 (m, 4H), 1.17-0.94 (m, 15H), 0.91-0.82 (m, 5H).

Transition temperature: C 83.9 S$_B$ 166.7 N 266.6 I.

Maximum temperature (T$_{NI}$)=197.7° C.; dielectric anisotropy (Δε)=14.1; optical anisotropy (Δn)=0.117; and viscosity (η)=52.9 mPa·s.

Moreover, the measurement sample was prepared from 5 wt % of the compound (S-1) and 95 wt % of the mother liquid crystal (A). This is because crystals were precipitated at the usual ratio (15 wt %:85 wt %).

TABLE 1

Physical Properties of Compound (No. 23) and Comparative compound (S-1)

Compound (No. 23)

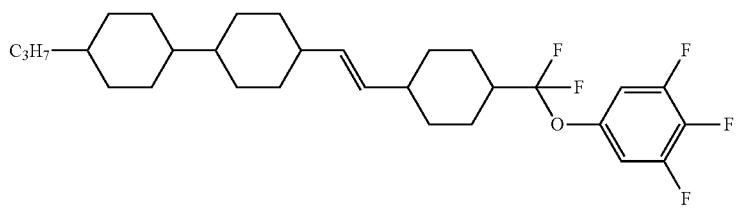

| | |
|---|---|
| Maximum temperature (T$_{NI}$) | 203.0° C. |
| Dielectric anisotropy (Δε) | 12.2 |
| Optical anisotropy (Δn) | 0.104 |
| Viscosity (η) | 48.0 mPa·s |

TABLE 1-continued

Physical Properties of Compound (No. 23) and Comparative compound (S-1)

Comparative compound (S-1)

![Structure of comparative compound S-1: C3H7-cyclohexyl-cyclohexyl-cyclohexyl-CF2-O-trifluorophenyl]

| Maximum temperature (T$_{NI}$) | 197.7° C. |
| Dielectric anisotropy (Δε) | 14.1 |
| Optical anisotropy (Δn) | 0.117 |
| Viscosity (η) | 52.9 mPa · s |

The physical properties of the compound (No. 23) obtained in Synthesis Example 3 and the comparative compound (S-1) are summarized in Table 1. From Table 1, it is known that the compound (No. 23) is excellent in terms of high maximum temperature and small viscosity.

Comparative Example 2

Comparison of Low-Temperature Compatibility

A composition (X-1) was prepared from 10 wt % of the compound (No. 23) and 90 wt % of the mother liquid crystal (A). 0.5 ml of the composition (X-1) and a glass capillary tube were placed in a 10 ml vial, and the vial was capped under a nitrogen gas stream. The cap portion was sealed using parafilm, and the resultant was then stored in a freezer at −20° C. Next, a composition (X-2) was prepared from 20 wt % of the compound (No. 23) and 80 wt % of the mother liquid crystal (B). By the same procedure, this composition was sealed in a vial and stored in a freezer at −20° C. 30 days later, upon observation of the two compositions, the nematic phase was maintained, while neither appearance of a smectic phase nor precipitation of crystals could be confirmed.

A composition (X-3) was prepared from 5 wt % of the comparative compound (S-1) and 95 wt % of the mother liquid crystal (A). A composition (X-4) was prepared from 5 wt % of the comparative compound (S-1) and 95 wt % of the mother liquid crystal (B). The compositions (X-3) and (X-4) were stored in a freezer at −20° C. by the same procedure as above, and 5 days later, precipitation of crystals was confirmed for the composition (X-3). In addition, 10 days later, precipitation of crystals was confirmed for the composition (X-4).

The above results are summarized in Table 2. A liquid crystal composition containing the compound (No. 23) of the invention is capable of maintaining the nematic phase even at low temperature. It can be concluded that the compound of the invention has excellent compatibility with other liquid crystal compounds and is therefore very useful.

TABLE 2

Comparison of Low-temperature Compatibility

| Sample for measurement | Components of sample | | Conditions (−20° C., 30 days) |
|---|---|---|---|
| Composition (X-1) | 10 wt % of compound (No. 23) | 90 wt % of mother liquid crystal (A) | Nematic phase was maintained |
| Composition (X-2) | 20 wt % of compound (No. 23) | 80 wt % of mother liquid crystal (B) | Nematic phase was maintained |
| Composition (X-3) | 5 wt % of comparative compound (S-1) | 95 wt % of mother liquid crystal (A) | 5 days later, crystals were precipitated |
| Composition (X-4) | 5 wt % of comparative compound (S-1) | 95 wt % of mother liquid crystal (B) | 10 days later, crystals were precipitated |

Examples of compounds synthesized in accordance with the above-described synthesis method of the compound (1) and the synthesis procedures described in Synthesis Examples 1 to 5 include the compounds (No. 1) to (No. 370) shown below.

| No. | |
|---|---|
| 1 | 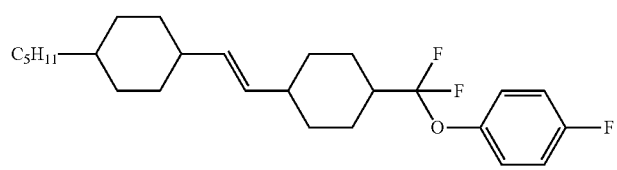 |

-continued
| No. | |
|---|---|
| 2 | 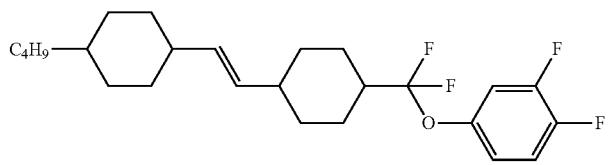 |
| 3 | 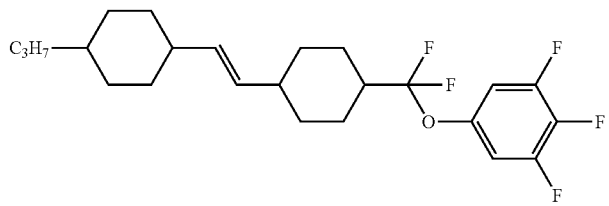 |
C 32.0 N 106.7 I
$T_{NI}$ = 85.7° C., Δε = 12.2 Δn = 0.077, η = 18.0 mPa · s
| | |
|---|---|
| 4 | 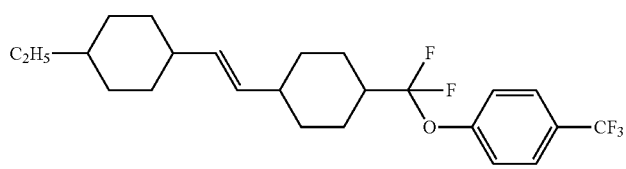 [SMILES: CCC1CCC(/C=C/C2CCC(C(F)(F)Oc3ccc(C(F)(F)F)cc3)CC2)CC1] |
| 5 | 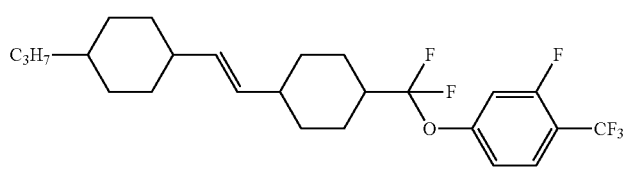 |
C 71.6 N 119.1 I
$T_{NI}$ = 91.0° C., Δε = 15.5 Δn = 0.084, η = 34.6 mPa · s
| | |
|---|---|
| 6 | 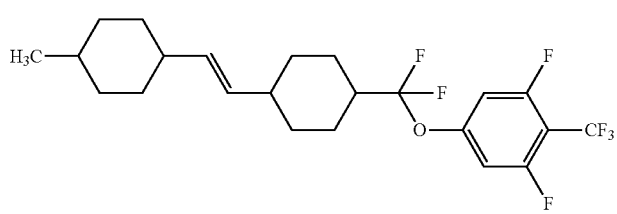 [SMILES: CC1CCC(/C=C/C2CCC(C(F)(F)Oc3cc(F)c(C(F)(F)F)c(F)c3)CC2)CC1] |
| 7 | 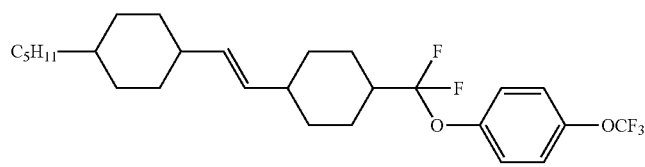 |
| 8 | 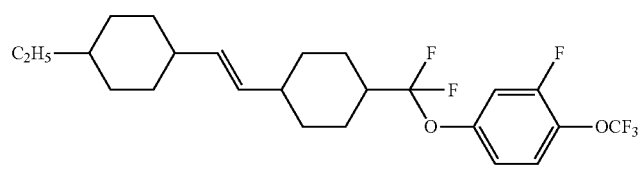 [SMILES: CCC1CCC(/C=C/C2CCC(C(F)(F)Oc3ccc(OC(F)(F)F)c(F)c3)CC2)CC1] |

-continued
| No. | |
|---|---|
| 9 | 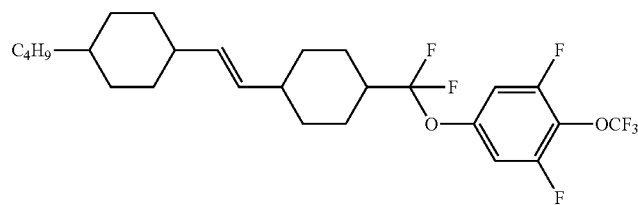 |
| 10 | 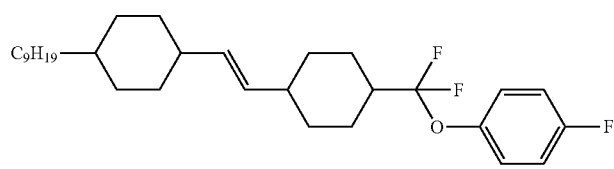 |
| 11 | 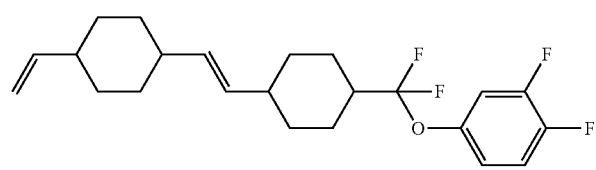 [SMILES: C=CC1CCC(/C=C/C2CCC(C(F)(F)Oc3ccc(F)c(F)c3)CC2)CC1] |
| 12 | 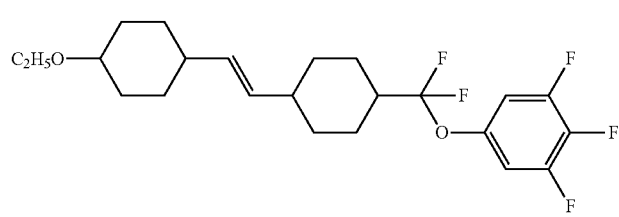 |
| 13 | 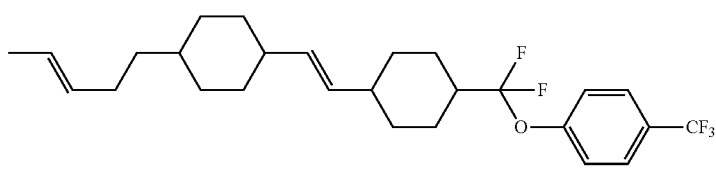 [SMILES: C/C=C/CCC1CCC(/C=C/C2CCC(C(F)(F)Oc3ccc(C(F)(F)F)cc3)CC2)CC1] |
| 14 | 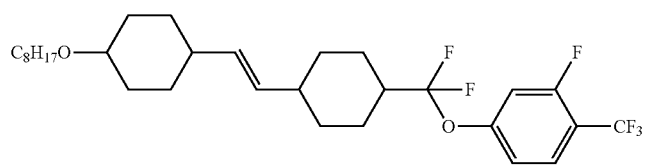 |
| 15 | 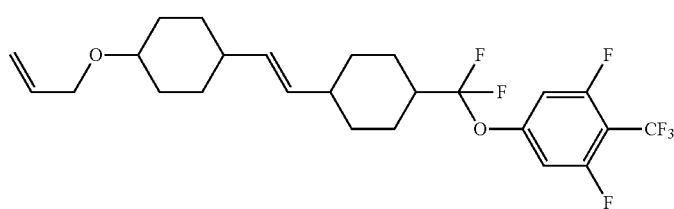 [SMILES: C=CCOC1CCC(/C=C/C2CCC(C(F)(F)Oc3cc(F)c(C(F)(F)F)c(F)c3)CC2)CC1] |
| 16 | 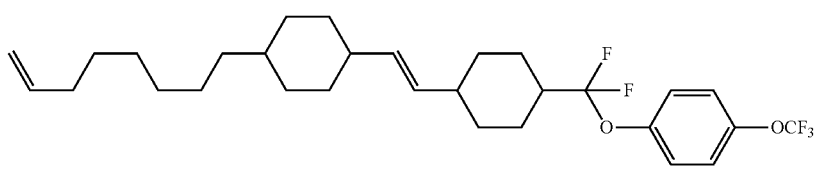 |

| No. | |
|---|---|
| 17 | 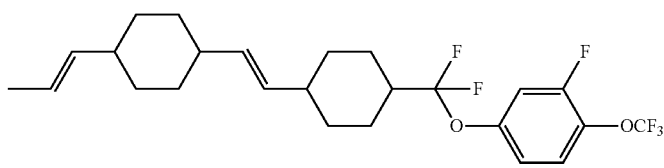 [SMILES: C/C=C/C1CCC(/C=C/C2CCC(C(F)(F)Oc3ccc(OC(F)(F)F)c(F)c3)CC2)CC1] |
| 18 | 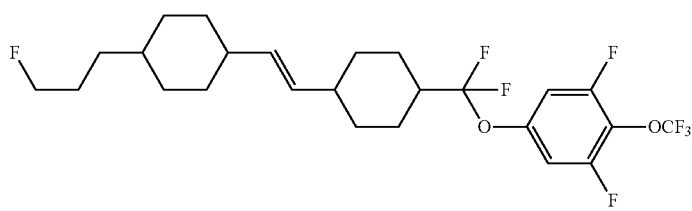 [SMILES: FCCCC1CCC(/C=C/C2CCC(C(F)(F)Oc3cc(F)c(OC(F)(F)F)c(F)c3)CC2)CC1] |
| 19 | 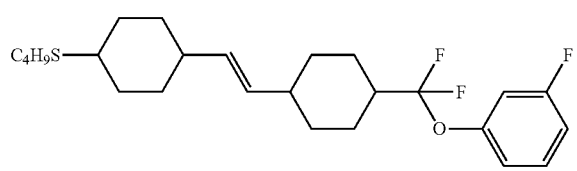 |
| 20 | 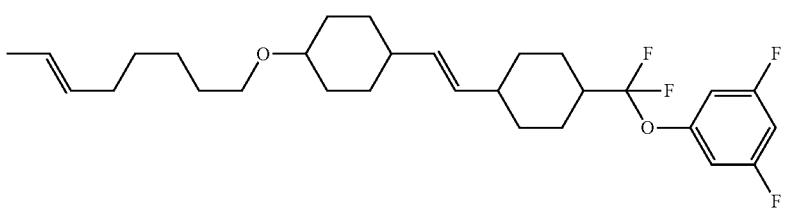 |
| 21 | 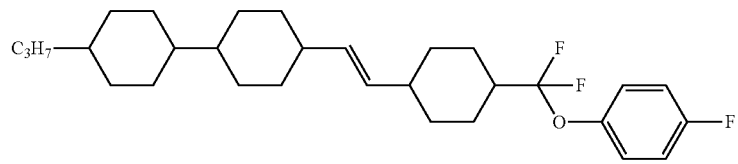 |
| 22 | 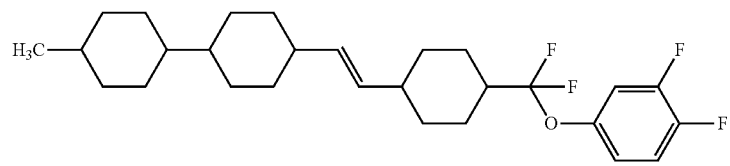 [SMILES: CC1CCC(C2CCC(/C=C/C3CCC(C(F)(F)Oc4ccc(F)c(F)c4)CC3)CC2)CC1] |
| 23 | 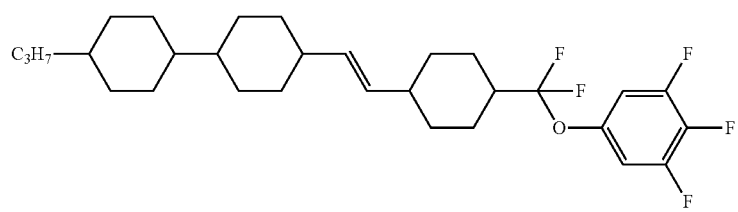 |
| | C −10.3 C 49.4 SB 149.2 N 274.3 I<br>$T_{NI}$ = 203.0° C., Δε = 12.2 Δn = 0.104, η = 48.0 mPa · s |
| 24 | 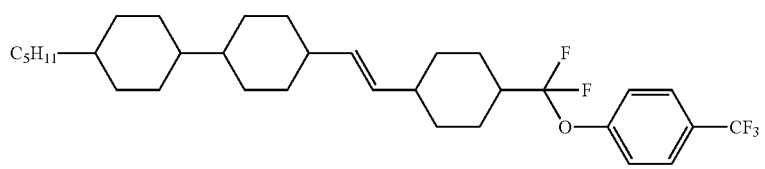 |

| No. | |
|---|---|
| 25 | 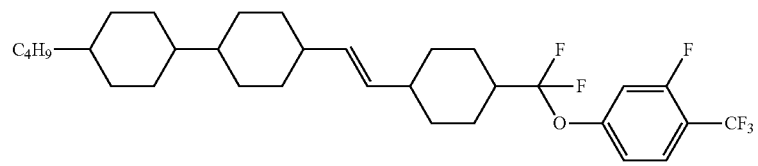 |
| 26 | 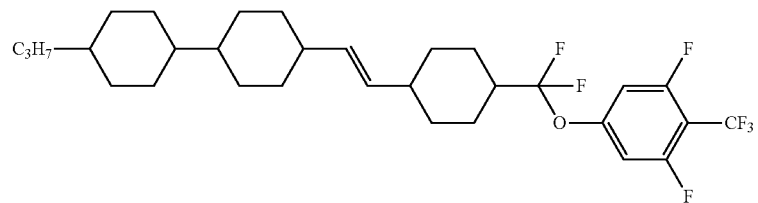
C 95.3 C 98.8 SB 142.0 N 263.4 I
$T_{NI} = 187.7°$ C., $\Delta\varepsilon = 18.1$ $\Delta n = 0.097$, $\eta = 60.9$ mPa · s |
| 27 | 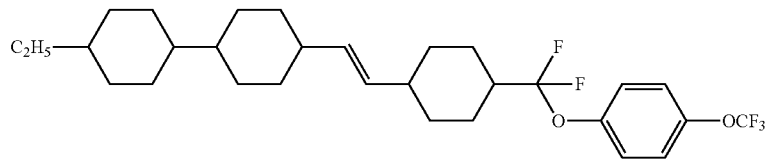 [SMILES: CCC1CCC(C2CCC(/C=C/C3CCC(C(F)(F)Oc4ccc(OC(F)(F)F)cc4)CC3)CC2)CC1] |
| 28 | 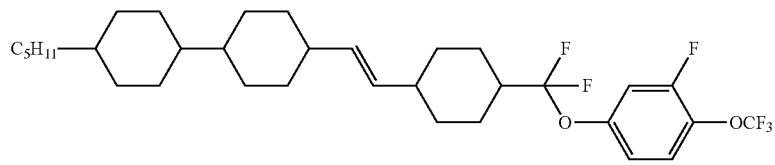 |
| 29 | 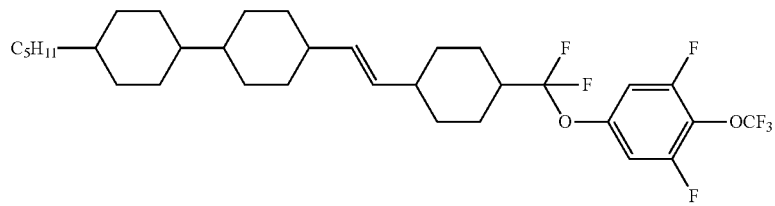 |
| 30 | 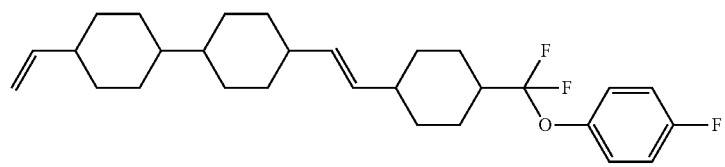 [SMILES: C=CC1CCC(C2CCC(/C=C/C3CCC(C(F)(F)Oc4ccc(F)cc4)CC3)CC2)CC1] |
| 31 | 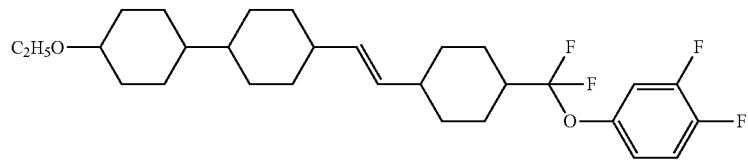 |
| 32 | 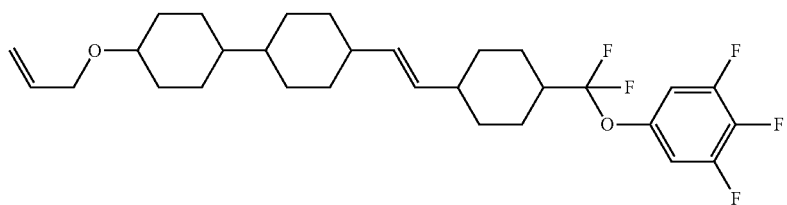 [SMILES: C=CCOC1CCC(C2CCC(/C=C/C3CCC(C(F)(F)Oc4cc(F)c(F)c(F)c4)CC3)CC2)CC1] |

| No. | |
|---|---|
| 33 | 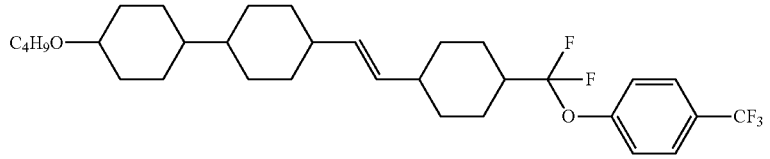 |
| 34 | 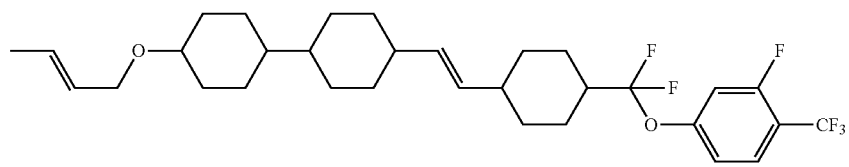 [SMILES: C/C=C/COC1CCC(C2CCC(/C=C/C3CCC(C(F)(F)Oc4ccc(C(F)(F)F)c(F)c4)CC3)CC2)CC1] |
| 35 | 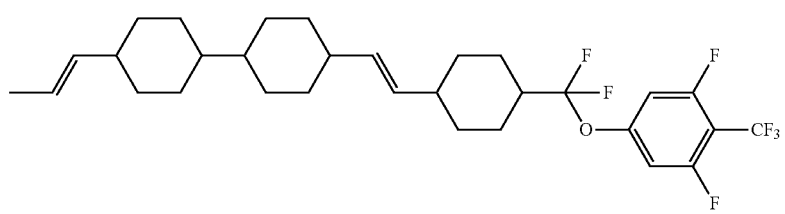 [SMILES: C/C=C/C1CCC(C2CCC(/C=C/C3CCC(C(F)(F)Oc4cc(F)c(C(F)(F)F)c(F)c4)CC3)CC2)CC1] |
| 36 | 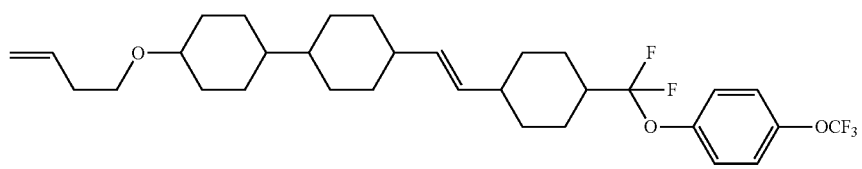 |
| 37 | 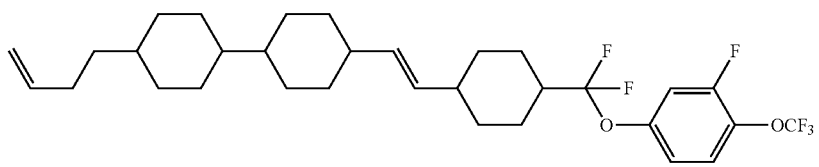 [SMILES: C=CCCC1CCC(C2CCC(/C=C/C3CCC(C(F)(F)Oc4ccc(OC(F)(F)F)c(F)c4)CC3)CC2)CC1] |
| 38 | 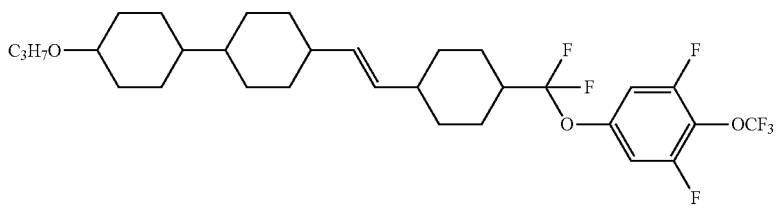 |
| 39 | 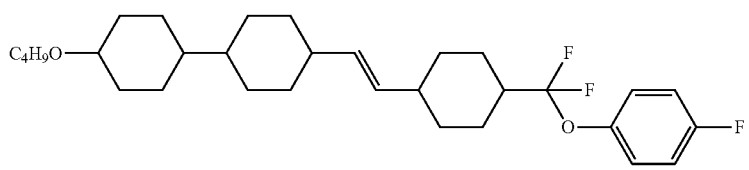 |
| 40 | 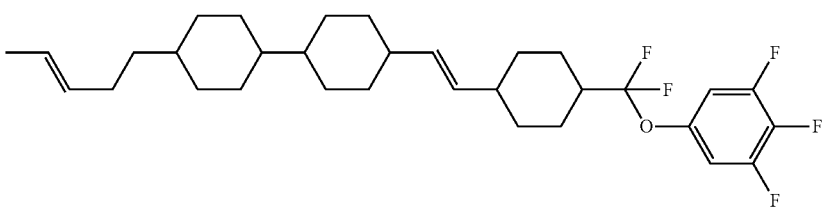 [SMILES: C/C=C/CCC1CCC(C2CCC(/C=C/C3CCC(C(F)(F)Oc4cc(F)c(F)c(F)c4)CC3)CC2)CC1] |

-continued
| No. | |
|---|---|
| 41 | 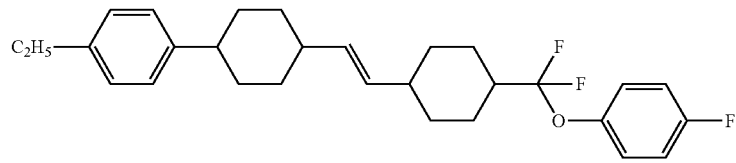 [SMILES: CCc1ccc(C2CCC(/C=C/C3CCC(C(F)(F)Oc4ccc(F)cc4)CC3)CC2)cc1] |
| 42 | 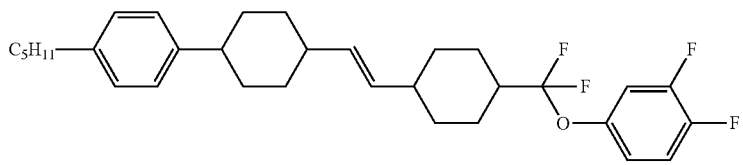 |
| 43 | 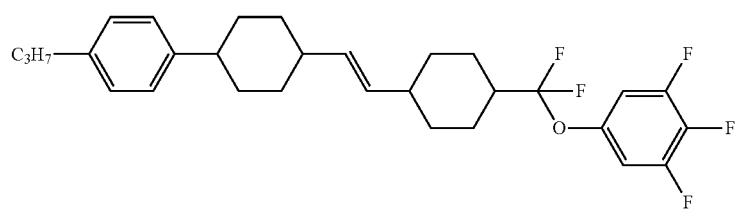 |
| 44 | 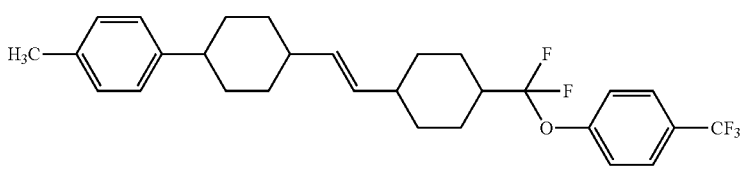 [SMILES: Cc1ccc(C2CCC(/C=C/C3CCC(C(F)(F)Oc4ccc(C(F)(F)F)cc4)CC3)CC2)cc1] |
| 45 | 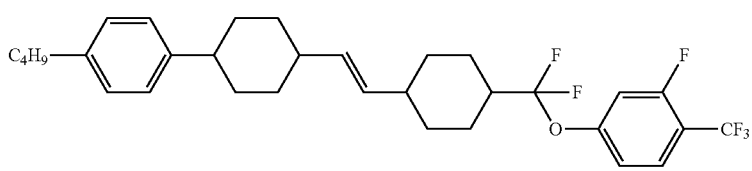 |
| 46 | 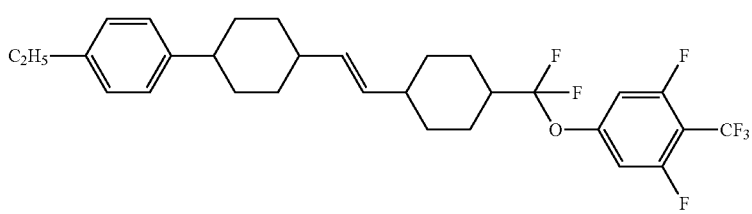 [SMILES: CCc1ccc(C2CCC(/C=C/C3CCC(C(F)(F)Oc4cc(F)c(C(F)(F)F)c(F)c4)CC3)CC2)cc1] |
| 47 | 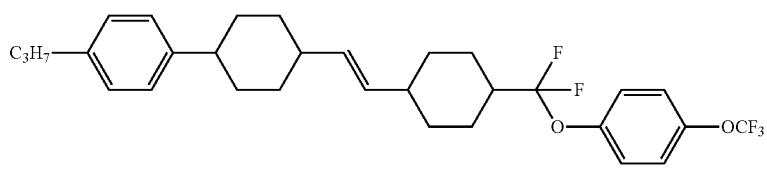 |
| 48 | 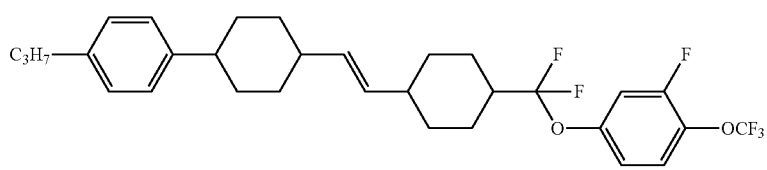 |

| No. | |
|---|---|
| 49 | 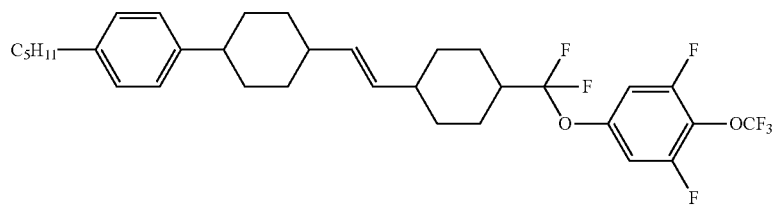 |
| 50 | 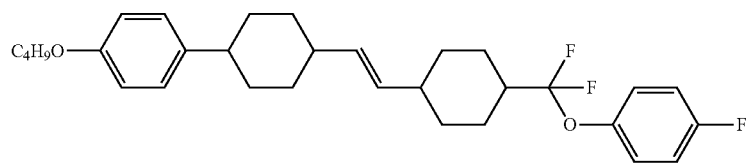 |
| 51 | 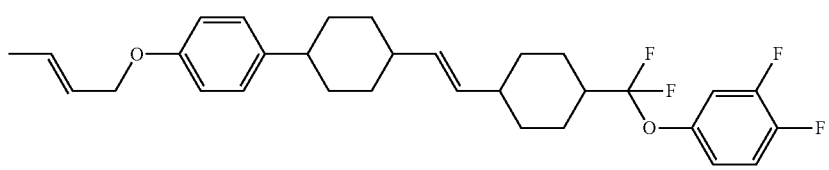 [SMILES: C/C=C/COc1ccc(C2CCC(/C=C/C3CCC(C(F)(F)Oc4ccc(F)c(F)c4)CC3)CC2)cc1] |
| 52 | 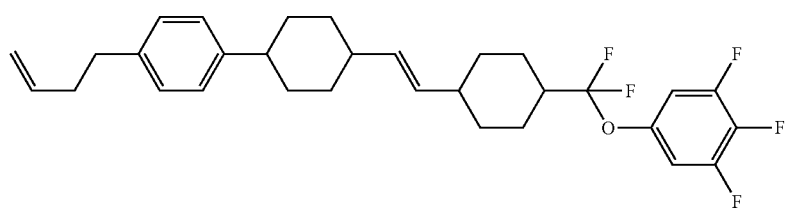 [SMILES: C=CCCc1ccc(C2CCC(/C=C/C3CCC(C(F)(F)Oc4cc(F)c(F)c(F)c4)CC3)CC2)cc1] |
| 53 | 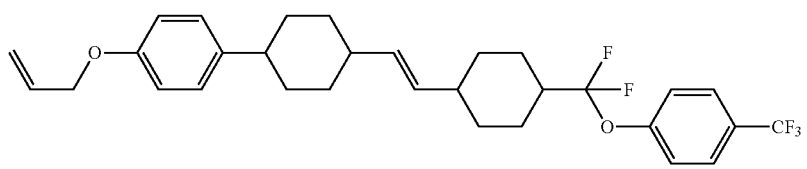 |
| 54 | 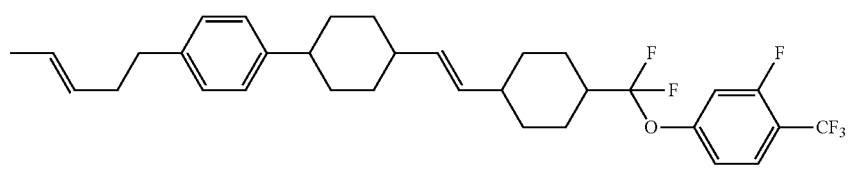 |
| 55 | 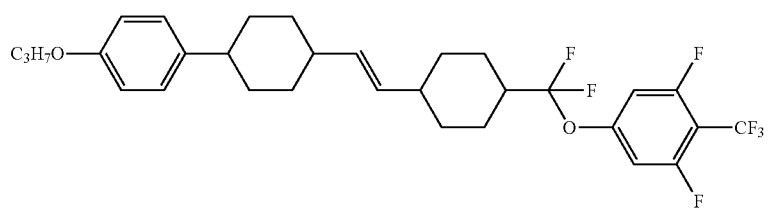 |
| 56 | 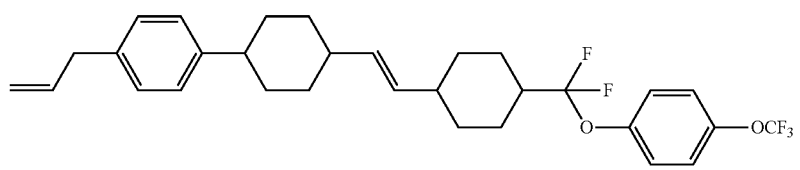 [SMILES: C=CCc1ccc(C2CCC(/C=C/C3CCC(C(F)(F)Oc4ccc(OC(F)(F)F)cc4)CC3)CC2)cc1] |

-continued
| No. | |
|---|---|
| 57 | 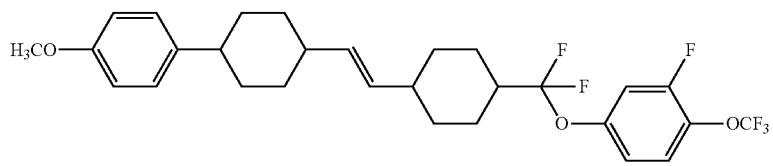 [SMILES: COc1ccc(C2CCC(/C=C/C3CCC(C(F)(F)Oc4ccc(OC(F)(F)F)c(F)c4)CC3)CC2)cc1] |
| 58 | 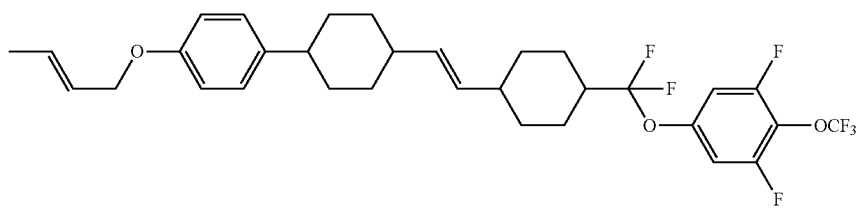 [SMILES: C/C=C/COc1ccc(C2CCC(/C=C/C3CCC(C(F)(F)Oc4cc(F)c(OC(F)(F)F)c(F)c4)CC3)CC2)cc1] |
| 59 | 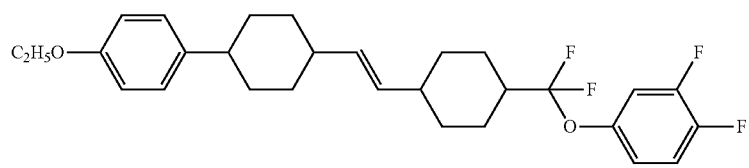 |
| 60 | 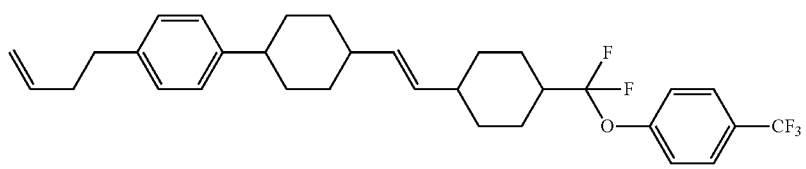 |
| 61 | 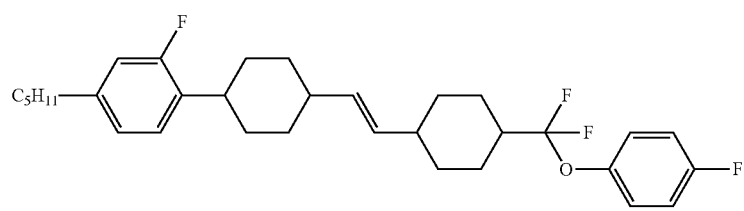 |
| 62 | 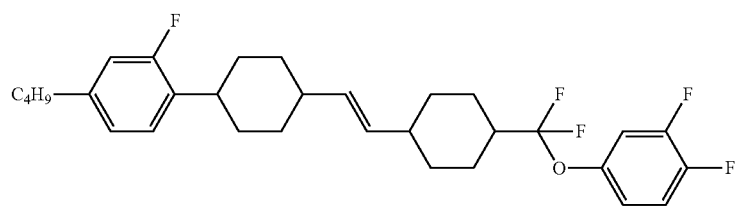 |
| 63 | 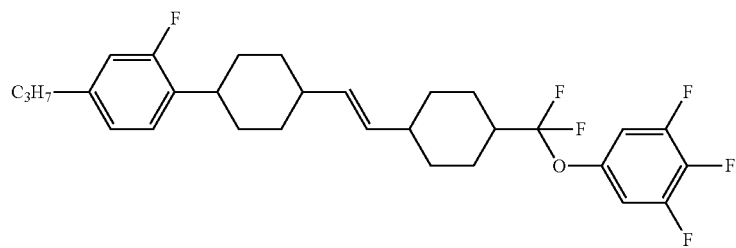 |
| 64 | 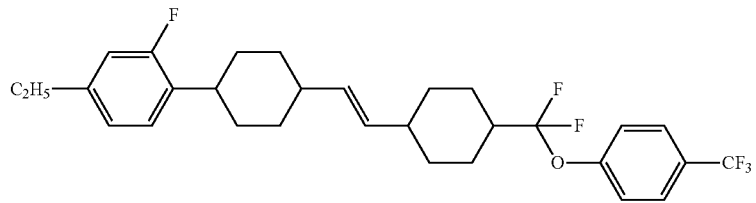 |

-continued
| No. | |
|---|---|
| 65 | 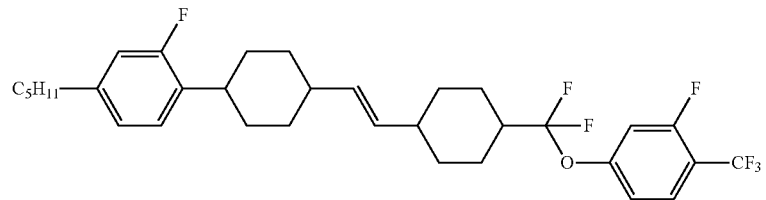 |
| 66 | 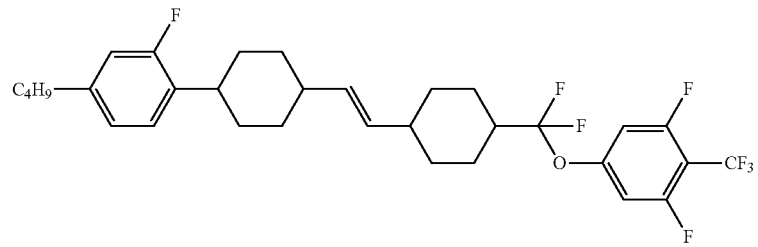 |
| 67 | 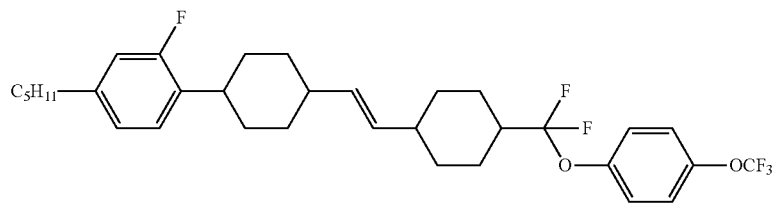 |
| 68 | 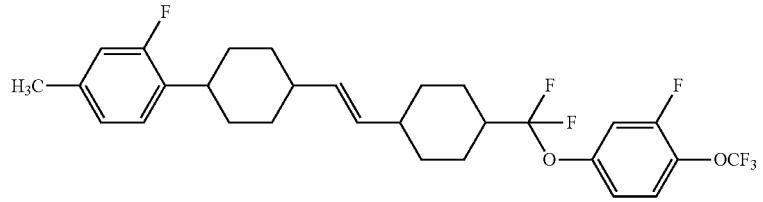 [SMILES: Cc1ccc(C2CCC(/C=C/C3CCC(C(F)(F)Oc4ccc(OC(F)(F)F)c(F)c4)CC3)CC2)c(F)c1] |
| 69 | 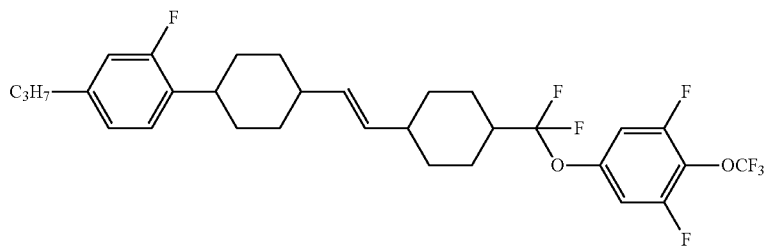 |
| 70 | 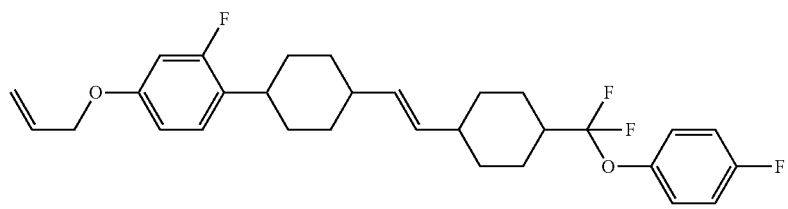 |
| 71 | 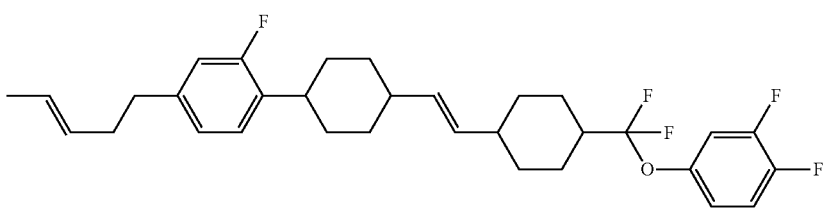 |

-continued
| No. | |
|---|---|
| 72 | 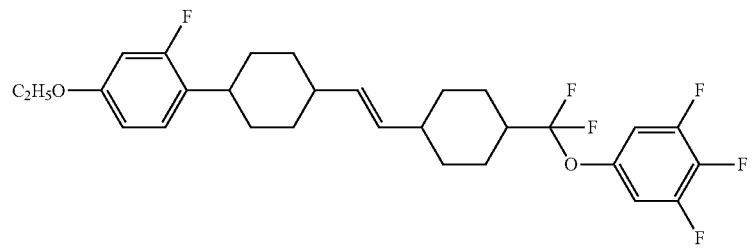 |
| 73 | 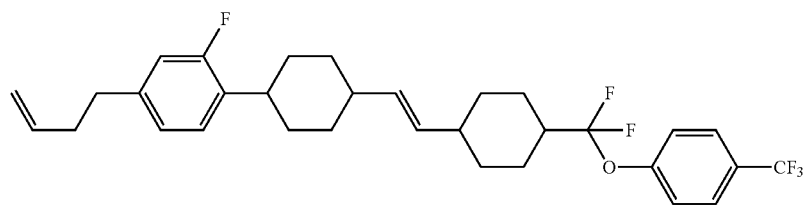 [SMILES: C=CCCc1ccc(C2CCC(/C=C/C3CCC(C(F)(F)Oc4ccc(C(F)(F)F)cc4)CC3)CC2)c(F)c1] |
| 74 | 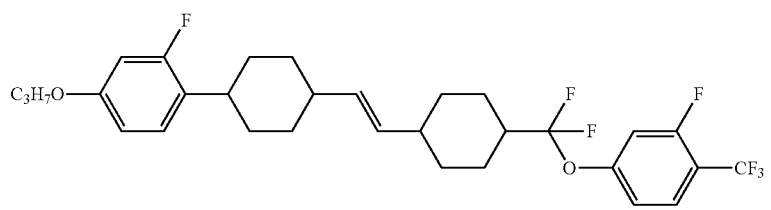 |
| 75 | 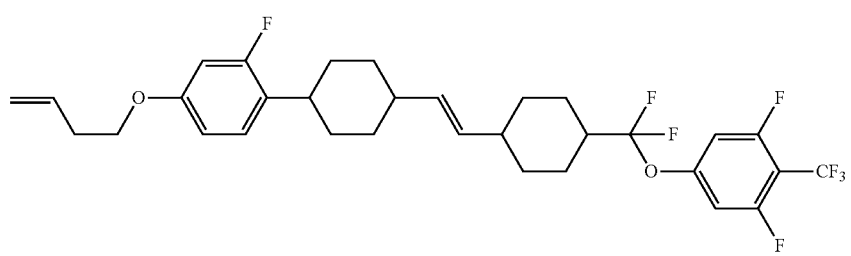 [SMILES: C=CCCOc1ccc(C2CCC(/C=C/C3CCC(C(F)(F)Oc4cc(F)c(C(F)(F)F)c(F)c4)CC3)CC2)c(F)c1] |
| 76 | 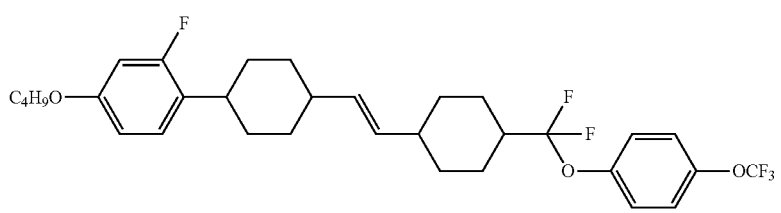 |
| 77 | 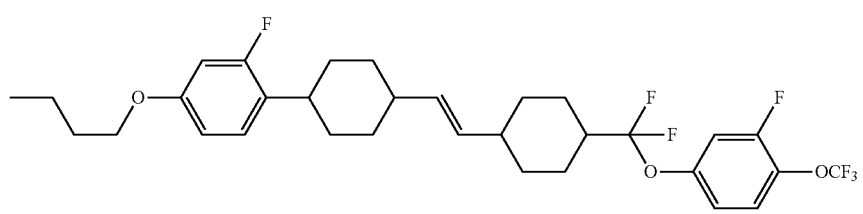 [SMILES: CCCCOc1ccc(C2CCC(/C=C/C3CCC(C(F)(F)Oc4ccc(OC(F)(F)F)c(F)c4)CC3)CC2)c(F)c1] |
| 78 | 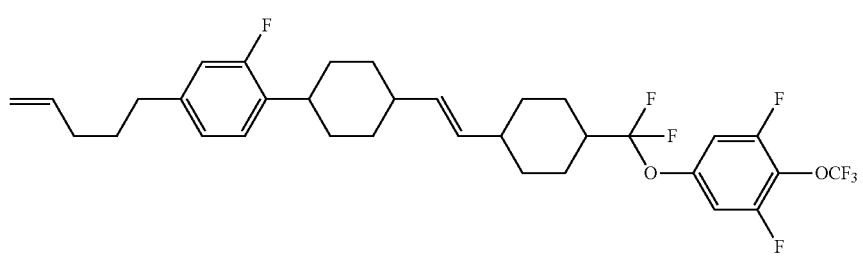 [SMILES: C=CCCCc1ccc(C2CCC(/C=C/C3CCC(C(F)(F)Oc4cc(F)c(OC(F)(F)F)c(F)c4)CC3)CC2)c(F)c1] |

| No. | |
|---|---|
| 79 | 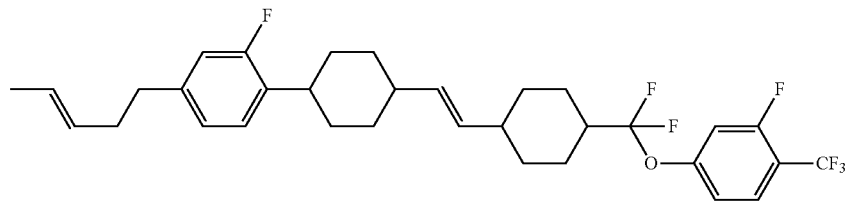 [SMILES: C/C=C/CCc1ccc(C2CCC(/C=C/C3CCC(C(F)(F)Oc4ccc(C(F)(F)F)c(F)c4)CC3)CC2)c(F)c1] |
| 80 | 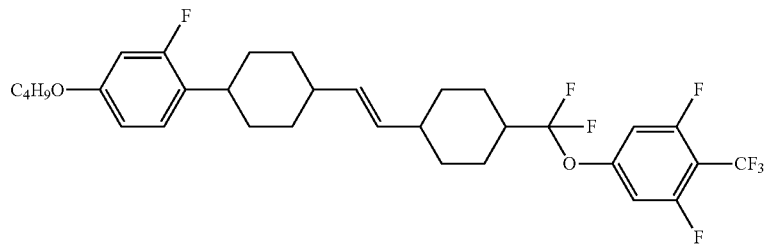 |
| 81 | 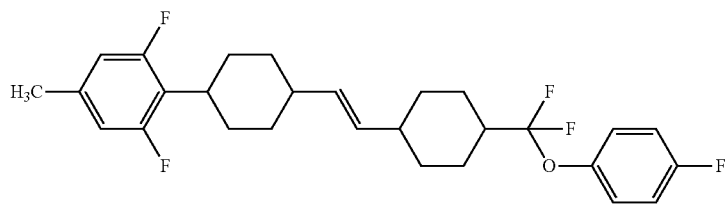 [SMILES: Cc1cc(F)c(C2CCC(/C=C/C3CCC(C(F)(F)Oc4ccc(F)cc4)CC3)CC2)c(F)c1] |
| 82 | 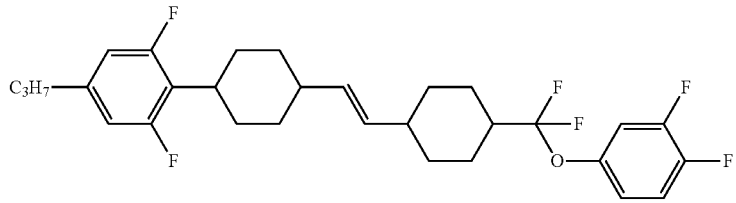 |
| 83 | 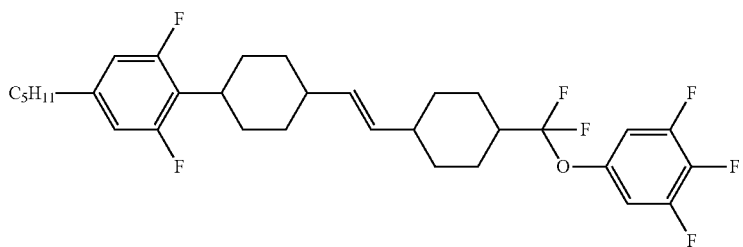 |
| 84 | 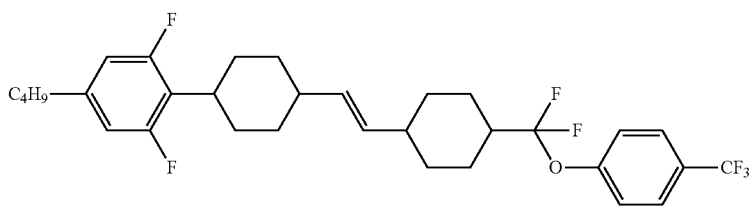 |
| 85 | 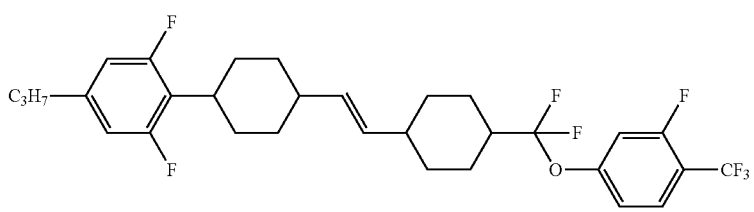 |

| No. | |
|---|---|
| 86 | 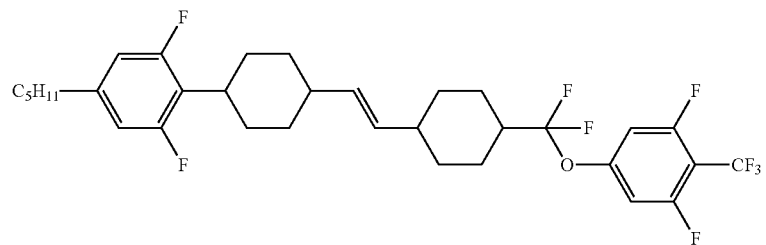 |
| 87 | 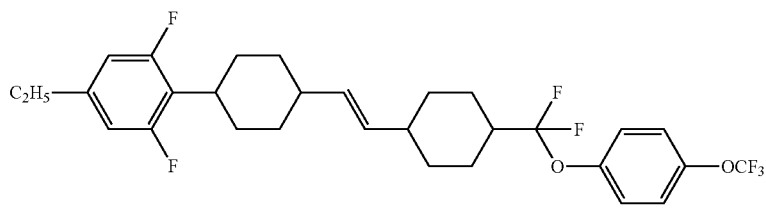 [SMILES: CCc1cc(F)c(C2CCC(/C=C/C3CCC(C(F)(F)Oc4ccc(OC(F)(F)F)cc4)CC3)CC2)c(F)c1] |
| 88 | 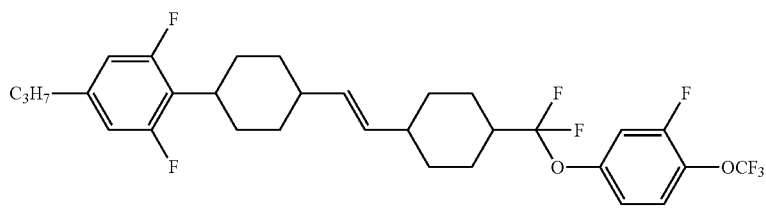 |
| 89 | 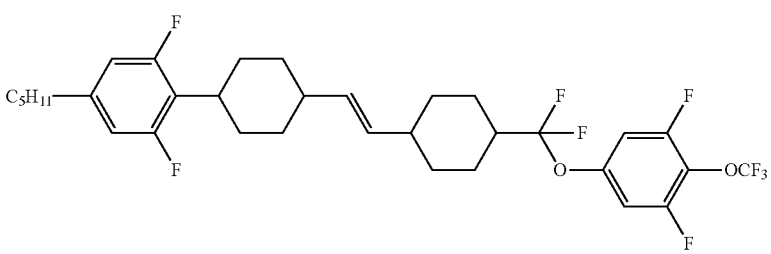 |
| 90 | 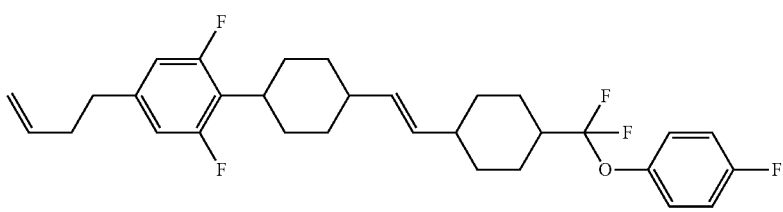 [SMILES: C=CCCc1cc(F)c(C2CCC(/C=C/C3CCC(C(F)(F)Oc4ccc(F)cc4)CC3)CC2)c(F)c1] |
| 91 | 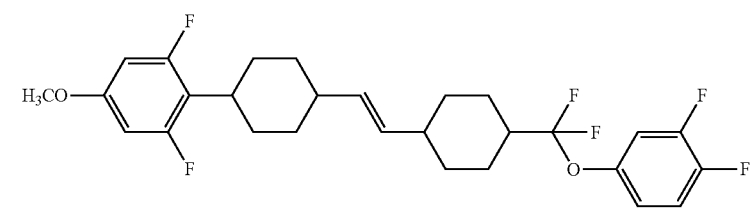 |
| 92 | 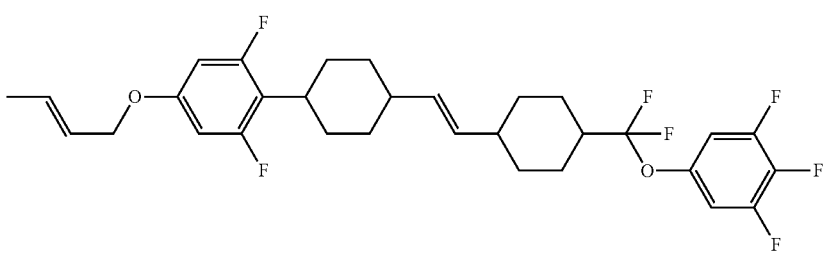 [SMILES: C/C=C/COc1cc(F)c(C2CCC(/C=C/C3CCC(C(F)(F)Oc4cc(F)c(F)c(F)c4)CC3)CC2)c(F)c1] |

-continued
| No. |  |
|---|---|
| 93 | 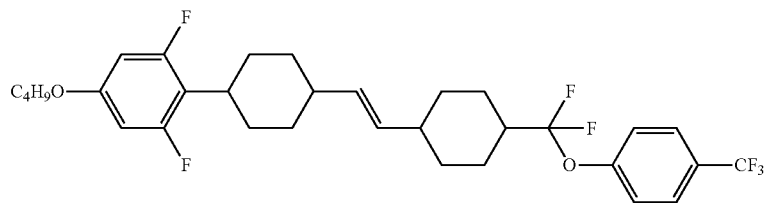 |
| 94 | 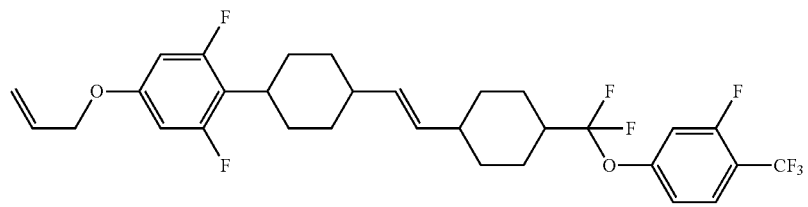 [SMILES: C=CCOc1cc(F)c(C2CCC(/C=C/C3CCC(C(F)(F)Oc4ccc(C(F)(F)F)c(F)c4)CC3)CC2)c(F)c1] |
| 95 | 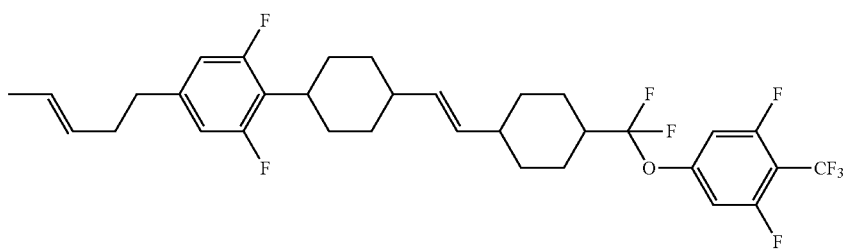 [SMILES: C/C=C/CCc1cc(F)c(C2CCC(/C=C/C3CCC(C(F)(F)Oc4cc(F)c(C(F)(F)F)c(F)c4)CC3)CC2)c(F)c1] |
| 96 | 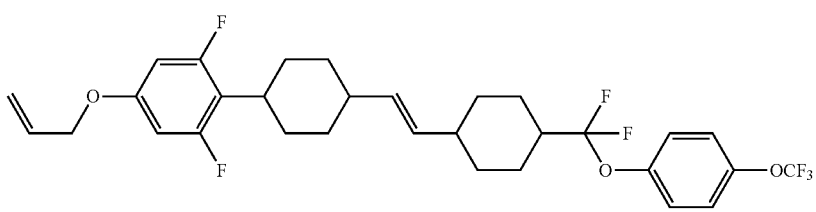 [SMILES: C=CCOc1cc(F)c(C2CCC(/C=C/C3CCC(C(F)(F)Oc4ccc(OC(F)(F)F)cc4)CC3)CC2)c(F)c1] |
| 97 | 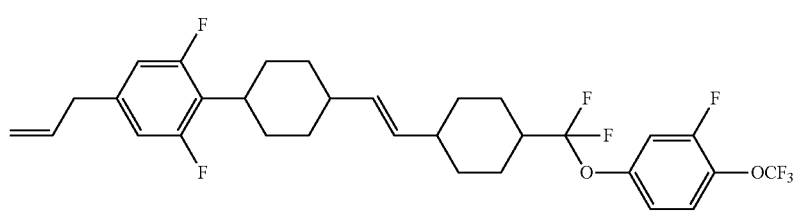 [SMILES: C=CCc1cc(F)c(C2CCC(/C=C/C3CCC(C(F)(F)Oc4ccc(OC(F)(F)F)c(F)c4)CC3)CC2)c(F)c1] |
| 98 | 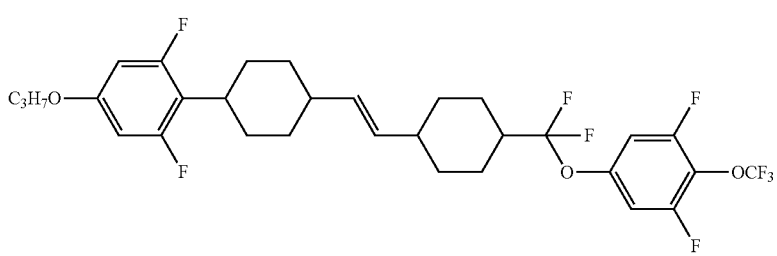 |
| 99 | 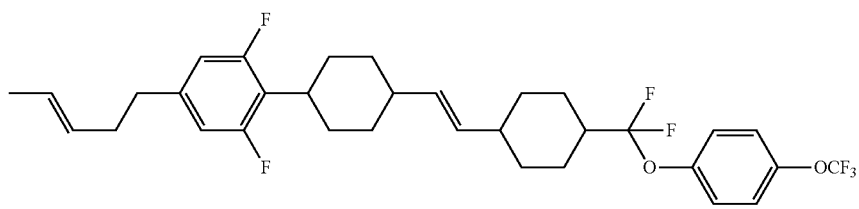 [SMILES: C/C=C/CCc1cc(F)c(C2CCC(/C=C/C3CCC(C(F)(F)Oc4ccc(OC(F)(F)F)cc4)CC3)CC2)c(F)c1] |

| No. | |
|---|---|
| 100 | 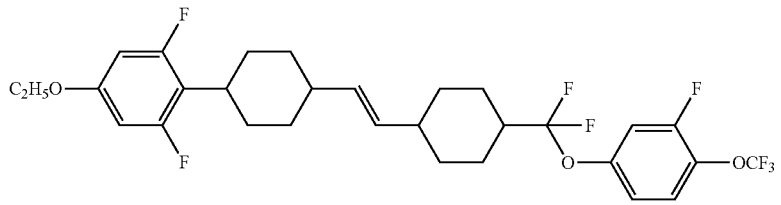 |
| 101 | 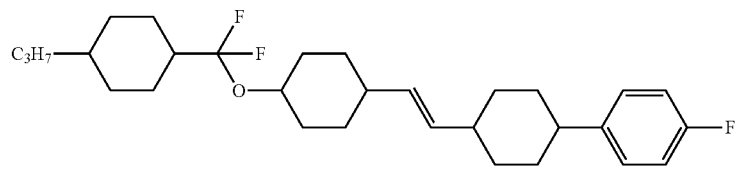 |
| 102 | 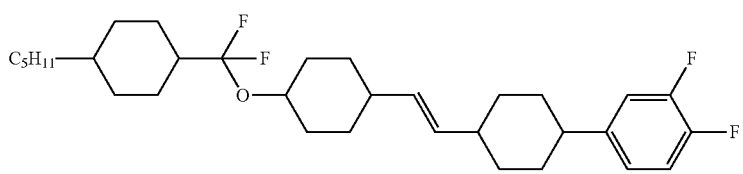 |
| 103 | 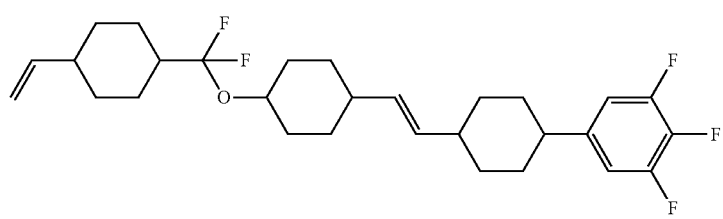 [SMILES: C=CC1CCC(C(F)(F)OC2CCC(/C=C/C3CCC(c4cc(F)c(F)c(F)c4)CC3)CC2)CC1] |
| 104 | 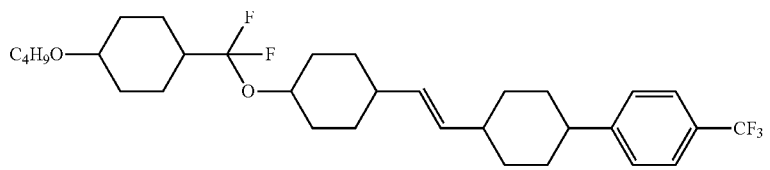 |
| 105 | 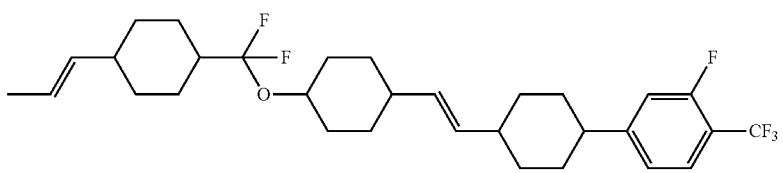 [SMILES: C/C=C/C1CCC(C(F)(F)OC2CCC(/C=C/C3CCC(c4ccc(C(F)(F)F)c(F)c4)CC3)CC2)CC1] |
| 106 | 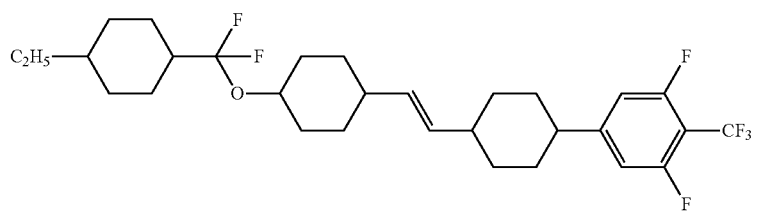 [SMILES: CCC1CCC(C(F)(F)OC2CCC(/C=C/C3CCC(c4cc(F)c(C(F)(F)F)c(F)c4)CC3)CC2)CC1] |
| 107 | 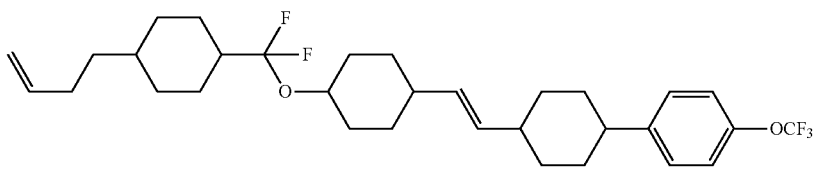 |

-continued
| No. | |
|---|---|
| 108 | 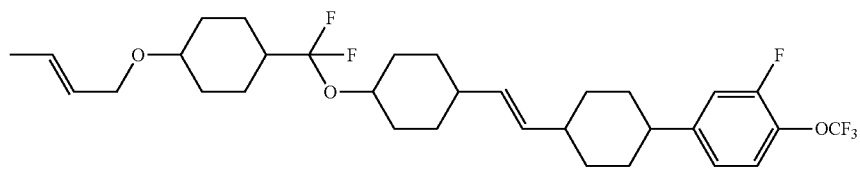 [SMILES: C/C=C/COC1CCC(C(F)(F)OC2CCC(/C=C/C3CCC(c4ccc(OC(F)(F)F)c(F)c4)CC3)CC2)CC1] |
| 109 | 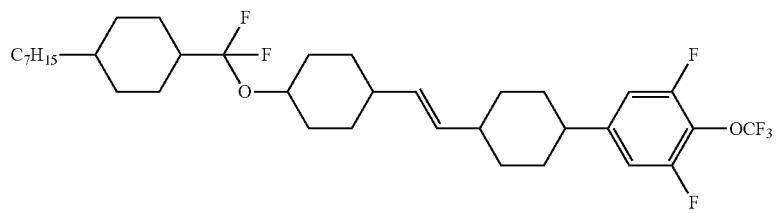 |
| 110 | 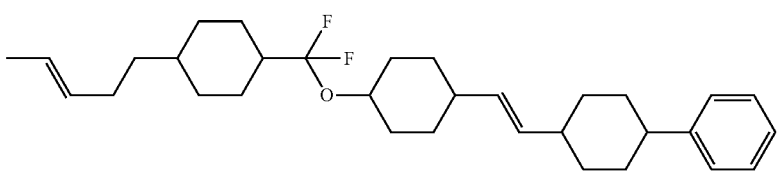 [SMILES: C/C=C/CCC1CCC(C(F)(F)OC2CCC(/C=C/C3CCC(c4ccccc4)CC3)CC2)CC1] |
| 111 | 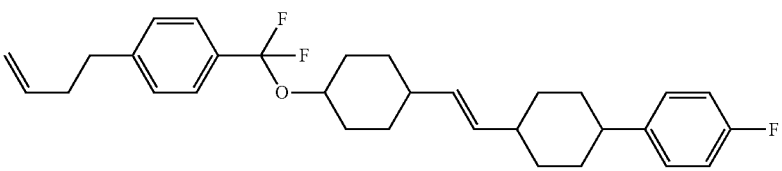 [SMILES: C=CCCc1ccc(C(F)(F)OC2CCC(/C=C/C3CCC(c4ccc(F)cc4)CC3)CC2)cc1] |
| 112 | 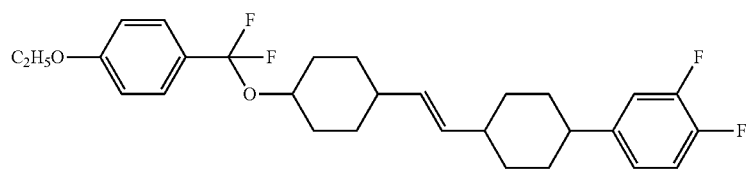 |
| 113 | 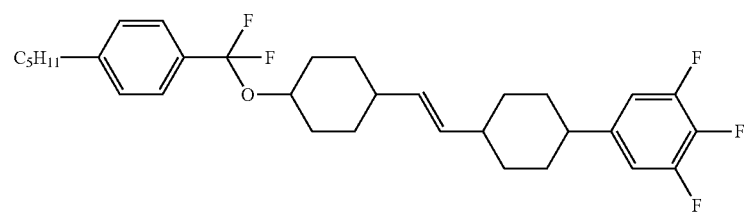 |
| 114 | 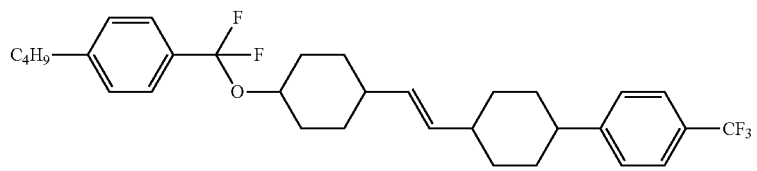 |
| 115 | 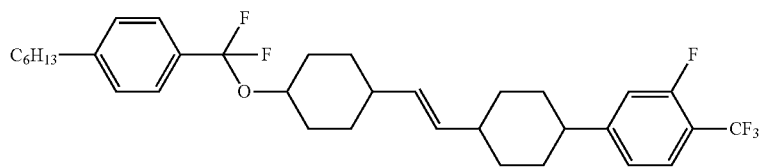 |

-continued
| No. | |
|---|---|
| 116 | 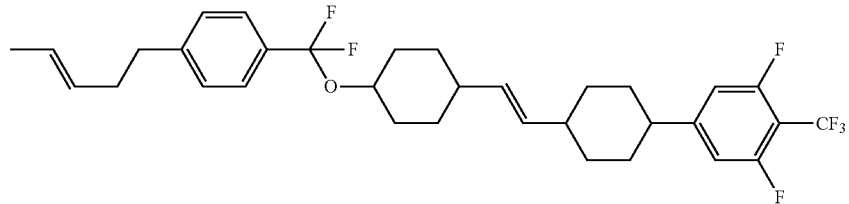 [SMILES: C/C=C/CCc1ccc(C(F)(F)OC2CCC(/C=C/C3CCC(c4cc(F)c(C(F)(F)F)c(F)c4)CC3)CC2)cc1] |
| 117 | 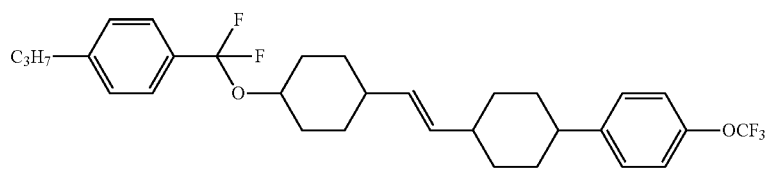 |
| 118 | 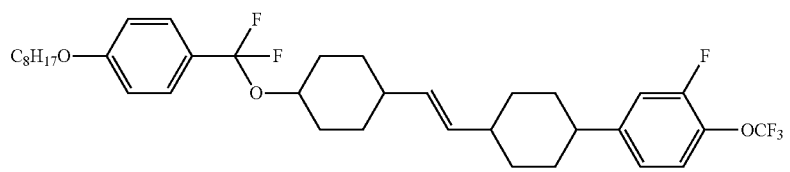 |
| 119 | 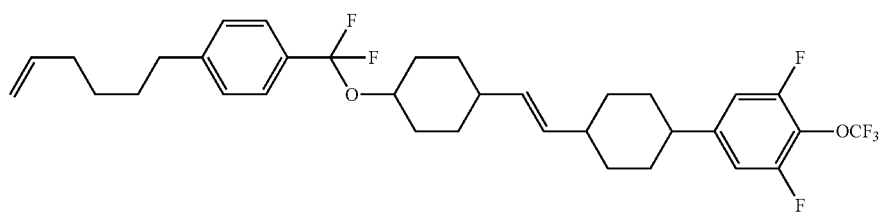 [SMILES: C=CCCCCc1ccc(C(F)(F)OC2CCC(/C=C/C3CCC(c4cc(F)c(OC(F)(F)F)c(F)c4)CC3)CC2)cc1] |
| 120 | 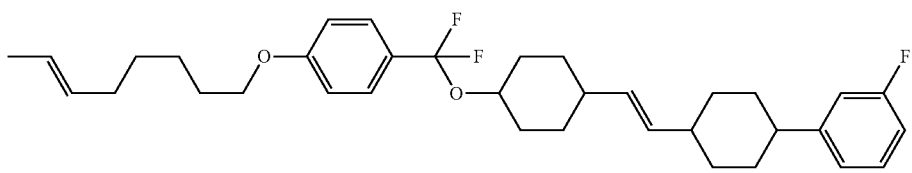 [SMILES: C/C=C/CCCCCOc1ccc(C(F)(F)OC2CCC(/C=C/C3CCC(c4cccc(F)c4)CC3)CC2)cc1] |
| 121 | 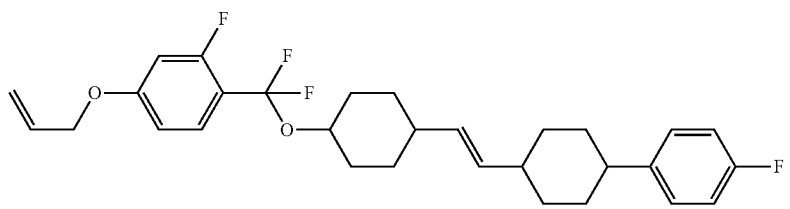 [SMILES: C=CCOc1ccc(C(F)(F)OC2CCC(/C=C/C3CCC(c4ccc(F)cc4)CC3)CC2)c(F)c1] |
| 122 | 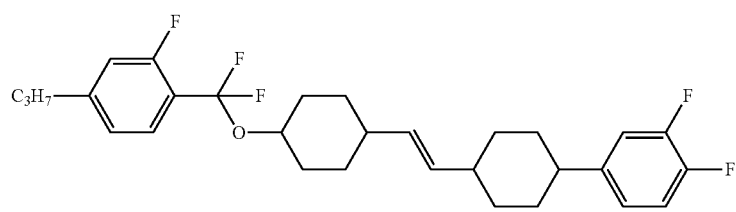 |

-continued
| No. | |
|---|---|
| 123 | 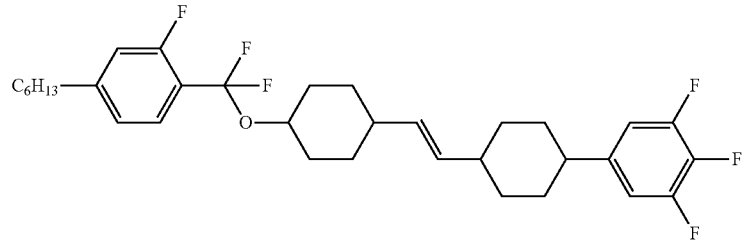 |
| 124 | 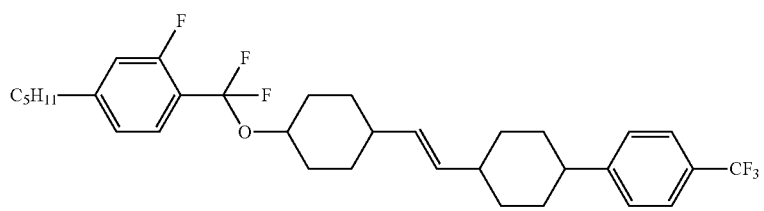 |
| 125 | 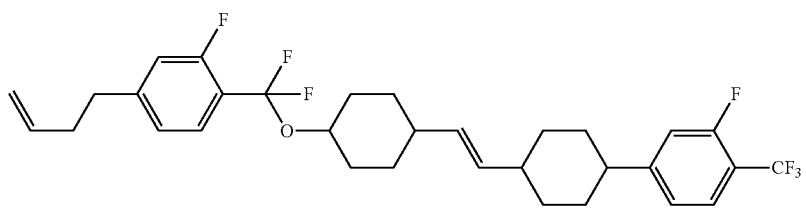 [SMILES: C=CCCc1ccc(C(F)(F)OC2CCC(/C=C/C3CCC(c4ccc(C(F)(F)F)c(F)c4)CC3)CC2)c(F)c1] |
| 126 | 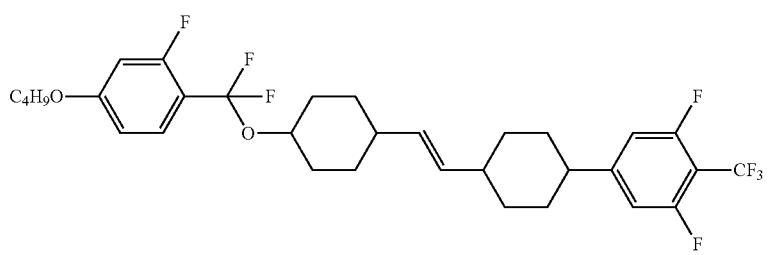 |
| 127 | 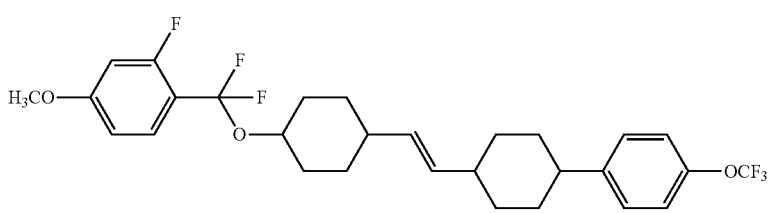 [SMILES: COc1ccc(C(F)(F)OC2CCC(/C=C/C3CCC(c4ccc(OC(F)(F)F)cc4)CC3)CC2)c(F)c1] |
| 128 | 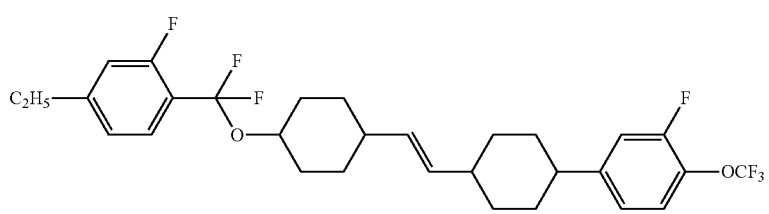 [SMILES: CCc1ccc(C(F)(F)OC2CCC(/C=C/C3CCC(c4ccc(OC(F)(F)F)c(F)c4)CC3)CC2)c(F)c1] |
| 129 | 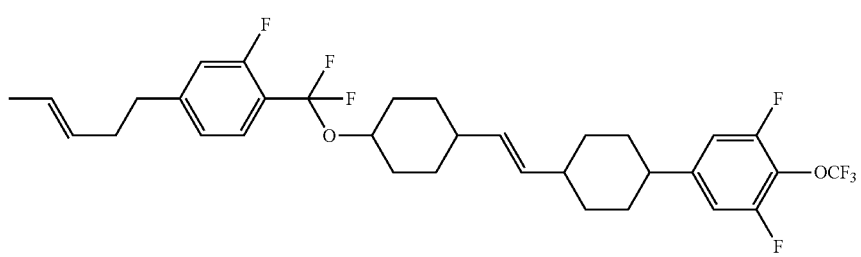 [SMILES: C/C=C/CCc1ccc(C(F)(F)OC2CCC(/C=C/C3CCC(c4cc(F)c(OC(F)(F)F)c(F)c4)CC3)CC2)c(F)c1] |

| No. |
|---|
| 130 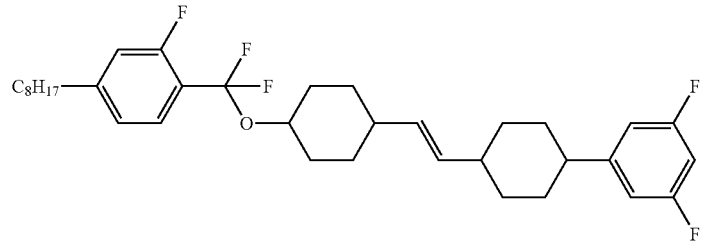 |
| 131 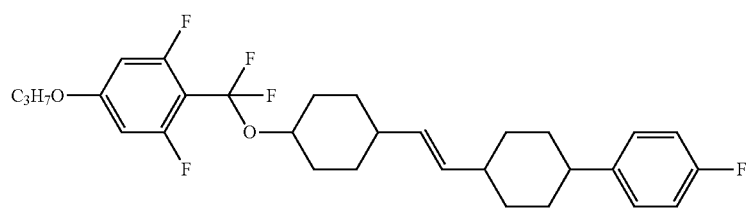 |
| 132 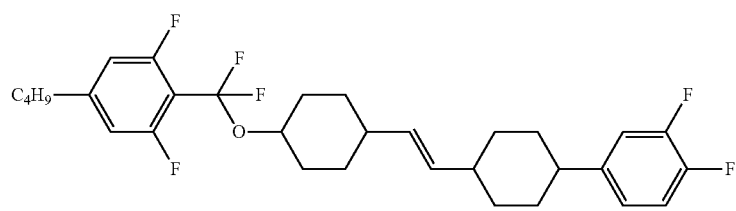 |
| 133 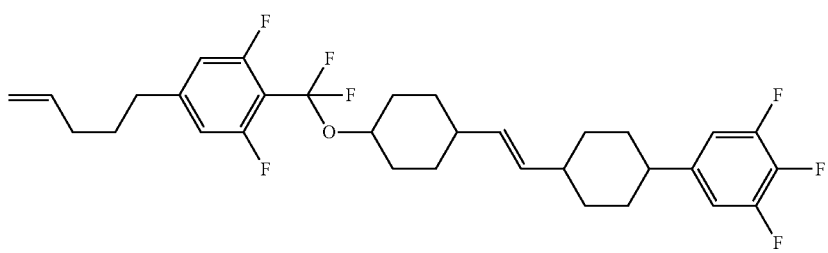 [SMILES: C=CCCCc1cc(F)c(C(F)(F)OC2CCC(/C=C/C3CCC(c4cc(F)c(F)c(F)c4)CC3)CC2)c(F)c1] |
| 134 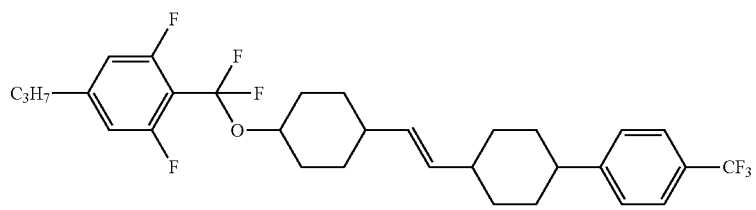 |
| 135 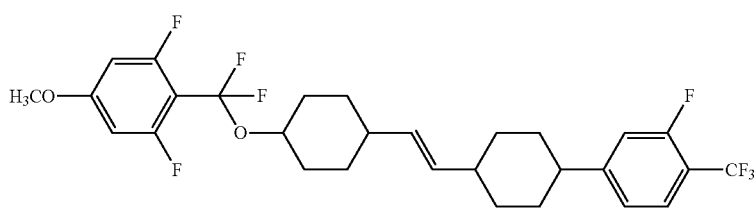 [SMILES: COc1cc(F)c(C(F)(F)OC2CCC(/C=C/C3CCC(c4ccc(C(F)(F)F)c(F)c4)CC3)CC2)c(F)c1] |

-continued
| No. | |
|---|---|
| 136 | 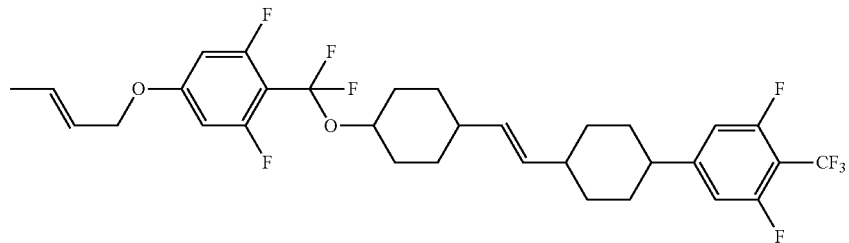 [SMILES: C/C=C/COc1cc(F)c(C(F)(F)OC2CCC(/C=C/C3CCC(c4cc(F)c(C(F)(F)F)c(F)c4)CC3)CC2)c(F)c1] |
| 137 | 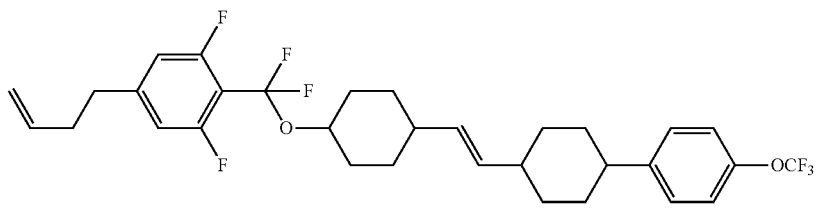 [SMILES: C=CCCc1cc(F)c(C(F)(F)OC2CCC(/C=C/C3CCC(c4ccc(OC(F)(F)F)cc4)CC3)CC2)c(F)c1] |
| 138 | 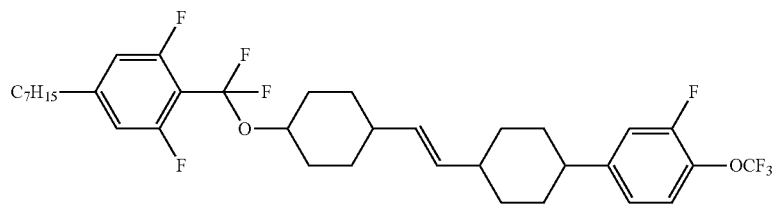 |
| 139 | 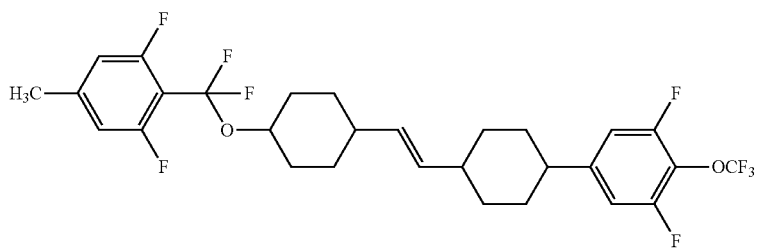 [SMILES: Cc1cc(F)c(C(F)(F)OC2CCC(/C=C/C3CCC(c4cc(F)c(OC(F)(F)F)c(F)c4)CC3)CC2)c(F)c1] |
| 140 | 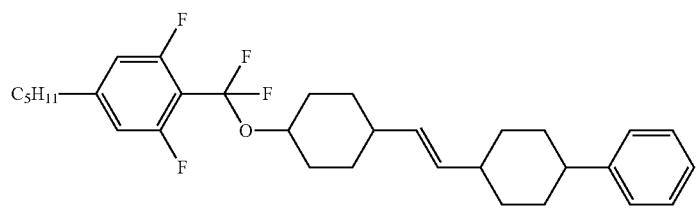 |
| 141 | 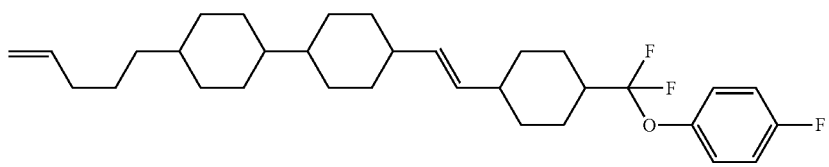 [SMILES: C=CCCCC1CCC(C2CCC(/C=C/C3CCC(C(F)(F)Oc4ccc(F)cc4)CC3)CC2)CC1] |
| 142 | 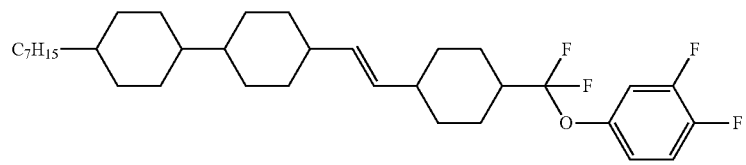 |

-continued
| No. | |
|---|---|
| 143 | 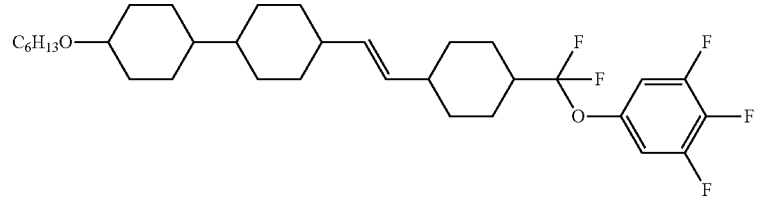 |
| 144 | 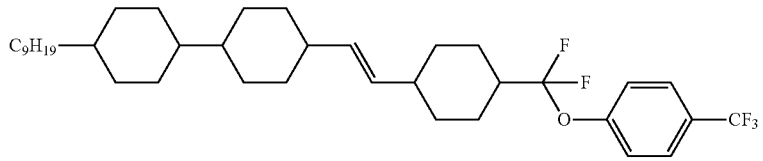 |
| 145 | 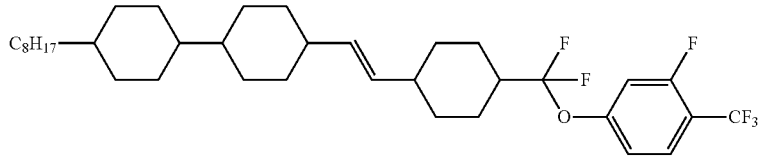 |
| 146 | 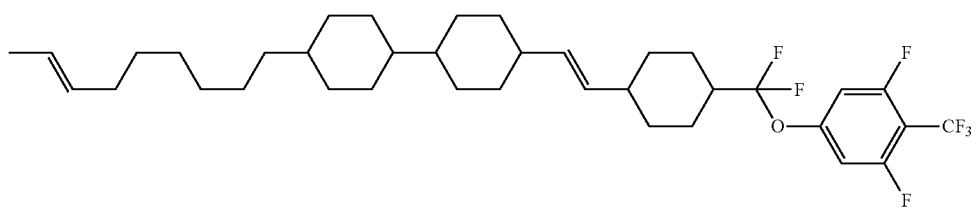 [SMILES: C/C=C/CCCCCCC1CCC(C2CCC(/C=C/C3CCC(C(F)(F)Oc4cc(F)c(C(F)(F)F)c(F)c4)CC3)CC2)CC1] |
| 147 | 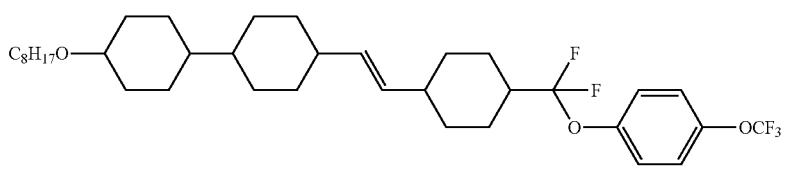 |
| 148 | 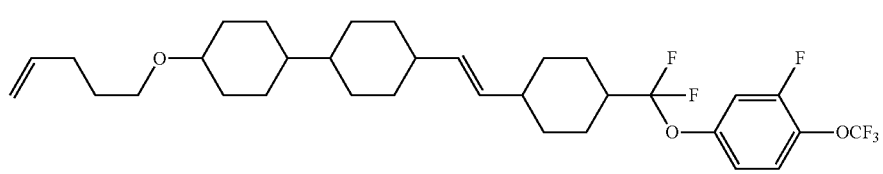 [SMILES: C=CCCCOC1CCC(C2CCC(/C=C/C3CCC(C(F)(F)Oc4ccc(OC(F)(F)F)c(F)c4)CC3)CC2)CC1] |
| 149 | 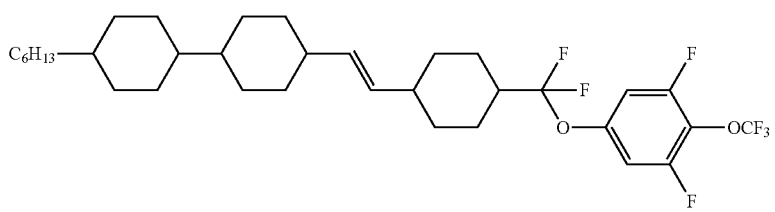 |
| 150 | 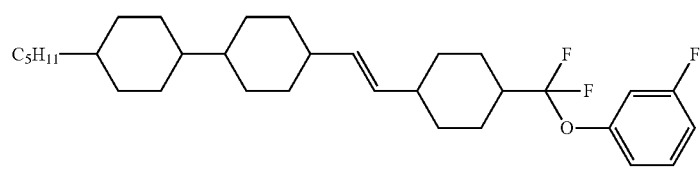 |

| No. | |
|---|---|
| 151 | 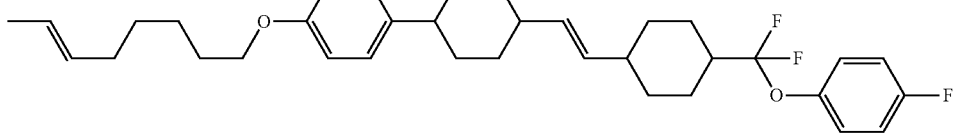 |
| 152 | 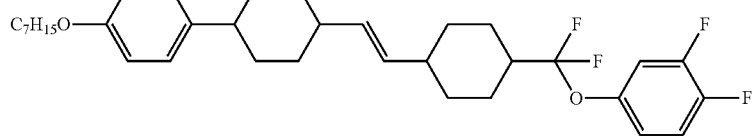 |
| 153 | 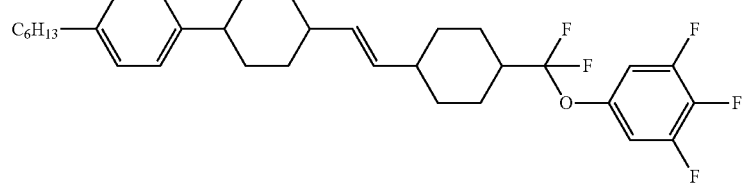 |
| 154 | 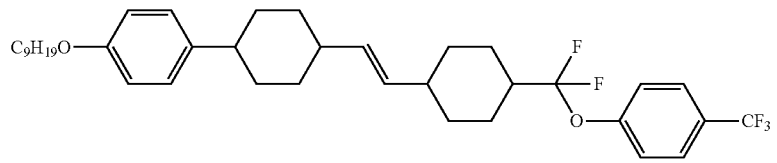 |
| 155 | 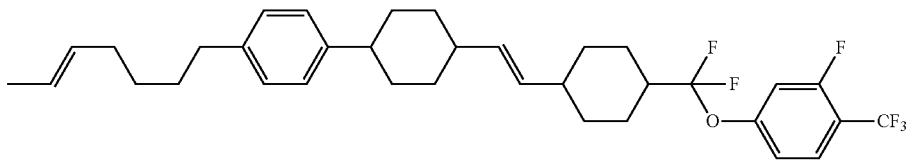 [SMILES: C/C=C/CCCCc1ccc(C2CCC(/C=C/C3CCC(C(F)(F)Oc4ccc(C(F)(F)F)c(F)c4)CC3)CC2)cc1] |
| 156 | 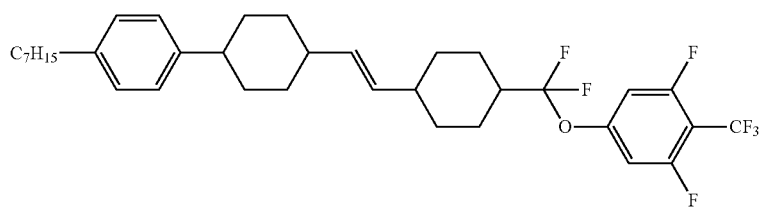 |
| 157 | 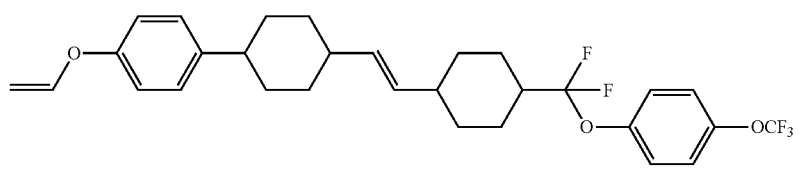 [SMILES: C=COc1ccc(C2CCC(/C=C/C3CCC(C(F)(F)Oc4ccc(OC(F)(F)F)cc4)CC3)CC2)cc1] |
| 158 | 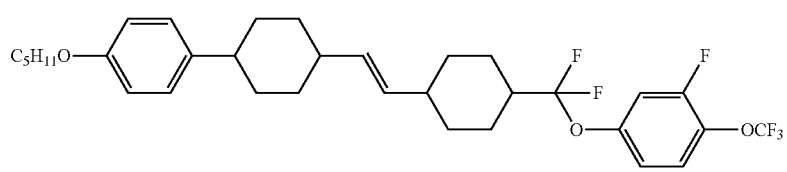 |

| No. | |
|---|---|
| 159 | 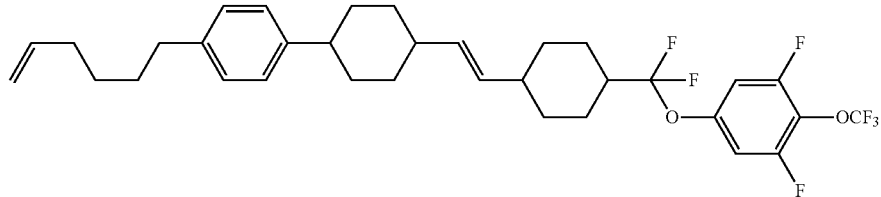 [SMILES: C=CCCCCc1ccc(C2CCC(/C=C/C3CCC(C(F)(F)Oc4cc(F)c(OC(F)(F)F)c(F)c4)CC3)CC2)cc1] |
| 160 | 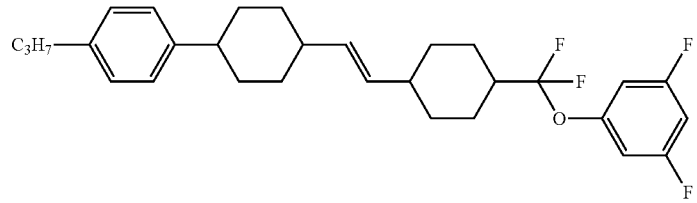 |
| 161 | 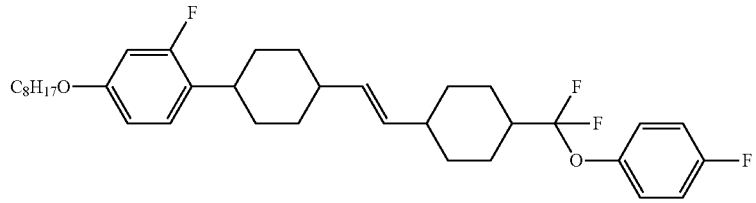 |
| 162 | 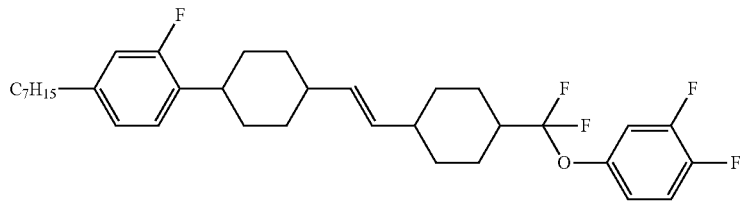 |
| 163 | 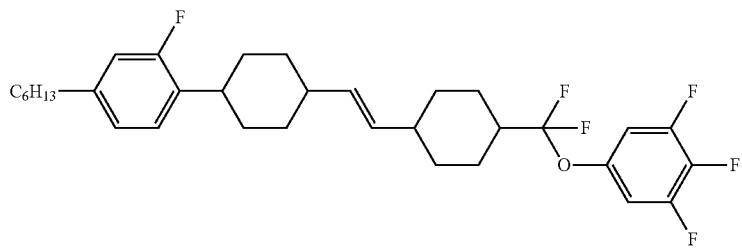 |
| 164 | 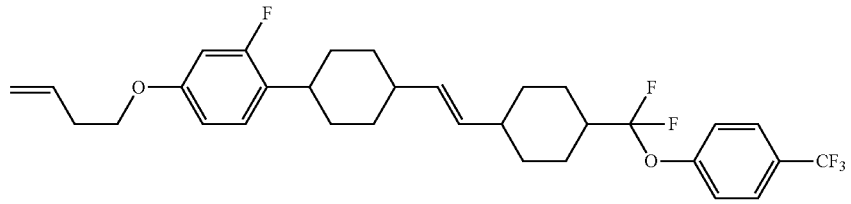 [SMILES: C=CCCOc1ccc(C2CCC(/C=C/C3CCC(C(F)(F)Oc4ccc(C(F)(F)F)cc4)CC3)CC2)c(F)c1] |
| 165 | 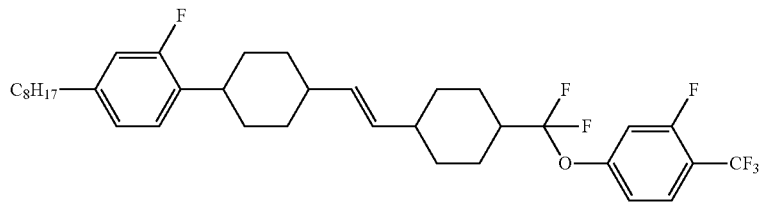 |

| No. | |
|---|---|
| 166 | 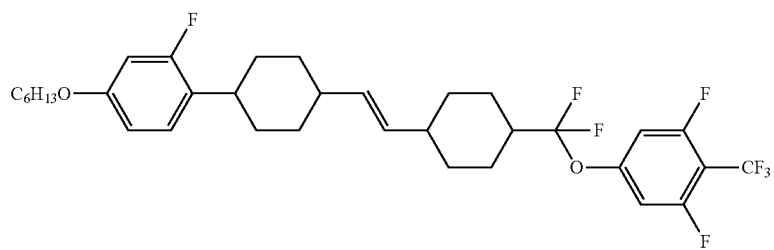 |
| 167 | 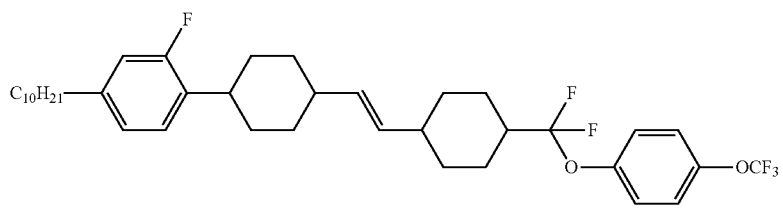 |
| 168 | 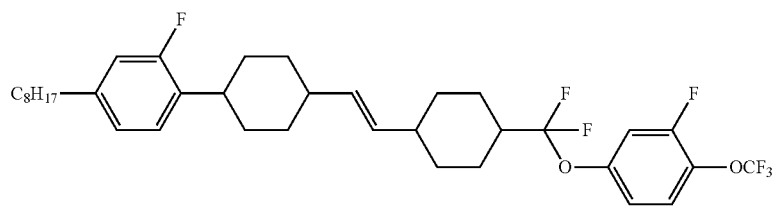 |
| 169 | 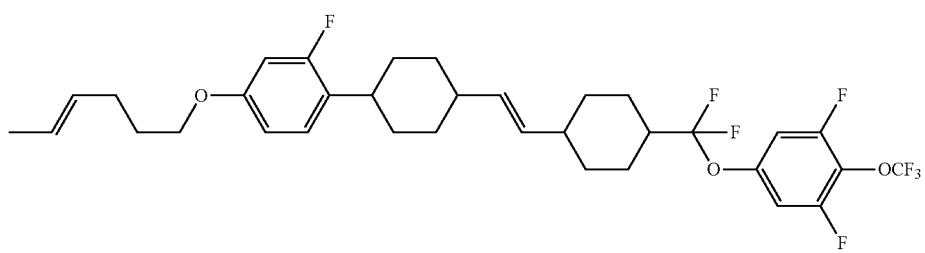 [SMILES: C/C=C/CCCOc1ccc(C2CCC(/C=C/C3CCC(C(F)(F)Oc4cc(F)c(OC(F)(F)F)c(F)c4)CC3)CC2)c(F)c1] |
| 170 | 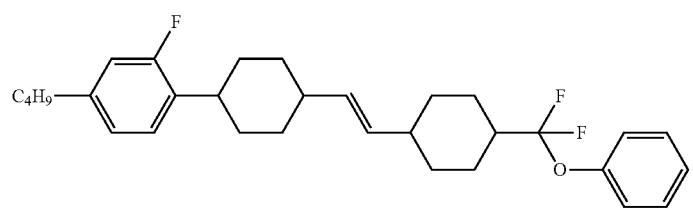 |
| 171 | 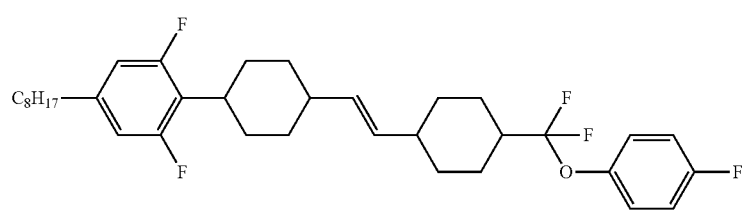 |
| 172 | 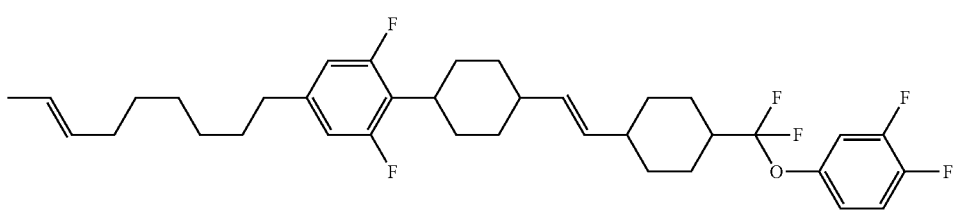 [SMILES: C/C=C/CCCCCCc1cc(F)c(C2CCC(/C=C/C3CCC(C(F)(F)Oc4ccc(F)c(F)c4)CC3)CC2)c(F)c1] |

-continued
| No. | |
|---|---|
| 173 | 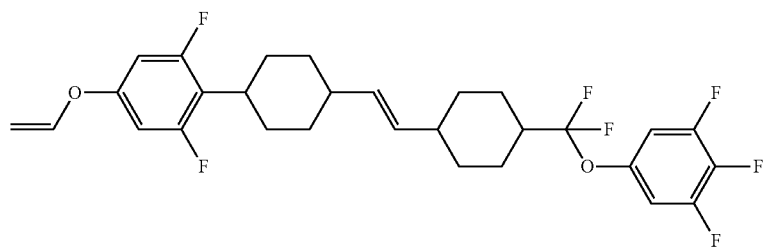 [SMILES: C=COc1cc(F)c(C2CCC(/C=C/C3CCC(C(F)(F)Oc4cc(F)c(F)c(F)c4)CC3)CC2)c(F)c1] |
| 174 | 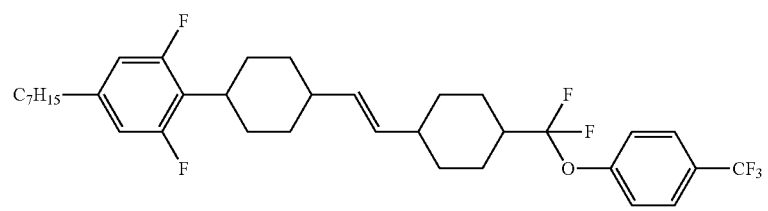 |
| 175 | 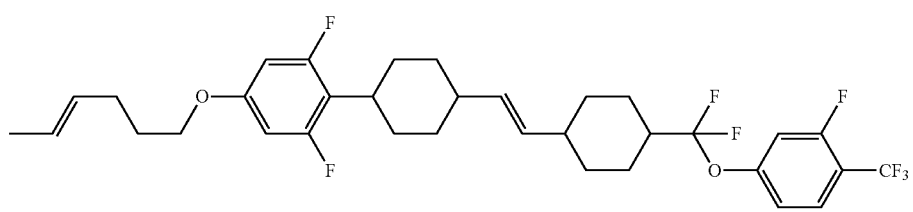 [SMILES: C/C=C/CCCOc1cc(F)c(C2CCC(/C=C/C3CCC(C(F)(F)Oc4ccc(C(F)(F)F)c(F)c4)CC3)CC2)c(F)c1] |
| 176 | 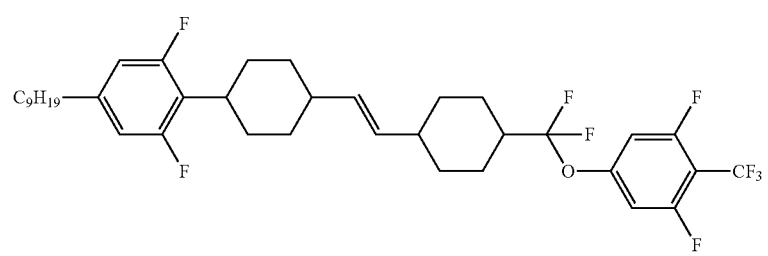 |
| 177 | 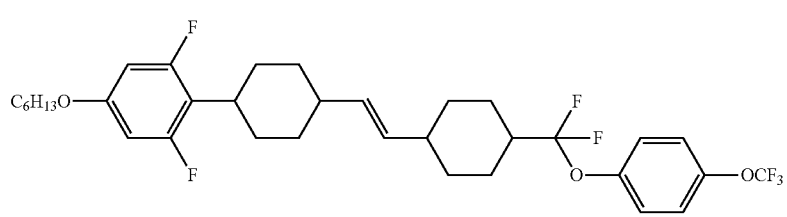 |
| 178 | 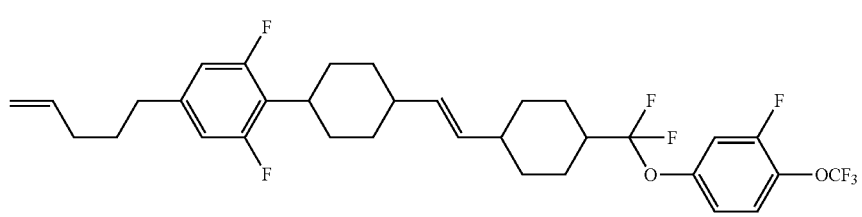 |
| 179 | 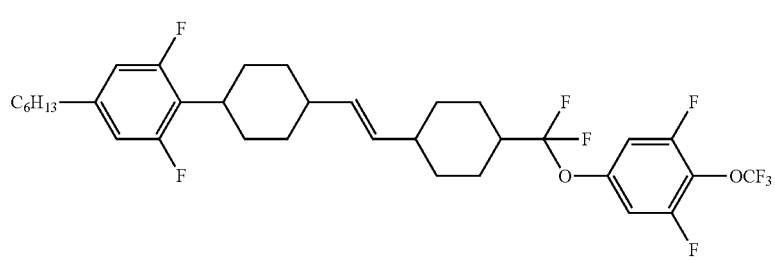 |

| No. | |
|---|---|
| 180 | 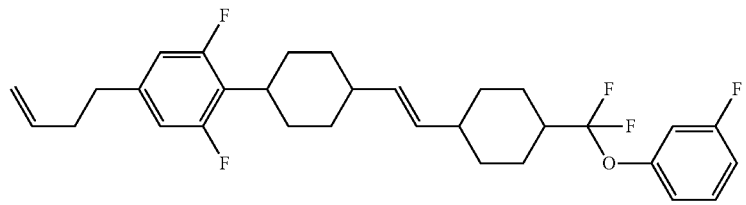 [SMILES: C=CCCc1cc(F)c(C2CCC(/C=C/C3CCC(C(F)(F)Oc4cccc(F)c4)CC3)CC2)c(F)c1] |
| 181 | 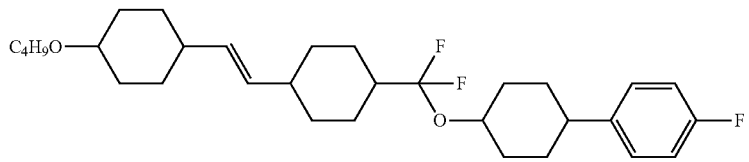 |
| 182 | 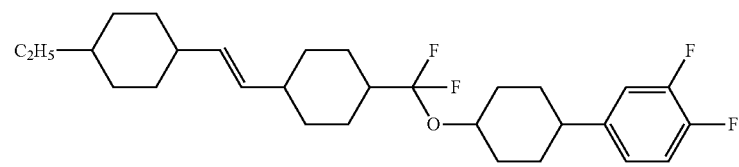 [SMILES: CCC1CCC(/C=C/C2CCC(C(F)(F)OC3CCC(c4ccc(F)c(F)c4)CC3)CC2)CC1] |
| 183 | 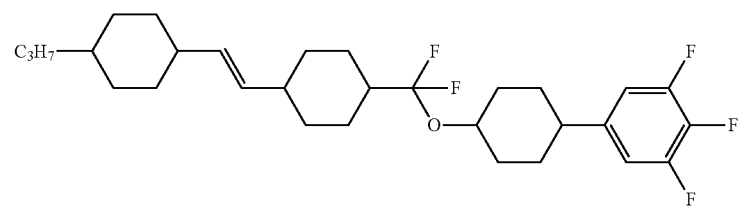 |
| 184 | 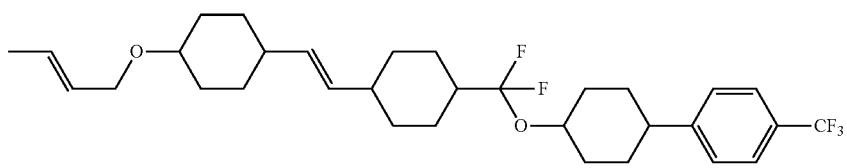 |
| 185 | 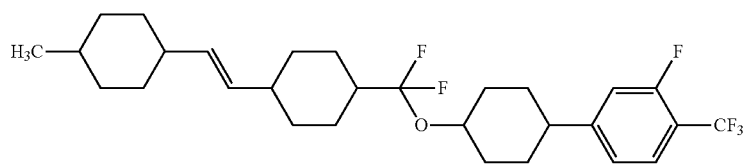 [SMILES: CC1CCC(/C=C/C2CCC(C(F)(F)OC3CCC(c4ccc(C(F)(F)F)c(F)c4)CC3)CC2)CC1] |
| 186 | 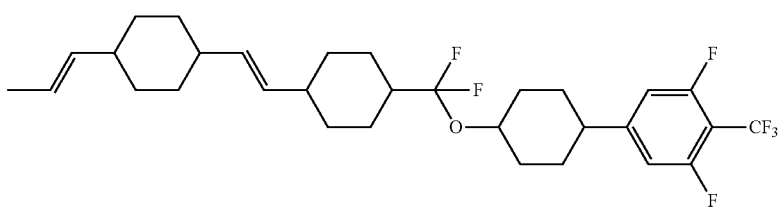 [SMILES: C/C=C/C1CCC(/C=C/C2CCC(C(F)(F)OC3CCC(c4cc(F)c(C(F)(F)F)c(F)c4)CC3)CC2)CC1] |
| 187 | 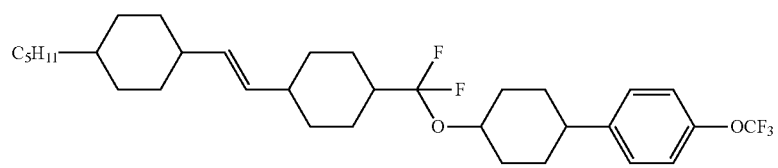 |

-continued
| No. | |
|---|---|
| 188 | 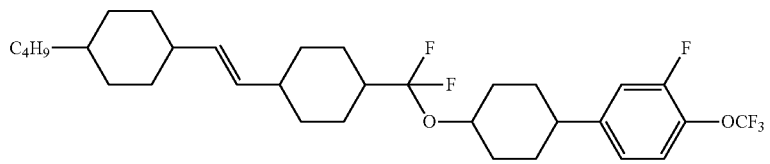 |
| 189 | 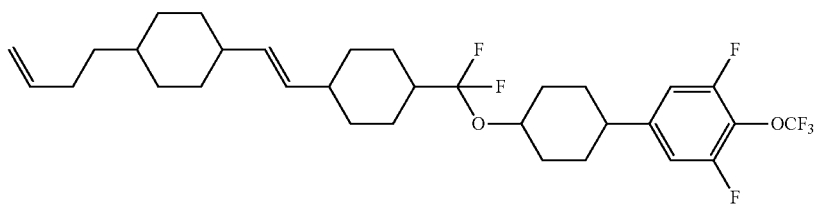 [SMILES: C=CCCC1CCC(/C=C/C2CCC(C(F)(F)OC3CCC(c4cc(F)c(OC(F)(F)F)c(F)c4)CC3)CC2)CC1] |
| 190 | 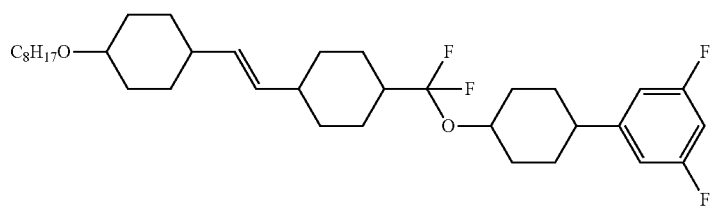 |
| 191 | 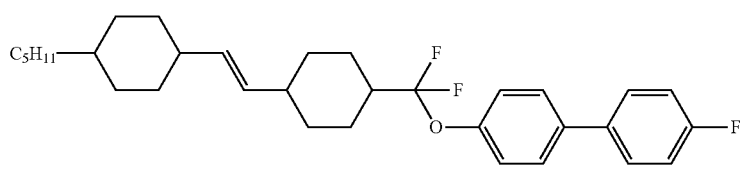 |
| 192 | 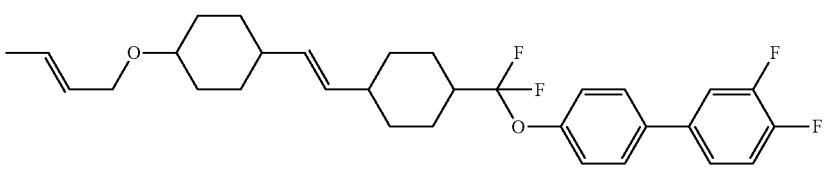 [SMILES: C/C=C/COC1CCC(/C=C/C2CCC(C(F)(F)Oc3ccc(-c4ccc(F)c(F)c4)cc3)CC2)CC1] |
| 193 | 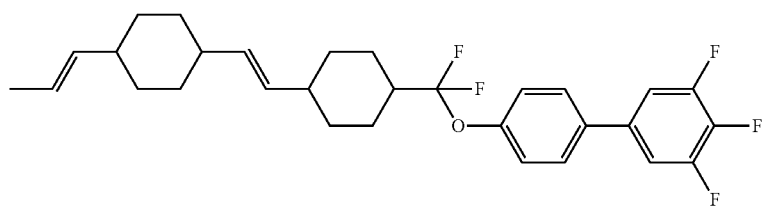 [SMILES: C/C=C/C1CCC(/C=C/C2CCC(C(F)(F)Oc3ccc(-c4cc(F)c(F)c(F)c4)cc3)CC2)CC1] |
| 191 | 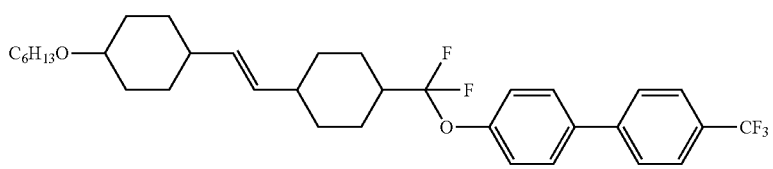 |
| 195 | 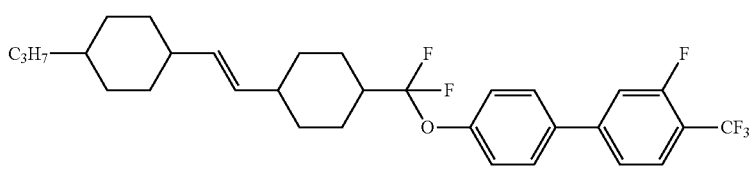 |

| No. | |
|---|---|
| 196 | 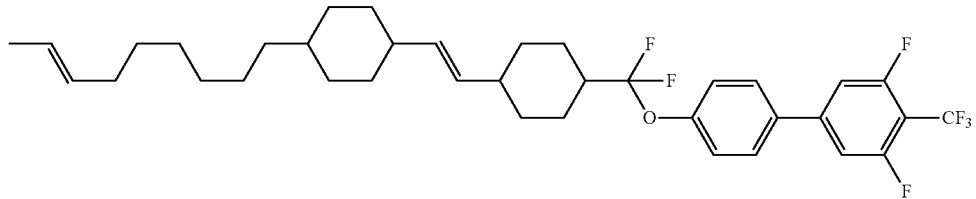 [SMILES: C/C=C/CCCCCCC1CCC(/C=C/C2CCC(C(F)(F)Oc3ccc(-c4cc(F)c(C(F)(F)F)c(F)c4)cc3)CC2)CC1] |
| 197 | 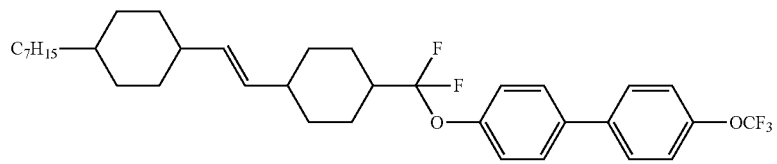 |
| 198 | 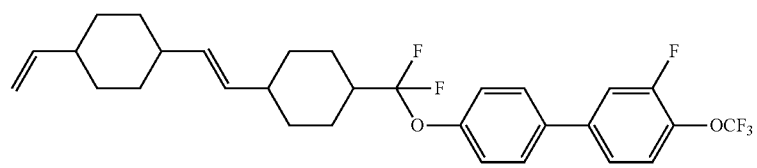 [SMILES: C=CC1CCC(/C=C/C2CCC(C(F)(F)Oc3ccc(-c4ccc(OC(F)(F)F)c(F)c4)cc3)CC2)CC1] |
| 199 | 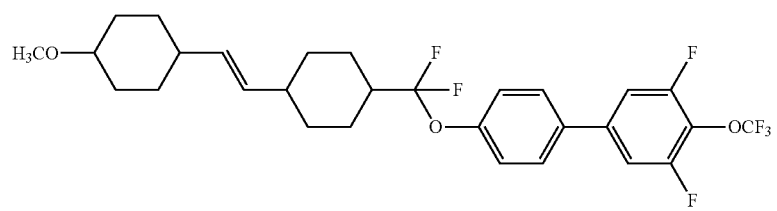 [SMILES: COC1CCC(/C=C/C2CCC(C(F)(F)Oc3ccc(-c4cc(F)c(OC(F)(F)F)c(F)c4)cc3)CC2)CC1] |
| 200 | 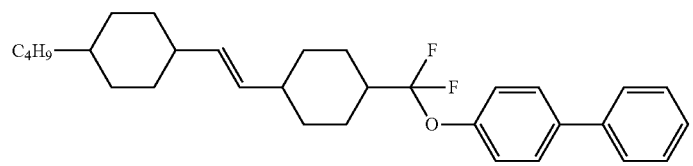 |
| 201 | 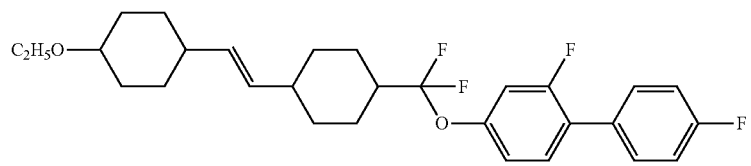 |
| 202 | 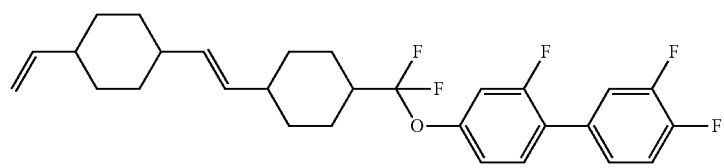 [SMILES: C=CC1CCC(/C=C/C2CCC(C(F)(F)Oc3ccc(-c4ccc(F)c(F)c4)c(F)c3)CC2)CC1] |
| 203 | 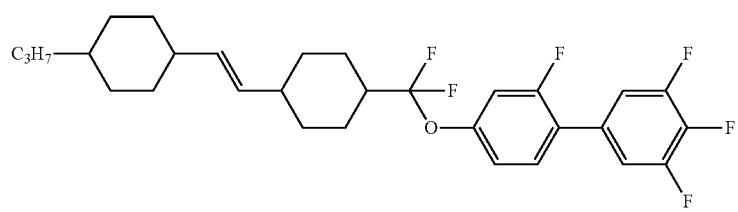 |

| No. | |
|---|---|
| 204 | 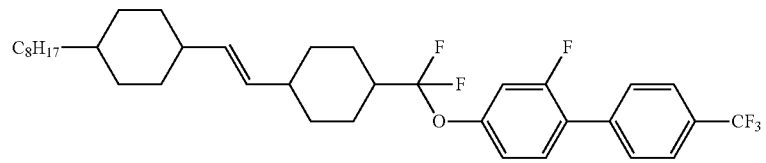 |
| 205 | 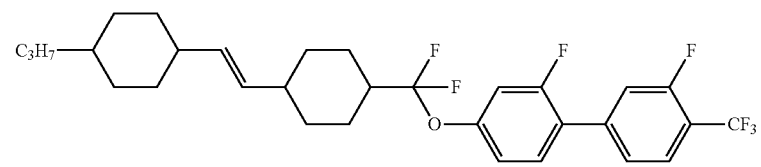 |
| 206 | 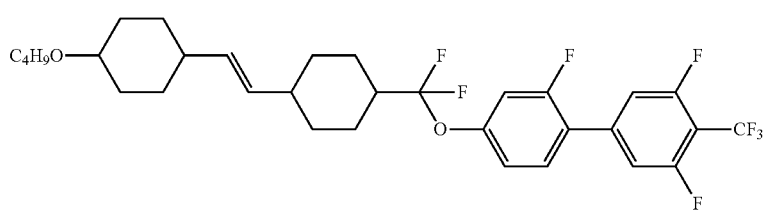 |
| 207 | 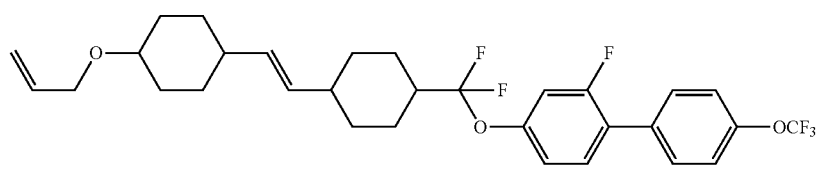 [SMILES: C=CCOC1CCC(/C=C/C2CCC(C(F)(F)Oc3ccc(-c4ccc(OC(F)(F)F)cc4)c(F)c3)CC2)CC1] |
| 208 | 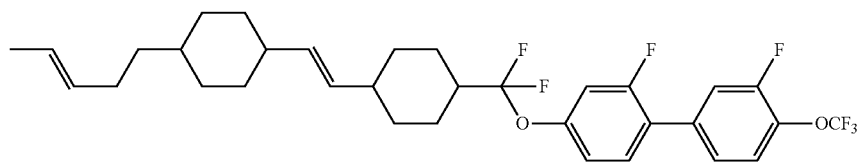 |
| 209 | 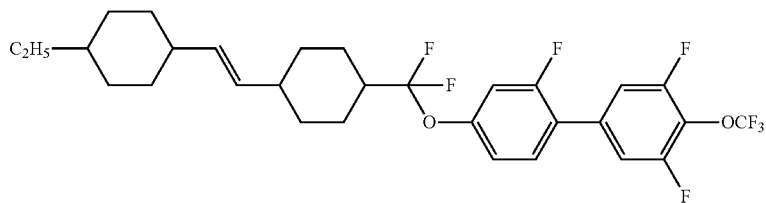 |
| 210 | 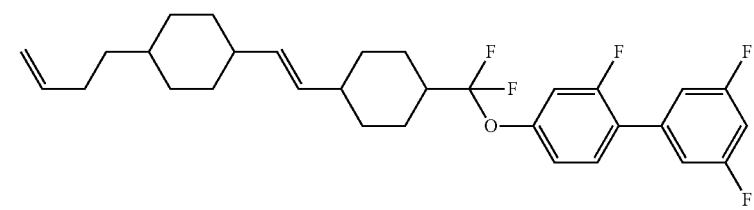 [SMILES: C=CCCC1CCC(/C=C/C2CCC(C(F)(F)Oc3ccc(-c4cc(F)cc(F)c4)c(F)c3)CC2)CC1] |
| 211 | 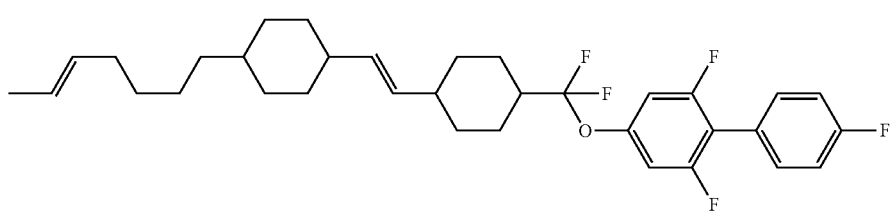 [SMILES: C/C=C/CCCCC1CCC(/C=C/C2CCC(C(F)(F)Oc3cc(F)c(-c4ccc(F)cc4)c(F)c3)CC2)CC1] |

-continued
| No. | |
|---|---|
| 212 | 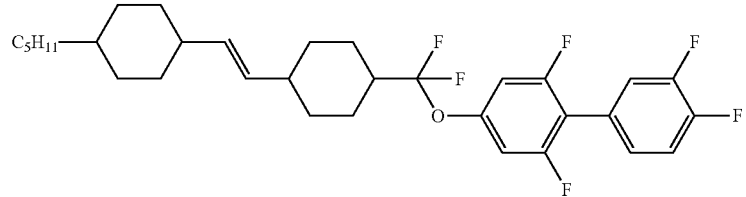 |
| 213 | 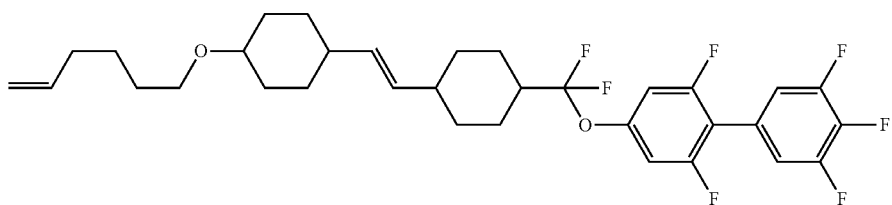 [SMILES: C=CCCCCOC1CCC(/C=C/C2CCC(C(F)(F)Oc3cc(F)c(-c4cc(F)c(F)c(F)c4)c(F)c3)CC2)CC1] |
| 214 | 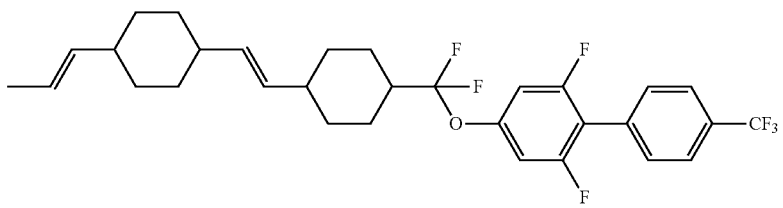 [SMILES: C/C=C/C1CCC(/C=C/C2CCC(C(F)(F)Oc3cc(F)c(-c4ccc(C(F)(F)F)cc4)c(F)c3)CC2)CC1] |
| 215 | 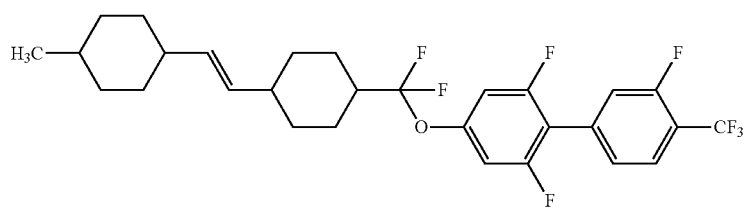 [SMILES: CC1CCC(/C=C/C2CCC(C(F)(F)Oc3cc(F)c(-c4ccc(C(F)(F)F)c(F)c4)c(F)c3)CC2)CC1] |
| 216 | 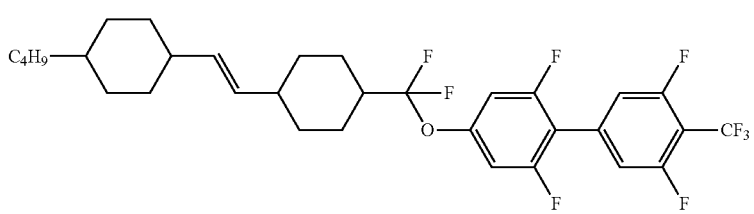 |
| 217 | 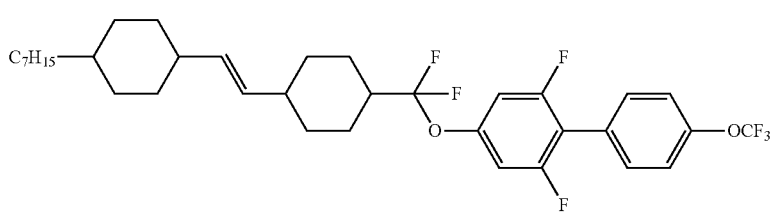 |
| 218 | 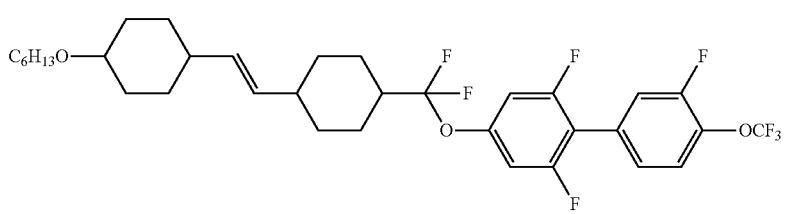 |

-continued
| No. | |
|---|---|
| 219 | 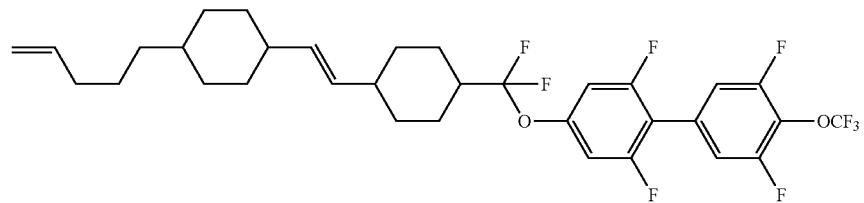 [SMILES: C=CCCCC1CCC(/C=C/C2CCC(C(F)(F)Oc3cc(F)c(-c4cc(F)c(OC(F)(F)F)c(F)c4)c(F)c3)CC2)CC1] |
| 220 | 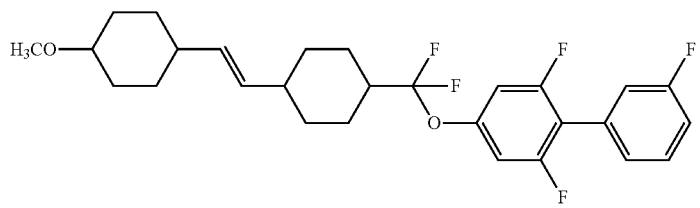 [SMILES: COC1CCC(/C=C/C2CCC(C(F)(F)Oc3cc(F)c(-c4cccc(F)c4)c(F)c3)CC2)CC1] |
| 221 | 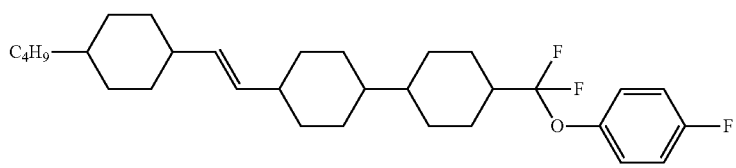 |
| 222 | 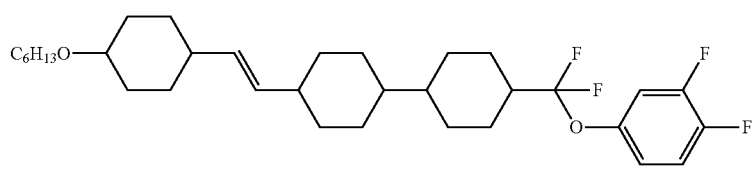 |
| 223 | 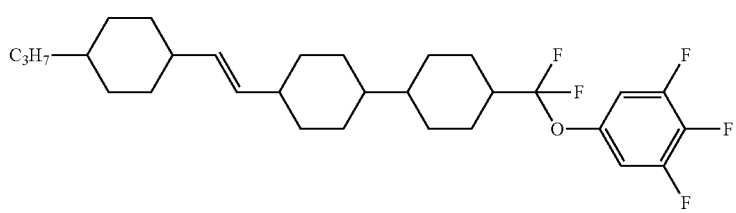 |
| | C 69.6 SB 127.8 N 254.7 I<br>$T_{NI}$ = 195.0° C., $\Delta\epsilon$ = 12.2 $\Delta$n = 0.104, $\eta$ = 59.4 mPa · s |
| 224 | 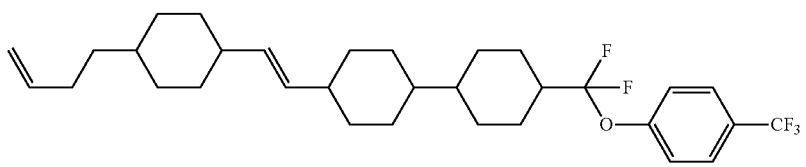 [SMILES: C=CCCC1CCC(/C=C/C2CCC(C3CCC(C(F)(F)Oc4ccc(C(F)(F)F)cc4)CC3)CC2)CC1] |
| 225 | 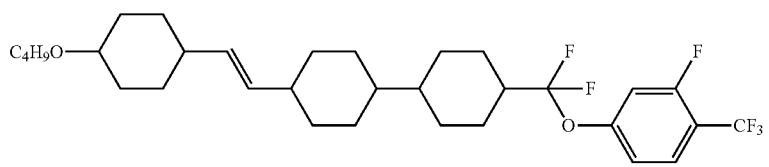 |
| 226 | 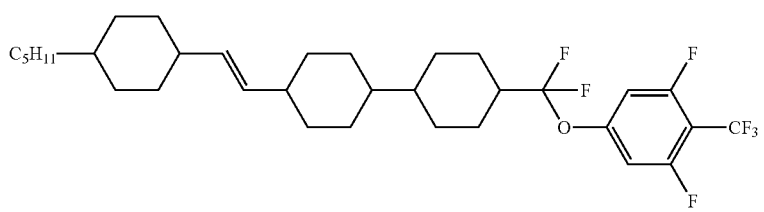 |

| No. | |
|---|---|
| 227 | 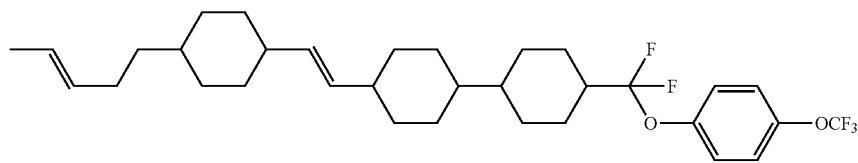 [SMILES: C/C=C/CCC1CCC(/C=C/C2CCC(C3CCC(C(F)(F)Oc4ccc(OC(F)(F)F)cc4)CC3)CC2)CC1] |
| 228 | 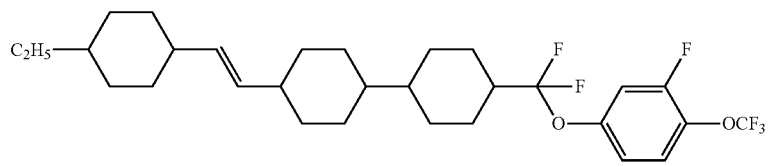 [SMILES: CCC1CCC(/C=C/C2CCC(C3CCC(C(F)(F)Oc4ccc(OC(F)(F)F)c(F)c4)CC3)CC2)CC1] |
| 229 | 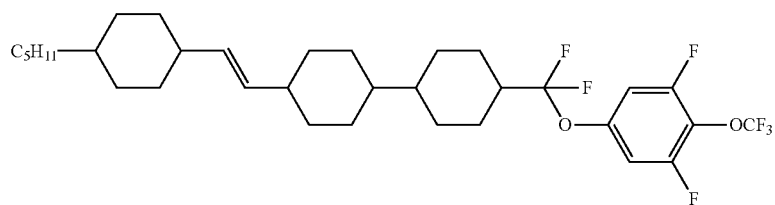 |
| 230 | 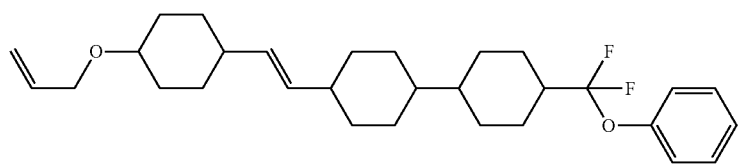 [SMILES: C=CCOC1CCC(/C=C/C2CCC(C3CCC(C(F)(F)Oc4ccccc4)CC3)CC2)CC1] |
| 231 | 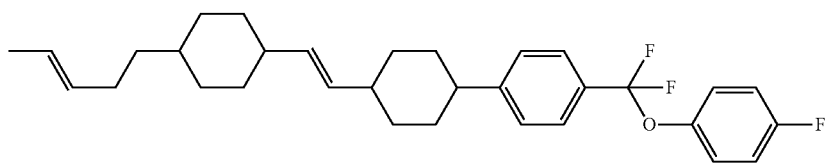 [SMILES: C/C=C/CCC1CCC(/C=C/C2CCC(c3ccc(C(F)(F)Oc4ccc(F)cc4)cc3)CC2)CC1] |
| 232 | 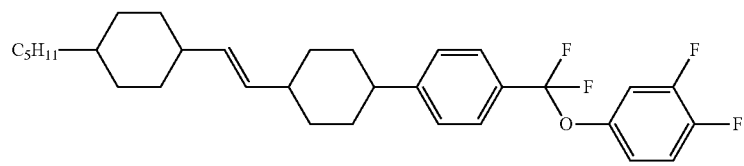 |
| 233 | 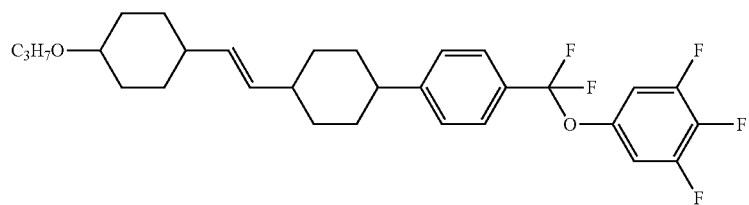 |
| 234 | 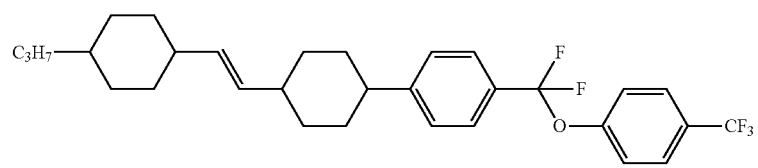 |

-continued
| No. | |
|---|---|
| 235 | 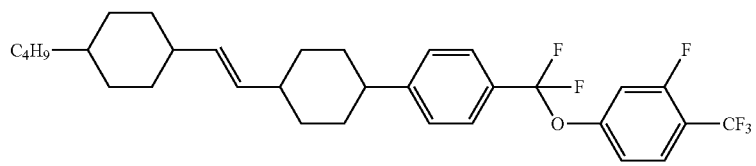 |
| 236 | 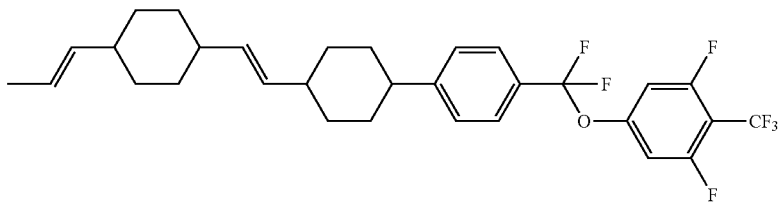 [SMILES: C/C=C/C1CCC(/C=C/C2CCC(c3ccc(C(F)(F)Oc4cc(F)c(C(F)(F)F)c(F)c4)cc3)CC2)CC1] |
| 237 | 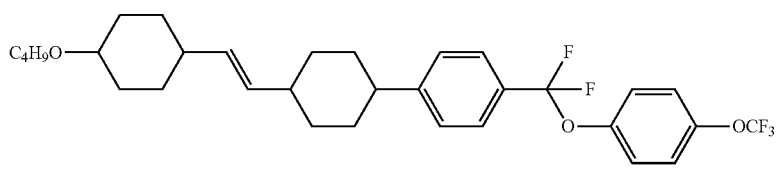 |
| 238 | 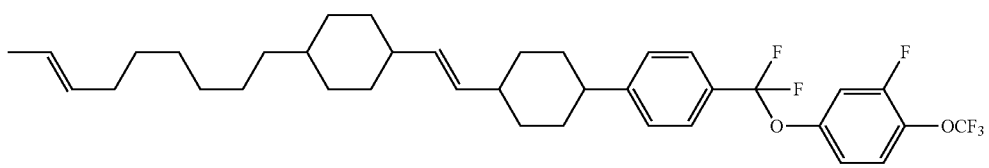 [SMILES: C/C=C/CCCCCCC1CCC(/C=C/C2CCC(c3ccc(C(F)(F)Oc4ccc(OC(F)(F)F)c(F)c4)cc3)CC2)CC1] |
| 239 | 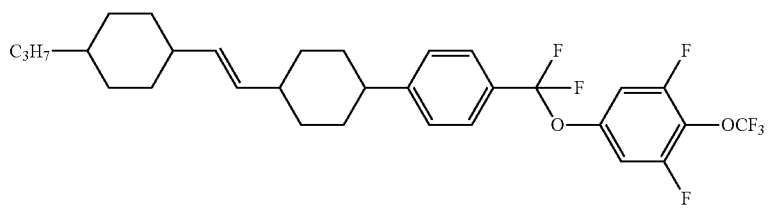 |
| 240 | 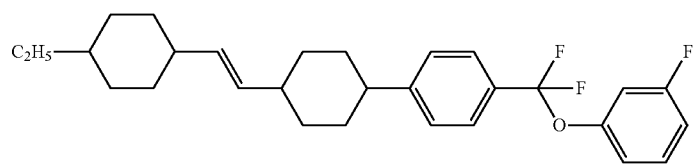 [SMILES: CCC1CCC(/C=C/C2CCC(c3ccc(C(F)(F)Oc4cccc(F)c4)cc3)CC2)CC1] |
| 241 | 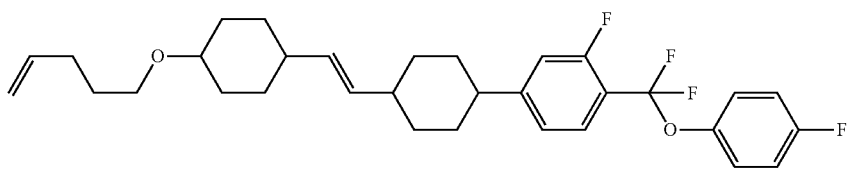 [SMILES: C=CCCCOC1CCC(/C=C/C2CCC(c3ccc(C(F)(F)Oc4ccc(F)cc4)c(F)c3)CC2)CC1] |
| 242 | 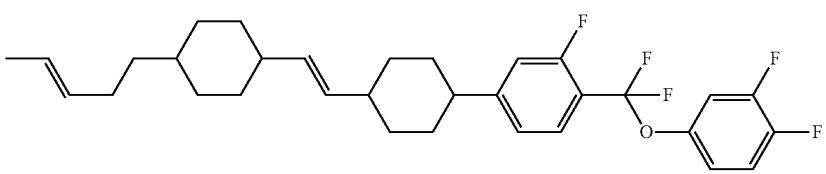 [SMILES: C/C=C/CCC1CCC(/C=C/C2CCC(c3ccc(C(F)(F)Oc4ccc(F)c(F)c4)c(F)c3)CC2)CC1] |

-continued
| No. | |
|---|---|
| 243 | 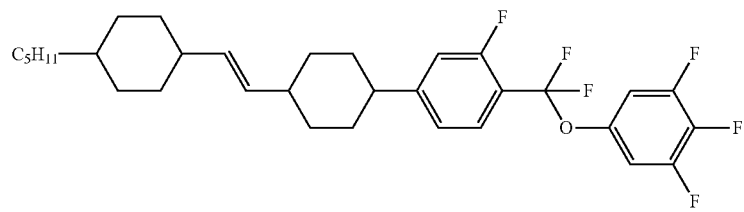 |
| 244 | 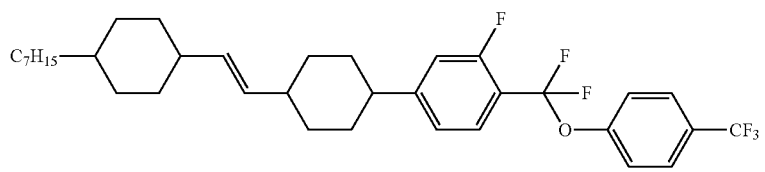 |
| 245 | 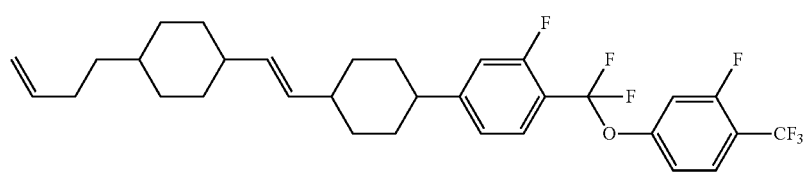 [SMILES: C=CCCC1CCC(/C=C/C2CCC(c3ccc(C(F)(F)Oc4ccc(C(F)(F)F)c(F)c4)c(F)c3)CC2)CC1] |
| 246 | 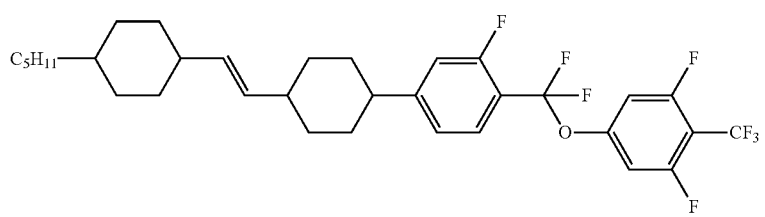 |
| 247 | 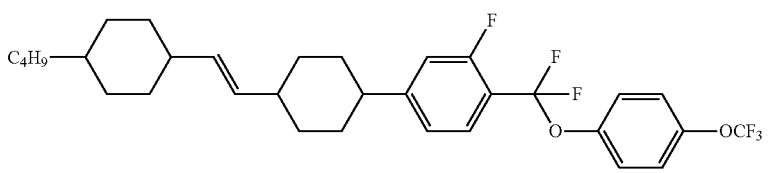 |
| 248 | 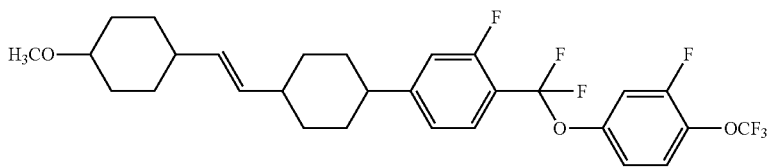 |
| 249 | 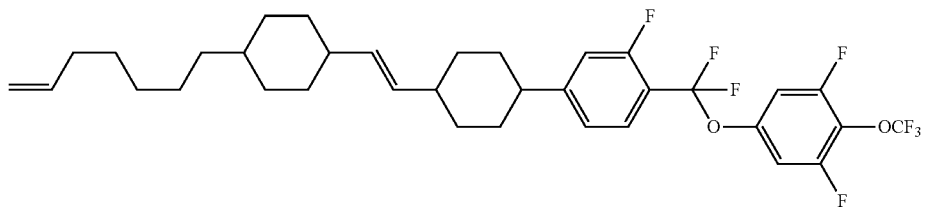 [SMILES: C=CCCCCCC1CCC(/C=C/C2CCC(c3ccc(C(F)(F)Oc4cc(F)c(OC(F)(F)F)c(F)c4)c(F)c3)CC2)CC1] |
| 250 | 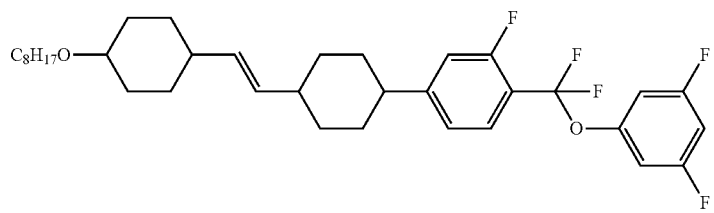 |

-continued
| No. | |
|---|---|
| 251 | 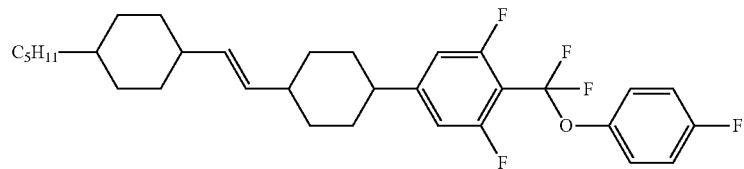 |
| 252 | 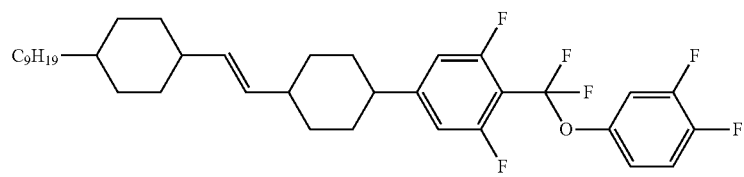 |
| 253 | 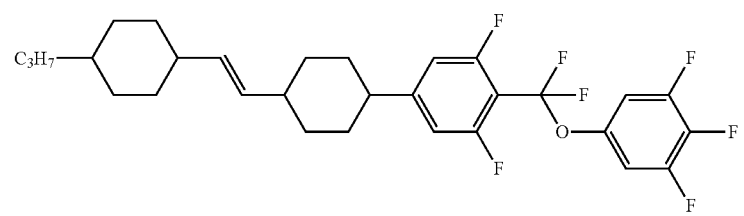 |
| 254 | 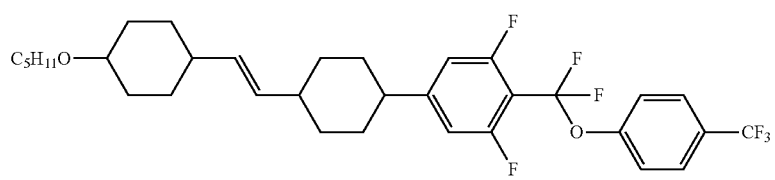 |
| 255 | 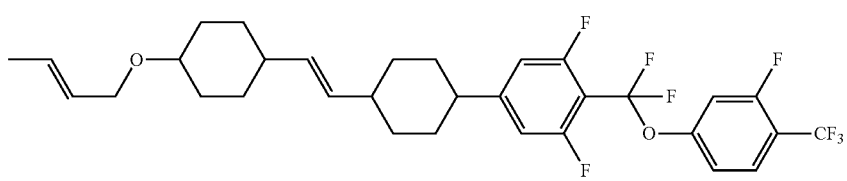 [SMILES: C/C=C/COC1CCC(/C=C/C2CCC(c3cc(F)c(C(F)(F)Oc4ccc(C(F)(F)F)c(F)c4)c(F)c3)CC2)CC1] |
| 256 | 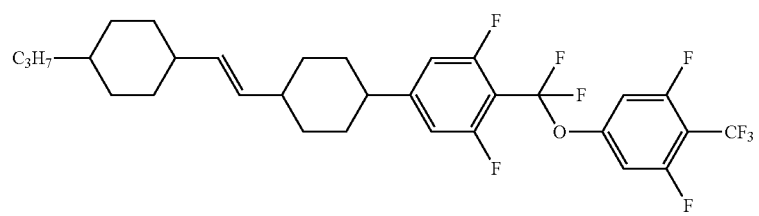 |
| 257 | 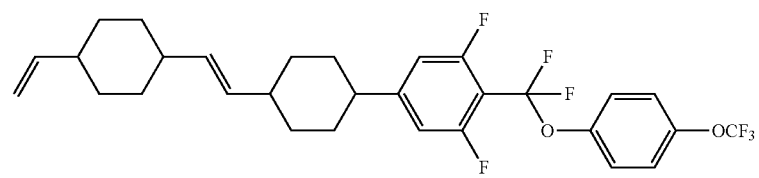 [SMILES: C=CC1CCC(/C=C/C2CCC(c3cc(F)c(C(F)(F)Oc4ccc(OC(F)(F)F)cc4)c(F)c3)CC2)CC1] |
| 258 | 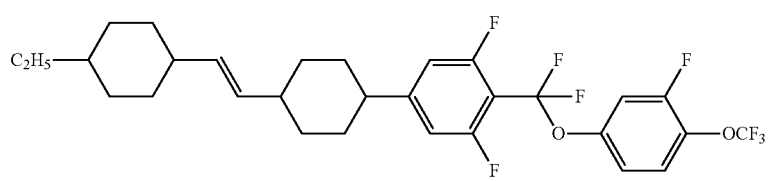 [SMILES: CCC1CCC(/C=C/C2CCC(c3cc(F)c(C(F)(F)Oc4ccc(OC(F)(F)F)c(F)c4)c(F)c3)CC2)CC1] |

| No. | |
|---|---|
| 259 | 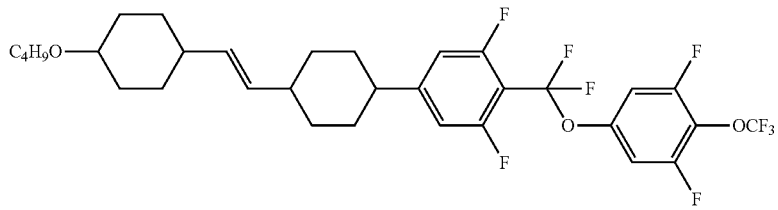 |
| 260 | 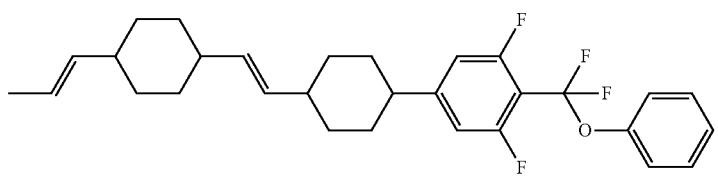 [SMILES: C/C=C/C1CCC(/C=C/C2CCC(c3cc(F)c(C(F)(F)Oc4ccccc4)c(F)c3)CC2)CC1] |
| 261 | 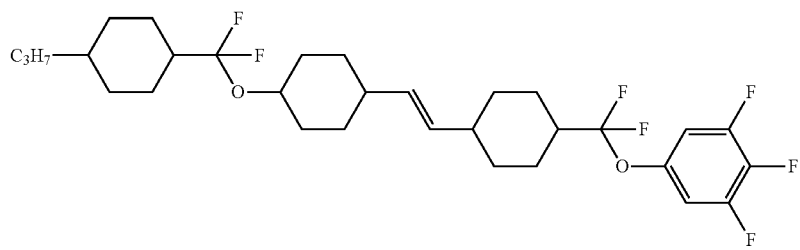 |
| 262 | 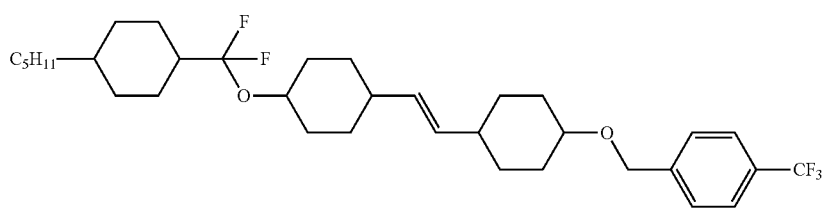 |
| 263 | 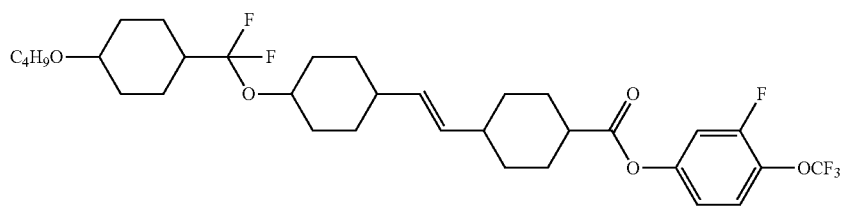 |
| 264 | 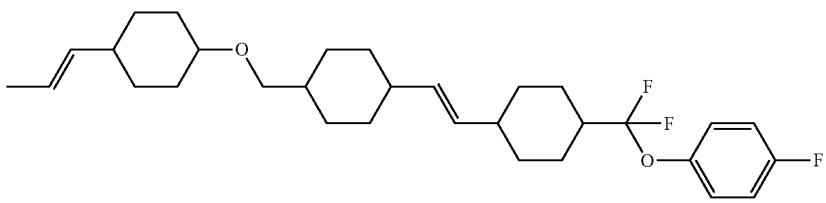 [SMILES: C/C=C/C1CCC(OCC2CCC(/C=C/C3CCC(C(F)(F)Oc4ccc(F)cc4)CC3)CC2)CC1] |
| 265 | 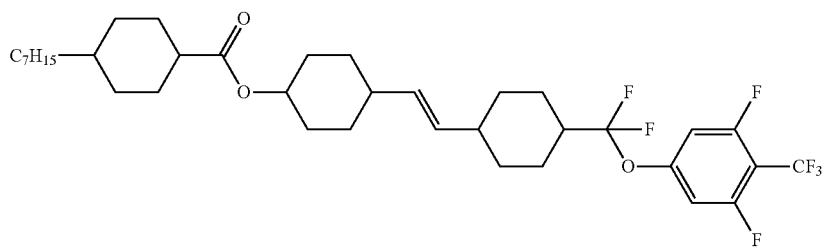 |

-continued
| No. | |
|---|---|
| 266 | 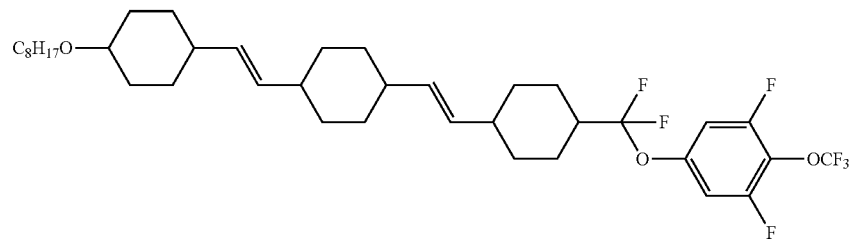 |
| 267 | 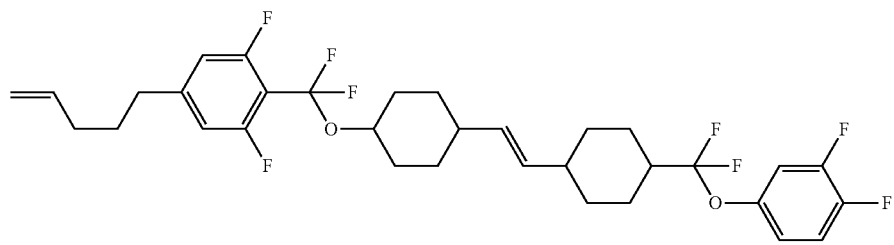 [SMILES: C=CCCCc1cc(F)c(C(F)(F)OC2CCC(/C=C/C3CCC(C(F)(F)Oc4ccc(F)c(F)c4)CC3)CC2)c(F)c1] |
| 268 | 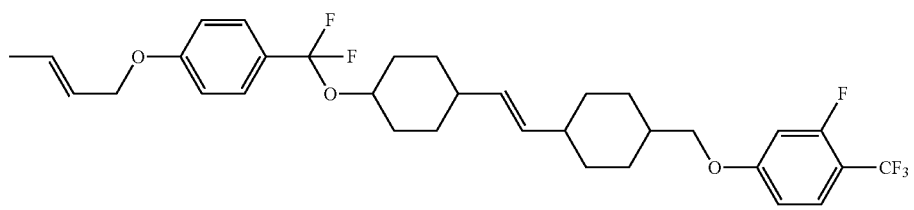 [SMILES: C/C=C/COc1ccc(C(F)(F)OC2CCC(/C=C/C3CCC(COc4ccc(C(F)(F)F)c(F)c4)CC3)CC2)cc1] |
| 269 | 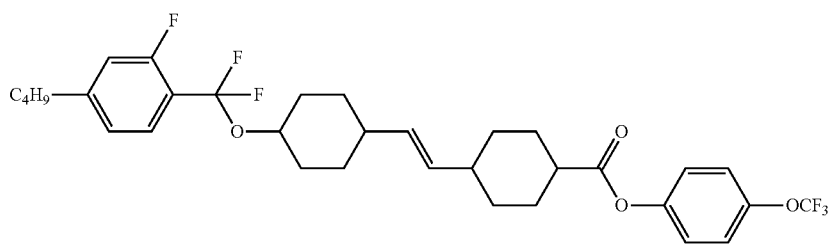 |
| 270 | 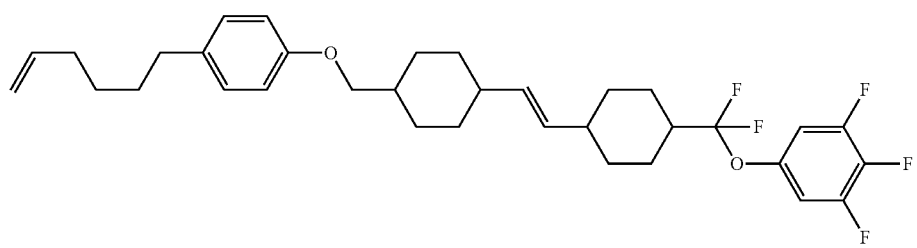 [SMILES: C=CCCCCc1ccc(OCC2CCC(/C=C/C3CCC(C(F)(F)Oc4cc(F)c(F)c(F)c4)CC3)CC2)cc1] |
| 271 | 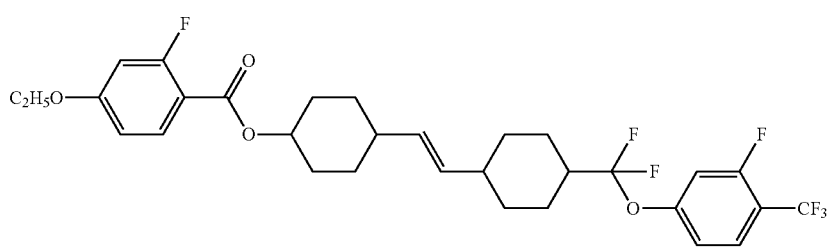 |

| No. | |
|---|---|
| 272 | 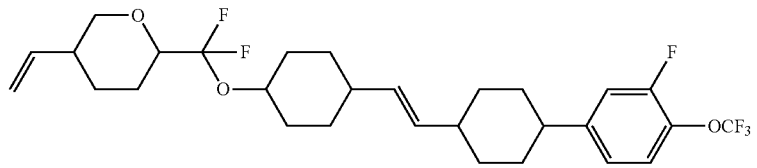 [SMILES: C=CC1CCC(C(F)(F)OC2CCC(/C=C/C3CCC(c4ccc(OC(F)(F)F)c(F)c4)CC3)CC2)OC1] |
| 273 | 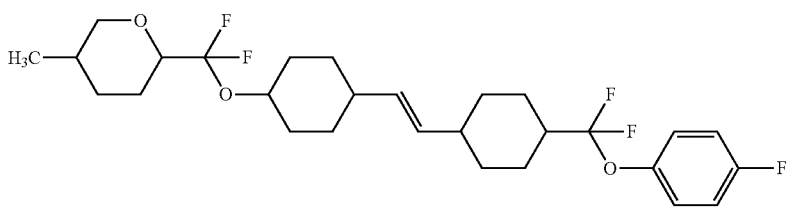 [SMILES: CC1CCC(C(F)(F)OC2CCC(/C=C/C3CCC(C(F)(F)Oc4ccc(F)cc4)CC3)CC2)OC1] |
| 274 | 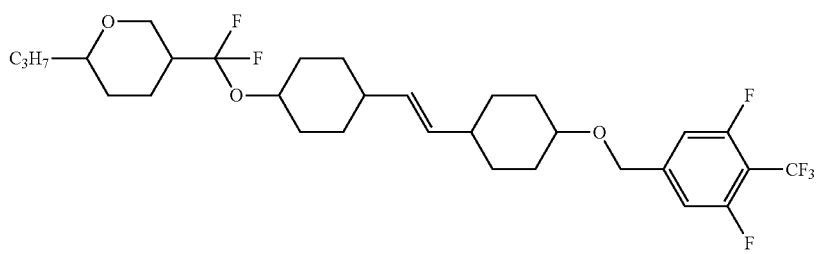 |
| 275 | 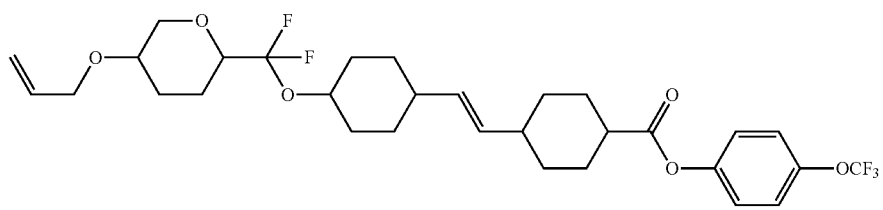 [SMILES: C=CCOC1CCC(C(F)(F)OC2CCC(/C=C/C3CCC(C(=O)Oc4ccc(OC(F)(F)F)cc4)CC3)CC2)OC1] |
| 276 | 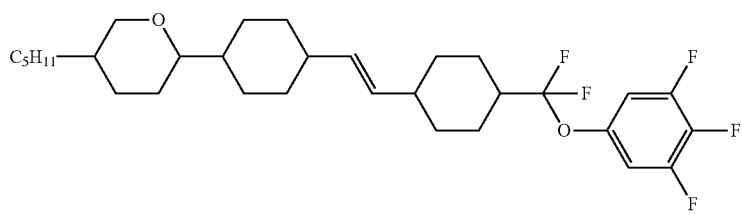 |
| 277 | 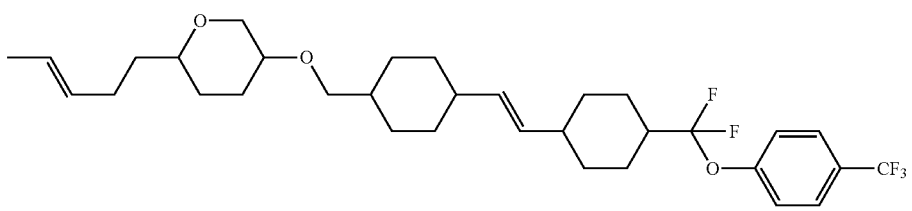 [SMILES: C/C=C/CCC1CCC(OCC2CCC(/C=C/C3CCC(C(F)(F)Oc4ccc(C(F)(F)F)cc4)CC3)CC2)CO1] |
| 278 | 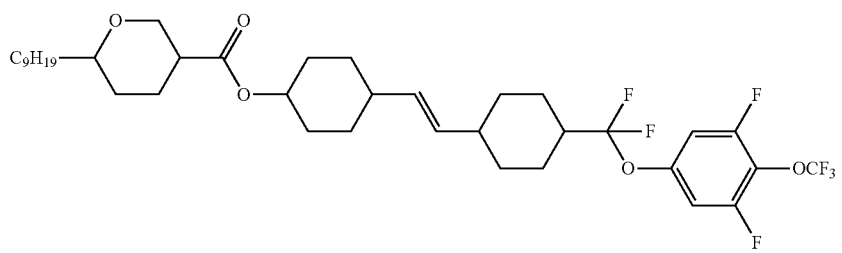 |

-continued
| No. | |
|---|---|
| 279 | 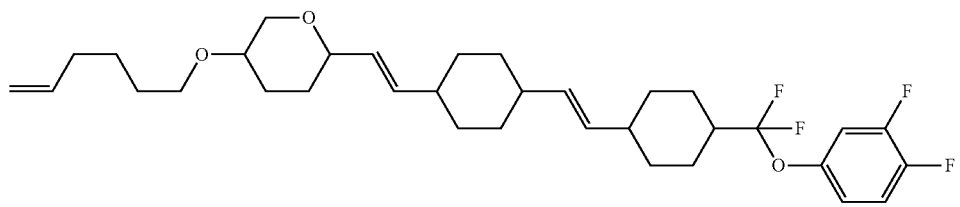 [SMILES: C=CCCCCOC1CCC(/C=C/C2CCC(/C=C/C3CCC(C(F)(F)Oc4ccc(F)c(F)c4)CC3)CC2)OC1] |
| 280 | 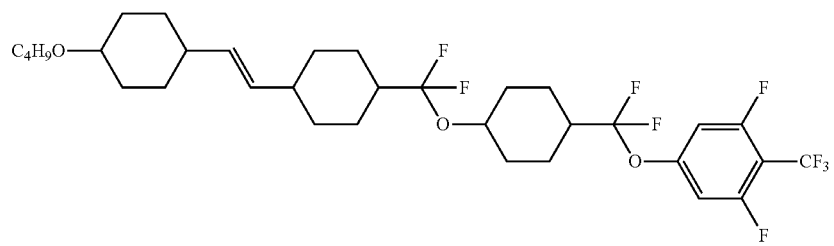 |
| 281 | 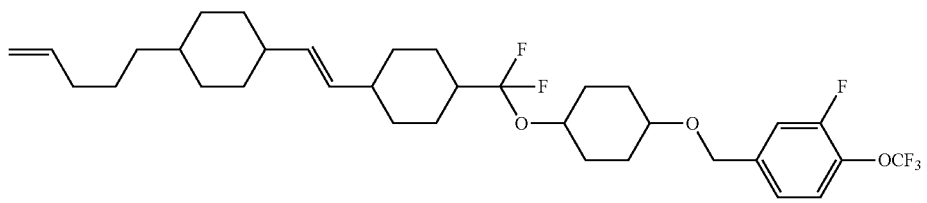 [SMILES: C=CCCCC1CCC(/C=C/C2CCC(C(F)(F)OC3CCC(OCc4ccc(OC(F)(F)F)c(F)c4)CC3)CC2)CC1] |
| 282 | 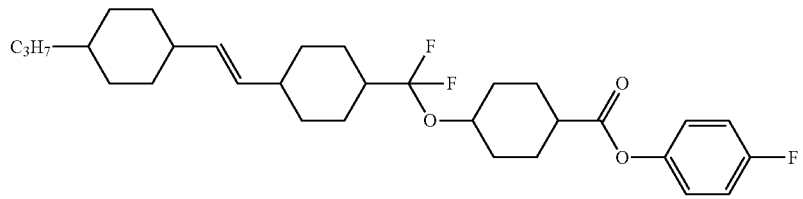 |
| 283 | 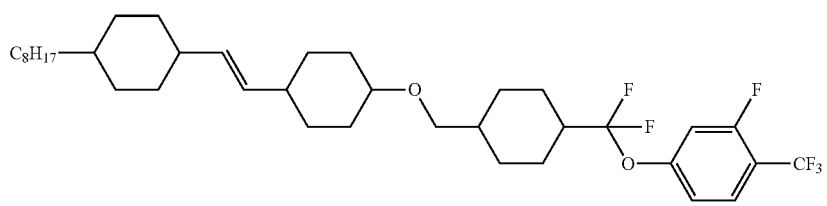 |
| 284 | 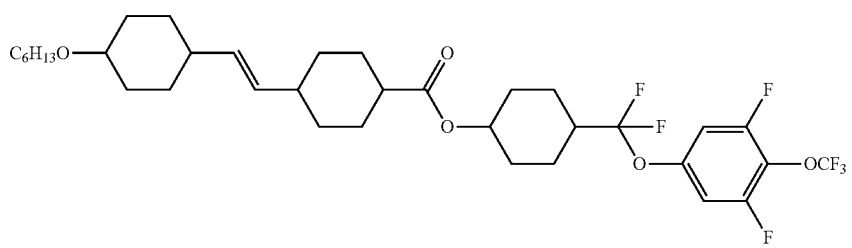 |
| 285 | 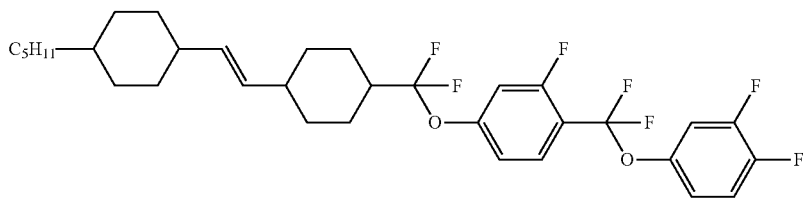 |

| No. | |
|---|---|
| 286 | 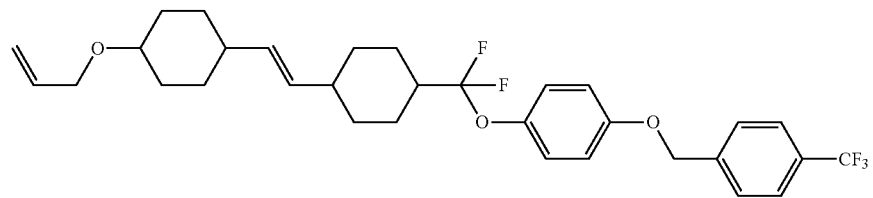 [SMILES: C=CCOC1CCC(/C=C/C2CCC(C(F)(F)Oc3ccc(OCc4ccc(C(F)(F)F)cc4)cc3)CC2)CC1] |
| 287 | 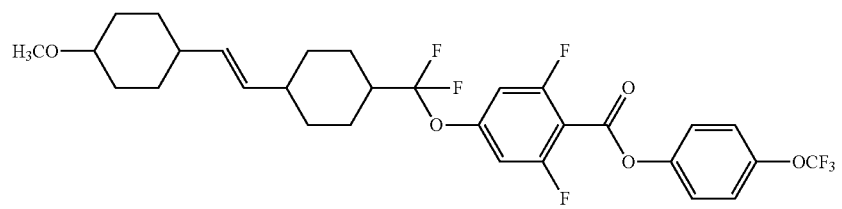 [SMILES: COC1CCC(/C=C/C2CCC(C(F)(F)Oc3cc(F)c(C(=O)Oc4ccc(OC(F)(F)F)cc4)c(F)c3)CC2)CC1] |
| 288 | 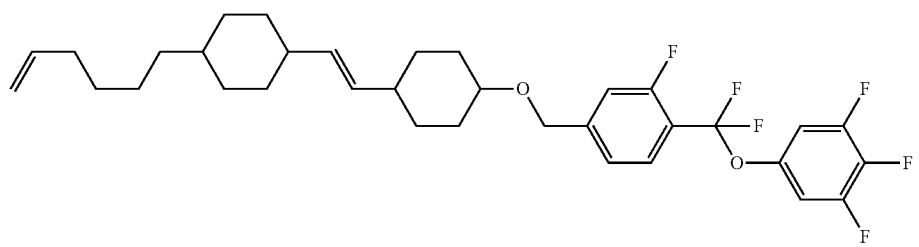 [SMILES: C=CCCCCC1CCC(/C=C/C2CCC(OCc3ccc(C(F)(F)Oc4cc(F)c(F)c(F)c4)c(F)c3)CC2)CC1] |
| 289 | 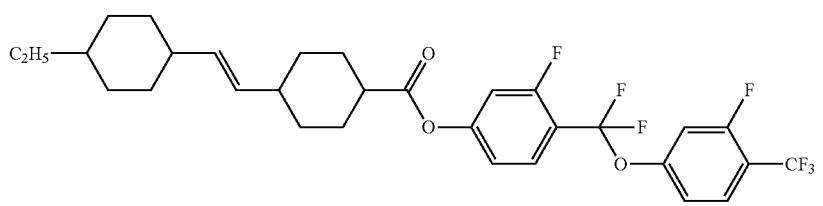 [SMILES: CCC1CCC(/C=C/C2CCC(C(=O)Oc3ccc(C(F)(F)Oc4ccc(C(F)(F)F)c(F)c4)c(F)c3)CC2)CC1] |
| 290 | 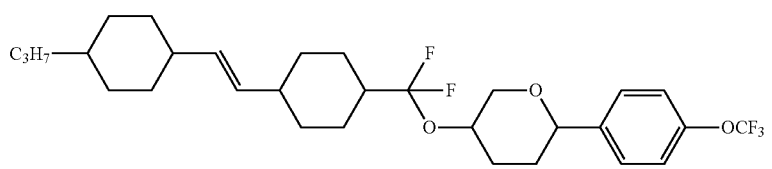 |
| 291 | 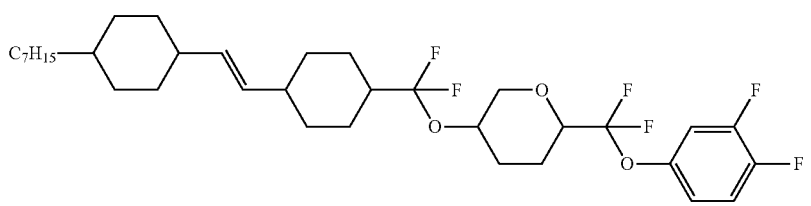 |
| 292 | 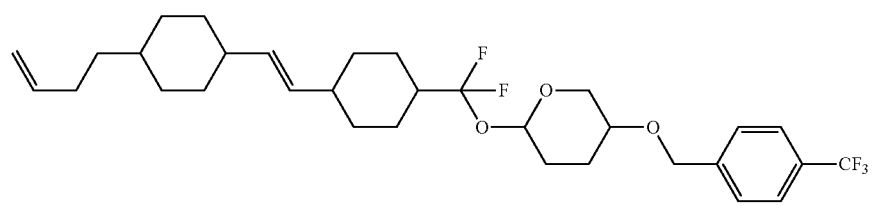 [SMILES: C=CCCC1CCC(/C=C/C2CCC(C(F)(F)OC3CCC(OCc4ccc(C(F)(F)F)cc4)CO3)CC2)CC1] |

| No. |
|---|
| 293 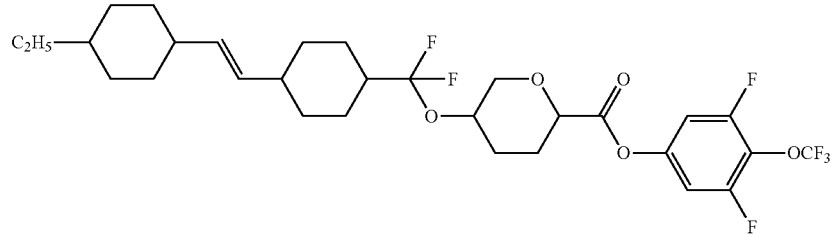 [SMILES: CCC1CCC(/C=C/C2CCC(C(F)(F)OC3CCC(C(=O)Oc4cc(F)c(OC(F)(F)F)c(F)c4)OC3)CC2)CC1] |
| 294 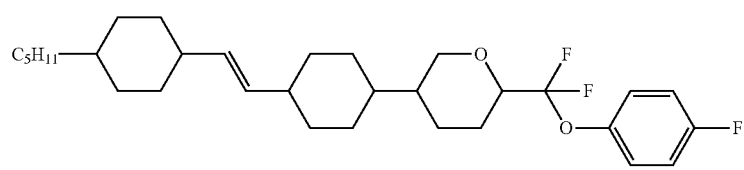 |
| 295 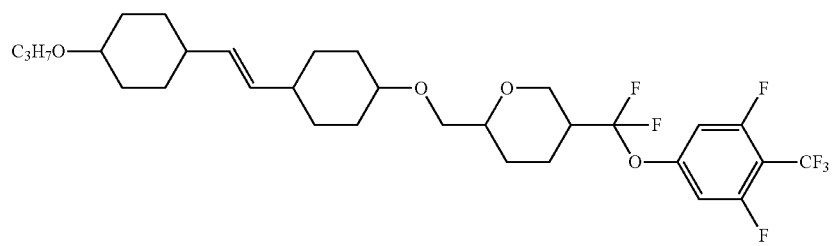 |
| 296 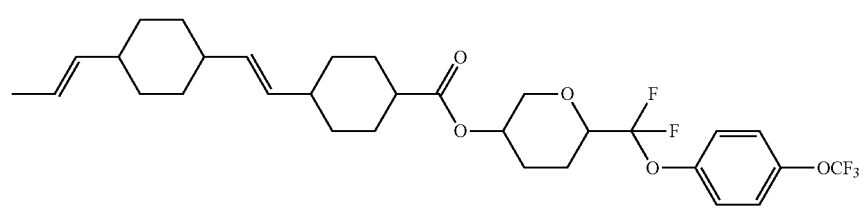 [SMILES: C/C=C/C1CCC(/C=C/C2CCC(C(=O)OC3CCC(C(F)(F)Oc4ccc(OC(F)(F)F)cc4)OC3)CC2)CC1] |
| 297 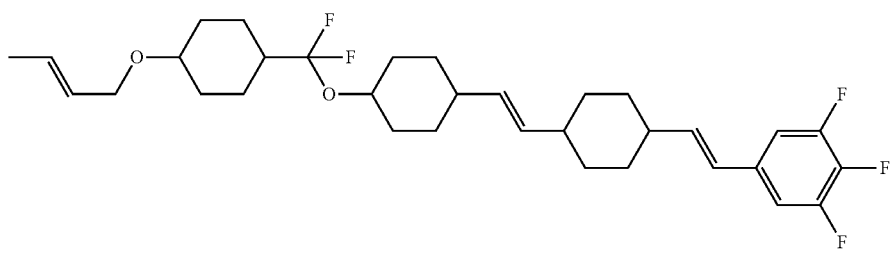 [SMILES: C/C=C/COC1CCC(C(F)(F)OC2CCC(/C=C/C3CCC(/C=C/c4cc(F)c(F)c(F)c4)CC3)CC2)CC1] |
| 298 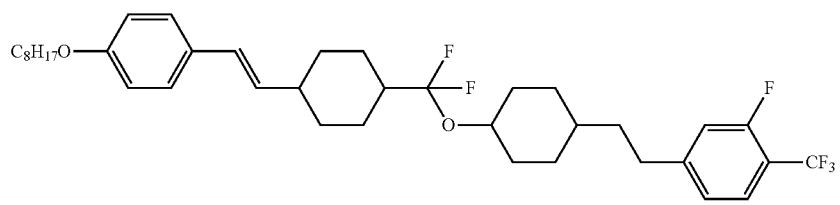 |
| 299 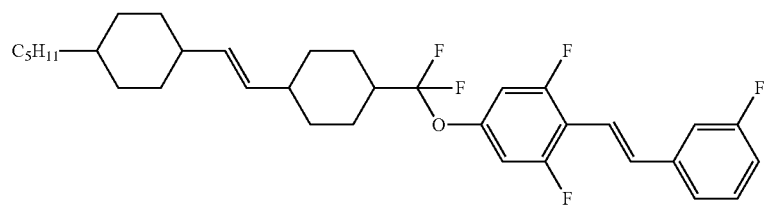 |

| No. |
| --- |
| 300 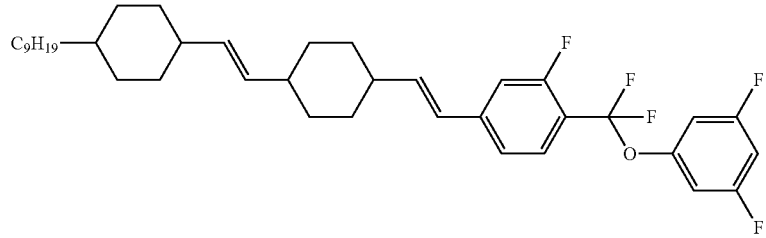 |
| 301 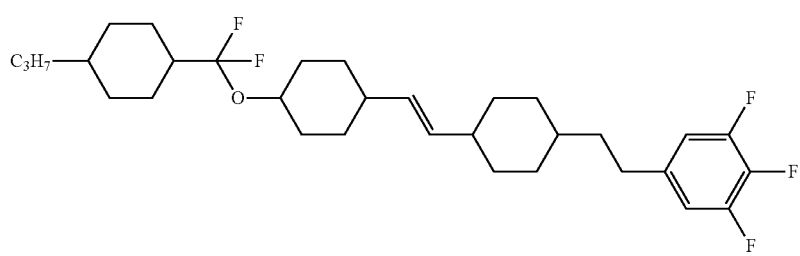 |
| 302 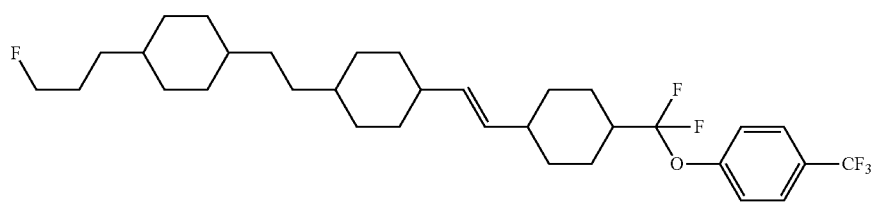 [SMILES: FCCCC1CCC(CCC2CCC(/C=C/C3CCC(C(F)(F)Oc4ccc(C(F)(F)F)cc4)CC3)CC2)CC1] |
| 303 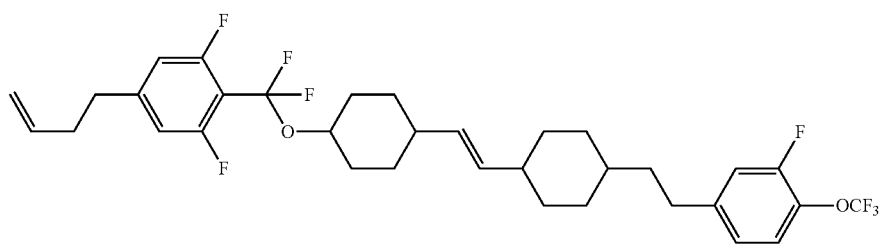 [SMILES: C=CCCc1cc(F)c(C(F)(F)OC2CCC(/C=C/C3CCC(CCc4ccc(OC(F)(F)F)c(F)c4)CC3)CC2)c(F)c1] |
| 304 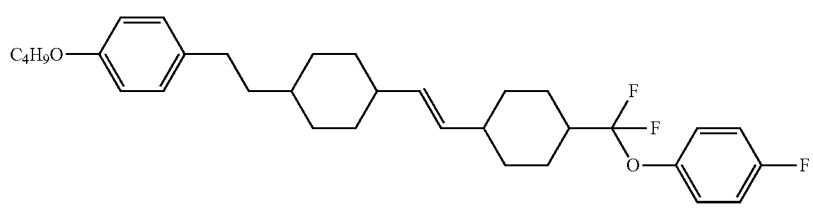 |
| 305 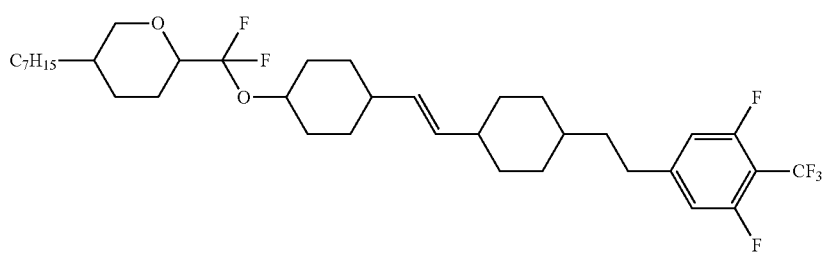 |

-continued
| No. | |
|---|---|
| 306 | 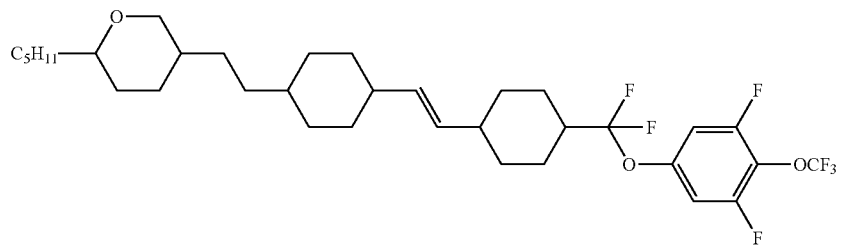 |
| 307 | 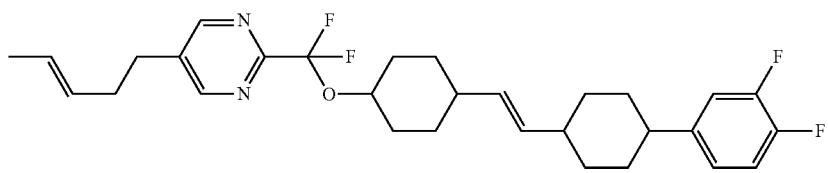 [SMILES: C/C=C/CCc1cnc(C(F)(F)OC2CCC(/C=C/C3CCC(c4ccc(F)c(F)c4)CC3)CC2)nc1] |
| 308 | 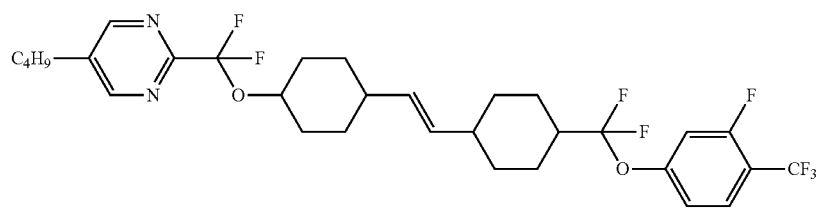 |
| 309 | 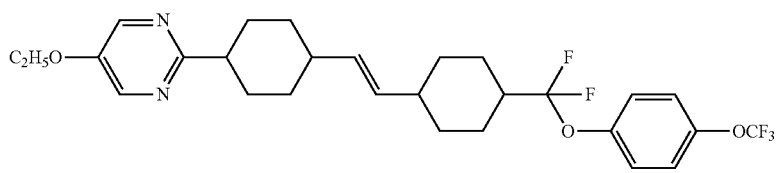 |
| 310 | 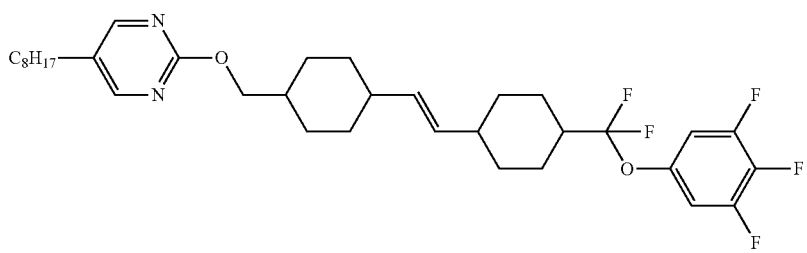 |
| 311 | 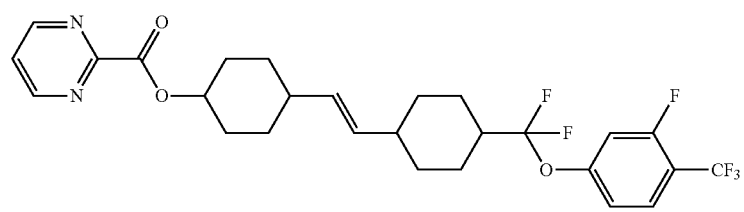 [SMILES: O=C(OC1CCC(/C=C/C2CCC(C(F)(F)Oc3ccc(C(F)(F)F)c(F)c3)CC2)CC1)c1ncccn1] |
| 312 | 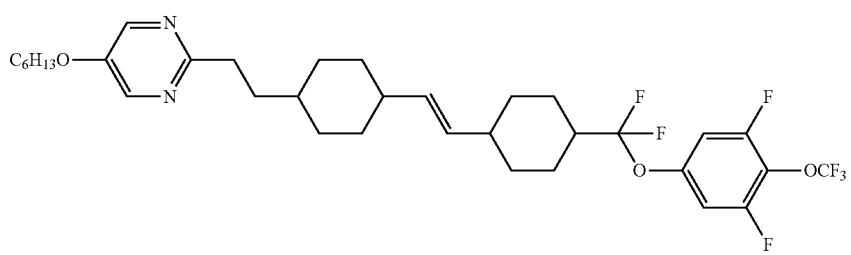 |

| No. | |
|---|---|
| 313 | 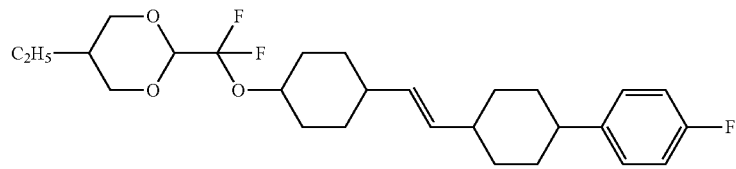 |
| 314 | 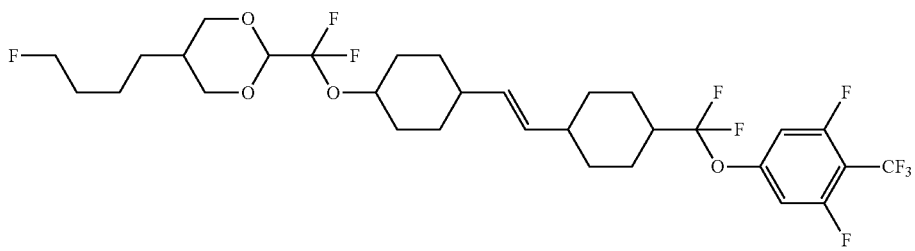 [SMILES: FCCCCC1COC(C(F)(F)OC2CCC(/C=C/C3CCC(C(F)(F)Oc4cc(F)c(C(F)(F)F)c(F)c4)CC3)CC2)OC1] |
| 315 | 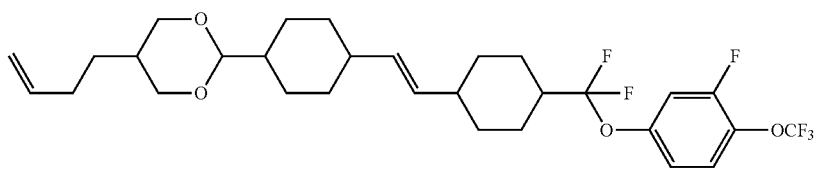 [SMILES: C=CCCC1COC(C2CCC(/C=C/C3CCC(C(F)(F)Oc4ccc(OC(F)(F)F)c(F)c4)CC3)CC2)OC1] |
| 316 | 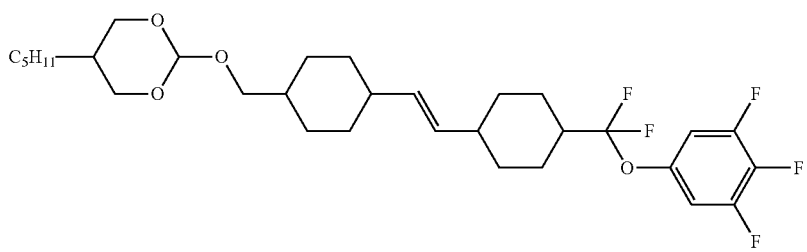 |
| 317 | 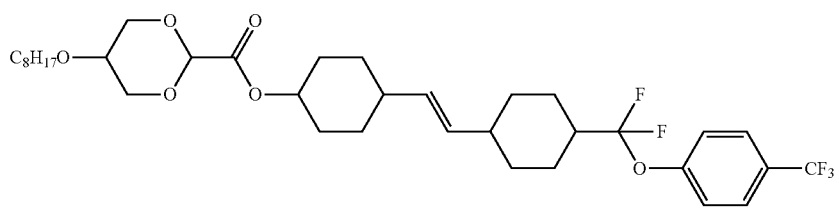 |
| 318 | 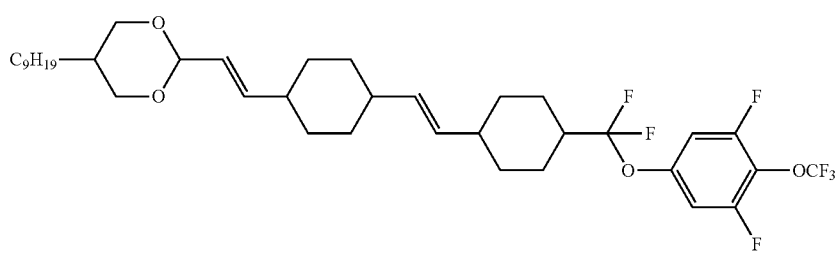 |
| 319 | 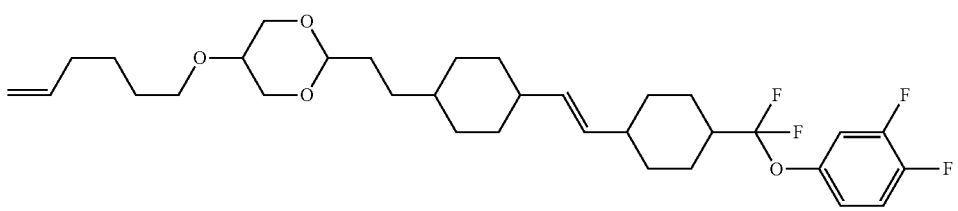 [SMILES: C=CCCCCOC1COC(CCC2CCC(/C=C/C3CCC(C(F)(F)Oc4ccc(F)c(F)c4)CC3)CC2)OC1] |

| No. | |
|---|---|
| 320 | 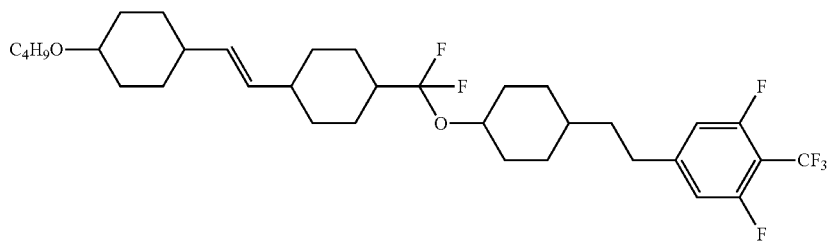 |
| 321 | 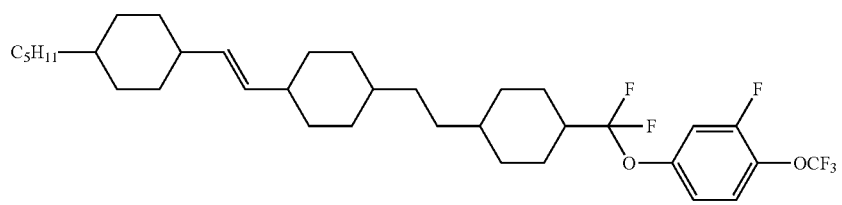 |
| 322 | 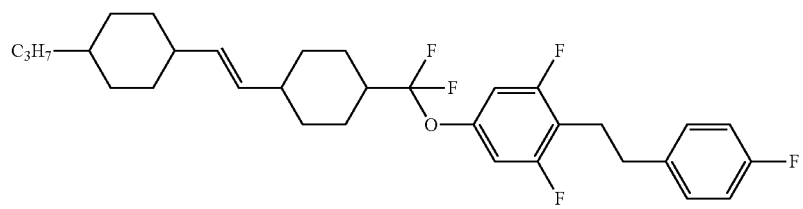 |
| 323 | 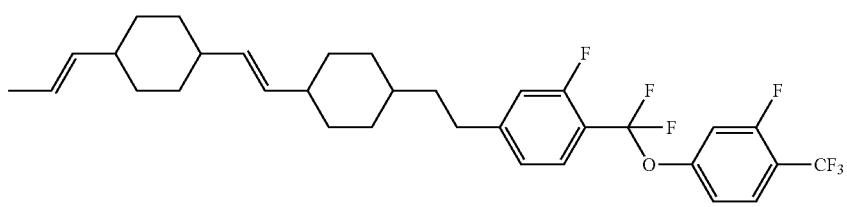 [SMILES: C/C=C/C1CCC(/C=C/C2CCC(CCc3ccc(C(F)(F)Oc4ccc(C(F)(F)F)c(F)c4)c(F)c3)CC2)CC1] |
| 324 | 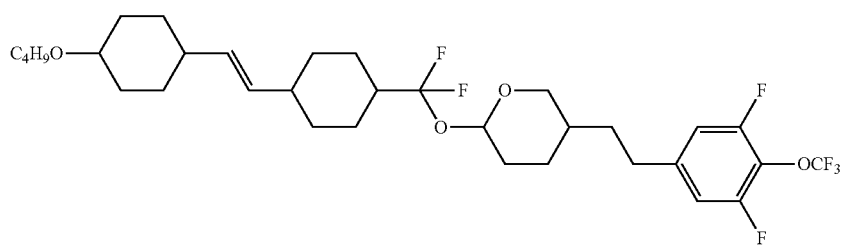 |
| 325 | 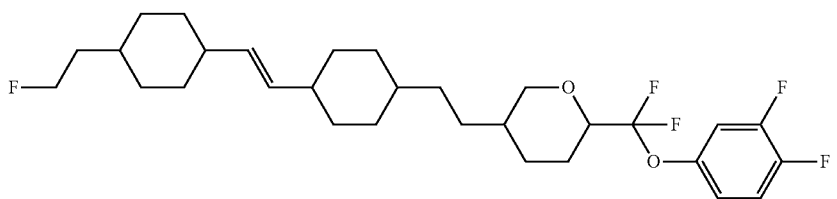 [SMILES: FCCC1CCC(/C=C/C2CCC(CCC3CCC(C(F)(F)Oc4ccc(F)c(F)c4)OC3)CC2)CC1] |
| 326 | 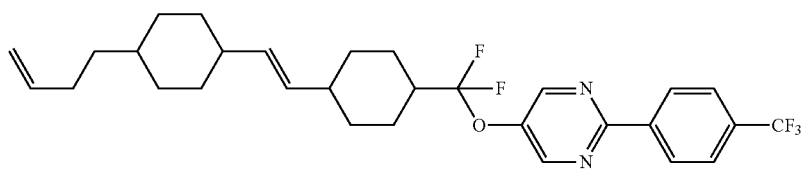 [SMILES: C=CCCC1CCC(/C=C/C2CCC(C(F)(F)Oc3cnc(-c4ccc(C(F)(F)F)cc4)nc3)CC2)CC1] |

| No. | |
|---|---|
| 327 | 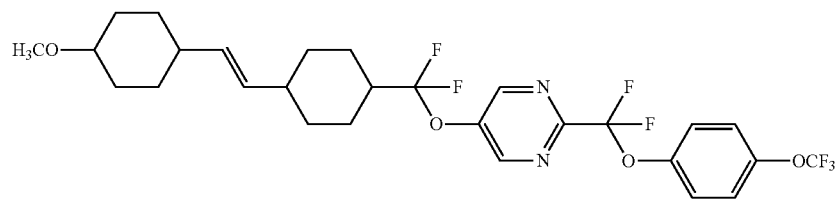 [SMILES: COC1CCC(/C=C/C2CCC(C(F)(F)Oc3cnc(C(F)(F)Oc4ccc(OC(F)(F)F)cc4)nc3)CC2)CC1] |
| 328 | 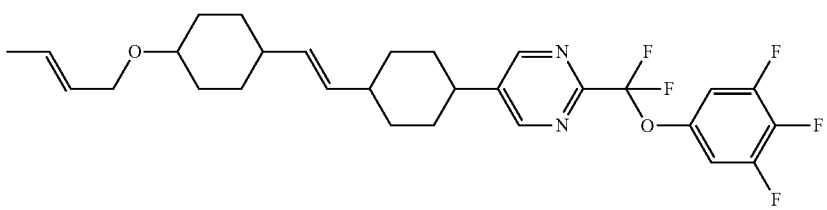 [SMILES: C/C=C/COC1CCC(/C=C/C2CCC(c3cnc(C(F)(F)Oc4cc(F)c(F)c(F)c4)nc3)CC2)CC1] |
| 329 | 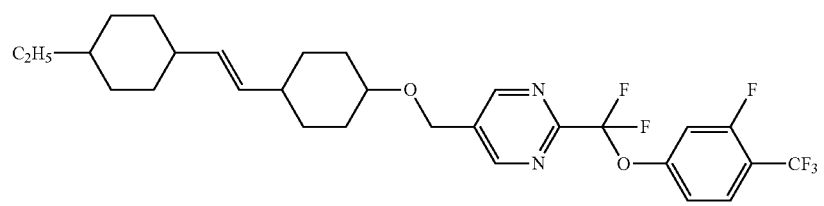 [SMILES: CCC1CCC(/C=C/C2CCC(OCc3cnc(C(F)(F)Oc4ccc(C(F)(F)F)c(F)c4)nc3)CC2)CC1] |
| 330 | 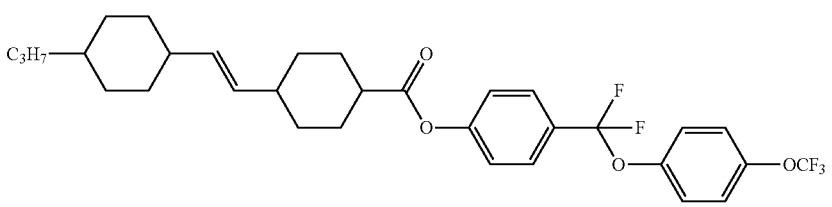 |
| 331 | 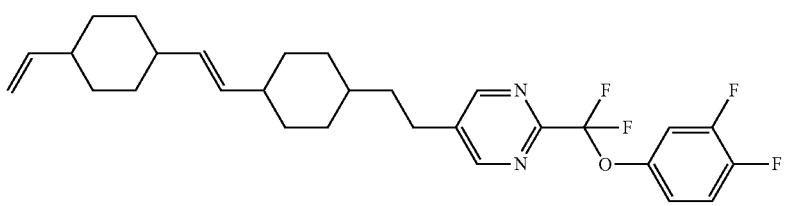 [SMILES: C=CC1CCC(/C=C/C2CCC(CCc3cnc(C(F)(F)Oc4ccc(F)c(F)c4)nc3)CC2)CC1] |
| 332 | 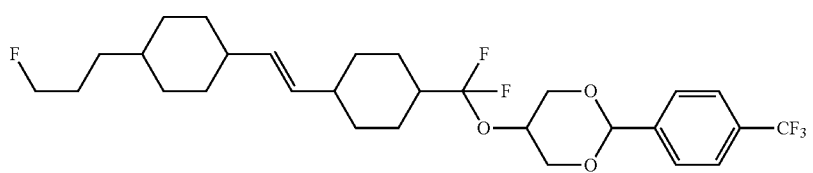 [SMILES: FCCCC1CCC(/C=C/C2CCC(C(F)(F)OC3COC(c4ccc(C(F)(F)F)cc4)OC3)CC2)CC1] |
| 333 | 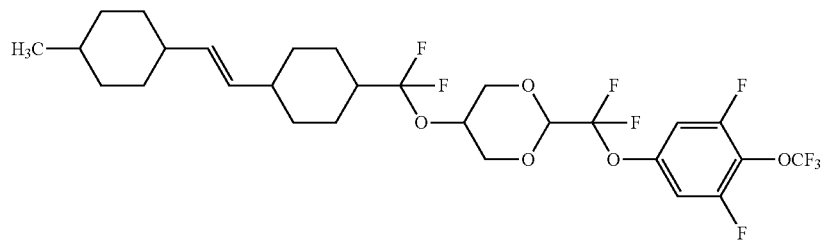 [SMILES: CC1CCC(/C=C/C2CCC(C(F)(F)OC3COC(C(F)(F)Oc4cc(F)c(OC(F)(F)F)c(F)c4)OC3)CC2)CC1] |

US 10,155,905 B2
185 186
-continued
| No. | |
|---|---|
| 334 | 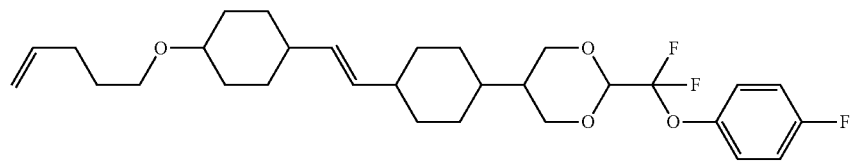 [SMILES: C=CCCCOC1CCC(/C=C/C2CCC(C3COC(C(F)(F)Oc4ccc(F)cc4)OC3)CC2)CC1] |
| 335 | 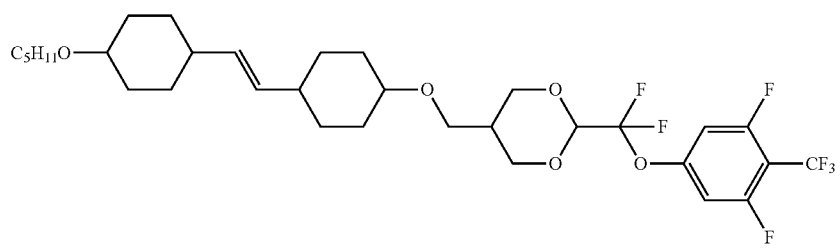 |
| 336 | 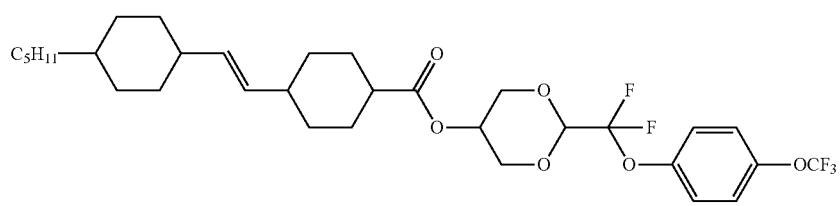 |
| 337 | 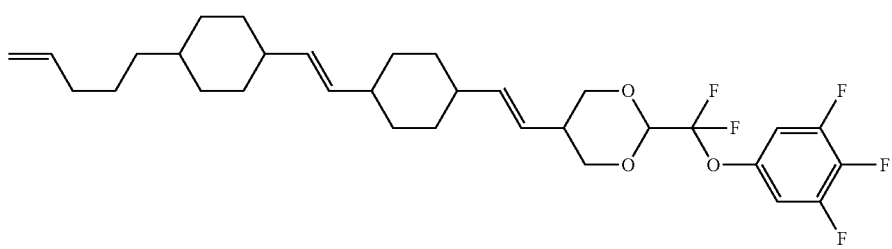 [SMILES: C=CCCCC1CCC(/C=C/C2CCC(/C=C/C3COC(C(F)(F)Oc4cc(F)c(F)c(F)c4)OC3)CC2)CC1] |
| 338 | 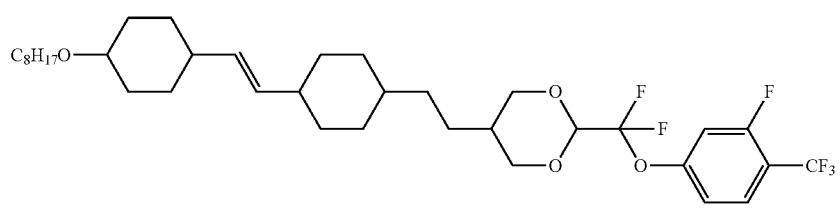 |
| 339 | 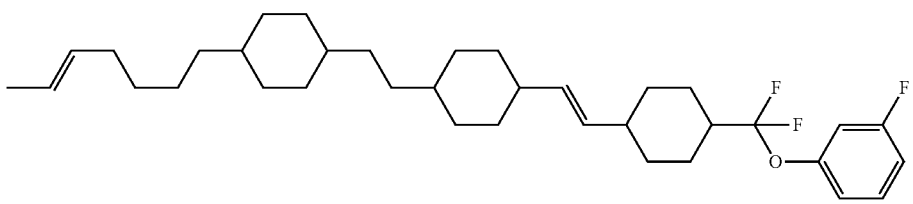 [SMILES: C/C=C/CCCCC1CCC(CCC2CCC(/C=C/C3CCC(C(F)(F)Oc4cccc(F)c4)CC3)CC2)CC1] |
| 340 | 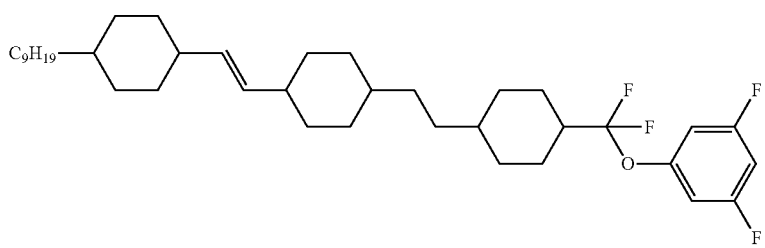 |

| No. | |
|---|---|
| 341 | 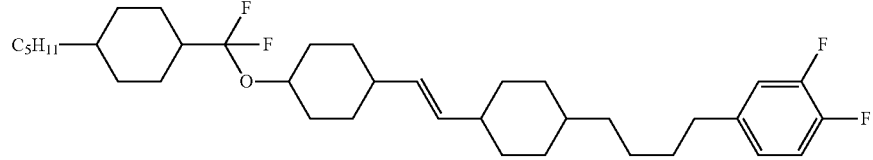 |
| 342 | 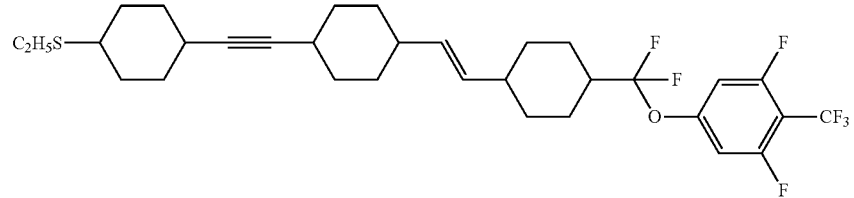 |
| 343 | 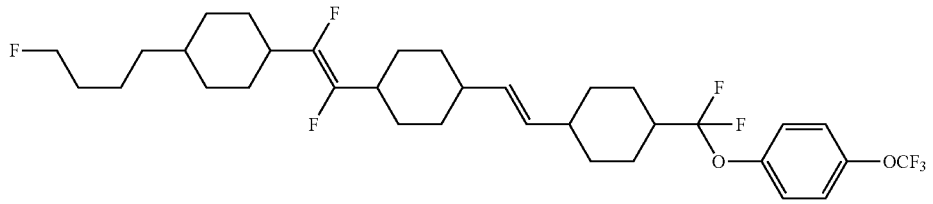 [SMILES: FCCCCC1CCC(/C(F)=C(\F)C2CCC(/C=C/C3CCC(C(F)(F)Oc4ccc(OC(F)(F)F)cc4)CC3)CC2)CC1] |
| 344 | 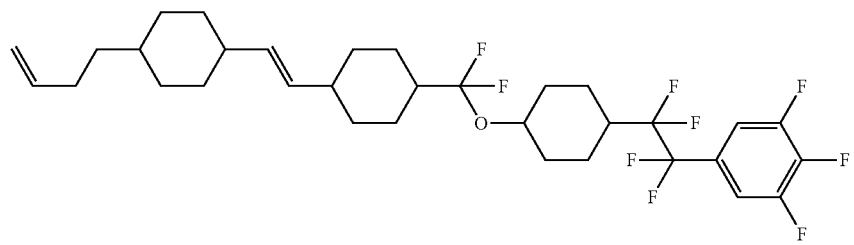 [SMILES: C=CCCC1CCC(/C=C/C2CCC(C(F)(F)OC3CCC(C(F)(F)C(F)(F)c4cc(F)c(F)c(F)c4)CC3)CC2)CC1] |
| 345 | 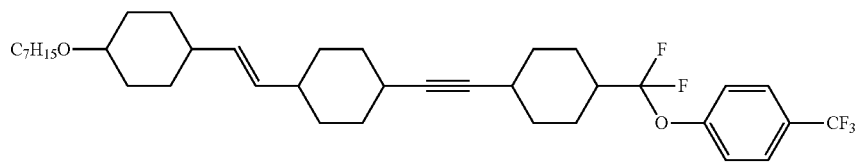 |
| 346 | 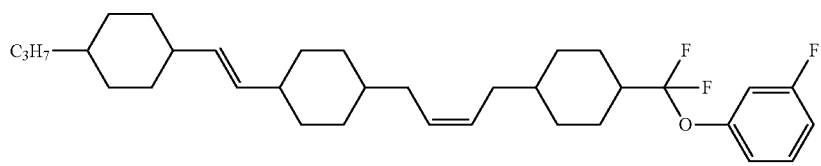 |
| 347 | 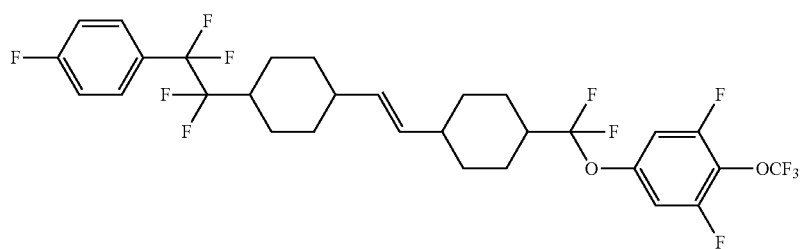 [SMILES: Fc1ccc(C(F)(F)C(F)(F)C2CCC(/C=C/C3CCC(C(F)(F)Oc4cc(F)c(OC(F)(F)F)c(F)c4)CC3)CC2)cc1] |

-continued
| No. | |
|---|---|
| 348 | 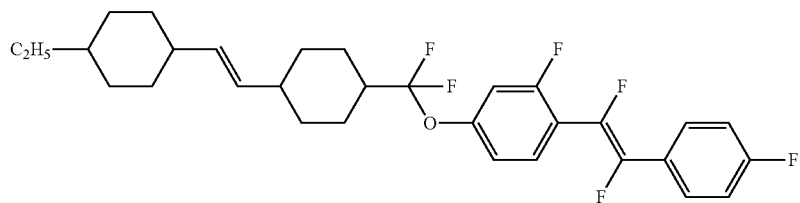 [SMILES: CCC1CCC(/C=C/C2CCC(C(F)(F)Oc3ccc(/C(F)=C(\F)c4ccc(F)cc4)c(F)c3)CC2)CC1] |
| 349 | 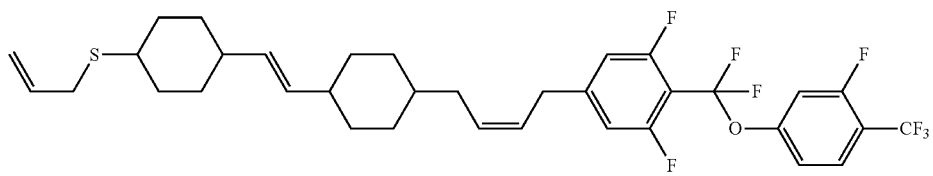 |
| 350 | 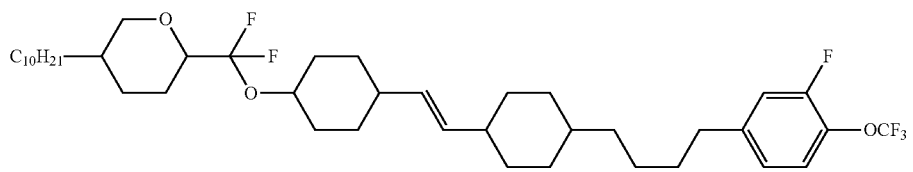 |
| 351 | 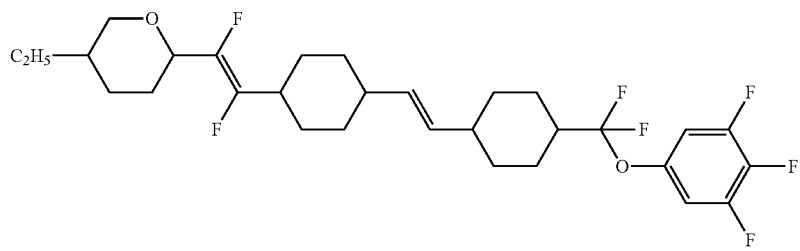 [SMILES: CCC1CCC(/C(F)=C(\F)C2CCC(/C=C/C3CCC(C(F)(F)Oc4cc(F)c(F)c(F)c4)CC3)CC2)OC1] |
| 352 | 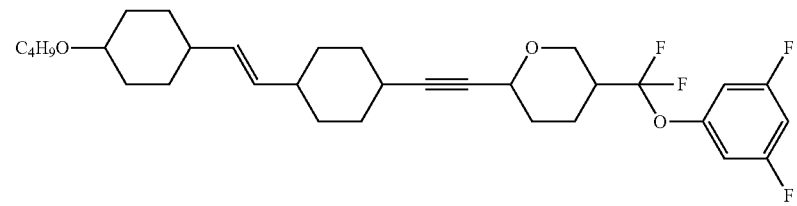 |
| 353 | 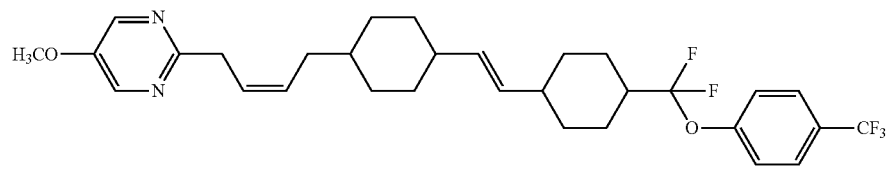 [SMILES: COc1cnc(C/C=C\CC2CCC(/C=C/C3CCC(C(F)(F)Oc4ccc(C(F)(F)F)cc4)CC3)CC2)nc1] |
| 354 | 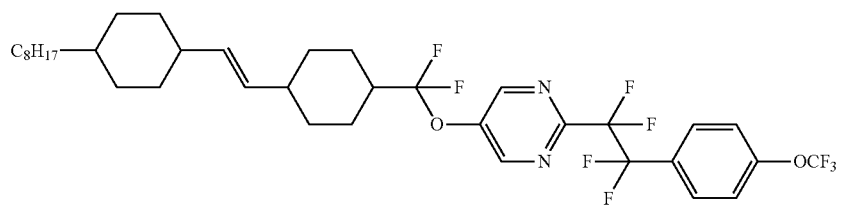 |
| 355 | 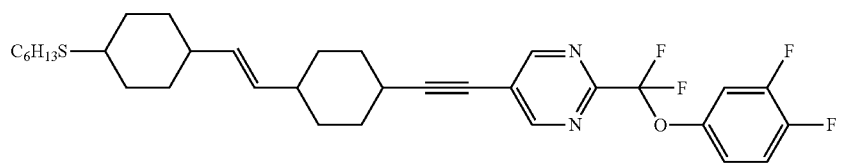 |

| No. | |
|---|---|
| 356 | 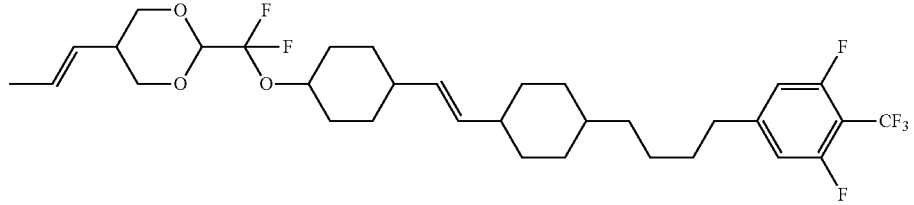 [SMILES: C/C=C/C1COC(C(F)(F)OC2CCC(/C=C/C3CCC(CCCCc4cc(F)c(C(F)(F)F)c(F)c4)CC3)CC2)OC1] |
| 357 | 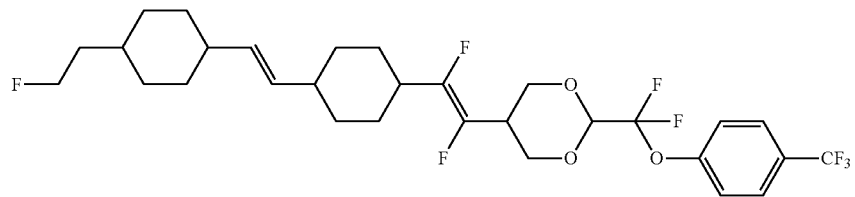 [SMILES: FCCC1CCC(/C=C/C2CCC(/C(F)=C(\F)C3COC(C(F)(F)Oc4ccc(C(F)(F)F)cc4)OC3)CC2)CC1] |
| 358 | 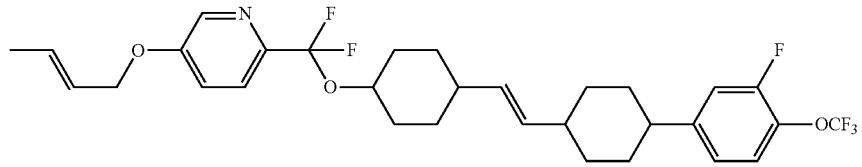 [SMILES: C/C=C/COc1ccc(C(F)(F)OC2CCC(/C=C/C3CCC(c4ccc(OC(F)(F)F)c(F)c4)CC3)CC2)nc1] |
| 359 | 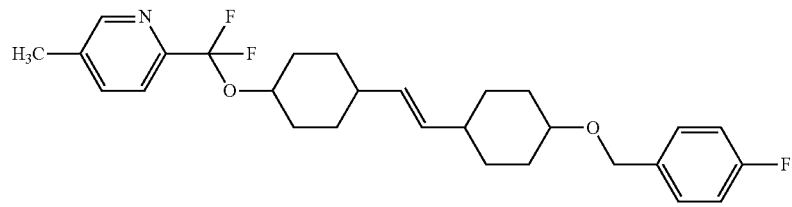 [SMILES: Cc1ccc(C(F)(F)OC2CCC(/C=C/C3CCC(OCc4ccc(F)cc4)CC3)CC2)nc1] |
| 360 | 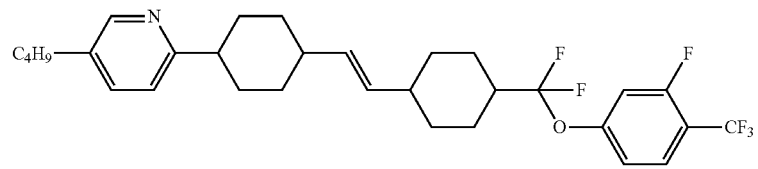 |
| 361 | 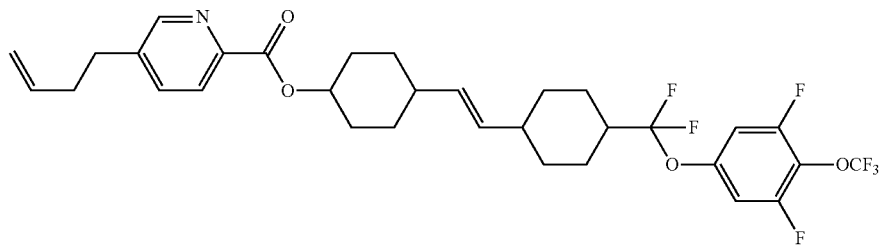 [SMILES: C=CCCc1ccc(C(=O)OC2CCC(/C=C/C3CCC(C(F)(F)Oc4cc(F)c(OC(F)(F)F)c(F)c4)CC3)CC2)nc1] |
| 362 | 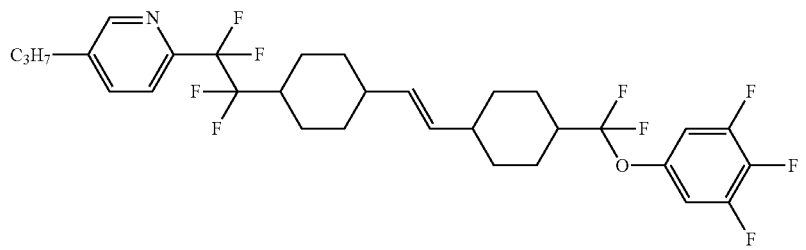 |

-continued
| No. | |
|---|---|
| 363 | 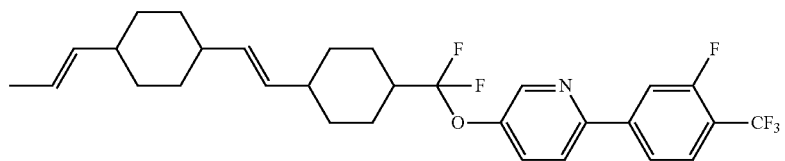 [SMILES: C/C=C/C1CCC(/C=C/C2CCC(C(F)(F)Oc3ccc(-c4ccc(C(F)(F)F)c(F)c4)nc3)CC2)CC1] |
| 364 | 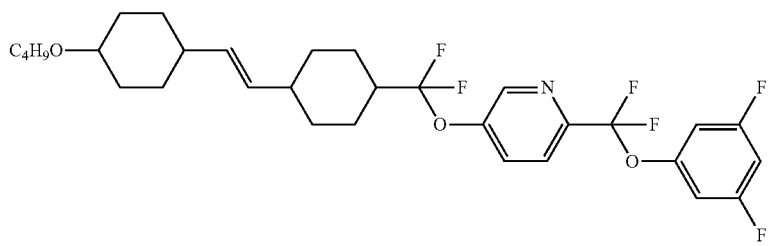 |
| 365 | 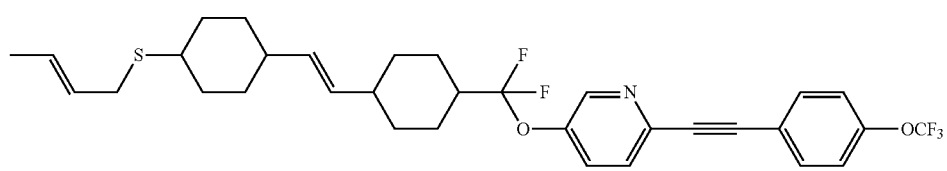 [SMILES: C/C=C/CSC1CCC(/C=C/C2CCC(C(F)(F)Oc3ccc(C#Cc4ccc(OC(F)(F)F)cc4)nc3)CC2)CC1] |
| 366 | 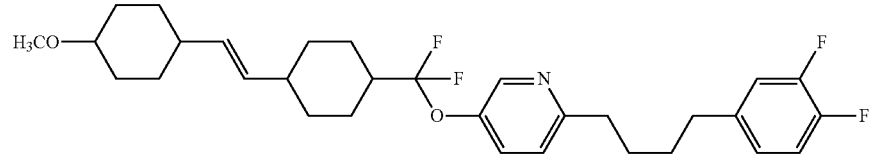 [SMILES: COC1CCC(/C=C/C2CCC(C(F)(F)Oc3ccc(CCCCc4ccc(F)c(F)c4)nc3)CC2)CC1] |
| 367 | 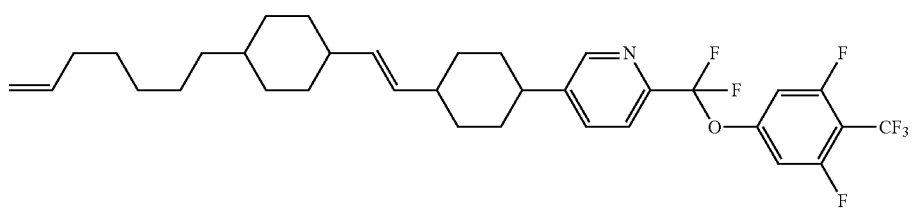 [SMILES: C=CCCCCCC1CCC(/C=C/C2CCC(c3ccc(C(F)(F)Oc4cc(F)c(C(F)(F)F)c(F)c4)nc3)CC2)CC1] |
| 368 | 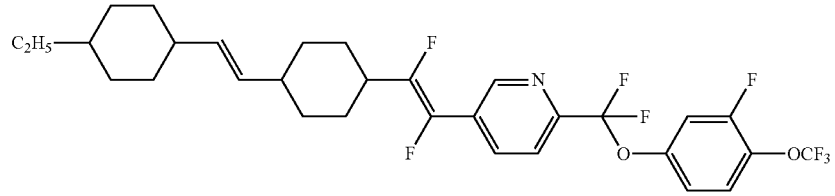 [SMILES: CCC1CCC(/C=C/C2CCC(/C(F)=C(\F)c3ccc(C(F)(F)Oc4ccc(OC(F)(F)F)c(F)c4)nc3)CC2)CC1] |
| 369 | 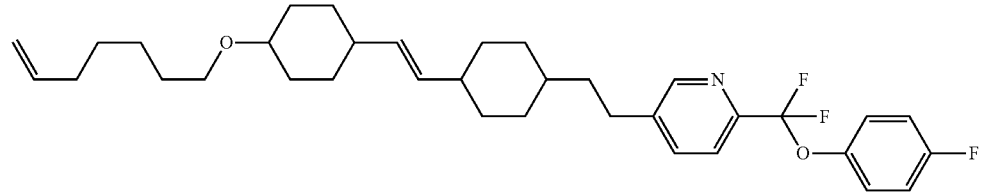 [SMILES: C=CCCCCCOC1CCC(/C=C/C2CCC(CCc3ccc(C(F)(F)Oc4ccc(F)cc4)nc3)CC2)CC1] |
| 370 | 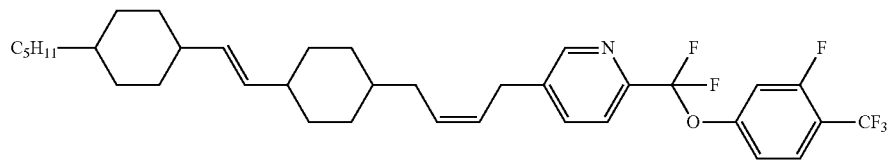 |

2. Examples of Composition

The composition of the invention is explained in detail according to examples. The invention includes a mixture of a composition of Use Example 1 and a composition of Use Example 2. The invention also includes a mixture obtained by mixing at least two compositions of the use examples. The compounds in the use examples are represented by symbols based on the definitions in the following Table 3. In Table 3, the stereo configuration of 1,4-cyclohexylene is trans. In the use examples, the number in the parentheses following the symbol indicates a chemical formula to which the compound belongs. The symbol (-) means other liquid crystal compounds. The ratio (percentage) of a liquid crystal compound is a weight percentage (wt %) based on the weight of a liquid crystal composition. Finally, physical property values of the composition were summarized. The physical properties were measured according to the methods described previously, and the measured values themselves were recorded without change (without extrapolation).

TABLE 3

Method of Description of Compound Using Symbols
R—(A$_1$)—Z$_1$— . . . —Z$_n$—(A$_n$)—R'

| 1) Left terminal group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right terminal group —R' | Symbol |
|---|---|
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |

| 3) Linking group —$Z_n$— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

| 4) Ring structure —$A_n$— | Symbol |
|---|---|
| 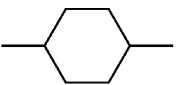 | H |
|  | B |

TABLE 3-continued

Method of Description of Compound Using Symbols
R—(A$_1$)—Z$_1$— . . . —Z$_n$—(A$_n$)—R'

| | |
|---|---|
| 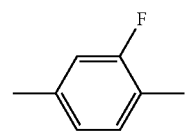 | B(F) |
| 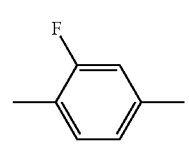 | B(2F) |
| 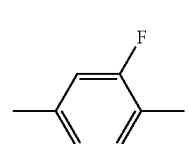 | B(F,F) |
| 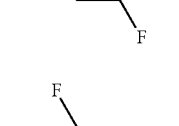 | B(2F,5F) |
| 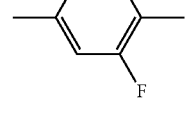 | B(2F,3F) |
| 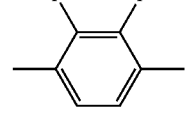 | Py |
| 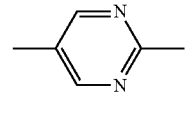 | G |
| 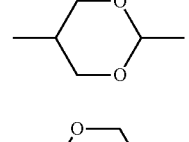 | Dh |
| 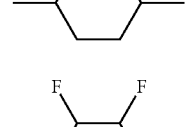 | Cro |
| 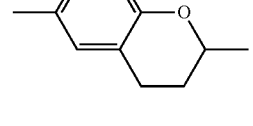 | B(2F,3CL) |

TABLE 3-continued

Method of Description of Compound Using Symbols
R—(A₁)—Z₁— . . . —Zₙ—(Aₙ)—R'

5) Examples of description

Example 1: 3-HHVHXB(F,F)—F

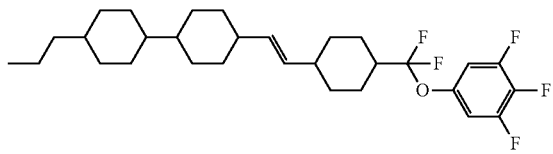 [SMILES: CCCC1CCC(C2CCC(/C=C/C3CCC(C(F)(F)Oc4cc(F)c(F)c(F)c4)CC3)CC2)CC1]

Example 2: 3-HBB(F,F)—F

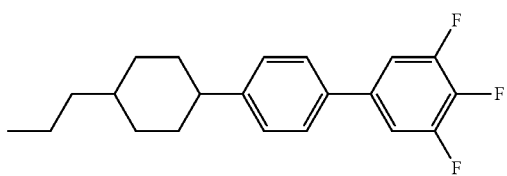 [SMILES: CCCC1CCC(c2ccc(-c3cc(F)c(F)c(F)c3)cc2)CC1]

Example 3: 3-HH-4

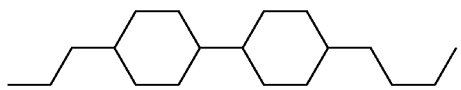 [SMILES: CCCCC1CCC(C2CCC(CCC)CC2)CC1]

Example 4: 3-HBB(2F,3F)—O2

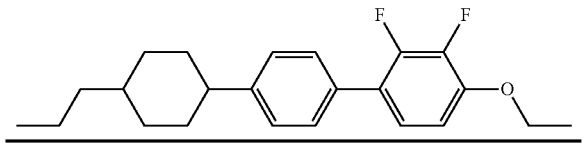

Use Example 1

| | | |
|---|---|---|
| 3-HVHXB(F,F)—F | (No. 3) | 10% |
| 3-HB—O2 | (2-5) | 8% |
| 5-HB—CL | (5-2) | 9% |
| 3-HBB(F,F)—F | (6-24) | 7% |
| 3-PyB(F)—F | (5-15) | 10% |
| 5-PyB(F)—F | (5-15) | 10% |
| 3-PyBB—F | (6-80) | 10% |
| 4-PyBB—F | (6-80) | 10% |
| 5-PyBB—F | (6-80) | 10% |
| 5-HBB(F)B-2 | (4-5) | 9% |
| 5-HBB(F)B-3 | (4-5) | 7% |

NI=98.1° C.; η=39.6 mPa·s; Δn=0.184; and Δε=8.8

Use Example 2

| | | |
|---|---|---|
| 3-HVHXB(F)—CF3 | (No. 5) | 9% |
| 2-HB—C | (8-1) | 5% |
| 3-HB—C | (8-1) | 12% |
| 3-HB—O2 | (2-5) | 13% |
| 2-BTB-1 | (2-10) | 3% |
| 3-HHB—F | (6-1) | 4% |
| 3-HHB-1 | (3-1) | 7% |
| 3-HHB—O1 | (3-1) | 5% |
| 3-HHB-3 | (3-1) | 12% |
| 3-HHEB—F | (6-10) | 4% |
| 5-HHEB—F | (6-10) | 4% |
| 2-HHB(F)—F | (6-2) | 5% |
| 3-HHB(F)—F | (6-2) | 6% |
| 5-HHB(F)—F | (6-2) | 5% |
| 3-HHB(F,F)—F | (6-3) | 6% |

NI=99.6° C.; η=20.6 mPa·s; Δn=0.100; and Δε=5.7.

Use Example 3

| | | |
|---|---|---|
| 3-HHVHXB(F,F)—F | (No. 23) | 10% |
| 7-HB(F,F)—F | (5-4) | 3% |
| 3-HB—O2 | (2-5) | 7% |
| 2-HHB(F)—F | (6-2) | 9% |
| 3-HHB(F)—F | (6-2) | 8% |
| 5-HHB(F)—F | (6-2) | 9% |
| 2-HBB(F)—F | (6-23) | 8% |
| 3-HBB(F)—F | (6-23) | 9% |
| 5-HBB(F)—F | (6-23) | 15% |
| 2-HBB—F | (6-22) | 4% |
| 3-HBB—F | (6-22) | 3% |
| 5-HBB—F | (6-22) | 3% |
| 3-HBB(F,F)—F | (6-24) | 4% |
| 5-HBB(F,F)—F | (6-24) | 8% |

NI=97.3° C.; η=26.5 mPa·s; Δn=0.114; and Δε=6.2.

Use Example 4

| | | |
|---|---|---|
| 3-HHVHXB(F,F)—CF3 | (No. 26) | 5% |
| 5-HB—CL | (5-2) | 14% |
| 3-HB—O2 | (2-5) | 15% |
| 3-HHB—F | (6-1) | 4% |
| 3-HHB—CL | (6-1) | 3% |
| 4-HHB—CL | (6-1) | 4% |
| 3-HHB(F)—F | (6-2) | 10% |
| 4-HHB(F)—F | (6-2) | 9% |
| 5-HHB(F)—F | (6-2) | 8% |
| 7-HHB(F)—F | (6-2) | 8% |
| 5-HBB(F)—F | (6-23) | 3% |
| 1O1—HBBH-5 | (4-1) | 3% |
| 3-HHBB(F,F)—F | (7-6) | 2% |
| 4-HHBB(F,F)—F | (7-6) | 3% |
| 5-HHBB(F,F)—F | (7-6) | 3% |
| 3-HH2BB(F,F)—F | (7-15) | 3% |
| 4-HH2BB(F,F)—F | (7-15) | 3% |

NI=113.7° C.; η=21.9 mPa·s; Δn=0.098; and Δε=4.7.

Use Example 5

| | | |
|---|---|---|
| 3-HVHHXB(F,F)—F | (No. 223) | 10% |
| 3-HHB(F,F)—F | (6-3) | 9% |
| 3-H2HB(F,F)—F | (6-15) | 8% |
| 4-H2HB(F,F)—F | (6-15) | 8% |
| 5-H2HB(F,F)—F | (6-15) | 8% |
| 3-HBB(F,F)—F | (6-24) | 17% |
| 5-HBB(F,F)—F | (6-24) | 16% |
| 3-H2BB(F,F)—F | (6-27) | 10% |
| 5-HHBB(F,F)—F | (7-6) | 3% |
| 5-HHEBB—F | (7-17) | 2% |
| 3-HH2BB(F,F)—F | (7-15) | 3% |
| 1O1—HBBH-4 | (4-1) | 3% |
| 1O1—HBBH-5 | (4-1) | 3% |

NI=108.1° C.; η=36.6 mPa·s; Δn=0.113; and Δε=9.2.

The helical pitch was 65.4 μm when the compound (Op-05) was added to the composition in a ratio of 0.25 wt %.

Use Example 6

| | | |
|---|---|---|
| 3-BHVHXB(F,F)—F | (No. 43) | 5% |
| 5-HB—F | (5-2) | 12% |
| 6-HB—F | (5-2) | 9% |
| 7-HB—F | (5-2) | 7% |
| 2-HHB—OCF3 | (6-1) | 6% |
| 3-HHB—OCF3 | (6-1) | 7% |
| 4-HHB—OCF3 | (6-1) | 7% |
| 5-HHB—OCF3 | (6-1) | 5% |
| 3-HH2B—OCF3 | (6-4) | 4% |
| 5-HH2B—OCF3 | (6-4) | 3% |
| 3-HHB(F,F)—OCF2H | (6-3) | 4% |
| 3-HHB(F,F)—OCF3 | (6-3) | 4% |
| 3-HH2B(F)—F | (6-5) | 3% |
| 3-HBB(F)—F | (6-23) | 10% |
| 5-HBB(F)—F | (6-23) | 8% |
| 5-HBBH-3 | (4-1) | 3% |
| 3-HB(F)BH-3 | (4-2) | 3% |

Use Example 7

| | | |
|---|---|---|
| 3-HVXHB(F,F)—F | (No. 183) | 4% |
| 5-HB—CL | (5-2) | 11% |
| 3-HB—O2 | (2-5) | 8% |
| 3-HHB-1 | (3-1) | 5% |
| 3-HHB(F,F)—F | (6-3) | 8% |
| 3-HBB(F,F)—F | (6-24) | 19% |
| 5-HBB(F,F)—F | (6-24) | 15% |
| 3-HHEB(F,F)—F | (6-12) | 8% |
| 4-HHEB(F,F)—F | (6-12) | 3% |
| 5-HHEB(F,F)—F | (6-12) | 3% |
| 2-HBEB(F,F)—F | (6-39) | 3% |
| 3-HBEB(F,F)—F | (6-39) | 3% |
| 5-HBEB(F,F)—F | (6-39) | 4% |
| 3-HHBB(F,F)—F | (7-6) | 6% |

Use Example 8

| | | |
|---|---|---|
| 3-HVHB(F,F)XB(F,F)—F | (No. 253) | 3% |
| 3-HB—CL | (5-2) | 6% |
| 5-HB—CL | (5-2) | 4% |
| 3-HHB—OCF3 | (6-1) | 5% |
| 3-H2HB—OCF3 | (6-13) | 5% |
| 5-H4HB—OCF3 | (6-19) | 14% |
| V—HHB(F)—F | (6-2) | 5% |
| 3-HHB(F)—F | (6-2) | 4% |
| 5-HHB(F)—F | (6-2) | 5% |
| 3-H4HB(F,F)—CF3 | (6-21) | 8% |
| 5-H4HB(F,F)—CF3 | (6-21) | 10% |
| 5-H2HB(F,F)—F | (6-15) | 5% |
| 5-H4HB(F,F)—F | (6-21) | 6% |
| 2-H2BB(F)—F | (6-26) | 5% |
| 3-H2BB(F)—F | (6-26) | 10% |
| 3-HBEB(F,F)—F | (6-39) | 5% |

Use Example 9

| | | |
|---|---|---|
| 3-HHVHXB(F,F)—F | (No. 23) | 8% |
| 5-HB—CL | (5-2) | 17% |
| 7-HB(F,F)—F | (5-4) | 3% |
| 3-HB—O2 | (2-5) | 12% |
| 5-HB—O2 | (2-5) | 9% |
| 7-HB-1 | (2-5) | 5% |
| 3-HHB-1 | (3-1) | 8% |
| 3-HHB—O1 | (3-1) | 4% |
| 2-HHB(F)—F | (6-2) | 7% |
| 3-HHB(F)—F | (6-2) | 7% |
| 5-HHB(F)—F | (6-2) | 7% |
| 3-HHB(F,F)—F | (6-3) | 5% |
| 3-H2HB(F,F)—F | (6-15) | 4% |
| 4-H2HB(F,F)—F | (6-15) | 4% |

NI=75.1° C.; η=17.0 mPa·s; Δn=0.080; and Δε=4.0.

Use Example 10

| | | |
|---|---|---|
| 3-HVHHXB(F,F)—F | (No. 223) | 10% |
| 5-HB—CL | (5-2) | 3% |
| 7-HB(F)—F | (5-3) | 6% |
| 3-HB—O2 | (2-5) | 15% |
| 5-HB—O2 | (2-5) | 14% |
| 3-HHEB—F | (6-10) | 8% |
| 5-HHEB—F | (6-10) | 7% |
| 3-HHEB(F,F)—F | (6-39) | 8% |
| 4-HHEB(F,F)—F | (6-39) | 5% |
| 4-HGB(F,F)—F | (6-103) | 5% |
| 5-HGB(F,F)—F | (6-103) | 5% |
| 2-H2GB(F,F)—F | (6-106) | 4% |
| 3-H2GB(F,F)—F | (6-106) | 5% |
| 5-GHB(F,F)—F | (6-109) | 5% |

NI=79.9° C.; η=19.8 mPa·s; Δn=0.074; and Δε=6.8.

Use Example 11

| | | |
|---|---|---|
| 3-HHVHXB(F,F)—F | (No. 23) | 9% |
| 3-HB—O1 | (2-5) | 15% |
| 3-HH-4 | (2-1) | 5% |
| 3-HB(2F,3F)—O2 | (9-1) | 10% |
| 5-HB(2F,3F)—O2 | (9-1) | 12% |
| 2-HHB(2F,3F)-1 | (10-1) | 11% |
| 3-HHB(2F,3F)-1 | (10-1) | 9% |
| 3-HHB(2F,3F)—O2 | (10-1) | 11% |
| 5-HHB(2F,3F)—O2 | (10-1) | 12% |
| 3-HHB-1 | (3-1) | 6% |

NI=95.2° C.; η=36.6 mPa·s; Δn=0.091; and Δε=−3.0.

Use Example 12

| | | |
|---|---|---|
| 3-HHVHXB(F,F)—CF3 | (No. 26) | 4% |
| 2-HH-5 | (2-1) | 3% |
| 3-HH-4 | (2-1) | 14% |
| 3-HH-5 | (2-1) | 4% |
| 3-HB—O2 | (2-5) | 12% |
| 3-H2B(2F,3F)—O2 | (9-4) | 15% |
| 5-H2B(2F,3F)—O2 | (9-4) | 15% |
| 3-HHB(2F,3CL)—O2 | (10-12) | 4% |
| 2-HBB(2F,3F)—O2 | (10-7) | 3% |
| 3-HBB(2F,3F)—O2 | (10-7) | 8% |
| 5-HBB(2F,3F)—O2 | (10-7) | 8% |
| 3-HHB-1 | (3-1) | 3% |
| 3-HHB-3 | (3-1) | 4% |
| 3-HHB—O1 | (3-1) | 3% |

NI=78.0° C.; η=20.0 mPa·s; Δn=0.092; and Δε=−3.9.

Use Example 13

| | | |
|---|---|---|
| 3-HVHHXB(F,F)—F | (No. 223) | 7% |
| 2-HH-3 | (2-1) | 21% |
| 3-HH-4 | (2-1) | 9% |
| 1-BB-3 | (2-8) | 9% |
| 3-HB—O2 | (2-5) | 2% |
| 3-BB(2F,3F)—O2 | (9-3) | 9% |
| 5-BB(2F,3F)—O2 | (9-3) | 6% |
| 2-HH1OB(2F,3F)—O2 | (10-5) | 11% |
| 3-HH1OB(2F,3F)—O2 | (10-5) | 18% |
| 3-HHB-1 | (3-1) | 3% |
| 3-HHB—O1 | (3-1) | 3% |
| 5-B(F)BB-2 | (3-8) | 2% |

NI=78.2° C.; η=16.5 mPa·s; Δn=0.097; and Δε=−2.8.

Use Example 14

| | | |
|---|---|---|
| 3-BHVHXB(F,F)—F | (No. 43) | 5% |
| 2-HH-3 | (2-1) | 16% |
| 7-HB-1 | (2-5) | 9% |
| 5-HB—O2 | (2-5) | 8% |
| 3-HB(2F,3F)—O2 | (9-1) | 17% |
| 5-HB(2F,3F)—O2 | (9-1) | 16% |
| 3-HHB(2F,3CL)—O2 | (10-12) | 3% |
| 4-HHB(2F,3CL)—O2 | (10-12) | 3% |
| 5-HHB(2F,3CL)—O2 | (10-12) | 2% |
| 3-HH1OCro(7F,8F)-5 | (13-6) | 4% |
| 5-HBB(F)B-2 | (4-5) | 9% |
| 5-HBB(F)B-3 | (4-5) | 8% |

Use Example 15

| | | |
|---|---|---|
| 3-HVHXHB(F,F)—F | (No. 183) | 5% |
| 1-BB-3 | (2-8) | 9% |
| 3-HH—V | (2-1) | 27% |
| 3-BB(2F,3F)—O2 | (9-3) | 12% |
| 2-HH1OB(2F,3F)—O2 | (10-5) | 20% |
| 3-HH1OB(2F,3F)—O2 | (10-5) | 14% |
| 3-HHB-1 | (3-1) | 8% |
| 5-B(F)BB-2 | (3-8) | 5% |

Use Example 16

| | | |
|---|---|---|
| 3-HVHB(F,F)XB(F,F)—F | (No. 253) | 4% |
| 2-HH-3 | (2-1) | 6% |
| 3-HH-V1 | (2-1) | 10% |
| 1V2—HH-1 | (2-1) | 8% |
| 1V2—HH-3 | (2-1) | 7% |
| 3-BB(2F,3F)—O2 | (9-3) | 8% |
| 5-BB(2F,3F)—O2 | (9-3) | 4% |
| 3-H1OB(2F,3F)—O2 | (9-5) | 7% |
| 2-HH1OB(2F,3F)—O2 | (10-5) | 8% |
| 3-HH1OB(2F,3F)—O2 | (10-5) | 18% |
| 3-HDhB(2F,3F)—O2 | (10-3) | 7% |
| 3-HHB-1 | (3-1) | 3% |
| 2-BB(2F,3F)B-3 | (11-1) | 10% |

Use Example 17

| | | |
|---|---|---|
| 3-HVHXB(F,F)—F | (No. 3) | 8% |
| 3-HHVHXB(F,F)—CF3 | (No. 26) | 5% |
| 1V2—BEB(F,F)—C | (8-15) | 4% |
| 3-HB—C | (8-1) | 15% |
| 2-BTB-1 | (2-10) | 10% |
| 3-HB—O2 | (2-5) | 15% |
| 5-HB—O2 | (2-5) | 13% |
| 3-HHB-1 | (3-1) | 5% |
| VFF—HHB-1 | (3-1) | 7% |
| VFF2—HHB-1 | (3-1) | 9% |
| 3-H2BTB-2 | (3-17) | 3% |
| 3-H2BTB-3 | (3-17) | 3% |
| 3-H2BTB-4 | (3-17) | 3% |

NI=80.2° C.; η=15.2 mPa·s; Δn=0.129; and Δε=7.0.

INDUSTRIAL APPLICABILITY

The liquid crystal compound of the invention has excellent physical properties. The liquid crystal composition that contains this compound can be widely utilized in liquid crystal display devices used for personal computers, televisions and so on.

What is claimed is:

1. A compound represented by formula (1-g),

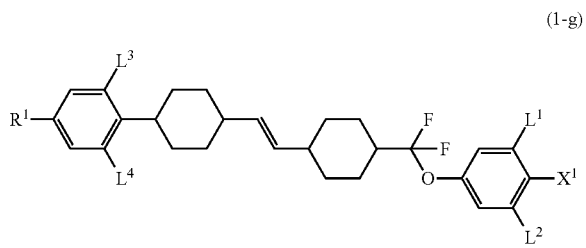

(1-g)

wherein in formula (1-g),
$R^1$ is alkyl having 1 to 10 carbons or alkenyl having 2 to 10 carbons, wherein at least one —CH$_2$— in the alkyl or alkenyl is optionally replaced with —O—;
$X^1$ is hydrogen, fluorine, —CF$_3$, or —OCF$_3$; and
$L^1$, $L^2$, $L^3$ and $L^4$ are independently hydrogen or fluorine, wherein at least one of $L^1$ and $L^2$ is fluorine.

2. The compound of claim 1, represented by any one of formulae (1-k) to (1-m),

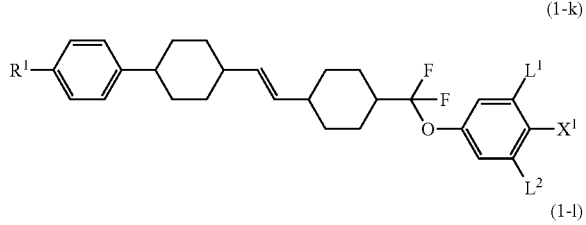

(1-k)

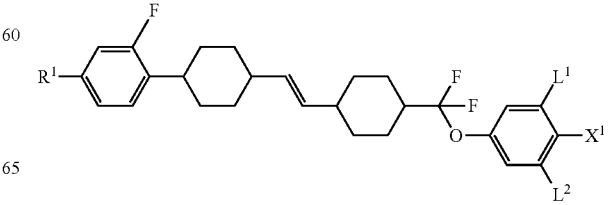

(1-l)

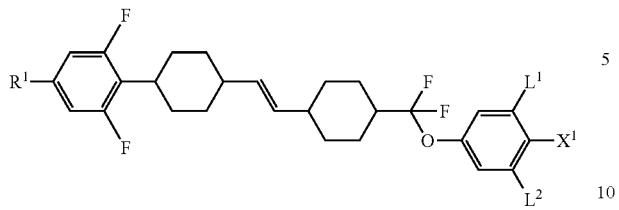

(1-m)

wherein in formulae (1-k) to (1-m),

R$^1$ is alkyl having 1 to 5 carbons or alkenyl having 2 to 5 carbons, wherein at least one —CH$_2$— in the alkyl or alkenyl is optionally replaced with —O—;

X$^1$ is hydrogen, fluorine, —CF$_3$, or —OCF$_3$; and

L$^1$ and L$^2$ are independently hydrogen or fluorine, wherein at least one of L$^1$ and L$^2$ is fluorine.

3. The compound of claim 2, wherein in formulae (1-k) to (1-m) of claim 2, R$^1$ is alkyl having 1 to 5 carbons or alkenyl having 2 to 5 carbons; X$^1$ is fluorine; and L$^1$ and L$^2$ are independently hydrogen or fluorine, wherein at least one of L$^1$ and L$^2$ is fluorine.

4. The compound of claim 2, wherein in formulae (1-k) to (1-m) of claim 2, R$^1$ is alkyl having 1 to 5 carbons or alkenyl having 2 to 5 carbons; X$^1$ is —CF$_3$; and L$^1$ and L$^2$ are independently hydrogen or fluorine, wherein at least one of L$^1$ and L$^2$ is fluorine.

5. The compound of claim 2, wherein in formulae (1-k) to (1-m) of claim 2, R$^1$ is alkyl having 1 to 5 carbons or alkenyl having 2 to 5 carbons; X$^1$ is —OCF$_3$; and L$^1$ and L$^2$ are independently hydrogen or fluorine, wherein at least one of L$^1$ and L$^2$ is fluorine.

6. A liquid crystal composition containing at least one compound of claim 1.

7. The liquid crystal composition of claim 6, further containing at least one compound selected from the group consisting of compounds represented by formulae (2) to (4),

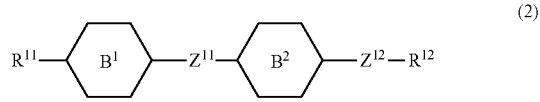

(2)

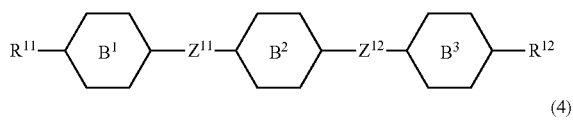

(3)

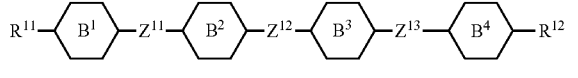

(4)

wherein in formulae (2) to (4),

R$^{11}$ and R$^{12}$ are independently alkyl having 1 to 10 carbons or alkenyl having 2 to 10 carbons, wherein at least one —CH$_2$— in the alkyl or alkenyl is optionally replaced with —O—, and at least one hydrogen in the alkyl or alkenyl is optionally replaced with fluorine;

ring B$^1$, ring B$^2$, ring B$^3$, and ring B$^4$ are independently 1,4-cyclohexylene, 1,4-phenylene, 2-fluoro-1,4-phenylene, 2,5-difluoro-1,4-phenylene, or pyrimidine-2,5-diyl; and Z$^{11}$, Z$^{12}$, and Z$^{13}$ are independently a single bond, —CH$_2$CH$_2$—, —CH=CH—, —C≡C—, or —COO—.

8. The liquid crystal composition of claim 6, further containing at least one compound selected from the group consisting of compounds represented by formulae (5) to (7),

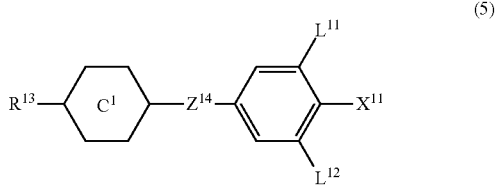

(5)

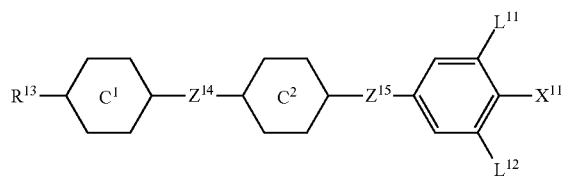

(6)

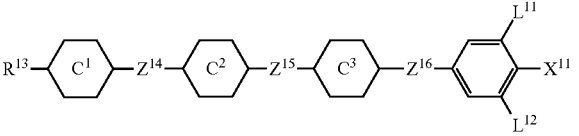

(7)

wherein in formulae (5) to (7),

R$^{13}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

X$^{11}$ is fluorine, chlorine, —OCF$_3$, —OCHF$_2$, —CF$_3$, —CHF$_2$, —CH$_2$F, —OCF$_2$CHF$_2$, or —OCF$_2$CHFCF$_3$;

ring C$^1$, ring C$^2$ and ring C$^3$ are independently 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

Z$^{14}$, Z$^{15}$, and Z$^{16}$ are independently a single bond, —CH$_2$CH$_2$—, —CH=CH—, —C≡C—, —COO—, —CF$_2$O—, —OCF$_2$—, —CH$_2$O—, or —(CH$_2$)$_4$—; and L$^{11}$ and L$^{12}$ are independently hydrogen or fluorine.

9. The liquid crystal composition of claim 6, further containing at least one compound represented by formula (8),

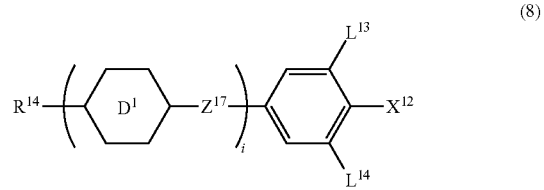

(8)

wherein in formula (8),

R$^{14}$ is alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

$X^{12}$ is —C≡N or —C≡C—C≡N;

ring $D^1$ is 1,4-cyclohexylene, 1,4-phenylene in which at least one hydrogen is optionally replaced with fluorine, tetrahydropyran-2,5-diyl, 1,3-dioxane-2,5-diyl, or pyrimidine-2,5-diyl;

$Z^{17}$ is a single bond, —CH$_2$CH$_2$—, —C≡C—, —COO—, —CF$_2$O—, —OCF$_2$—, or —CH$_2$O—;

$L^{13}$ and $L^{14}$ are independently hydrogen or fluorine; and i is 1, 2, 3, or 4.

10. The liquid crystal composition of claim 6, further containing at least one compound selected from the group consisting of compounds represented by formulae (9) to (15), nylene in which at least one hydrogen is optionally replaced with fluorine, tetrahydropyran-2,5-diyl, or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —CH$_2$CH$_2$—, —COO—, —CH$_2$O—, —OCF$_2$—, or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and

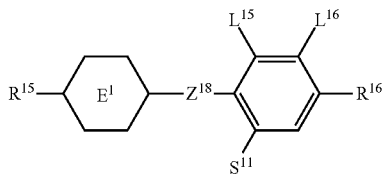

(9)

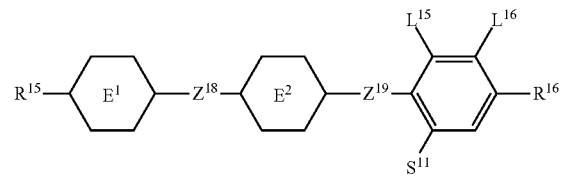

(10)

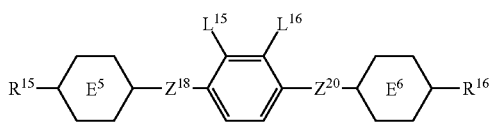

(11)

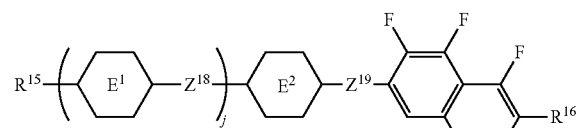

(12)

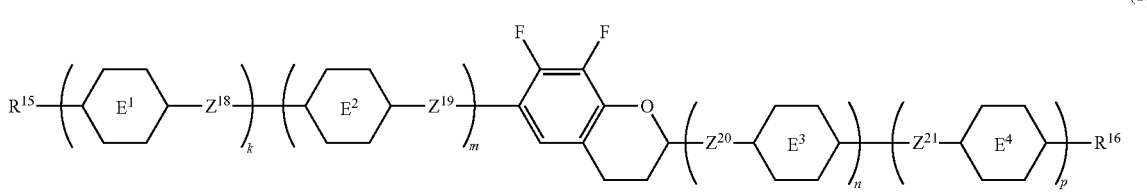

(13)

(14)

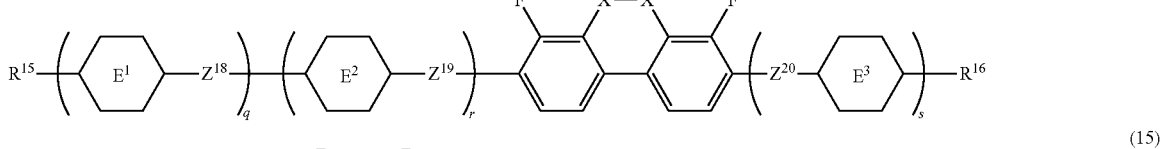

(15)

wherein in formulae (9) to (15), $R^{15}$ and $R^{16}$ are independently alkyl having 1 to 10 carbons or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

$R^{17}$ is hydrogen, fluorine, alkyl having 1 to 10 carbons, or alkenyl having 2 to 10 carbons, wherein at least one —CH$_2$— in the alkyl and alkenyl is optionally replaced with —O—, and at least one hydrogen in the alkyl and alkenyl is optionally replaced with fluorine;

ring $E^1$, ring $E^2$, ring $E^3$, and ring $E^4$ are independently 1,4-cyclohexylene, 1,4-cyclohexenylene, 1,4-phej, k, m, n, p, q, r and s are independently 0 or 1, the sum of k, m, n and p is 1 or 2, the sum of q, r and s is 0, 1, 2, or 3, and t is 1, 2, or 3.

11. The liquid crystal composition of claim 6, further containing at least one of a polymerizable compound, a polymerization initiator, a polymerization inhibitor, an optically active compound, an antioxidant, an ultraviolet absorbent, a light stabilizer, a heat stabilizer, a dye and a defoamer.

12. A liquid crystal display device, containing the liquid crystal composition of claim 6.

* * * * *